United States Patent
Biilmann Rønn et al.

(10) Patent No.: US 11,548,950 B2
(45) Date of Patent: Jan. 10, 2023

(54) AGENT, USES AND METHODS FOR TREATMENT

(71) Applicant: H. Lundbeck A/S, Valby (DK)

(72) Inventors: Lars Christian Biilmann Rønn, Valby (DK); Ibrahim John Malik, Valby (DK); Jeffrey B. Stavenhagen, Valby (DK); Søren Christensen, Valby (DK); Jan Egebjerg, Valby (DK); Arnout Gerritsen, Utrecht (NL); Edward van den Brink, Utrecht (NL); Paul Parren, Utrecht (NL); Rob de Jong, Utrecht (NL)

(73) Assignee: H. Lundbeck A/S, Valby (DK)

( * ) Notice: Subject to any disclaimer, the term of this patent is extended or adjusted under 35 U.S.C. 154(b) by 41 days.

(21) Appl. No.: 17/097,457

(22) Filed: Nov. 13, 2020

(65) Prior Publication Data

US 2021/0269524 A1 Sep. 2, 2021

Related U.S. Application Data

(63) Continuation of application No. 16/521,279, filed on Jul. 24, 2019, now Pat. No. 10,889,650, which is a (Continued)

(51) Int. Cl.
*C07K 16/00* (2006.01)
*A61K 51/10* (2006.01)
(Continued)

(52) U.S. Cl.
CPC ........ *C07K 16/286* (2013.01); *A61K 39/3955* (2013.01); *A61P 25/28* (2018.01); *C07K 16/28* (2013.01); *A61K 2039/505* (2013.01); *C07K 2317/20* (2013.01); *C07K 2317/21* (2013.01); *C07K 2317/24* (2013.01); *C07K 2317/33* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,179,337 A | 12/1979 | Davis et al. | |
| 4,495,285 A | 1/1985 | Shimizu et al. | |

(Continued)

FOREIGN PATENT DOCUMENTS

| | | |
|---|---|---|
| WO | WO 92/03918 A1 | 3/1992 |
| WO | WO 92/22645 A1 | 12/1992 |

(Continued)

OTHER PUBLICATIONS

International Search Report and Written Opinion dated Oct. 26, 2016 in connection with Application No. PCT/EP2016/066516. 24 pages.

(Continued)

*Primary Examiner* — Aurora M Fontainhas
(74) *Attorney, Agent, or Firm* — Wolf, Greenfield & Sacks, P.C.

(57) ABSTRACT

The present invention relates to monoclonal anti-Sortilin antibodies which have been found useful correcting a deficient level progranulin (PGRN). In particular, these antibodies can be used in the treatment of frontotemporal dementia (FTD) and amyotrophic lateral sclerosis (ALS).

19 Claims, 40 Drawing Sheets

Specification includes a Sequence Listing.

Related U.S. Application Data continuation of application No. 15/743,549, filed as application No. PCT/EP2016/066516 on Jul. 12, 2016, now Pat. No. 10,479,835.

(51) Int. Cl.
| | |
|---|---|
| *C07K 16/28* | (2006.01) |
| *A61P 25/28* | (2006.01) |
| *A61K 39/395* | (2006.01) |
| *A61K 39/00* | (2006.01) |

(56) References Cited

U.S. PATENT DOCUMENTS

| | | | |
|---|---|---|---|
| 4,609,546 | A | 9/1986 | Hiratani |
| 4,681,581 | A | 7/1987 | Coates |
| 4,735,210 | A | 4/1988 | Goldenberg |
| 4,766,106 | A | 8/1988 | Katre et al. |
| 4,946,778 | A | 8/1990 | Ladner et al. |
| 5,101,827 | A | 4/1992 | Goldenberg |
| 5,101,990 | A | 4/1992 | Krishnakumar et al. |
| 5,102,990 | A | 4/1992 | Rhodes |
| 5,225,539 | A | 7/1993 | Winter |
| 5,530,101 | A | 6/1996 | Queen et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,585,089 | A | 12/1996 | Queen et al. |
| 5,589,466 | A | 12/1996 | Feigner et al. |
| 5,625,126 | A | 4/1997 | Lonberg et al. |
| RE35,500 | E | 5/1997 | Rhodes |
| 5,633,425 | A | 5/1997 | Lonberg et al. |
| 5,648,471 | A | 7/1997 | Buttram et al. |
| 5,661,016 | A | 8/1997 | Lonberg et al. |
| 5,697,902 | A | 12/1997 | Goldenberg |
| 5,741,957 | A | 4/1998 | Doboer et al. |
| 5,750,172 | A | 5/1998 | Meade et al. |
| 5,756,687 | A | 5/1998 | Denman et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,827,690 | A | 10/1998 | Meade et al. |
| 5,859,205 | A | 1/1999 | Adair et al. |
| 5,874,299 | A | 2/1999 | Lonberg et al. |
| 5,877,397 | A | 3/1999 | Lonberg et al. |
| 5,973,972 | A | 10/1999 | Kwon et al. |
| 6,077,835 | A | 6/2000 | Hanson et al. |
| 6,407,213 | B1 | 6/2002 | Carter et al. |
| 6,881,557 | B2 | 4/2005 | Foote |
| 10,428,147 | B2 | 10/2019 | Biilmann Rønn et al. |
| 10,479,835 | B2 | 11/2019 | Biilmann Rønn et al. |
| 10,889,650 | B2 | 1/2021 | Biilmann Rønn et al. |
| 10,894,833 | B2 | 1/2021 | Biilmann Rønn et al. |
| 2010/0028333 | A1 | 2/2010 | Getty et al. |
| 2011/0144312 | A1 | 6/2011 | Kato et al. |
| 2012/0039865 | A1 | 2/2012 | Strittmatter et al. |
| 2017/0267761 | A1 | 9/2017 | Biilmann Rønn et al. |
| 2018/0305455 | A1 | 10/2018 | Biilmann Rønn et al. |
| 2019/0023788 | A1 | 1/2019 | Rønn et al. |
| 2020/0024348 | A1 | 1/2020 | Schwabe et al. |
| 2020/0190188 | A1 | 6/2020 | Biilmann Rønn et al. |
| 2021/0292414 | A1 | 9/2021 | Biilmann Rønn et al. |

FOREIGN PATENT DOCUMENTS

| | | |
|---|---|---|
| WO | WO 93/01227 A1 | 1/1993 |
| WO | WO 94/25585 A1 | 11/1994 |
| WO | WO 98/24884 A1 | 6/1998 |
| WO | WO 00/46147 A2 | 8/2000 |
| WO | WO 00/70087 A1 | 11/2000 |
| WO | WO 01/09187 A2 | 2/2001 |
| WO | WO 01/14424 A2 | 3/2001 |
| WO | WO 02/43478 A2 | 6/2002 |
| WO | WO 2004/056385 A2 | 7/2004 |
| WO | WO 2007/059782 A1 | 5/2007 |
| WO | WO 2008/074329 A2 | 6/2008 |
| WO | WO 2009/097006 A2 | 8/2009 |
| WO | WO 2009/132656 A2 | 11/2009 |
| WO | WO 2010/022175 A1 | 2/2010 |
| WO | WO 2010/069331 A2 | 6/2010 |
| WO | WO 2014/071131 A1 | 5/2014 |
| WO | WO 2016/164637 A1 | 10/2016 |
| WO | WO 2017/009327 A1 | 1/2017 |

OTHER PUBLICATIONS

Invitation to Pay Additional Fees dated Oct. 30, 2018 in connection with Application No. PCT/EP2018/069460. 17 pages.

International Search Report and Written Opinion dated May 21, 2019 in connection with for Application No. PCT/EP2018/069460. 20 pages.

[No Author Listed] Purified Mouse Anti-Neurotensin Receptor 3. BD Transduction Laboratories. 2 pages. Retrieved from the internet <https://www.bdbiosciences.com/ds/pm/tds/612100.pdf> Last accessed Jul. 23, 2020.

Altschul, 1991 Amino Acid Substitution Matrices From An Information Theoretic Perspective, J. Mol. Biol. 219, 555-565.

Aslanidis et al., Ligation-independent cloning of PCR products (LIC-PCR). Nucleic Acids Res 1990;18(20): 6069-74.

Baker et al, Mutations in progranulin cause tau-negative frontotemporal dementia linked to chromosome 17. Nature. Aug. 24, 2006;442(7105):916-9.

Barderas et al., Affinity maturation of antibodies assisted by in silico modeling. 2008. Proc. Natl. Acad. Sci. 2008;105(26):9029-9034.

Benvenisty et al., Direct introduction of genes into rats and expression of the genes. PNAS USA. 1986;83:9551-55.

Bird et al., Single-chain antigen-binding proteins. Science. 1988;242:423-426.

Böer et al., Yeast expression platforms. Appl. Microbiol. Biotechnol. 2007;77(3):513-523.

Bostrom et al., Chapter 19: Improving Antibody Binding Affinity And Specificity For Therapeutic Development. Methods Mol. Biol. 2009;525:353-376.

Boxer et al, Frontotemporal degeneration, the next therapeutic frontier: Molecules and animal models for frontotemporal degeneration drug development. Alzheimers Dement. Mar. 2013;9(2):176-88.

Brouwers et al., Genetic variability in progranulin contributes to risk for clinically diagnosed Alzheimer disease. Neurology. Aug. 26, 2008;71(9):656-64.

Carlo et al., Sorting receptor sortilin-a culprit in cardiovascular and neurological diseases. J Mol Med (Berl). Sep. 2014;92(9):905-11.

Carrasquillo et al., Genome-wide screen identifies rs646776 near sortilin as a regulator of progranulin levels in human plasma. Am J Hum Genet. Dec. 10, 2010;87(6):890-7.

Carter et al., Humanization Of An Anti-p185her2 Antibody For Human Cancer Therapy, Proc. Natl. Acad. Sci. (U.S.A.) 1992;89:4285-4289.

Celik, et al., Production of recombinant proteins by yeast cells. Biotechnol. Adv. 2012;30(5), 1108-1118.

Chen et al., B cell development in mice that lack one or both immunoglobulin kappa light chain genes. EMBO J. Mar. 1993;12(3):821-30.

Chen et al., Immunoglobulin gene rearrangement in B cell deficient mice generated by targeted deletion of the JH locus. Int Immunology. 1993;5(6):647-656.

Chen et al., Progranulin does not bind tumor necrosis factor (TNF) receptors and is not a direct regulator of TNF-dependent signaling or bioactivity in immune or neuronal cells. J Neurosci. 2013;33(21):9202-9213.

Chothia et al., Canonical structures For The Hypervariable domains Of Immunoglobulins. J. Mol. Biol. 1987;196:901-917.

Clackson et al., Making antibody fragments using phage display libraries. Nature. Aug. 15, 1991;352(6336):624-8.

Co et al., Chimeric And Humanized Antibodies With Specificity For The CD33 Antigen. J. Immunol. 1992;148:1149-1154.

Co et al., Humanized Antibodies For Antiviral Therapy. Proc. Natl. Acad. Sci. (U.S.A.). 1991;88:2869-2873.

(56) References Cited

OTHER PUBLICATIONS

Corsaro et al., Enhancing the efficiency of DNA-mediated gene transfer in mammalian cells. Somatic Cell Genet. Sep. 1981;7(5):603-16.

Cruts et al, Loss of progranulin function in frontotemporal lobar degeneration. Trends in Genetics. 2008;24:186-194.

Cruts et al, Null mutations in progranulin cause ubiquitin-positive frontotemporal dementia linked to chromosome 17q21. Nature. 2006;442: 920-924.

De Muynck et al, The neurotrophic properties of progranulin depend on the granulin E domain but do not require sortilin binding. Neurobiology of Aging. 2013;34(11):2541-2547.

Dumont et al, Human cell lines for biopharmaceutical manufacturing: history, status and future perspectives, Crit Rev Biotechnol. 2016;36(6):1110-1122.

Eddy, Where Did The BLOSUM62 Alignment Score Matrix Come From? Nature Biotech. 2004;22(8):1035-1036.

Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.

Evans et al., Rapid expression of an anti-human C5 chimeric Fab utilizing a vector that replicates in COS and 293 cells. J. Immunol. Meth. 1995;184:123-38.

Finlay et al., Affinity Maturation of a Humanized Rat Antibody for Anti-RAGE Therapy: Comprehensive Mutagenesis Reveals a High Level of Mutational Plasticity Both Inside and Outside the Complementarity-Determining Regions. J. Mol. Biol. 2009;388(3):541-558.

Fishwild et al., High-avidity human IgGk monoclonal antibodies from a novel strain of minilocus transgenic mice. Nature Biotechnology. 1996;14:845-851.

Ghaemimanesh et al., Production and Characterization of a Novel Monoclonal Antibody Against Human Sortilin. Monoclon Antib Immunodiagn Immunother. Dec. 2015;34(6):390-5. doi: 10.1089/mab.2015.0042.

Glaser et al., Antibody engineering by codon-based mutagenesis in a filamentous phage vector system. J Immunol. Dec. 15, 1992;149(12):3903-13.

Gonzales et al., SDR Grafting Of A Murine Antibody Using Multiple Human Germline Templates To Minimize Its Immunogenicity. Mol. Immunol. 2004;41:863-872.

Gorman et al., Reshaping A Therapeutic CD4 Antibody, Proc. Natl. Acad. Sci. (U.S.A.). 1991;88:4181-4185.

Grant et al., Expression and Secretion Vectors for Yeast. Methods in Enzymol. 1987;153:516-544.

Gunasekaran et al., Enhancing antibody Fc Heterodimer formation through electrostatic steering effects: Applications to bispecific molecules and monovalent IgG. J Biolog Chem. 2010;285(5):19637-46.

Gustchina et al., Affinity maturation by targeted diversification of the cdr-h2 loop of a monoclonal fab derived from a synthetic naïve human antibody library and directed against the internal trimeric coiled-coil of gp41 yields a set of Fabs with improved HIV-1 neutralization potency and breadth. Virology. 2009;393(1):112-119.

Hackel et al., Stability And CDR Composition Biases Enrich Binder Functionality Landscapes. J. Mol. Biol. 2010;401(1):84-96.

Harding et al., Class switching in human immunoglobulin transgenic mice. N Ann NY Acad Sci. 1995;764:536-546.

He et al., Progranulin (granulin-epithelin precursor, PC-cell-derived growth factor, acrogranin) mediates tissue repair and tumorigenesis. J. Mol. Med. 2003;57:600-612.

Henikoff et al., Amino acid substitution matrices from protein blocks, Proc. Natl. Acad. Sci. (USA). 1992;89:10915-10919.

Holliger et al., "Diabodies": small bivalent and bispecific antibody fragments. Proc Natl Acad Sci U S A. Jul. 15, 1993;90(14):6444-8.

Holliger, Chapter 31: Expression of Antibody Fragments. Methods Mol. Biol. 2002;178:349-357.

Holt et al., Doman antibodies: proteins for therapy. Trends Biotechnol. Nov. 2003;2i(11) :484-90.

Hu et al., Sortilin-mediated endocytosis determines levels of the frontotemporal dementia protein, progranulin. Neuron. Nov. 18, 2010;68(4):654-67.

Huston et al., Protein engineering of antibody binding sites: recovery of specific activity in an anti-digoxin single-chain Fv analogue produced in *Escherichia coli*. Proc. Natl. Acad. Sci. (U.S.A.) 1988;85:5879-5883.

Ito et al., Conjoint pathologic cascades mediated by ALS/FTLD-U linked RNA-binding proteins TDP-43 and FUS. Neurology. Oct. 25, 2011;77(17):1636-43.

Karlin et al., Methods For Assessing The Statistical Significance Of Molecular Sequence Features By Using General Scoring Schemes. Proc. Natl. Acad. Sci. (USA). 1990;87:2264-2268.

Kettleborough et al., Humanization Of A Mouse Monoclonal Antibody By CDR-Grafting: The Importance Of Framework Residues On Loop Conformation. Protein Engineering. 1991;4:773-83.

Köhler et al., Continuous cultures of fused cells secreting antibody of predefined specificity. Nature. Aug. 7, 1975;256(5517):495-7.

Krause et al., An Insertion Mutation That Distorts Antibody Binding Site Architecture Enhances Function Of A Human Antibody. MBio. 2011:2(1) pii: e00345-10. doi: 10.1128/mBio.00345-10.

Kuan et al., Affinity-matured anti-glycoprotein NMB recombinant immuno toxins targeting; malignant gliomas and melanomas. Int J Cancer. Jul. 1, 2011;129(1):111-21. doi:; 10.1002/ijc.25645. Epub Nov. 3, 2010.

Kurth et al., Site-Specific Conjugation Of A Radioiodinated Phenethylamine Derivative To A Monoclonal Antibody Results In Increased Radioactivity Localization In Tumor. J. Med. Chem. 1993;36(9):1255-1261.

Labrijn et al., Efficient generation of stable bispecific IgG1 by controlled Fab-arm exchange. PNAS. Mar. 26, 2013;110(13):5145-50.

Le Ber et al., Demographic, neurological and behavioural characteristics and brain perfusion SPECT in frontal variant of frontotemporal dementia. Brain. 2006;129:3051-65.

Lee et al., Targeted manipulation of the sortilin-progranulin axis rescues progranulin haploinsufficiency. Hum Mol Genet. Mar. 15, 2014;23(6):1467-78. doi: 10.1093/hmg/ddt534. Epub Oct. 26, 2013.

Li et al., Expression of recombinant proteins in *Picha pastoris*. Appl Biochem Biotechnol. 2007;142(2):105-124. DOI: 10.1007/s12010-007-0003-x.

Liau et al., Identification of a human glioma-associated growth factor gene, granulin, using differential immuno-absorption. Cancer Res. 2000. 60:1353-1360.

Lindegren et al., Chloramine-T In High-Specific-Activity Radioiodination Of Antibodies Using N-Succinimidyl-3-(Trimethylstannyl)Benzoate As An Intermediate. Nucl. Med. Biol. 1998;25(7):659-665.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Lobuglio et al., Mouse/Human Chimeric Monoclonal Antibody In Man: Kinetics And Immune Response. Proc. Natl. Acad. Sci. (U.S.A.). 1989;86:4220-4224.

Lonberg et al., Antigen-sepcific human antibodies from mice comprising four distinct genetic modifications. Nature. 1994;368:856-9.

Lonberg et al., Human antibodies from transgenic mice. Intern. Rev. Immunol. 1995;13:65-93.

Lu et al., Mediation of estrogen mitogenic effect in human breast cancer MCF-7 cells by PC-cell-derived growth factor (PCDGF/granulin precursor). Proc. Natl Acad Sci U.S.A. 2001;98:142-147.

Mabry et al., Engineering of stable bispecific antibodies targeting IL-17A and IL-23. PEDS. 2010;23(3):115-127.

Maeda et al., Construction Of Reshaped Human Antibodies With HIV-Neutralizing Activity. Human Antibodies Hybridoma. 1991;2:124-134.

Mariuzza et al., The structural basis of antigen-antibody recognition. Annu Rev Biophys Chem. 1987;16:139-59.

Marks et al., By-passing immunization. Human antibodies from V-gene libraries displayed on phage. J Mol Biol. Dec. 5, 1991;222(3):581-97.

(56) References Cited

OTHER PUBLICATIONS

Mattanovich et al., Chapter 17: Recombinant Protein Production in Yeasts. Methods Mol. Biol. 2012; 824:329-358.

McCafferty et al., Phage antibodies: filamentous phage displaying antibody variable domains. Nature. 1990;348:552-554.

Metz et al., Bispecific antibody derivatives with restricted binding functionalities that are activated by proteolytic processing. Protein Engineering. 2012; 25(10):571-580.

Minami et al., Progranulin protects against amyloid β deposition and toxicity in Alzheimer's disease mouse models. Nat Med. Oct. 2014;20(10):1157-64.

Monami et al., Proepithelin Promotes Migration and Invasion of 5637 Bladder Cancer Cells through the Activation of ERK1/2 and the Formation of a Paxillin/FAK/ERK Complex. Cancer Res. 2006;66(14):7103-10.

Montgomery et al., Affinity maturation and characterization of a human monoclonal antibody against HIV-1 gp41. MAbs. Sep.-Oct. 2009;1(5):462-74. Epub Sep. 8, 2009.

Moore et al., A novel bispecific antibody format enables simultaneous bivalent and monovalent co-engagement of distinct target antigens. MAbs. Nov.-Dec. 2011;3(6):546-57. doi: 10.4161/mabs.3.6.18123. Epub Nov. 1, 2011.

Nguyen et al., Progranulin: at the interface of neurodegenerative and metabolic diseases. Trends Endocrinol Metab. Dec. 2013;24(12):597-606.

Nykjær et al, Sortilin: a receptor to regulate neuronal viability and function. Trends Neurosci. Apr. 2012;35(4):261-70. doi: 10.1016/j.tins.2012.01.003. Epub Feb. 16, 2012. Review.

Nykjaer et al., Sortilin is essential for proNGF-induced neuronal cell death. Nature. Feb. 26, 2004;427(6977):843-8.

Quistgaard et al, Ligands bind to Sortilin in the tunnel of a ten-bladed beta-propeller domain. Nat Struct Mol Biol. Jan. 2009;16(1):96-8. doi: 10.1038/nsmb.1543. Epub Jan. 4, 2009.

Quistgaard et al, Revisiting the structure of the Vps10 domain of human sortilin and its interaction with neurotensin. Protein Sci. Sep. 2014;23(9):1291-300. doi: 10.1002/pro.2512. Epub Jul. 22, 2014.

Rademakers et al, Advances in understanding the molecular basis of frontotemporal dementia. Nat Rev Neurol. Aug. 2012;8(8) 423-34.

Rasmussen et al., Transient p53 suppression increases reprogramming of human fibroblasts without affecting apoptosis and DNA damage. Stem Cell Reports. Sep. 9, 2014;3(3):404-13. doi: 10.1016/j.stemcr.2014.07.006. Epub Aug. 21, 2014.

Rea et al., Site-specifically radioiodinated antibody for targeting tumors. Cancer Res. 1990;50(3 Suppl):857s-861s.

Revets et al., Nanobodies as novel agents for cancer therapy. Expert Opin Biol Ther. Jan. 2005;5(1):111-24.

Ridgway et al., 'Knobs-into-holes' engineering of antibody CH3 domains for heavy chain heterodimerization. Protein Eng. Jul. 1996;9(7):617-21.

Riechmann et al., Reshaping human antibodies for therapy. Nature. Mar. 24, 1988;332(6162):323-7.

Sato et al., Reshaping a human antibody to inhibit the interleukin 6-dependent tumor cell ; growth. Cancer Res. Feb. 15, 1993;53(4):851-6.

Schakowski et al., A Novel Minimal-Size Vector (MIDGE) Improves Transgene Expression in Colon Carcinoma Cells and Avoids Transfection of Undesired DNA. Mol Ther. 2001;3(5):793-800.

Schrøder et al., The identification of AF38469: An orally bioavailable inhibitor of the VPS10P family sorting receptor Sortilin. Bioorg Med Chem Lett. Jan. 1, 2014;24(1):177-80.

Serrero, Autocrine growth factor revisited: PC-cell-derived growth factor (progranulin), a critical player in breast cancer tumorigenesis. Biochem Biophys. Res. Commun. 2003;308:409-413.

Sheng et al., Progranulin polymorphism rs5848 is associated with increased risk of Alzheimer's disease. Gene. Jun. 1, 2014;542(2):141-5.

Spreter Von Kreudenstein et al., Improving biophysical properties of a bispecific antibody scaffold to aid developability: quality by molecular design. MAbs. 2013; 5(2);646-54.

Steidl et al., In Vitro Affinity Maturation Of Human GM-CSF Antibodies By Targeted CDR-Diversification. Mol. Immunol. 2008;46(1):135-144.

Strop et al., Generating Bispecific Human IgG1 and IgG2 Antibodies from Any Antibody Pair. JMB. 2012;420:204-19.

Sykes et al., Linear expression elements: a repid, in vivo, method to screen for gene functions. Nat Biotech. Apr. 1997;17:355-9.

Takamura et al., Sortilin is required for toxic action of Aβ oligomers (AβOs): extracellular AβOs trigger apoptosis, and intraneuronal AβOs impair degradation pathways. Life Sci. Dec. 10, 2012;91(23-24):1177-86. doi: 10.1016/j.lfs.2012.04.038. Epub May 3, 2012.

Tang et al., The growth factor progranulin binds to TNF receptors and is therapeutic against inflammatory arthritis in mice. Science. Apr. 22, 2011;332(6028):478-84. doi: 10.1126/science.1199214. Epub Mar. 10, 2011.

Tangkeangsirisin et al., PC cell-derived growth factor (PCDGF/GP88, progranulin) stimulates migration, invasiveness and VEGF expression in breast cancer cells. Carcinogenesis. Sep. 2004;25(9):1587-92. Epub Apr. 29, 2004.

Taylor et al., A transgenic mouse that expresses a diversity of human sequence heavy and light chain immunoglobulins. Nucleic Acids Res. Dec. 11, 1992;20(23):6287-95.

Taylor et al., Human immunoglobulin transgenes undergo rearrangement, somatic mutation and class switching in mice that lack endogenous IgM. Int Immunol. Apr. 1994;6(4):579-91.

Tempest et al., Reshaping a human monoclonal antibody to inhibit human respiratory syncytial virus infection in vivo. Biotechnology (N Y). Mar. 1991;9(3):266-71.

Tuaillon et al., Biased utilization of DHQ52 and JH4 gene segments in a human Ig transgenic minilocus is independent of antigenic selection. J Immunol. Mar. 5, 1994;152(6):2912-20.

Van Der Vaart, Expression of VHH antibody fragments in *Saccharomyces; cerevisiae*. Methods Mol Biol. 2002;178:359-66. Review.

Van Heeke et al., Expression of human asparagine synthetase in *Escherichia coli*. J Biol Chem. Apr. 5, 1989;264(10):5503-9.

Verhoeyen et al., Reshaping Human Antibodies: Grafting An Antilysozyme Activity. Science. Mar. 25, 1988;239:1534-1536.

Vincent et al., Neurotensin and neurotensin receptors. Trends Pharmacol Sci. Jul. 1999;20(7):302-9.

Ward et al., Binding activities of a repertoire of single immunoglobulin variable domains secreted from *Escherichia coli*. Nature. Oct. 12, 1989;341(6242):544-6.

Wigler et al., Biochemical transfer of single-copy eucaryotic genes using total cellular DNA as donor. Cell. Jul. 1978;14(3):725-31.

Wu et al., Stepwise in vitro affinity maturation of Vitaxin, an alphav beta3-specific humanized mAb. Proc Natl Acad Sci U S A. May 26, 1998;95(11):6037-42.

Yelton et al., Affinity maturation of the BR96 anti-carcinoma antibody by codon-based mutagenesis. J Immunol. Aug. 15, 1995;155(4):1994-2004.

Zheng et al., C-terminus of progranulin interacts with the beta-propeller region of sortilin to regulate progranulin trafficking. PLoS One. 2011;6(6):e21023. doi: 10.1371/journal.pone.0021023. Epub Jun. 15, 2011.

Zhu et al., Conversion of proepithelin to epithelins: roles of SLPI and elastase in host defense and wound repair. Cell. Dec. 13, 2002;111(6):867-78.

Arnett et al., Pro-NGF, sortilin, and p75NTR: potential mediators of injury-induced apoptosis in the mouse dorsal root ganglion. Brain Res. Dec. 5, 2007;1183:32-42. Epub Oct. 26, 2007.

1224 primary hits; 154 cloned and expressed

↓ Sortilin binding and domain assignment 62 selected clones based on sortilin binding
A(6), B(0), C(2), D(17), E(26), D+(6), Tet(2), other(3)

↓ PGRN-sortilin HTRF binding 20 inhibited PGRN-sortilin binding
15D domain, 3 D+ domain identified ↓ Crossblock analysis 19 cross blocking mAbs
Confirmed the 15 D domain, 3 D+ domain ABs

↓ PGRN ELISA

The 19 Abs increased excellular PGRN
3 Abs tested in vivo and found to increase plasma PGRN

FIG. 1

FIG. 2A
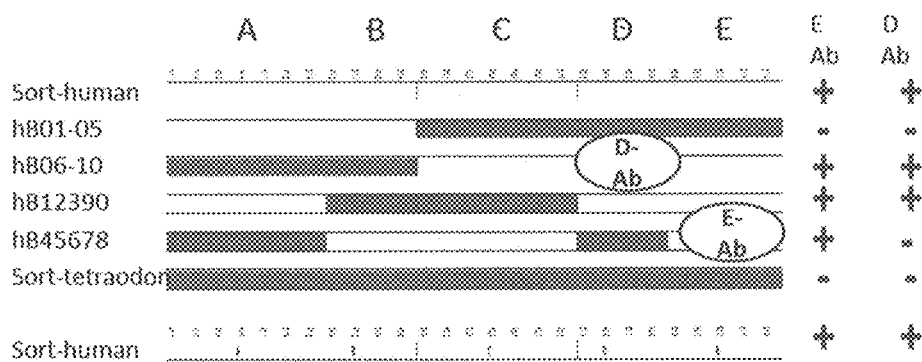
FIG. 2B
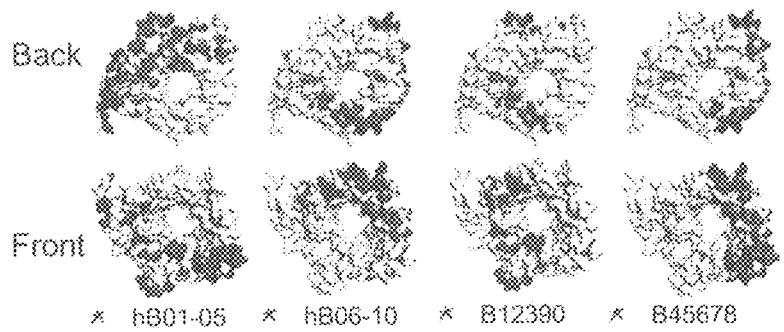
FIG. 2C
| mAbs | Domain | hSort | hB01-05 | hB06-10 | B12390 | B45678 | Tet |
|---|---|---|---|---|---|---|---|
| 6 | A | + | + | - | + | - | - |
| 0 | B | + | + | - | - | + | - |
| 2 | C | + | - | + | - | + | - |
| 17 | D | + | - | + | + | - | - |
| 26 | E | + | - | + | + | + | - |
| 6 | D+ | + | - | - | + | - | - |
| 2 | Tet | + | + | + | + | + | + |
| 3 | Other | + | +/- | +/- | +/- | + | - |

| mAb | Domain | hSort | hB01-05 | hB06-10 | B12390 | B45678 | Tet |
|---|---|---|---|---|---|---|---|
| 002 | D | 2,40 | NB | 43,30 | 2,44 | NB | NB |
| 044 | D | 1,38 | NB | 21,20 | 1,03 | NB | NB |
| 045 | D | 1,56 | NB | 9,60 | 1,10 | NB | NB |
| 68 | D+ | 1,80 | NB | NB | 1,87 | NB | NB |
| 088 | D | 2,49 | NB | 9,55 | 1,57 | NB | NB |
| 093-01 | D | 3,47 | NB | 44,53 | 2,13 | NB | NB |
| 093-05 | D | 2,88 | NB | 43,24 | 1,78 | NB | NB |
| 193 | D | 2,07 | NB | 5,57 | 0,83 | NB | NB |
| 531 | D+ | 5,50 | NB | NB | 2,29 | NB | NB |
| 548 | D+ | 4,49 | NB | NB | 3,36 | NB | NB |
| 562 | D | 2,23 | NB | 24,56 | 1,34 | NB | NB |
| 566 | D | 2,93 | NB | 42,55 | 2,12 | NB | NB |
| 811 | D | 1,81 | NB | 8,00 | 1,08 | NB | NB |
| 849 | D | 1,01 | NB | 17,08 | 0,78 | NB | NB |
| 924 | D | 6,76 | NB | 20,01 | 3,83 | NB | NB |
| 1276 | D | 2,24 | NB | 8,78 | 0,93 | NB | NB |
| 1289 | D | 1,62 | NB | 15,23 | 0,96 | NB | NB |
| 1320 | D | 19,14 | NB | 55,43 | 12,32 | NB | NB |

| | |
|---|---|
| + | EC50 0.1-10 ng/ml |
| + | EC50 >10 ng/ml |
| NB | no binding |

FIG. 3

| mAb | Domain | hSort | hB01-05 | hB06-10 | B12390 | B45678 | Tet |
|---|---|---|---|---|---|---|---|
| 1F2F4 | D | 1,56 | NB | 9,60 | 1,10 | NB | NB |
| 5E1F6 | D | 1,14 | NB | 0,72 | 0,59 | NB | NB |

| + | binding |
|---|---|
| NB | no binding |

FIG. 4

* antibody too weak to fit a dose-response curve. 6% inhibition at 1μM

** ctrl antibody too weak to fit a dose-response curve. 37% inhibition at 1μM

| Ab | highest conc (nM) | % inh highest conc | IC50 (nM) | Domain |
|---|---|---|---|---|
| IgG1-6003-002 | 500 | 91 | 4,3 | D |
| IgG1-6003-044 | 1000 | 101 | 3,4 | D |
| IgG1-6003-045 | 1000 | 102 | 3,9 | D |
| IgG1-6003-068 | 1000 | 92 | 22 | D+ |
| IgG1-6003-088 | 1000 | 96 | 2,5 | D |
| IgG1-6003-093-L01 | 1000 | 82 | 13 | D |
| IgG1-6003-093-L05 | 1000 | 95 | 35 | D |
| IgG1-6003-193 | 1000 | 93 | 1,8 | D |
| IgG1-6003-531 | 1000 | 102 | 2,5 | D+ |
| IgG1-6003-548 | 600 | 87 | 11 | D+ |
| IgG1-6003-562 | 1000 | 100 | 5,8 | D |
| IgG1-6003-566 | 1000 | 100 | 2,6 | D |
| IgG1-6003-811 | 1000 | 102 | 4,4 | D |
| IgG1-6003-849 | 1000 | 101 | 3,8 | D |
| IgG1-6003-924 | 1000 | 100 | 3,3 | D |
| IgG1-6003-1276 | 1000 | 108 | 2,5 | D |
| IgG1-6003-1289 | 800 | 98 | 3,0 | D |
| IgG1-6003-1320 | 900 | 75 | 32 | D |
| IgG1-B12 | 1000 | 37 | - | - |

FIG. 6

| Domain | antibody | D+ 548 | D+ 531 | D 002 | D 044 | D 045 | D 088 | D 193 | D 562 | D 566 | D 811 | D 878 | D 1289 | D 849 |
|---|---|---|---|---|---|---|---|---|---|---|---|---|---|---|
| D+ | 548 | 0.04 | 0.01 | 0.00 | 0.04 | 0.00 | 0.01 | 0.00 | 0.02 | 0.00 | 0.02 | 0.00 | 0.01 | 0.03 |
| D+ | 531 | 0.02 | 0.00 | -0.01 | 0.01 | 0.01 | 0.00 | 0.00 | 0.01 | 0.01 | 0.01 | 0.01 | 0.01 | 0.01 |
| D | 002 | 0.00 | -0.02 | -0.02 | 0.00 | 0.02 | -0.02 | -0.02 | 0.03 | -0.02 | -0.01 | -0.02 | -0.01 | 0.03 |
| D | 044 | 0.02 | 0.00 | -0.01 | 0.00 | 0.02 | 0.00 | -0.01 | 0.00 | 0.00 | 0.00 | -0.01 | -0.01 | 0.00 |
| D | 045 | 0.02 | 0.00 | 0.00 | 0.01 | 0.03 | 0.01 | 0.00 | 0.01 | 0.00 | 0.01 | 0.00 | 0.00 | 0.01 |
| D | 088 | 0.02 | 0.02 | 0.00 | 0.02 | 0.02 | 0.02 | 0.01 | 0.02 | 0.02 | 0.03 | 0.00 | 0.00 | 0.00 |
| D | 193 | 0.03 | 0.00 | -0.01 | 0.01 | 0.01 | -0.03 | -0.03 | 0.01 | 0.00 | 0.01 | 0.00 | -0.02 | 0.02 |
| D | 562 | 0.01 | 0.02 | -0.04 | -0.01 | -0.01 | -0.02 | -0.02 | -0.02 | -0.03 | -0.02 | 0.00 | -0.02 | 0.00 |
| D | 566 | 0.00 | -0.02 | -0.02 | 0.00 | 0.00 | -0.03 | -0.01 | -0.01 | -0.02 | -0.01 | -0.01 | 0.00 | -0.03 |
| D | 811 | -0.01 | -0.02 | -0.01 | -0.01 | 0.00 | -0.02 | -0.03 | 0.00 | -0.03 | -0.01 | -0.01 | -0.01 | 0.00 |
| D | 878 | -0.01 | -0.01 | 0.00 | 0.00 | -0.02 | -0.03 | -0.02 | 0.01 | 0.00 | 0.00 | -0.02 | 0.00 | -0.02 |
| D | 1289 | 0.01 | 0.00 | 0.00 | 0.00 | 0.01 | -0.01 | 0.00 | 0.00 | 0.00 | 0.01 | -0.01 | 0.01 | 0.00 |
| D | 849 | 0.01 | 0.00 | 0.00 | 0.01 | 0.03 | 0.00 | 0.00 | 0.01 | 0.01 | 0.01 | 0.00 | 0.01 | 0.00 |
| D | 1276 | 0.01 | 0.00 | 0.00 | 0.00 | 0.01 | 0.00 | -0.01 | 0.00 | 0.00 | 0.01 | 0.00 | 0.01 | 0.01 |
| D | 924 | 0.01 | 0.01 | 0.00 | 0.00 | 0.00 | 0.00 | 0.01 | 0.01 | 0.00 | 0.01 | 0.00 | 0.01 | 0.00 |
| D | 093-L01 | 0.02 | 0.01 | 0.00 | 0.01 | 0.03 | 0.00 | -0.01 | 0.01 | 0.01 | 0.01 | 0.00 | 0.02 | 0.02 |
| D | 093-L05 | 0.01 | 0.00 | 0.00 | 0.00 | 0.01 | 0.00 | -0.01 | 0.00 | 0.01 | 0.01 | 0.00 | 0.01 | 0.00 |
| D | 5E1F6 | -0.01 | 0.00 | 0.00 | -0.02 | 0.01 | 0.00 | -0.02 | 0.00 | -0.01 | 0.00 | 0.00 | 0.01 | 0.00 |
| D | 1F2F4 | -0.01 | 0.00 | 0.01 | 0.01 | -0.01 | 0.00 | -0.01 | 0.00 | -0.01 | -0.01 | -0.02 | 0.00 | -0.01 |
| D+ | 068 | -0.01 | 0.00 | 0.00 | 0.00 | 0.01 | 0.00 | 0.00 | 0.00 | -0.01 | -0.01 | 0.00 | 0.01 | -0.01 |
| D | 1320 | -0.01 | 0.00 | 0.01 | 0.01 | 0.00 | 0.00 | -0.01 | 0.00 | -0.01 | -0.01 | -0.01 | 0.00 | -0.01 |

FIG. 7A

| Domain | antibody | 1276 D | 924 D | 093-L01 D | 093-L05 D | 5E1F6 D | 1F2F4 D | 068 D+ | 1320 D | A1 A |
|---|---|---|---|---|---|---|---|---|---|---|
| | | 1276 | 924 | 093-L01 | 093-L05 | 5E1F6 | 1F2F4 | 068 | 1320 | AbA1 |
| D+ | 548 | 0.02 | 0.02 | 0.04 | 0.01 | 0.02 | x | 0.00 | 0.04 | 0.07 |
| D+ | 531 | 0.01 | 0.01 | 0.01 | 0.02 | 0.02 | x | 0.00 | 0.04 | 0.69 |
| D | 002 | 0.02 | 0.03 | 0.00 | 0.01 | 0.07 | x | -0.02 | 0.02 | 0.57 |
| D | 044 | 0.01 | 0.01 | 0.00 | 0.03 | 0.02 | x | -0.01 | 0.01 | 0.49 |
| D | 045 | 0.01 | 0.01 | 0.01 | 0.03 | 0.01 | x | 0.00 | 0.01 | 0.52 |
| D | 088 | 0.01 | 0.02 | 0.01 | 0.02 | 0.01 | x | -0.02 | 0.03 | 0.77 |
| D | 193 | 0.03 | 0.02 | 0.03 | 0.02 | 0.03 | x | -0.01 | 0.04 | 0.42 |
| D | 562 | 0.00 | 0.00 | 0.00 | 0.02 | 0.01 | -0.01 | -0.04 | 0.01 | 0.23 |
| D | 566 | -0.03 | -0.01 | 0.01 | 0.01 | -0.02 | x | -0.02 | 0.01 | 0.58 |
| D | 811 | 0.00 | 0.01 | 0.00 | 0.00 | 0.01 | x | -0.02 | 0.00 | 0.77 |
| D | 1289 | -0.02 | -0.02 | -0.02 | 0.01 | -0.02 | x | -0.01 | 0.01 | 0.45 |
| D | 849 | -0.01 | 0.01 | 0.00 | 0.00 | 0.01 | x | 0.00 | 0.01 | 0.73 |
| D | 1276 | 0.01 | 0.05 | 0.00 | 0.01 | 0.01 | x | 0.00 | 0.00 | 0.70 |
| D | 924 | 0.01 | 0.01 | 0.01 | 0.01 | 0.01 | x | 0.00 | 0.02 | 0.52 |
| D | 093-L01 | 0.00 | 0.02 | 0.01 | 0.02 | 0.02 | x | -0.01 | 0.01 | 0.65 |
| D | 093-L05 | 0.01 | 0.02 | 0.01 | 0.02 | 0.01 | x | -0.01 | 0.03 | 0.62 |
| D | 5E1F6 | 0.02 | 0.02 | 0.02 | 0.01 | 0.02 | 0.02 | -0.01 | 0.03 | 0.39 |
| D+ | 1F2F4 | 0.00 | 0.04 | 0.02 | 0.02 | 0.01 | 0.01 | -0.01 | 0.01 | 0.41 |
| D+ | 068 | -0.01 | 0.01 | -0.02 | 0.01 | 0.01 | x | -0.01 | 0.01 | 0.52 |
| D | 1320 | -0.01 | 0.00 | 0.04 | 0.00 | -0.01 | 0.00 | -0.01 | 0.00 | 0.19 |

FIG. 7B

| Domain | antibody | 530 E AbE1 | 784 E AbE2 | 010 E AbE3 | 471 E AbE4 | 532 E AbE5 | 910 E AbE6 | 550 Tetra Abtet | 826 E AbE7 | 942 A AbA2 |
|---|---|---|---|---|---|---|---|---|---|---|
| D+ | 548 | 0.01 | 0.03 | 0.22 | 0.26 | 0.27 | 0.22 | 0.06 | 0.01 | 0.05 |
| D+ | 531 | 0.28 | 0.60 | 0.83 | 0.92 | 0.93 | 0.87 | 0.69 | 0.51 | 0.22 |
| D | 002 | 0.25 | 0.52 | 0.74 | 0.70 | 0.79 | 0.78 | 0.67 | 0.42 | 0.19 |
| D | 044 | 0.18 | 0.42 | 0.64 | 0.73 | 0.68 | 0.68 | 0.56 | 0.32 | 0.20 |
| D | 045 | 0.23 | 0.47 | 0.67 | 0.72 | 0.72 | 0.70 | 0.60 | 0.36 | 0.19 |
| D | 088 | 0.42 | 0.79 | 1.00 | 1.19 | 1.13 | 1.09 | 0.96 | 0.64 | 0.24 |
| D | 193 | 0.19 | 0.38 | 0.54 | 0.57 | 0.52 | 0.53 | 0.43 | 0.27 | 0.19 |
| D | 562 | b | 0.23 | 0.39 | 0.36 | 0.33 | 0.33 | 0.24 | 0.13 | 0.13 |
| D | 566 | 0.25 | 0.55 | 0.77 | 0.88 | 0.87 | 0.79 | 0.60 | 0.35 | 0.24 |
| D | 811 | 0.42 | 0.79 | 1.02 | 1.17 | 1.13 | 1.09 | 0.97 | 0.65 | 0.24 |
| D | 1289 | 0.18 | 0.43 | 0.56 | 0.67 | 0.63 | 0.64 | 0.47 | 0.29 | 0.18 |
| D | 849 | 0.37 | 0.74 | 0.96 | 1.11 | 1.08 | 1.04 | 0.90 | 0.58 | 0.25 |
| D | 1276 | 0.39 | 0.74 | 0.93 | 1.03 | 1.00 | 0.97 | 0.83 | 0.57 | 0.26 |
| D | 924 | 0.25 | 0.50 | 0.66 | 0.67 | 0.69 | 0.65 | 0.52 | 0.33 | 0.22 |
| D | 093-L01 | 0.31 | 0.64 | 0.82 | 0.93 | 0.92 | 0.87 | 0.78 | 0.49 | 0.23 |
| D | 093-L05 | 0.29 | 0.58 | 0.80 | 0.89 | 0.88 | 0.84 | 0.69 | 0.45 | 0.22 |
| D | 5E1F6 | 0.19 | 0.39 | 0.62 | 0.57 | 0.59 | 0.54 | 0.40 | 0.27 | 0.18 |
| D | 1F2F4 | 0.16 | 0.38 | 0.60 | 0.63 | 0.62 | 0.58 | 0.44 | 0.26 | 0.18 |
| D+ | 068 | 0.26 | 0.58 | 0.80 | 0.94 | 0.94 | 0.89 | 0.80 | 0.43 | 0.12 |
| D | 1320 | b | b | 0.22 | 0.28 | 0.28 | 0.29 | 0.17 | b | b |

FIG. 7C

| Ab No | PGRN % | Ab No | PGRN % |
|---|---|---|---|
| 002 | 142 | 849 | 149 |
| 044 | 166 | 1276 | 163 |
| 045 | 202 | 924 | 125 |
| 088 | 121 | 093-L01 | 116 |
| 193 | 207 | 093-L05 | 140 |
| 562 | 139 | 1320 | 114 |
| 566 | 139 | 1F2F4 | 282 |
| 811 | 146 | 5E1F6 | 177 |
| 1289 | 117 | | |
| 548 | 139 | 68 | 201 |
| 531 | 140 | | |

FIG. 11 data: means ± SEM; *, p<0.05, p<0.01, *p<0.001, mab#45 vs PBS, two-way ANOVA followed by Bonferroni post-test

| time (h) | mab#45 | | | PBS | | |
|---|---|---|---|---|---|---|
| | Y | SEM | N | Y | SEM | N |
| 2 | 4.587163 | 0.684416 | 10 | 2.854475 | 0.411770 | 8 |
| 4 | 3.654225 | 0.453960 | 10 | 1.303813 | 0.129774 | 8 |
| 6 | 3.826151 | 0.499164 | 10 | 1.157348 | 0.103958 | 8 |
| 8 | 3.941664 | 0.495235 | 10 | 1.084373 | 0.102409 | 8 |
| 10 | 3.744573 | 0.396738 | 10 | 0.885935 | 0.139000 | 8 |
| 12 | 3.498750 | 0.369875 | 10 | 0.880561 | 0.161299 | 8 |
| 14 | 3.287708 | 0.362766 | 10 | 0.966836 | 0.190743 | 8 |
| 16 | 3.372367 | 0.365127 | 10 | 1.031850 | 0.180413 | 8 |
| 18 | 2.962828 | 0.298671 | 10 | 0.817940 | 0.158949 | 8 |
| 20 | 2.868518 | 0.343551 | 10 | 0.681344 | 0.153457 | 8 |
| 22 | 2.173472 | 0.322407 | 10 | 0.673761 | 0.122029 | 8 |
| 24 | 1.604464 | 0.377046 | 10 | 0.583756 | 0.123556 | 8 |

SEQUENCE LISTING

```
<160> NUMBER OF SEQ ID NOS: 198

<210> SEQ ID NO 1
<211> LENGTH: 16
<212> TYPE: PRT
<213> ORGANISM: Artificial
<220> FEATURE:
<223> OTHER INFORMATION: 5E1 CDR1 Light Chain

<400> SEQUENCE: 1

Lys Ser Ser Gln Ser Leu Leu Asp Ser Asn Gly Lys Thr Tyr Leu Asn
1               5                   10                  15

<210> SEQ ID NO 2
<211> LENGTH: 7
<212> TYPE: PRT
<213> ORGANISM: Artificial
<220> FEATURE:
<223> OTHER INFORMATION: 5E1 CDR2 Light Chain

<400> SEQUENCE: 2

Leu Val Ser Lys Leu Asp Ser
1               5

<210> SEQ ID NO 3
<211> LENGTH: 9
<212> TYPE: PRT
<213> ORGANISM: Artificial
<220> FEATURE:
<223> OTHER INFORMATION: 5E1 CDR 3 Light Chain

<400> SEQUENCE: 3

Cys Gln Gly Thr His Phe Pro Leu Thr
1               5

<210> SEQ ID NO 4
<211> LENGTH: 10
<212> TYPE: PRT
<213> ORGANISM: Artificial
<220> FEATURE:
<223> OTHER INFORMATION: 5E1 CDR 1 Heavy Chain

<400> SEQUENCE: 4

Gly Phe Ile Phe Ser Ile Tyr Gly Met Ser
1               5                   10
```

<210> SEQ ID NO 5
<211> LENGTH: 17
<212> TYPE: PRT
<213> ORGANISM: Artificial
<220> FEATURE:
<223> OTHER INFORMATION: 5E1 CDR 2 Heavy Chain

<400> SEQUENCE: 5

Met Ile Ser Ser Gly Gly Ile Tyr Thr Gln Tyr Pro Asp Ser Val Lys
1               5                   10                  15

Gly

<210> SEQ ID NO 6
<211> LENGTH: 8
<212> TYPE: PRT
<213> ORGANISM: Artificial
<220> FEATURE:
<223> OTHER INFORMATION: 5E1 CDR 3 Heavy Chain

<400> SEQUENCE: 6

His Asp Asp Ser Trp Phe Ala Tyr
1               5

<210> SEQ ID NO 7
<211> LENGTH: 113
<212> TYPE: PRT
<213> ORGANISM: Artificial
<220> FEATURE:
<223> OTHER INFORMATION: 5E1 VL

<400> SEQUENCE: 7

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Cys Gln Gly
                85                  90                  95

Thr His Phe Pro Leu Thr Phe Gly Ala Gly Thr Lys Leu Glu Leu Lys
            100                 105                 110

Arg

<210> SEQ ID NO 8
<211> LENGTH: 117
<212> TYPE: PRT
<213> ORGANISM: Artificial
<220> FEATURE:
<223> OTHER INFORMATION: 5E1 VH

<400> SEQUENCE: 8

Glu Val His Leu Val Glu Ser Gly Gly Asp Leu Val Asn Pro Gly Gly
1               5                   10                  15

Ser Leu Lys Leu Ser Cys Glu Ala Ser Gly Phe Ile Phe Ser Ile Tyr
            20                  25                  30

Gly Met Ser Trp Val Arg Gln Thr Pro Asp Lys Arg Leu Glu Trp Val

```
                35                  40                  45
Ala Met Ile Ser Ser Gly Gly Ile Tyr Thr Gln Tyr Pro Asp Ser Val
         50                  55                  60
Lys Gly Arg Phe Thr Ile Ser Arg Asp Asn Ala Lys Asn Thr Leu Tyr
 65                  70                  75                  80
Leu Gln Met Ser Gly Leu Lys Ser Glu Asp Thr Gly Thr Tyr His Cys
                 85                  90                  95
Thr Arg His Asp Asp Ser Trp Phe Ala Tyr Trp Gly Gln Gly Thr Leu
            100                 105                 110
Val Thr Val Ser Ala
        115

<210> SEQ ID NO 9
<211> LENGTH: 14
<212> TYPE: PRT
<213> ORGANISM: Artificial
<220> FEATURE:
<223> OTHER INFORMATION: 1F2 (Lambda) CDR1 Light Chain

<400> SEQUENCE: 9

Arg Ser Ser Thr Gly Ala Val Thr Thr Ser Asn Tyr Ala Asn
 1               5                  10

<210> SEQ ID NO 10
<211> LENGTH: 7
<212> TYPE: PRT
<213> ORGANISM: Artificial
<220> FEATURE:
<223> OTHER INFORMATION: 1F2 (Lambda) CDR2 Light Chain

<400> SEQUENCE: 10

Gly Thr Asn Asn Arg Ala Pro
 1               5

<210> SEQ ID NO 11
<211> LENGTH: 10
<212> TYPE: PRT
<213> ORGANISM: Artificial
<220> FEATURE:
<223> OTHER INFORMATION: 1F2 (Lambda) CDR3 Light Chain

<400> SEQUENCE: 11

Ala Leu Trp Tyr Ser Asn His Phe Trp Val
 1               5                  10

<210> SEQ ID NO 12
<211> LENGTH: 10
<212> TYPE: PRT
<213> ORGANISM: Artificial
<220> FEATURE:
<223> OTHER INFORMATION: 1F2 (Lambda) CDR1 Heavy Chain

<400> SEQUENCE: 12

Gly Phe Thr Phe Ser Ser Tyr Gly Met Ser
 1               5                  10

<210> SEQ ID NO 13
<211> LENGTH: 17
<212> TYPE: PRT
<213> ORGANISM: Artificial
<220> FEATURE:
<223> OTHER INFORMATION: 1F2 (Lambda) CDR2 Heavy Chain

<400> SEQUENCE: 13
```

```
Ile Ile Ser Ser Gly Gly Ser Tyr Thr His Tyr Pro Asp Ser Val Lys
1               5                   10                  15

Gly
```

```
<210> SEQ ID NO 14
<211> LENGTH: 9
<212> TYPE: PRT
<213> ORGANISM: Artificial
<220> FEATURE:
<223> OTHER INFORMATION: 1F2 (Lambda) CDR3 Heavy Chain

<400> SEQUENCE: 14

Leu Cys Gly Pro Leu Cys Ser Gly Tyr
1               5
```

```
<210> SEQ ID NO 15
<211> LENGTH: 112
<212> TYPE: PRT
<213> ORGANISM: Artificial
<220> FEATURE:
<223> OTHER INFORMATION: 1F2 (Lambda) VL

<400> SEQUENCE: 15

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Phe Trp Val Phe Gly Gly Gly Thr Lys Leu Thr Val Leu Gly Arg
            100                 105                 110
```

```
<210> SEQ ID NO 16
<211> LENGTH: 118
<212> TYPE: PRT
<213> ORGANISM: Artificial
<220> FEATURE:
<223> OTHER INFORMATION: 1F2 (Lambda) VH

<400> SEQUENCE: 16

Glu Val Gln Leu Val Glu Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Ile Ile Ser Ser Gly Gly Ser Tyr Thr His Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg Leu Cys Gly Pro Leu Cys Ser Gly Tyr Trp Gly Gln Gly Thr
            100                 105                 110
```

Ser Val Thr Val Ser Ser
        115

<210> SEQ ID NO 17
<211> LENGTH: 12
<212> TYPE: PRT
<213> ORGANISM: Artificial
<220> FEATURE:
<223> OTHER INFORMATION: 068 CDR1 Light Chain

<400> SEQUENCE: 17

Arg Ala Ser Gln Ser Val Ser Ser Asn Tyr Leu Ala
1               5                   10

<210> SEQ ID NO 18
<211> LENGTH: 7
<212> TYPE: PRT
<213> ORGANISM: Artificial
<220> FEATURE:
<223> OTHER INFORMATION: 068 CDR2 Light Chain

<400> SEQUENCE: 18

Gly Ala Ser Ser Arg Ala Thr
1               5

<210> SEQ ID NO 19
<211> LENGTH: 9
<212> TYPE: PRT
<213> ORGANISM: Artificial
<220> FEATURE:
<223> OTHER INFORMATION: 068 CDR3 Light Chain

<400> SEQUENCE: 19

Gln Gln Tyr Gly Ser Ser Pro Leu Thr
1               5

<210> SEQ ID NO 20
<211> LENGTH: 10
<212> TYPE: PRT
<213> ORGANISM: Artificial
<220> FEATURE:
<223> OTHER INFORMATION: 068 CDR1 Heavy Chain

<400> SEQUENCE: 20

Gly Phe Thr Phe Ser Ile Tyr Gly Met His
1               5                   10

<210> SEQ ID NO 21
<211> LENGTH: 17
<212> TYPE: PRT
<213> ORGANISM: Artificial
<220> FEATURE:
<223> OTHER INFORMATION: 068 CDR2 Heavy Chain

<400> SEQUENCE: 21

Val Ile Ser Tyr Asp Gly Ser Ser Lys Tyr Tyr Ala Asp Ser Val Lys
1               5                   10                  15

Gly

<210> SEQ ID NO 22
<211> LENGTH: 11
<212> TYPE: PRT
<213> ORGANISM: Artificial
<220> FEATURE:
<223> OTHER INFORMATION: 068 CDR3 Heavy Chain

<400> SEQUENCE: 22

Asp Arg Ala Leu Leu Thr Gly Val Phe Asp Tyr
1               5                   10

<210> SEQ ID NO 23
<211> LENGTH: 108
<212> TYPE: PRT
<213> ORGANISM: Artificial
<220> FEATURE:
<223> OTHER INFORMATION: 068 VL

<400> SEQUENCE: 23

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 24
<211> LENGTH: 120
<212> TYPE: PRT
<213> ORGANISM: Artificial
<220> FEATURE:
<223> OTHER INFORMATION: 068 VH

<400> SEQUENCE: 24

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ile Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Ala Leu Leu Thr Gly Val Phe Asp Tyr Trp Gly Gln
            100                 105                 110

Gly Thr Leu Val Thr Val Ser Ser
        115                 120

<210> SEQ ID NO 25
<211> LENGTH: 11
<212> TYPE: PRT
<213> ORGANISM: Artificial
<220> FEATURE:
<223> OTHER INFORMATION: 1320 CDR1 Light Chain

<400> SEQUENCE: 25

Arg Ala Ser Gln Ser Val Ser Ser Tyr Leu Ala
1               5                   10

<210> SEQ ID NO 26
<211> LENGTH: 7
<212> TYPE: PRT
<213> ORGANISM: Artificial
<220> FEATURE:
<223> OTHER INFORMATION: 1320 CDR2 Light Chain

<400> SEQUENCE: 26

Asp Ala Ser Asn Arg Ala Thr
1               5

<210> SEQ ID NO 27
<211> LENGTH: 9
<212> TYPE: PRT
<213> ORGANISM: Artificial
<220> FEATURE:
<223> OTHER INFORMATION: 1320 CDR3 Light Chain

<400> SEQUENCE: 27

Gln Gln Arg Thr Asn Trp Ser Ile Thr
1               5

<210> SEQ ID NO 28
<211> LENGTH: 10
<212> TYPE: PRT
<213> ORGANISM: Artificial
<220> FEATURE:
<223> OTHER INFORMATION: 1320 CDR1 Heavy Chain

<400> SEQUENCE: 28

Gly Phe Thr Phe Ser Ser Tyr Val Met Ser
1               5                   10

<210> SEQ ID NO 29
<211> LENGTH: 17
<212> TYPE: PRT
<213> ORGANISM: Artificial
<220> FEATURE:
<223> OTHER INFORMATION: 1320 CDR2 Heavy Chain

<400> SEQUENCE: 29

Ala Ile Ser Gly Ser Gly Gly Ser Thr Tyr Tyr Ala Asp Ser Val Lys
1               5                   10                  15
Gly

<210> SEQ ID NO 30
<211> LENGTH: 7
<212> TYPE: PRT
<213> ORGANISM: Artificial
<220> FEATURE:
<223> OTHER INFORMATION: 1320 CDR3 Heavy Chain

<400> SEQUENCE: 30

Leu Ile Trp Gly Trp Asp Ile
1               5

<210> SEQ ID NO 31
<211> LENGTH: 107
<212> TYPE: PRT
<213> ORGANISM: Artificial
<220> FEATURE:
<223> OTHER INFORMATION: 1320 VL -continued

```
<400> SEQUENCE: 31

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Arg Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Ser Ile Ser Ser Leu Glu Pro
65                  70                  75                  80

Glu Asp Phe Ala Val Tyr Tyr Cys Gln Gln Arg Thr Asn Trp Ser Ile
                85                  90                  95

Thr Phe Gly Gln Gly Thr Arg Leu Glu Ile Lys
            100                 105

<210> SEQ ID NO 32
<211> LENGTH: 116
<212> TYPE: PRT
<213> ORGANISM: Artificial
<220> FEATURE:
<223> OTHER INFORMATION: 1320 VH

<400> SEQUENCE: 32

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Ile Trp Gly Trp Asp Ile Trp Gly Gln Gly Thr Met Val
            100                 105                 110

Thr Val Ser Ser
        115

<210> SEQ ID NO 33
<211> LENGTH: 12
<212> TYPE: PRT
<213> ORGANISM: Artificial
<220> FEATURE:
<223> OTHER INFORMATION: 93-05 CDR1 Light Chain

<400> SEQUENCE: 33

Arg Ala Ser Gln Ser Val Ser Ser Ser Tyr Leu Ala
1               5                   10

<210> SEQ ID NO 34
<211> LENGTH: 7
<212> TYPE: PRT
<213> ORGANISM: Artificial
<220> FEATURE:
<223> OTHER INFORMATION: 93-05 CDR2 Light Chain

<400> SEQUENCE: 34
```

```
Gly Ala Ser Ser Arg Ala Thr
1               5

<210> SEQ ID NO 35
<211> LENGTH: 9
<212> TYPE: PRT
<213> ORGANISM: Artificial
<220> FEATURE:
<223> OTHER INFORMATION: 93-05 CDR3 Light Chain

<400> SEQUENCE: 35

Gln Gln Tyr Gly Ser Ser Pro Phe Thr
1               5

<210> SEQ ID NO 36
<211> LENGTH: 10
<212> TYPE: PRT
<213> ORGANISM: Artificial
<220> FEATURE:
<223> OTHER INFORMATION: 93-05 CDR1 Heavy Chain

<400> SEQUENCE: 36

Gly Phe Thr Phe Ser Ser Tyr Ala Met Ser
1               5                   10

<210> SEQ ID NO 37
<211> LENGTH: 17
<212> TYPE: PRT
<213> ORGANISM: Artificial
<220> FEATURE:
<223> OTHER INFORMATION: 93-05 CDR2 Heavy Chain

<400> SEQUENCE: 37

Ala Ile Ser Gly Ser Gly Gly Ser Thr Tyr Tyr Ala Asp Ser Val Lys
1               5                   10                  15

Gly

<210> SEQ ID NO 38
<211> LENGTH: 11
<212> TYPE: PRT
<213> ORGANISM: Artificial
<220> FEATURE:
<223> OTHER INFORMATION: 93-05 CDR3 Heavy Chain

<400> SEQUENCE: 38

Ile Ala Ala Ala Gly Thr Asn Tyr Phe Asp Tyr
1               5                   10

<210> SEQ ID NO 39
<211> LENGTH: 108
<212> TYPE: PRT
<213> ORGANISM: Artificial
<220> FEATURE:
<223> OTHER INFORMATION: 93-05 VL

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60
```

-continued

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 40
<211> LENGTH: 120
<212> TYPE: PRT
<213> ORGANISM: Artificial
<220> FEATURE:
<223> OTHER INFORMATION: 93-05 VH

<400> SEQUENCE: 40

Val Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Met His Thr Leu Phe
65                  70                  75                  80

Leu Gln Ile Asn Ser Leu Arg Ala Glu Asp Thr Ala Val Tyr Tyr Cys
                85                  90                  95

Val Ala Ile Ala Ala Ala Gly Thr Asn Tyr Phe Asp Tyr Trp Gly Gln
            100                 105                 110

Gly Thr Leu Val Thr Val Ser Ser
        115                 120

<210> SEQ ID NO 41
<211> LENGTH: 12
<212> TYPE: PRT
<213> ORGANISM: Artificial
<220> FEATURE:
<223> OTHER INFORMATION: 93-01 CDR1 Light Chain

<400> SEQUENCE: 41

Arg Ala Ser Gln Ser Val Ser Ser Ser Tyr Leu Ala
1               5                   10

<210> SEQ ID NO 42
<211> LENGTH: 7
<212> TYPE: PRT
<213> ORGANISM: Artificial
<220> FEATURE:
<223> OTHER INFORMATION: 93-01 CDR2 Light Chain

<400> SEQUENCE: 42

Gly Ala Ser Ser Arg Ala Thr
1               5

<210> SEQ ID NO 43
<211> LENGTH: 9
<212> TYPE: PRT
<213> ORGANISM: Artificial
<220> FEATURE:
<223> OTHER INFORMATION: 93-01 CDR3 Light Chain

<400> SEQUENCE: 43

```
Gln Gln Tyr Gly Ser Ser Pro Phe Thr
1               5

<210> SEQ ID NO 44
<211> LENGTH: 10
<212> TYPE: PRT
<213> ORGANISM: Artificial
<220> FEATURE:
<223> OTHER INFORMATION: 93-01 CDR1 Heavy Chain

<400> SEQUENCE: 44

Gly Phe Thr Phe Ser Ser Tyr Ala Met Ser
1               5                   10

<210> SEQ ID NO 45
<211> LENGTH: 17
<212> TYPE: PRT
<213> ORGANISM: Artificial
<220> FEATURE:
<223> OTHER INFORMATION: 93-01 CDR2 Heavy Chain

<400> SEQUENCE: 45

Ala Ile Ser Gly Ser Gly Gly Ser Thr Tyr Tyr Ala Asp Ser Val Lys
1               5                   10                  15

Gly

<210> SEQ ID NO 46
<211> LENGTH: 11
<212> TYPE: PRT
<213> ORGANISM: Artificial
<220> FEATURE:
<223> OTHER INFORMATION: 93-01 CDR3 Heavy Chain

<400> SEQUENCE: 46

Ile Ala Ala Ala Gly Thr Asn Tyr Phe Asp Tyr
1               5                   10

<210> SEQ ID NO 47
<211> LENGTH: 108
<212> TYPE: PRT
<213> ORGANISM: Artificial
<220> FEATURE:
<223> OTHER INFORMATION: 93-01 VL

<400> SEQUENCE: 47

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys
            100                 105

<210> SEQ ID NO 48
<211> LENGTH: 120
```

-continued

```
<212> TYPE: PRT
<213> ORGANISM: Artificial
<220> FEATURE:
<223> OTHER INFORMATION: 93-01 VH

<400> SEQUENCE: 48

Val Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Met His Thr Leu Phe
65                  70                  75                  80

Leu Gln Ile Asn Ser Leu Arg Ala Glu Asp Thr Ala Val Tyr Tyr Cys
                85                  90                  95

Val Ala Ile Ala Ala Ala Gly Thr Asn Tyr Phe Asp Tyr Trp Gly Gln
            100                 105                 110

Gly Thr Leu Val Thr Val Ser Ser
        115                 120

<210> SEQ ID NO 49
<211> LENGTH: 12
<212> TYPE: PRT
<213> ORGANISM: Artificial
<220> FEATURE:
<223> OTHER INFORMATION: 924 CDR1 Light Chain

<400> SEQUENCE: 49

Arg Ala Ser Gln Ser Val Ser Ser Ser Tyr Leu Ala
1               5                   10

<210> SEQ ID NO 50
<211> LENGTH: 7
<212> TYPE: PRT
<213> ORGANISM: Artificial
<220> FEATURE:
<223> OTHER INFORMATION: 924 CDR2 Light Chain

<400> SEQUENCE: 50

Gly Ala Ser Ser Arg Ala Thr
1               5

<210> SEQ ID NO 51
<211> LENGTH: 9
<212> TYPE: PRT
<213> ORGANISM: Artificial
<220> FEATURE:
<223> OTHER INFORMATION: 924 CDR3 Light Chain

<400> SEQUENCE: 51

Gln Gln Tyr Gly Ser Ser Pro Ile Thr
1               5

<210> SEQ ID NO 52
<211> LENGTH: 12
<212> TYPE: PRT
<213> ORGANISM: Artificial
<220> FEATURE:
<223> OTHER INFORMATION: 924 CDR1 Heavy Chain

<400> SEQUENCE: 52
```

Gly Gly Ser Ile Ser Ser Gly Asn Tyr Tyr Trp Asn
1               5                   10

<210> SEQ ID NO 53
<211> LENGTH: 16
<212> TYPE: PRT
<213> ORGANISM: Artificial
<220> FEATURE:
<223> OTHER INFORMATION: 924 CDR2 Heavy Chain

<400> SEQUENCE: 53

Tyr Ile Tyr Tyr Ser Gly Ser Thr Tyr Tyr Asn Pro Ser Leu Lys Ser
1               5                   10                  15

<210> SEQ ID NO 54
<211> LENGTH: 11
<212> TYPE: PRT
<213> ORGANISM: Artificial
<220> FEATURE:
<223> OTHER INFORMATION: 924 CDR3 Heavy Chain

<400> SEQUENCE: 54

Leu Ile Thr Ser Gln Asn Phe Phe Phe Asp Tyr
1               5                   10

<210> SEQ ID NO 55
<211> LENGTH: 108
<212> TYPE: PRT
<213> ORGANISM: Artificial
<220> FEATURE:
<223> OTHER INFORMATION: 924 VL

<400> SEQUENCE: 55

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 56
<211> LENGTH: 121
<212> TYPE: PRT
<213> ORGANISM: Artificial
<220> FEATURE:
<223> OTHER INFORMATION: 924 VH

<400> SEQUENCE: 56

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asn Tyr Tyr Trp Asn Trp Ile Arg Gln His Pro Gly Lys Gly Leu Glu
            35                  40                  45

```
Trp Ile Gly Tyr Ile Tyr Tyr Ser Gly Ser Thr Tyr Tyr Asn Pro Ser
        50                  55                  60
Leu Lys Ser Arg Val Thr Ile Ser Val Asp Thr Ser Lys Asn Gln Phe
 65                  70                  75                  80
Ser Leu Lys Leu Asn Ser Val Thr Ser Ala Asp Thr Ala Val Tyr Tyr
                 85                  90                  95
Cys Ala Ala Leu Ile Thr Ser Gln Asn Phe Phe Asp Tyr Trp Gly
            100                 105                 110
Gln Gly Thr Leu Val Thr Val Ser Ser
            115                 120

<210> SEQ ID NO 57
<211> LENGTH: 12
<212> TYPE: PRT
<213> ORGANISM: Artificial
<220> FEATURE:
<223> OTHER INFORMATION: 1276 CDR1 Light Chain

<400> SEQUENCE: 57

Arg Ala Ser Gln Ser Val Ser Ser Ser Tyr Leu Ala
 1               5                  10

<210> SEQ ID NO 58
<211> LENGTH: 7
<212> TYPE: PRT
<213> ORGANISM: Artificial
<220> FEATURE:
<223> OTHER INFORMATION: 1276 CDR2 Light Chain

<400> SEQUENCE: 58

Gly Ala Ser Ser Arg Ala Thr
 1               5

<210> SEQ ID NO 59
<211> LENGTH: 9
<212> TYPE: PRT
<213> ORGANISM: Artificial
<220> FEATURE:
<223> OTHER INFORMATION: 1276 CDR3 Light Chain

<400> SEQUENCE: 59

Gln Gln Tyr Gly Ser Ser Pro Ile Thr
 1               5

<210> SEQ ID NO 60
<211> LENGTH: 10
<212> TYPE: PRT
<213> ORGANISM: Artificial
<220> FEATURE:
<223> OTHER INFORMATION: 1276 CDR1 Heavy Chain

<400> SEQUENCE: 60

Gly Phe Thr Phe Asn Thr Phe Ala Met Asn
 1               5                  10

<210> SEQ ID NO 61
<211> LENGTH: 17
<212> TYPE: PRT
<213> ORGANISM: Artificial
<220> FEATURE:
<223> OTHER INFORMATION: 1276 CDR2 Heavy Chain

<400> SEQUENCE: 61

Ala Ile Thr Gly Ser Gly Gly Ser Thr Tyr Tyr Ala Asp Ser Val Lys
```

-continued

```
1               5                   10                  15
Gly

<210> SEQ ID NO 62
<211> LENGTH: 13
<212> TYPE: PRT
<213> ORGANISM: Artificial
<220> FEATURE:
<223> OTHER INFORMATION: 1276 CDR3 Heavy Chain

<400> SEQUENCE: 62

Pro Ile Thr Val Val Arg Gly Val Ser Ala Phe Asp Ile
1               5                   10

<210> SEQ ID NO 63
<211> LENGTH: 108
<212> TYPE: PRT
<213> ORGANISM: Artificial
<220> FEATURE:
<223> OTHER INFORMATION: 1276 VL

<400> SEQUENCE: 63

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 64
<211> LENGTH: 122
<212> TYPE: PRT
<213> ORGANISM: Artificial
<220> FEATURE:
<223> OTHER INFORMATION: 1276 VH

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Phe
            20                  25                  30

Ala Met Asn Trp Val Arg Gln Ala Pro Gly Lys Gly Leu Glu Trp Val
        35                  40                  45

Ser Ala Ile Thr Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Ile Thr Val Val Arg Gly Val Ser Ala Phe Asp Ile Trp
            100                 105                 110
```

Gly Gln Gly Thr Met Val Thr Val Ser Ser
        115                 120

<210> SEQ ID NO 65
<211> LENGTH: 12
<212> TYPE: PRT
<213> ORGANISM: Artificial
<220> FEATURE:
<223> OTHER INFORMATION: 849 CDR1 Light Chain

<400> SEQUENCE: 65

Arg Ala Ser Gln Ser Val Ser Ser Ser Tyr Leu Ala
1               5                   10

<210> SEQ ID NO 66
<211> LENGTH: 7
<212> TYPE: PRT
<213> ORGANISM: Artificial
<220> FEATURE:
<223> OTHER INFORMATION: 849 CDR2 Light Chain

<400> SEQUENCE: 66

Gly Ala Ser Ser Arg Ala Thr
1               5

<210> SEQ ID NO 67
<211> LENGTH: 9
<212> TYPE: PRT
<213> ORGANISM: Artificial
<220> FEATURE:
<223> OTHER INFORMATION: 849 CDR3 Light Chain

<400> SEQUENCE: 67

Gln Gln Tyr Gly Ser Ser Pro Leu Thr
1               5

<210> SEQ ID NO 68
<211> LENGTH: 10
<212> TYPE: PRT
<213> ORGANISM: Artificial
<220> FEATURE:
<223> OTHER INFORMATION: 849 CDR1 Heavy Chain

<400> SEQUENCE: 68

Gly Phe Thr Phe Asn Thr Phe Ala Met Asn
1               5                   10

<210> SEQ ID NO 69
<211> LENGTH: 17
<212> TYPE: PRT
<213> ORGANISM: Artificial
<220> FEATURE:
<223> OTHER INFORMATION: 849 CDR2 Heavy Chain

<400> SEQUENCE: 69

Ala Ile Ser Gly Ser Gly Gly Ser Thr Tyr Tyr Ala Asp Ser Val Lys
1               5                   10                  15
Gly

<210> SEQ ID NO 70
<211> LENGTH: 11
<212> TYPE: PRT
<213> ORGANISM: Artificial
<220> FEATURE:
<223> OTHER INFORMATION: 849 CDR3 Heavy Chain

<400> SEQUENCE: 70

Leu Val Arg Gly Val Arg Asp Ala Phe Asp Ile
1               5                   10

<210> SEQ ID NO 71
<211> LENGTH: 108
<212> TYPE: PRT
<213> ORGANISM: Artificial
<220> FEATURE:
<223> OTHER INFORMATION: 849 VL

<400> SEQUENCE: 71

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 72
<211> LENGTH: 120
<212> TYPE: PRT
<213> ORGANISM: Artificial
<220> FEATURE:
<223> OTHER INFORMATION: 849 VH

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Thr Phe
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Leu Val Arg Gly Val Arg Asp Ala Phe Asp Ile Trp Gly Gln
            100                 105                 110

Gly Thr Met Val Thr Val Ser Ser
        115                 120

<210> SEQ ID NO 73
<211> LENGTH: 12
<212> TYPE: PRT
<213> ORGANISM: Artificial
<220> FEATURE:
<223> OTHER INFORMATION: 531-02 CDR1 Light Chain

<400> SEQUENCE: 73

Arg Ala Ser Gln Ser Val Ser Ser Asp Leu Ala
1               5                   10

<210> SEQ ID NO 74
<211> LENGTH: 7
<212> TYPE: PRT
<213> ORGANISM: Artificial
<220> FEATURE:
<223> OTHER INFORMATION: 531-02 CDR2 Light Chain

<400> SEQUENCE: 74

Gly Ala Ser Ser Arg Ala Thr
1               5

<210> SEQ ID NO 75
<211> LENGTH: 9
<212> TYPE: PRT
<213> ORGANISM: Artificial
<220> FEATURE:
<223> OTHER INFORMATION: 531-02 CDR3 Light Chain

<400> SEQUENCE: 75

Gln Gln Tyr Gly Ser Ser Pro Leu Thr
1               5

<210> SEQ ID NO 76
<211> LENGTH: 10
<212> TYPE: PRT
<213> ORGANISM: Artificial
<220> FEATURE:
<223> OTHER INFORMATION: 531-02 CDR1 Heavy Chain

<400> SEQUENCE: 76

Gly Phe Thr Phe Ser Arg Tyr Val Met Ser
1               5                   10

<210> SEQ ID NO 77
<211> LENGTH: 17
<212> TYPE: PRT
<213> ORGANISM: Artificial
<220> FEATURE:
<223> OTHER INFORMATION: 531-02 CDR2 Heavy Chain

<400> SEQUENCE: 77

Thr Ile Ser Gly Ser Gly Gly Ser Thr Tyr Tyr Ala Asp Ser Val Lys
1               5                   10                  15

Gly

<210> SEQ ID NO 78
<211> LENGTH: 8
<212> TYPE: PRT
<213> ORGANISM: Artificial
<220> FEATURE:
<223> OTHER INFORMATION: 531-02 CDR3 Heavy Chain

<400> SEQUENCE: 78

Gly Ala Phe Gly Ala Phe Asp Ile
1               5

<210> SEQ ID NO 79
<211> LENGTH: 108
<212> TYPE: PRT
<213> ORGANISM: Artificial
<220> FEATURE:
<223> OTHER INFORMATION: 531-02 VL

<400> SEQUENCE: 79

-continued

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Asp Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 80
<211> LENGTH: 117
<212> TYPE: PRT
<213> ORGANISM: Artificial
<220> FEATURE:
<223> OTHER INFORMATION: 531-02 VH

<400> SEQUENCE: 80

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ser Thr Ile Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Glu Gly Ala Phe Gly Ala Phe Asp Ile Trp Gly Gln Gly Thr Met
            100                 105                 110

Val Thr Val Ser Ser
        115

<210> SEQ ID NO 81
<211> LENGTH: 12
<212> TYPE: PRT
<213> ORGANISM: Artificial
<220> FEATURE:
<223> OTHER INFORMATION: 548-01 CDR1 Light Chain

<400> SEQUENCE: 81

Arg Ala Ser Gln Ser Val Ser Ser Ser Tyr Leu Val
1               5                   10

<210> SEQ ID NO 82
<211> LENGTH: 7
<212> TYPE: PRT
<213> ORGANISM: Artificial
<220> FEATURE:
<223> OTHER INFORMATION: 548-01 CDR2 Light Chain

<400> SEQUENCE: 82

Gly Ala Ser Ser Arg Ala Thr
1               5

<210> SEQ ID NO 83
<211> LENGTH: 9
<212> TYPE: PRT
<213> ORGANISM: Artificial
<220> FEATURE:
<223> OTHER INFORMATION: 548-01 CDR3 Light Chain

<400> SEQUENCE: 83

Gln Gln Tyr Gly Ser Ser Pro Ile Thr
1               5

<210> SEQ ID NO 84
<211> LENGTH: 10
<212> TYPE: PRT
<213> ORGANISM: Artificial
<220> FEATURE:
<223> OTHER INFORMATION: 548-01 CDR1 Heavy Chain

<400> SEQUENCE: 84

Lys Phe Thr Phe Asn Thr Tyr Ala Met Asn
1               5                   10

<210> SEQ ID NO 85
<211> LENGTH: 17
<212> TYPE: PRT
<213> ORGANISM: Artificial
<220> FEATURE:
<223> OTHER INFORMATION: 548-01 CDR2 Heavy Chain

<400> SEQUENCE: 85

Ala Ile Ser Gly Ser Gly Ile Ser Ser Tyr Tyr Ala Asp Ser Val Asn
1               5                   10                  15

Gly

<210> SEQ ID NO 86
<211> LENGTH: 13
<212> TYPE: PRT
<213> ORGANISM: Artificial
<220> FEATURE:
<223> OTHER INFORMATION: 548-01 CDR3 Heavy Chain

<400> SEQUENCE: 86

Pro Ile Val Val Val Ser Ile Asp Met Ala Phe Asp Ile
1               5                   10

<210> SEQ ID NO 87
<211> LENGTH: 108
<212> TYPE: PRT
<213> ORGANISM: Artificial
<220> FEATURE:
<223> OTHER INFORMATION: 548-01 VL

<400> SEQUENCE: 87

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Val Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

```
Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105
```

<210> SEQ ID NO 88
<211> LENGTH: 122
<212> TYPE: PRT
<213> ORGANISM: Artificial
<220> FEATURE:
<223> OTHER INFORMATION: 548-01 VH

<400> SEQUENCE: 88

```
Glu Val Gln Leu Leu Glu Ser Gly Gly Leu Val Gln Pro Gly Gly
1               5                   10                  15

Ser Leu Arg Leu Ser Cys Thr Ala Ser Lys Phe Thr Phe Asn Thr Tyr
                20                  25                  30

Ala Met Asn Trp Val Arg Gln Ala Pro Gly Lys Gly Leu Glu Trp Val
                35                  40                  45

Ser Ala Ile Ser Gly Ser Gly Ile Ser Ser Tyr Tyr Ala Asp Ser Val
        50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Ile Val Val Ser Ile Asp Met Ala Phe Asp Ile Trp
                100                 105                 110

Gly Gln Gly Thr Met Val Thr Val Ser Ser
            115                 120
```

<210> SEQ ID NO 89
<211> LENGTH: 11
<212> TYPE: PRT
<213> ORGANISM: Artificial
<220> FEATURE:
<223> OTHER INFORMATION: 548-02 CDR1 Light Chain

<400> SEQUENCE: 89

```
Arg Ala Ser Gln Ser Val Ser Ser Tyr Leu Ala
1               5                   10
```

<210> SEQ ID NO 90
<211> LENGTH: 7
<212> TYPE: PRT
<213> ORGANISM: Artificial
<220> FEATURE:
<223> OTHER INFORMATION: 548-02 CDR2 Light Chain

<400> SEQUENCE: 90

```
Asp Ala Ser Asn Arg Ala Thr
1               5
```

<210> SEQ ID NO 91
<211> LENGTH: 9
<212> TYPE: PRT
<213> ORGANISM: Artificial
<220> FEATURE:
<223> OTHER INFORMATION: 548-02 CDR3 Light Chain

<400> SEQUENCE: 91

```
Gln Gln Arg Ser Asn Trp Pro Leu Thr
1               5

<210> SEQ ID NO 92
<211> LENGTH: 10
<212> TYPE: PRT
<213> ORGANISM: Artificial
<220> FEATURE:
<223> OTHER INFORMATION: 548-02 CDR1 Heavy Chain

<400> SEQUENCE: 92

Lys Phe Thr Phe Asn Thr Tyr Ala Met Asn
1               5                   10

<210> SEQ ID NO 93
<211> LENGTH: 17
<212> TYPE: PRT
<213> ORGANISM: Artificial
<220> FEATURE:
<223> OTHER INFORMATION: 548-02 CDR2 Heavy Chain

<400> SEQUENCE: 93

Ala Ile Ser Gly Ser Gly Ile Ser Ser Tyr Tyr Ala Asp Ser Val Asn
1               5                   10                  15

Gly

<210> SEQ ID NO 94
<211> LENGTH: 13
<212> TYPE: PRT
<213> ORGANISM: Artificial
<220> FEATURE:
<223> OTHER INFORMATION: 548-02 CDR3 Heavy Chain

<400> SEQUENCE: 94

Pro Ile Val Val Val Ser Ile Asp Met Ala Phe Asp Ile
1               5                   10

<210> SEQ ID NO 95
<211> LENGTH: 107
<212> TYPE: PRT
<213> ORGANISM: Artificial
<220> FEATURE:
<223> OTHER INFORMATION: 548-02 VL

<400> SEQUENCE: 95

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
        50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 96
<211> LENGTH: 122
<212> TYPE: PRT
```

```
<213> ORGANISM: Artificial
<220> FEATURE:
<223> OTHER INFORMATION: 548-02 VH

<400> SEQUENCE: 96
```

Glu Val Gln Leu Leu Glu Ser Gly Gly Gly Leu Val Gln Pro Gly Gly
1               5                   10                  15

Ser Leu Arg Leu Ser Cys Thr Ala Ser Lys Phe Thr Phe Asn Thr Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Ile Ser Ser Tyr Tyr Ala Asp Ser Val
50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Pro Ile Val Val Val Ser Ile Asp Met Ala Phe Asp Ile Trp
            100                 105                 110

Gly Gln Gly Thr Met Val Thr Val Ser Ser
        115                 120

```
<210> SEQ ID NO 97
<211> LENGTH: 12
<212> TYPE: PRT
<213> ORGANISM: Artificial
<220> FEATURE:
<223> OTHER INFORMATION: 1289-02 CDR1 Light Chain

<400> SEQUENCE: 97
```

Arg Ala Ser Gln Ser Val Ser Ser Ser Tyr Leu Ala
1               5                   10

```
<210> SEQ ID NO 98
<211> LENGTH: 7
<212> TYPE: PRT
<213> ORGANISM: Artificial
<220> FEATURE:
<223> OTHER INFORMATION: 1289-02 CDR2 Light Chain

<400> SEQUENCE: 98
```

Gly Ala Ser Ser Arg Ala Thr
1               5

```
<210> SEQ ID NO 99
<211> LENGTH: 9
<212> TYPE: PRT
<213> ORGANISM: Artificial
<220> FEATURE:
<223> OTHER INFORMATION: 1289-02 CDR3 Light Chain

<400> SEQUENCE: 99
```

Gln Gln Tyr Gly Ser Ser Pro Ile Thr
1               5

```
<210> SEQ ID NO 100
<211> LENGTH: 10
<212> TYPE: PRT
<213> ORGANISM: Artificial
<220> FEATURE:
<223> OTHER INFORMATION: 1289-02 CDR1 Heavy Chain

<400> SEQUENCE: 100
```

-continued

```
Gly Phe Thr Phe Ser Ser Phe Ala Met Ser
1               5                   10

<210> SEQ ID NO 101
<211> LENGTH: 17
<212> TYPE: PRT
<213> ORGANISM: Artificial
<220> FEATURE:
<223> OTHER INFORMATION: 1289-02 CDR2 Heavy Chain

<400> SEQUENCE: 101

Ala Ile Ser Gly Ser Gly Gly Ser Thr Tyr Tyr Ala Asp Ser Val Lys
1               5                   10                  15

Gly

<210> SEQ ID NO 102
<211> LENGTH: 13
<212> TYPE: PRT
<213> ORGANISM: Artificial
<220> FEATURE:
<223> OTHER INFORMATION: 1289-02 CDR3 Heavy Chain

<400> SEQUENCE: 102

Pro Ile Thr Leu Val Arg Gly Val Gly Ala Phe Asp Ile
1               5                   10

<210> SEQ ID NO 103
<211> LENGTH: 108
<212> TYPE: PRT
<213> ORGANISM: Artificial
<220> FEATURE:
<223> OTHER INFORMATION: 1289-02 VL

<400> SEQUENCE: 103

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 104
<211> LENGTH: 122
<212> TYPE: PRT
<213> ORGANISM: Artificial
<220> FEATURE:
<223> OTHER INFORMATION: 1289-02 VH

<400> SEQUENCE: 104

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Gly Leu Glu Trp Val
```

```
                35                  40                  45
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Ser
 65                  70                  75                  80

Leu Gln Met Asn Ser Leu Arg Ala Glu Asp Thr Ala Val Tyr Tyr Cys
                 85                  90                  95

Ala Thr Pro Ile Thr Leu Val Arg Gly Val Gly Ala Phe Asp Ile Trp
            100                 105                 110

Gly Gln Gly Thr Met Val Thr Val Ser Ser
        115                 120

<210> SEQ ID NO 105
<211> LENGTH: 12
<212> TYPE: PRT
<213> ORGANISM: Artificial
<220> FEATURE:
<223> OTHER INFORMATION: 811-02 CDR1 Light Chain

<400> SEQUENCE: 105

Arg Ala Ser Gln Ser Val Ser Ser Ser Tyr Leu Ala
1               5                   10

<210> SEQ ID NO 106
<211> LENGTH: 7
<212> TYPE: PRT
<213> ORGANISM: Artificial
<220> FEATURE:
<223> OTHER INFORMATION: 811-02 CDR2 Light Chain

<400> SEQUENCE: 106

Gly Ala Ser Ser Arg Ala Thr
1               5

<210> SEQ ID NO 107
<211> LENGTH: 10
<212> TYPE: PRT
<213> ORGANISM: Artificial
<220> FEATURE:
<223> OTHER INFORMATION: 811-02 CDR3 Light Chain

<400> SEQUENCE: 107

Gln Gln Tyr Gly Ser Ser Pro Pro Trp Thr
1               5                   10

<210> SEQ ID NO 108
<211> LENGTH: 10
<212> TYPE: PRT
<213> ORGANISM: Artificial
<220> FEATURE:
<223> OTHER INFORMATION: 811-02 CDR1 Heavy Chain

<400> SEQUENCE: 108

Gly Phe Thr Phe Ser Thr Phe Ala Met Asn
1               5                   10

<210> SEQ ID NO 109
<211> LENGTH: 17
<212> TYPE: PRT
<213> ORGANISM: Artificial
<220> FEATURE:
<223> OTHER INFORMATION: 811-02 CDR2 Heavy Chain

<400> SEQUENCE: 109
```

Ala Ile Ser Gly Ser Gly Gly Asn Thr Tyr Tyr Ala Asp Ser Val Lys
1               5                   10                  15

Gly

<210> SEQ ID NO 110
<211> LENGTH: 12
<212> TYPE: PRT
<213> ORGANISM: Artificial
<220> FEATURE:
<223> OTHER INFORMATION: 811-02 CDR3 Heavy Chain

<400> SEQUENCE: 110

Ile Pro Val Lys Leu Gly Asp Asp Ala Phe Asp Ile
1               5                   10

<210> SEQ ID NO 111
<211> LENGTH: 109
<212> TYPE: PRT
<213> ORGANISM: Artificial
<220> FEATURE:
<223> OTHER INFORMATION: 811-02 VL

<400> SEQUENCE: 111

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Pro Trp Thr Phe Gly Gln Gly Thr Lys Val Glu Ile Lys
            100                 105

<210> SEQ ID NO 112
<211> LENGTH: 121
<212> TYPE: PRT
<213> ORGANISM: Artificial
<220> FEATURE:
<223> OTHER INFORMATION: 811-02 VH

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Thr Phe
            20                  25                  30

Ala Met Asn Trp Val Arg Gln Ala Pro Gly Lys Gly Leu Glu Trp Val
        35                  40                  45

Ser Ala Ile Ser Gly Ser Gly Gly Asn Thr Tyr Tyr Ala Asp Ser Val
    50                  55                  60

Lys Gly Arg Phe Ile Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ile Pro Val Lys Leu Gly Asp Asp Ala Phe Asp Ile Trp Gly
            100                 105                 110

Gln Gly Thr Met Val Thr Val Ser Ser
        115                 120

<210> SEQ ID NO 113
<211> LENGTH: 12
<212> TYPE: PRT
<213> ORGANISM: Artificial
<220> FEATURE:
<223> OTHER INFORMATION: 566-01 CDR1 Light Chain

<400> SEQUENCE: 113

Arg Ala Ser Gln Ser Val Ser Ser Tyr Leu Ala
1               5                   10

<210> SEQ ID NO 114
<211> LENGTH: 7
<212> TYPE: PRT
<213> ORGANISM: Artificial
<220> FEATURE:
<223> OTHER INFORMATION: 566-01 CDR2 Light Chain

<400> SEQUENCE: 114

Gly Ala Ser Ser Arg Ala Thr
1               5

<210> SEQ ID NO 115
<211> LENGTH: 9
<212> TYPE: PRT
<213> ORGANISM: Artificial
<220> FEATURE:
<223> OTHER INFORMATION: 566-01 CDR3 Light Chain

<400> SEQUENCE: 115

Gln Gln Tyr Gly Ser Ser Pro Ile Thr
1               5

<210> SEQ ID NO 116
<211> LENGTH: 10
<212> TYPE: PRT
<213> ORGANISM: Artificial
<220> FEATURE:
<223> OTHER INFORMATION: 566-01 CDR1 Heavy Chain

<400> SEQUENCE: 116

Gly Phe Thr Phe Ser Thr Phe Ala Met Ser
1               5                   10

<210> SEQ ID NO 117
<211> LENGTH: 17
<212> TYPE: PRT
<213> ORGANISM: Artificial
<220> FEATURE:
<223> OTHER INFORMATION: 566-01 CDR2 Heavy Chain

<400> SEQUENCE: 117

Ala Ile Ser Gly Ser Gly Gly Ser Thr Tyr Tyr Ala Asp Ser Val Arg
1               5                   10                  15

Gly

<210> SEQ ID NO 118
<211> LENGTH: 12
<212> TYPE: PRT
<213> ORGANISM: Artificial
<220> FEATURE:
<223> OTHER INFORMATION: 566-01 CDR3 Heavy Chain

<400> SEQUENCE: 118

Pro Ile Thr Met Val Arg Gly Glu Ala Phe Asp Ile
1               5                   10

<210> SEQ ID NO 119
<211> LENGTH: 108
<212> TYPE: PRT
<213> ORGANISM: Artificial
<220> FEATURE:
<223> OTHER INFORMATION: 566-01 VL

<400> SEQUENCE: 119

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 120
<211> LENGTH: 121
<212> TYPE: PRT
<213> ORGANISM: Artificial
<220> FEATURE:
<223> OTHER INFORMATION: 566-01 VH

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Val Ala Ser Gly Phe Thr Phe Ser Thr Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Arg Gly Arg Phe Thr Val Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Ile Thr Met Val Arg Gly Glu Ala Phe Asp Ile Trp Gly
            100                 105                 110

Gln Gly Thr Met Val Thr Val Ser Ser
        115                 120

<210> SEQ ID NO 121
<211> LENGTH: 12
<212> TYPE: PRT
<213> ORGANISM: Artificial
<220> FEATURE:
<223> OTHER INFORMATION: 562 CDR1 Light Chain

<400> SEQUENCE: 121

Arg Ala Ser Gln Ser Val Ser Ser Tyr Leu Ala
1               5                   10

<210> SEQ ID NO 122
<211> LENGTH: 7
<212> TYPE: PRT
<213> ORGANISM: Artificial
<220> FEATURE:
<223> OTHER INFORMATION: 562 CDR2 Light Chain

<400> SEQUENCE: 122

Gly Ala Ser Ser Arg Ala Thr
1               5

<210> SEQ ID NO 123
<211> LENGTH: 9
<212> TYPE: PRT
<213> ORGANISM: Artificial
<220> FEATURE:
<223> OTHER INFORMATION: 562 CDR3 Light Chain

<400> SEQUENCE: 123

Gln Gln Tyr Gly Ser Ser Pro Ile Thr
1               5

<210> SEQ ID NO 124
<211> LENGTH: 10
<212> TYPE: PRT
<213> ORGANISM: Artificial
<220> FEATURE:
<223> OTHER INFORMATION: 562 CDR1 Heavy Chain

<400> SEQUENCE: 124

Gly Phe Thr Phe Ser Thr Phe Ala Met Ser
1               5                   10

<210> SEQ ID NO 125
<211> LENGTH: 17
<212> TYPE: PRT
<213> ORGANISM: Artificial
<220> FEATURE:
<223> OTHER INFORMATION: 562 CDR2 Heavy Chain

<400> SEQUENCE: 125

Ala Ile Ser Gly Ser Gly Gly Ser Thr Tyr Tyr Ala Asp Ser Val Lys
1               5                   10                  15

Gly

<210> SEQ ID NO 126
<211> LENGTH: 12
<212> TYPE: PRT
<213> ORGANISM: Artificial
<220> FEATURE:
<223> OTHER INFORMATION: 562 CDR3 Heavy Chain

<400> SEQUENCE: 126

Pro Ile Thr Val Val Arg Gly Glu Ala Phe Asp Ile
1               5                   10

<210> SEQ ID NO 127
<211> LENGTH: 108
<212> TYPE: PRT
<213> ORGANISM: Artificial
<220> FEATURE:
<223> OTHER INFORMATION: 562 VL

<400> SEQUENCE: 127

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Ile Thr Phe Gly Gln Gly Thr Arg Leu Glu Ile Lys
            100                 105

<210> SEQ ID NO 128
<211> LENGTH: 121
<212> TYPE: PRT
<213> ORGANISM: Artificial
<220> FEATURE:
<223> OTHER INFORMATION: 562 VH

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Glu Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Pro Ile Thr Val Val Arg Gly Glu Ala Phe Asp Ile Trp Gly
            100                 105                 110

Gln Gly Thr Met Val Thr Val Ser Ser
        115                 120

<210> SEQ ID NO 129
<211> LENGTH: 12
<212> TYPE: PRT
<213> ORGANISM: Artificial
<220> FEATURE:
<223> OTHER INFORMATION: 193 CDR1 Light Chain

<400> SEQUENCE: 129

Arg Ala Ser Gln Ser Val Ser Ser Ser Tyr Ile Ala
1               5                   10

<210> SEQ ID NO 130
<211> LENGTH: 7
<212> TYPE: PRT
<213> ORGANISM: Artificial
<220> FEATURE:
<223> OTHER INFORMATION: 193 CDR2 Light Chain

<400> SEQUENCE: 130

```
Gly Ala Ser Ser Arg Ala Thr
1               5
```

<210> SEQ ID NO 131
<211> LENGTH: 9
<212> TYPE: PRT
<213> ORGANISM: Artificial
<220> FEATURE:
<223> OTHER INFORMATION: 193 CDR3 Light Chain

<400> SEQUENCE: 131

```
Gln Gln Tyr Val Asn Ser Pro Leu Thr
1               5
```

<210> SEQ ID NO 132
<211> LENGTH: 10
<212> TYPE: PRT
<213> ORGANISM: Artificial
<220> FEATURE:
<223> OTHER INFORMATION: 193 CDR1 Heavy Chain

<400> SEQUENCE: 132

```
Gly Phe Thr Phe Thr Ser Phe Ala Met Ser
1               5                   10
```

<210> SEQ ID NO 133
<211> LENGTH: 17
<212> TYPE: PRT
<213> ORGANISM: Artificial
<220> FEATURE:
<223> OTHER INFORMATION: 193 CDR2 Heavy Chain

<400> SEQUENCE: 133

```
Gly Ile Ser Gly Ser Gly Gly Ser Thr Tyr Tyr Ala Asp Ser Val Lys
1               5                   10                  15

Gly
```

<210> SEQ ID NO 134
<211> LENGTH: 11
<212> TYPE: PRT
<213> ORGANISM: Artificial
<220> FEATURE:
<223> OTHER INFORMATION: 193 CDR3 Heavy Chain

<400> SEQUENCE: 134

```
Leu Val Arg Gly Val Ile Ile Val Phe Asp Ile
1               5                   10
```

<210> SEQ ID NO 135
<211> LENGTH: 108
<212> TYPE: PRT
<213> ORGANISM: Artificial
<220> FEATURE:
<223> OTHER INFORMATION: 193 VL

<400> SEQUENCE: 135

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Ile Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60
```

Gly Ser Gly Ser Gly Thr Asp Phe Ser Leu Thr Ile Ser Arg Leu Glu
65                  70                  75                  80

Pro Glu Asp Phe Ala Val Tyr Tyr Cys Gln Gln Tyr Val Asn Ser Pro
                85                  90                  95

Leu Thr Phe Gly Gly Gly Thr Lys Val Glu Ile Lys
            100                 105

<210> SEQ ID NO 136
<211> LENGTH: 120
<212> TYPE: PRT
<213> ORGANISM: Artificial
<220> FEATURE:
<223> OTHER INFORMATION: 193 VH

<400> SEQUENCE: 136

Glu Val Gln Leu Leu Glu Ser Gly Gly Gly Leu Val Leu Pro Gly Gly
1               5                   10                  15

Ser Leu Arg Leu Ser Cys Ala Ala Ser Gly Phe Thr Phe Thr Ser Phe
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ser Leu Val Arg Gly Val Ile Ile Val Phe Asp Ile Trp Gly Gln
            100                 105                 110

Gly Thr Met Val Thr Val Ser Ser
        115                 120

<210> SEQ ID NO 137
<211> LENGTH: 12
<212> TYPE: PRT
<213> ORGANISM: Artificial
<220> FEATURE:
<223> OTHER INFORMATION: 88 CDR1 Light Chain

<400> SEQUENCE: 137

Arg Ala Ser Gln Ser Val Ser Ser Ser Tyr Leu Ala
1               5                   10

<210> SEQ ID NO 138
<211> LENGTH: 7
<212> TYPE: PRT
<213> ORGANISM: Artificial
<220> FEATURE:
<223> OTHER INFORMATION: 88 CDR2 Light Chain

<400> SEQUENCE: 138

Gly Ala Ser Ser Arg Ala Thr
1               5

<210> SEQ ID NO 139
<211> LENGTH: 9
<212> TYPE: PRT
<213> ORGANISM: Artificial
<220> FEATURE:
<223> OTHER INFORMATION: 88 CDR3 Light Chain

<400> SEQUENCE: 139

Gln Gln Tyr Gly Ser Ser Pro Leu Thr
1               5

<210> SEQ ID NO 140
<211> LENGTH: 10
<212> TYPE: PRT
<213> ORGANISM: Artificial
<220> FEATURE:
<223> OTHER INFORMATION: 88 CDR1 Heavy Chain

<400> SEQUENCE: 140

Gly Phe Thr Phe Ser Thr Phe Ala Met Ser
1               5                   10

<210> SEQ ID NO 141
<211> LENGTH: 17
<212> TYPE: PRT
<213> ORGANISM: Artificial
<220> FEATURE:
<223> OTHER INFORMATION: 88 CDR2 Heavy Chain

<400> SEQUENCE: 141

Ala Ile Ser Gly Ser Gly Gly Thr Tyr Tyr Ala Asp Ser Val Lys
1               5                   10                  15
Gly

<210> SEQ ID NO 142
<211> LENGTH: 12
<212> TYPE: PRT
<213> ORGANISM: Artificial
<220> FEATURE:
<223> OTHER INFORMATION: 88 CDR3 Heavy Chain

<400> SEQUENCE: 142

Tyr Ile Val Ala Thr Ile Ala Asp Ala Phe Asp Ile
1               5                   10

<210> SEQ ID NO 143
<211> LENGTH: 108
<212> TYPE: PRT
<213> ORGANISM: Artificial
<220> FEATURE:
<223> OTHER INFORMATION: 88 VL

<400> SEQUENCE: 143

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 144
<211> LENGTH: 121

```
<212> TYPE: PRT
<213> ORGANISM: Artificial
<220> FEATURE:
<223> OTHER INFORMATION: 88 VH

<400> SEQUENCE: 144

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Tyr Ile Val Ala Thr Ile Ala Asp Ala Phe Asp Ile Trp Gly
            100                 105                 110

Gln Gly Thr Met Val Thr Val Ser Ser
        115                 120

<210> SEQ ID NO 145
<211> LENGTH: 12
<212> TYPE: PRT
<213> ORGANISM: Artificial
<220> FEATURE:
<223> OTHER INFORMATION: 045 CDR1 Light Chain

<400> SEQUENCE: 145

Arg Ala Ser Gln Ser Val Ser Ser Ser Tyr Leu Ala
1               5                   10

<210> SEQ ID NO 146
<211> LENGTH: 7
<212> TYPE: PRT
<213> ORGANISM: Artificial
<220> FEATURE:
<223> OTHER INFORMATION: 045 CDR2 Light Chain

<400> SEQUENCE: 146

Gly Ala Ser Ser Arg Ala Thr
1               5

<210> SEQ ID NO 147
<211> LENGTH: 9
<212> TYPE: PRT
<213> ORGANISM: Artificial
<220> FEATURE:
<223> OTHER INFORMATION: 045 CDR3 Light Chain

<400> SEQUENCE: 147

Gln His Tyr Gly Ser Ser Pro Leu Thr
1               5

<210> SEQ ID NO 148
<211> LENGTH: 10
<212> TYPE: PRT
<213> ORGANISM: Artificial
<220> FEATURE:
<223> OTHER INFORMATION: 045 CDR1 Heavy Chain

<400> SEQUENCE: 148
```

Gly Phe Thr Phe Asn Ser Tyr Ala Met Ser
1               5                   10

<210> SEQ ID NO 149
<211> LENGTH: 17
<212> TYPE: PRT
<213> ORGANISM: Artificial
<220> FEATURE:
<223> OTHER INFORMATION: 045 CDR2 Heavy Chain

<400> SEQUENCE: 149

Ala Ile Ser Gly Ser Gly Gly Ile Thr Tyr Tyr Ala Asp Ser Val Lys
1               5                   10                  15

Gly

<210> SEQ ID NO 150
<211> LENGTH: 11
<212> TYPE: PRT
<213> ORGANISM: Artificial
<220> FEATURE:
<223> OTHER INFORMATION: 045 CDR3 Heavy Chain

<400> SEQUENCE: 150

Met Val Arg Gly Val Ile Val Asn Phe Asp Tyr
1               5                   10

<210> SEQ ID NO 151
<211> LENGTH: 108
<212> TYPE: PRT
<213> ORGANISM: Artificial
<220> FEATURE:
<223> OTHER INFORMATION: 045 VL

<400> SEQUENCE: 151

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Gly Ser Ser Pro
                85                  90                  95

Leu Thr Phe Gly Gly Gly Thr Lys Val Glu Ile Lys
            100                 105

<210> SEQ ID NO 152
<211> LENGTH: 120
<212> TYPE: PRT
<213> ORGANISM: Artificial
<220> FEATURE:
<223> OTHER INFORMATION: 045 VH

<400> SEQUENCE: 152

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

```
Ala Met Ser Trp Val Arg Gln Ala Pro Gly Lys Gly Leu Glu Trp Val
            35                  40                  45

Ser Ala Ile Ser Gly Ser Gly Gly Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Ser Met Val Arg Gly Val Ile Val Asn Phe Asp Tyr Trp Gly Gln
            100                 105                 110

Gly Thr Leu Val Thr Val Ser Ser
        115                 120

<210> SEQ ID NO 153
<211> LENGTH: 12
<212> TYPE: PRT
<213> ORGANISM: Artificial
<220> FEATURE:
<223> OTHER INFORMATION: 044 CDR1 Light Chain

<400> SEQUENCE: 153

Arg Ala Ser Gln Ser Val Ser Ser Ser Tyr Leu Ala
1               5                   10

<210> SEQ ID NO 154
<211> LENGTH: 7
<212> TYPE: PRT
<213> ORGANISM: Artificial
<220> FEATURE:
<223> OTHER INFORMATION: 044 CDR2 Light Chain

<400> SEQUENCE: 154

Gly Ala Ser Ser Arg Ala Thr
1               5

<210> SEQ ID NO 155
<211> LENGTH: 9
<212> TYPE: PRT
<213> ORGANISM: Artificial
<220> FEATURE:
<223> OTHER INFORMATION: 044 CDR3 Light Chain

<400> SEQUENCE: 155

Gln Gln Tyr Gly Ser Ser Pro Leu Thr
1               5

<210> SEQ ID NO 156
<211> LENGTH: 10
<212> TYPE: PRT
<213> ORGANISM: Artificial
<220> FEATURE:
<223> OTHER INFORMATION: 044 CDR1 Heavy Chain

<400> SEQUENCE: 156

Gly Phe Thr Phe Ser Ser Tyr Ala Met Ser
1               5                   10

<210> SEQ ID NO 157
<211> LENGTH: 17
<212> TYPE: PRT
<213> ORGANISM: Artificial
<220> FEATURE:
<223> OTHER INFORMATION: 044 CDR2 Heavy Chain

<400> SEQUENCE: 157
```

Ala Ile Ser Gly Ser Gly Gly Asn Thr Tyr Tyr Ala Asp Ser Val Lys
1               5                   10                  15
Gly

<210> SEQ ID NO 158
<211> LENGTH: 11
<212> TYPE: PRT
<213> ORGANISM: Artificial
<220> FEATURE:
<223> OTHER INFORMATION: 044 CDR3 Heavy Chain

<400> SEQUENCE: 158

Met Val Arg Gly Val Phe Ile Asn Phe Asp Tyr
1               5                   10

<210> SEQ ID NO 159
<211> LENGTH: 108
<212> TYPE: PRT
<213> ORGANISM: Artificial
<220> FEATURE:
<223> OTHER INFORMATION: 044 VL

<400> SEQUENCE: 159

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
                100                 105

<210> SEQ ID NO 160
<211> LENGTH: 120
<212> TYPE: PRT
<213> ORGANISM: Artificial
<220> FEATURE:
<223> OTHER INFORMATION: 044 VH

<400> SEQUENCE: 160

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ser Ala Ile Ser Gly Ser Gly Gly Asn Thr Tyr Tyr Ala Asp Ser Val
        50                  55                  60

Lys Gly Arg Ser Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser Met Val Arg Gly Val Phe Ile Asn Phe Asp Tyr Trp Gly Gln

```
                100              105              110
Gly Thr Leu Val Thr Val Ser Ser
        115              120

<210> SEQ ID NO 161
<211> LENGTH: 12
<212> TYPE: PRT
<213> ORGANISM: Artificial
<220> FEATURE:
<223> OTHER INFORMATION: 002 CDR1 Light Chain

<400> SEQUENCE: 161

Arg Ala Ser Gln Ser Val Ser Ser Ser Tyr Leu Ala
1               5                   10

<210> SEQ ID NO 162
<211> LENGTH: 7
<212> TYPE: PRT
<213> ORGANISM: Artificial
<220> FEATURE:
<223> OTHER INFORMATION: 002 CDR2 Light Chain

<400> SEQUENCE: 162

Gly Ala Ser Ser Arg Ala Thr
1               5

<210> SEQ ID NO 163
<211> LENGTH: 8
<212> TYPE: PRT
<213> ORGANISM: Artificial
<220> FEATURE:
<223> OTHER INFORMATION: 002 CDR3 Light Chain

<400> SEQUENCE: 163

Gln Gln Tyr Gly Ser Ser Leu Thr
1               5

<210> SEQ ID NO 164
<211> LENGTH: 10
<212> TYPE: PRT
<213> ORGANISM: Artificial
<220> FEATURE:
<223> OTHER INFORMATION: 002 CDR1 Heavy Chain

<400> SEQUENCE: 164

Gly Phe Thr Phe Ser Ser Tyr Ala Met Ser
1               5                   10

<210> SEQ ID NO 165
<211> LENGTH: 17
<212> TYPE: PRT
<213> ORGANISM: Artificial
<220> FEATURE:
<223> OTHER INFORMATION: 002 CDR2 Heavy Chain

<400> SEQUENCE: 165

Ala Ile Ser Gly Ser Gly Gly Ser Thr Tyr Tyr Ala Asp Ser Val Lys
1               5                   10                  15

Gly

<210> SEQ ID NO 166
<211> LENGTH: 11
<212> TYPE: PRT
<213> ORGANISM: Artificial
<220> FEATURE:
<223> OTHER INFORMATION: 002 CDR3 Heavy Chain
```

-continued

```
<400> SEQUENCE: 166

Met Val Arg Gly Val Ile Ile Asn Phe Asp Tyr
1               5                   10

<210> SEQ ID NO 167
<211> LENGTH: 107
<212> TYPE: PRT
<213> ORGANISM: Artificial
<220> FEATURE:
<223> OTHER INFORMATION: 002 VL

<400> SEQUENCE: 167

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Leu
                85                  90                  95

Thr Phe Gly Gln Gly Thr Arg Leu Glu Ile Lys
            100                 105

<210> SEQ ID NO 168
<211> LENGTH: 120
<212> TYPE: PRT
<213> ORGANISM: Artificial
<220> FEATURE:
<223> OTHER INFORMATION: 002 VH

<400> SEQUENCE: 168

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Val Met Val Arg Gly Val Ile Ile Asn Phe Asp Tyr Trp Gly Gln
            100                 105                 110

Gly Thr Leu Val Thr Val Ser Ser
        115                 120

<210> SEQ ID NO 169
<211> LENGTH: 831
<212> TYPE: PRT
<213> ORGANISM: Artificial
<220> FEATURE:
<223> OTHER INFORMATION: full human Sortilin sequence isoform 1
```

<400> SEQUENCE: 169

```
Met Glu Arg Pro Trp Gly Ala Ala Asp Gly Leu Ser Arg Trp Pro His
1               5                   10                  15
Gly Leu Gly Leu Leu Leu Leu Gln Leu Leu Pro Pro Ser Thr Leu
            20                  25                  30
Ser Gln Asp Arg Leu Asp Ala Pro Pro Pro Ala Ala Pro Leu Pro
        35                  40                  45
Arg Trp Ser Gly Pro Ile Gly Val Ser Trp Gly Leu Arg Ala Ala Ala
    50                  55                  60
Ala Gly Ala Phe Pro Arg Gly Gly Arg Trp Arg Arg Ser Ala Pro
65              70                  75                  80
Gly Glu Asp Glu Glu Cys Gly Arg Val Arg Asp Phe Val Ala Lys Leu
                85                  90                  95
Ala Asn Asn Thr His Gln His Val Phe Asp Asp Leu Arg Gly Ser Val
            100                 105                 110
Ser Leu Ser Trp Val Gly Asp Ser Thr Gly Val Ile Leu Val Leu Thr
        115                 120                 125
Thr Phe His Val Pro Leu Val Ile Met Thr Phe Gly Gln Ser Lys Leu
    130                 135                 140
Tyr Arg Ser Glu Asp Tyr Gly Lys Asn Phe Lys Asp Ile Thr Asp Leu
145                 150                 155                 160
Ile Asn Asn Thr Phe Ile Arg Thr Glu Phe Gly Met Ala Ile Gly Pro
                165                 170                 175
Glu Asn Ser Gly Lys Val Val Leu Thr Ala Glu Val Ser Gly Gly Ser
            180                 185                 190
Arg Gly Gly Arg Ile Phe Arg Ser Ser Asp Phe Ala Lys Asn Phe Val
        195                 200                 205
Gln Thr Asp Leu Pro Phe His Pro Leu Thr Gln Met Met Tyr Ser Pro
    210                 215                 220
Gln Asn Ser Asp Tyr Leu Leu Ala Leu Ser Thr Glu Asn Gly Leu Trp
225                 230                 235                 240
Val Ser Lys Asn Phe Gly Gly Lys Trp Glu Glu Ile His Lys Ala Val
                245                 250                 255
Cys Leu Ala Lys Trp Gly Ser Asp Asn Thr Ile Phe Phe Thr Thr Tyr
            260                 265                 270
Ala Asn Gly Ser Cys Lys Ala Asp Leu Gly Ala Leu Glu Leu Trp Arg
        275                 280                 285
Thr Ser Asp Leu Gly Lys Ser Phe Lys Thr Ile Gly Val Lys Ile Tyr
    290                 295                 300
Ser Phe Gly Leu Gly Gly Arg Phe Leu Phe Ala Ser Val Met Ala Asp
305                 310                 315                 320
Lys Asp Thr Thr Arg Arg Ile His Val Ser Thr Asp Gln Gly Asp Thr
                325                 330                 335
Trp Ser Met Ala Gln Leu Pro Ser Val Gly Gln Glu Gln Phe Tyr Ser
            340                 345                 350
Ile Leu Ala Ala Asn Asp Asp Met Val Phe Met His Val Asp Glu Pro
        355                 360                 365
Gly Asp Thr Gly Phe Gly Thr Ile Phe Thr Ser Asp Asp Arg Gly Ile
    370                 375                 380
Val Tyr Ser Lys Ser Leu Asp Arg His Leu Tyr Thr Thr Thr Gly Gly
385                 390                 395                 400
Glu Thr Asp Phe Thr Asn Val Thr Ser Leu Arg Gly Val Tyr Ile Thr
                405                 410                 415
```

```
Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
            435                 440                 445

Asp Ala Thr Ala Lys Asn Lys Asn Glu Cys Ser Leu His Ile His Ala
450                 455                 460

Ser Tyr Ser Ile Ser Gln Lys Leu Asn Val Pro Met Ala Pro Leu Ser
465                 470                 475                 480

Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
            515                 520                 525

Asp Ser Gly Gly Ile Ile Val Ala Ile Glu His Ser Ser Arg Pro Ile
            530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
            595                 600                 605

Glu Arg Asn Cys Glu Glu Lys Asp Tyr Thr Ile Trp Leu Ala His Ser
            610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
                660                 665                 670

Phe Leu Cys Asp Phe Gly Tyr Tyr Arg Pro Glu Asn Asp Ser Lys Cys
            675                 680                 685

Val Glu Gln Pro Glu Leu Lys Gly His Asp Leu Glu Phe Cys Leu Tyr
            690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn Ser Val Pro Ile Ile Leu Ala Ile Val Gly Leu Met Leu
            755                 760                 765

Val Thr Val Val Ala Gly Val Leu Ile Val Lys Lys Tyr Val Cys Gly
            770                 775                 780

Gly Arg Phe Leu Val His Arg Tyr Ser Val Leu Gln Gln His Ala Glu
785                 790                 795                 800

Ala Asn Gly Val Asp Gly Val Asp Ala Leu Asp Thr Ala Ser His Thr
                805                 810                 815

Asn Lys Ser Gly Tyr His Asp Asp Ser Asp Glu Asp Leu Leu Glu
            820                 825                 830
```

```
<210> SEQ ID NO 170
<211> LENGTH: 88
<212> TYPE: PRT
<213> ORGANISM: Artificial
<220> FEATURE:
<223> OTHER INFORMATION: D region as identified by present invention

<400> SEQUENCE: 170

His Tyr Tyr Thr Ile Leu Asp Ser Gly Gly Ile Ile Val Ala Ile Glu
 1               5                  10                  15

His Ser Ser Arg Pro Ile Asn Val Ile Lys Phe Ser Thr Asp Glu Gly
                20                  25                  30

Gln Cys Trp Gln Thr Tyr Thr Phe Thr Arg Asp Pro Ile Tyr Phe Thr
            35                  40                  45

Gly Leu Ala Ser Glu Pro Gly Ala Arg Ser Met Asn Ile Ser Ile Trp
    50                  55                  60

Gly Phe Thr Glu Ser Phe Leu Thr Ser Gln Trp Val Ser Tyr Thr Ile
65                  70                  75                  80

Asp Phe Lys Asp Ile Leu Glu Arg
                85

<210> SEQ ID NO 171
<211> LENGTH: 700
<212> TYPE: PRT
<213> ORGANISM: Artificial
<220> FEATURE:
<223> OTHER INFORMATION: Sortilin hSORTECDBAP

<400> SEQUENCE: 171

Ser Ala Pro Gly Glu Asp Glu Cys Gly Arg Val Arg Asp Phe Val
 1               5                  10                  15

Ala Lys Leu Ala Asn Asn Thr His Gln His Val Phe Asp Asp Leu Arg
                20                  25                  30

Gly Ser Val Ser Leu Ser Trp Val Gly Asp Ser Thr Gly Val Ile Leu
            35                  40                  45

Val Leu Thr Thr Phe His Val Pro Leu Val Ile Met Thr Phe Gly Gln
    50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95

Ile Gly Pro Glu Asn Ser Gly Lys Val Val Leu Thr Ala Glu Val Ser
            100                 105                 110

Gly Gly Ser Arg Gly Gly Arg Ile Phe Arg Ser Ser Asp Phe Ala Lys
        115                 120                 125

Asn Phe Val Gln Thr Asp Leu Pro Phe His Pro Thr Gln Met Met
    130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Ala Val Cys Leu Ala Lys Trp Gly Ser Asp Asn Thr Ile Phe Phe
            180                 185                 190

Thr Thr Tyr Ala Asn Gly Ser Cys Lys Ala Asp Leu Gly Ala Leu Glu
        195                 200                 205

Leu Trp Arg Thr Ser Asp Leu Gly Lys Ser Phe Lys Thr Ile Gly Val
    210                 215                 220
```

```
Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
            245                 250                 255

Gly Asp Thr Trp Ser Met Ala Gln Leu Pro Ser Val Gly Gln Glu Gln
                260                 265                 270

Phe Tyr Ser Ile Leu Ala Ala Asn Asp Asp Met Val Phe Met His Val
            275                 280                 285

Asp Glu Pro Gly Asp Thr Gly Phe Gly Thr Ile Phe Thr Ser Asp Asp
        290                 295                 300

Arg Gly Ile Val Tyr Ser Lys Ser Leu Asp Arg His Leu Tyr Thr Thr
305                 310                 315                 320

Thr Gly Gly Glu Thr Asp Phe Thr Asn Val Thr Ser Leu Arg Gly Val
                325                 330                 335

Tyr Ile Thr Ser Val Leu Ser Glu Asp Asn Ser Ile Gln Thr Met Ile
            340                 345                 350

Thr Phe Asp Gln Gly Gly Arg Trp Thr His Leu Arg Lys Pro Glu Asn
        355                 360                 365

Ser Glu Cys Asp Ala Thr Ala Lys Asn Lys Asn Glu Cys Ser Leu His
370                 375                 380

Ile His Ala Ser Tyr Ser Ile Ser Gln Lys Leu Asn Val Pro Met Ala
385                 390                 395                 400

Pro Leu Ser Glu Pro Asn Ala Val Gly Ile Val Ile Ala His Gly Ser
                405                 410                 415

Val Gly Asp Ala Ile Ser Val Met Val Pro Asp Val Tyr Ile Ser Asp
            420                 425                 430

Asp Gly Gly Tyr Ser Trp Thr Lys Met Leu Glu Gly Pro His Tyr Tyr
        435                 440                 445

Thr Ile Leu Asp Ser Gly Gly Ile Ile Val Ala Ile Glu His Ser Ser
450                 455                 460

Arg Pro Ile Asn Val Ile Lys Phe Ser Thr Asp Glu Gly Gln Cys Trp
465                 470                 475                 480

Gln Thr Tyr Thr Phe Thr Arg Asp Pro Ile Tyr Phe Thr Gly Leu Ala
                485                 490                 495

Ser Glu Pro Gly Ala Arg Ser Met Asn Ile Ser Ile Trp Gly Phe Thr
            500                 505                 510

Glu Ser Phe Leu Thr Ser Gln Trp Val Ser Tyr Thr Ile Asp Phe Lys
        515                 520                 525

Asp Ile Leu Glu Arg Asn Cys Glu Glu Lys Asp Tyr Thr Ile Trp Leu
            530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
610                 615                 620

Cys Leu Tyr Gly Arg Glu Glu His Leu Thr Thr Asn Gly Tyr Arg Lys
625                 630                 635                 640
```

```
Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
        660                 665                 670

Gln Asn Ser Lys Ser Asn Gly Ser Ala Gly Gly Ser Gly Gly Leu Asn
            675                 680                 685

Asp Ile Phe Glu Ala Gln Lys Ile Glu Trp His Glu
        690                 695                 700

<210> SEQ ID NO 172
<211> LENGTH: 700
<212> TYPE: PRT
<213> ORGANISM: Artificial
<220> FEATURE:
<223> OTHER INFORMATION: Sortilin SORTECDBAP_hBACK

<400> SEQUENCE: 172

Ser Ala Pro Gly Glu Asp Glu Cys Gly Arg Val Arg Asp Phe Val
1               5                   10                  15

Ala Lys Leu Ala Asn Asn Thr His Gln His Ile Phe Asn Asp Leu Ser
            20                  25                  30

Gly Ser Val Ser Leu Ser Trp Val Gly Asp Ser Thr Gly Val Ile Leu
        35                  40                  45

Val Leu Thr Thr Phe Gln Val Pro Ile Phe Met Ile Thr Ile Gly Gln
50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Ser Asp Phe Gly Ile Ala
                85                  90                  95

Ile Gly Pro Glu Asn Ser Gly Lys Val Val Leu Thr Ala Asp Val Ser
            100                 105                 110

Gly Ser His Gly Ser Arg Ile Phe Arg Ser Ser Asp Phe Ala Lys Asn
        115                 120                 125

Phe Val Gln Gln Glu Leu Pro Phe Val Pro Leu Met Gln Ile Met Tyr
130                 135                 140

Ser Pro Gln Asn Ser Asp Tyr Leu Leu Ala Leu Ser Asn Lys Asn Glu
145                 150                 155                 160

Leu Trp Val Ser Lys Asn Phe Gly Gly Lys Trp Glu Lys Leu Tyr Asp
                165                 170                 175

Thr Val Cys Leu Ala Lys Trp Gly Ser Asp Asn Thr Ile Phe Phe Thr
            180                 185                 190

Ala Asn His Asn Gly Ser Cys Ser Asn Asp Arg Gly Met Leu Glu Leu
        195                 200                 205

Trp Arg Thr Ser Asp Leu Gly Lys Ser Phe Lys Thr Ile Gly Ser Lys
210                 215                 220

Ile Tyr Ser Phe Gly Leu Gly Gly Arg Phe Leu Phe Ala Ser Val Met
225                 230                 235                 240

Thr Gly Lys Gly Thr Leu Arg Ala Ile His Val Ser Thr Asp Gln Gly
                245                 250                 255

Asp Thr Trp Ser Met Ala Gln Leu Pro Pro Val Gly His Glu Gln Phe
            260                 265                 270

Tyr Ser Ile Leu Ala Ala Asn Asp Asp Met Val Phe Met His Val Asp
        275                 280                 285

Glu Pro Gly Asp Ser Gly Phe Gly Thr Ile Phe Thr Ser Asp Asp Arg
290                 295                 300
```

Gly Ile Val Tyr Ser Lys Ser Leu Glu Arg His Leu Tyr Thr Thr Thr
305                 310                 315                 320

Gly Gly Glu Thr Asp Phe Thr Asn Val Thr Ser Leu Arg Gly Val Tyr
            325                 330                 335

Ile Thr Ser Ile Leu Ala Glu Asp Lys Ser Val Gln Ser Met Ile Thr
                340                 345                 350

Phe Asp Gln Gly Gly Arg Trp Thr His Leu Arg Lys Pro Glu Asn Ser
            355                 360                 365

Lys Cys Asp Ala Thr Ala Arg Asp Pro Glu Lys Cys Ser Leu His Ile
370                 375                 380

His Ala Ala Tyr Ser Ile Ala Thr Gly Leu Asn Val Pro Met Leu Pro
385                 390                 395                 400

Leu Ser Glu Pro Asn Ala Val Gly Ile Val Ala His Gly Ser Val
                405                 410                 415

Gly Asp Ala Ile Ser Val Met Arg Pro Asp Val Tyr Ile Ser Asp Asp
                420                 425                 430

Gly Gly Tyr Ser Trp Thr Lys Ala Leu Glu Gly Pro His His Tyr Thr
            435                 440                 445

Ile Leu Asp Ser Gly Gly Ile Ile Val Ala Val Glu Gln Asn Ala His
450                 455                 460

Gln Gly Val Asn Gln Ile Lys Phe Ser Thr Asp Glu Gly Gln Cys Trp
465                 470                 475                 480

Gln Thr Tyr Asn Phe Thr Lys Asp Pro Ile Phe Phe Thr Gly Leu Ala
                485                 490                 495

Ser Glu Pro Gly Ala Arg Ser Met Asn Ile Ser Ile Trp Gly Tyr Arg
            500                 505                 510

Ser Ser Leu Phe His Gln Tyr Trp Ile Ser Tyr Thr Ile Asp Phe Lys
            515                 520                 525

Asp Ile Leu Glu Arg Asn Cys Glu Glu Lys Asp Tyr Thr Ile Trp Leu
530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
            595                 600                 605

Ser Lys Cys Val Glu Gln Pro Glu Leu Lys Gly His Asp Leu Glu Phe
610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Cys Thr Ser Asn Phe Leu Ser Pro Glu Lys
            660                 665                 670

Gln Asn Ser Lys Ser Asn Gly Ser Ala Gly Gly Ser Gly Leu Asn
675                 680                 685

Asp Ile Phe Glu Ala Gln Lys Ile Glu Trp His Glu
690                 695                 700

<210> SEQ ID NO 173
<211> LENGTH: 700
<212> TYPE: PRT

<210> ORGANISM: Artificial
<220> FEATURE:
<223> OTHER INFORMATION: Sortilin SORTECDBAP_tetra

<400> SEQUENCE: 173

```
Arg Ser Thr Glu Gln Gly Glu Ser Cys Ser Gly Leu Leu Gly Ala Asp
1               5                   10                  15

Ala Lys Leu Ala Gly Asn Thr His Gln His Ile Phe Asn Asp Leu Ser
            20                  25                  30

Gly Ser Val Ser Leu Ala Trp Val Gly Asp Gly Thr Gly Val Ile Leu
        35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Ser Phe Glu Asp Val
65                  70                  75                  80

Thr Asn Leu Ile Asn Asn Thr Phe Ile Arg Ser Asp Phe Gly Ile Ala
                85                  90                  95

Ile Gly Pro Glu Asn Ser Gly Lys Val Ile Leu Thr Ala Asp Val Ser
            100                 105                 110

Gly Ser His Gly Ser Arg Ile Phe Val Ser Ser Asp Phe Gly Lys Ser
        115                 120                 125

Phe Thr His Gln Glu Leu Pro Phe Val Pro Leu Met Gln Ile Thr Tyr
    130                 135                 140

Asn Pro Glu Asn Ser Asn Val Leu Leu Ala Leu Ser Asn Lys Asn Glu
145                 150                 155                 160

Leu Trp Leu Ser Glu Asp Phe Gly Thr Asn Trp Lys Lys Leu Tyr Asp
                165                 170                 175

Thr Val Cys Leu Ala Lys Trp Gly Arg Lys Gly Thr Ile Phe Phe Thr
            180                 185                 190

Ala Asn His Asn Gly Ser Cys Ser Asn Asp Arg Gly Met Leu Glu Leu
        195                 200                 205

Glu Arg Thr Thr Asp Tyr Gly Lys Ser Phe Lys Thr Val Ala Ser Lys
    210                 215                 220

Ile Tyr Ser Phe Gly Leu Gly Gly Lys Phe Leu Phe Ala Ser Val Met
225                 230                 235                 240

Thr Gly Lys Gly Thr Leu Arg Ala Ile His Val Ser Val Asp Asp Gly
                245                 250                 255

Asp Thr Trp Asn Met Ala Gln Leu Pro Pro Val Gly His Glu Gln Phe
            260                 265                 270

Tyr Ser Ile Leu Ala Ala Asn Asp Glu Met Val Phe Met His Val Asp
        275                 280                 285

Glu Pro Gly Asp Ser Gly Phe Gly Thr Ile Tyr Val Ser Asp Asp Arg
    290                 295                 300

Gly Thr Val Tyr Ser Lys Ser Leu Glu Arg His Leu Tyr Thr Thr Thr
305                 310                 315                 320

Gly Gly Glu Thr Asp Phe Ile Asn Val Thr Ser Leu Arg Gly Val Phe
                325                 330                 335

Thr Thr Ser Ile Leu Ala Glu Asp Lys Ser Val Gln Ser Val Ile Ser
            340                 345                 350

Phe Asp Gln Gly Gly Glu Trp Val Pro Leu Arg Lys Pro Ala Asp Ser
        355                 360                 365

Lys Cys Asp Ala Thr Ala Arg Asp Pro Glu Lys Cys Ser Leu His Ile
    370                 375                 380

His Ala Ala Tyr Ser Ile Ala Thr Gly Leu Asn Val Pro Met Leu Pro
```

```
                385                 390                 395                 400
Leu Ser Glu Pro Asn Ala Val Gly Leu Val Leu Ala His Gly Ser Val
                    405                 410                 415
Gly Asp Ala Ile Ser Val Met Arg Pro Asp Val Tyr Val Ser Asp Asp
                420                 425                 430
Gly Gly Tyr Thr Trp Ile Lys Ala Leu Glu Gly Pro His His Tyr Ala
            435                 440                 445
Ile Leu Asp Ser Gly Gly Leu Leu Val Ala Val Glu Gln Asn Ala His
        450                 455                 460
Gln Gly Val Asn Gln Ile Lys Phe Ser Thr Asp Glu Gly Gln Cys Trp
465                 470                 475                 480
Gly Val Tyr Asn Phe Thr Lys Asp Pro Ile Phe Thr Gly Leu Ala
                485                 490                 495
Ser Glu Pro Gly Ala Arg Ser Met Asn Val Ser Leu Trp Gly Tyr Arg
                    500                 505                 510
Ser Ser Leu Phe His Gln Tyr Trp Ile Ser Phe Thr Ile Asp Phe Arg
            515                 520                 525
Asp Leu Ile Thr Arg Asn Cys Thr Asp Lys Asp Tyr Val Gln Trp Leu
        530                 535                 540
Ala His Ser Asp Asp Ile Ser Asp Pro Asn Asp Gly Cys Met Leu Gly
545                 550                 555                 560
Tyr Lys Glu Lys Phe Leu Arg Leu Lys Lys Asp Ser Val Cys Leu Asn
                565                 570                 575
Gly Arg Asp Tyr Glu Val Asn Thr Gln Pro Thr Pro Cys Leu Cys Thr
                    580                 585                 590
Leu Asp Asp Phe Leu Cys Asp Phe Gly Tyr Tyr Arg Lys Glu Asn Ser
            595                 600                 605
Ser Glu Cys Val Glu Gln Pro Asp Leu Lys Gly Lys Val Leu Glu Phe
        610                 615                 620
Cys Leu His Gly Thr Glu Glu Leu Leu Thr Asn Gly Tyr Arg Lys
625                 630                 635                 640
Ile Pro Gly Asp Lys Cys Glu Gly Gly Gln Ile Pro Glu Arg Lys Glu
                645                 650                 655
Ile Asn Leu Arg Arg Arg Cys Val Ser Asp Leu Leu Gly Pro Glu Phe
                    660                 665                 670
Leu Val Lys Lys Ser Ser Gly Ala Gly Ser Gly Leu Asn
            675                 680                 685
Asp Ile Phe Glu Ala Gln Lys Ile Glu Trp His Glu
        690                 695                 700

<210> SEQ ID NO 174
<211> LENGTH: 701
<212> TYPE: PRT
<213> ORGANISM: Artificial
<220> FEATURE:
<223> OTHER INFORMATION: Sortilin  SORTECDBAP_hB01-05

<400> SEQUENCE: 174

Ser Ala Pro Gly Glu Asp Glu Cys Gly Arg Val Arg Asp Phe Val
1               5                   10                  15

Ala Lys Leu Ala Asn Asn Thr His Gln His Val Phe Asp Asp Leu Arg
                20                  25                  30

Gly Ser Val Ser Leu Ser Trp Val Gly Asp Ser Thr Gly Val Ile Leu
            35                  40                  45

Val Leu Thr Thr Phe His Val Pro Leu Val Ile Met Thr Phe Gly Gln
```

```
            50                  55                  60
Ser Lys Leu Tyr Arg Ser Glu Asp Tyr Gly Lys Asn Phe Lys Asp Ile
 65                  70                  75                  80

Thr Asp Leu Ile Asn Asn Thr Phe Ile Arg Thr Glu Phe Gly Met Ala
                 85                  90                  95

Ile Gly Pro Glu Asn Ser Gly Lys Val Val Leu Thr Ala Glu Val Ser
            100                 105                 110

Gly Gly Ser Arg Gly Arg Ile Phe Arg Ser Ser Asp Phe Ala Lys
        115                 120                 125

Asn Phe Val Gln Thr Asp Leu Pro Phe His Pro Leu Thr Gln Met Met
130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Ala Val Cys Leu Ala Lys Trp Gly Ser Asp Asn Thr Ile Phe Phe
            180                 185                 190

Thr Thr Tyr Ala Asn Gly Ser Cys Lys Ala Asp Leu Gly Ala Leu Glu
        195                 200                 205

Leu Trp Arg Thr Ser Asp Leu Gly Lys Ser Phe Lys Thr Ile Gly Val
210                 215                 220

Lys Ile Tyr Ser Phe Gly Leu Gly Gly Arg Phe Leu Phe Ala Ser Val
225                 230                 235                 240

Met Ala Asp Lys Asp Thr Thr Arg Arg Ile His Val Ser Thr Asp Gln
                245                 250                 255

Gly Asp Thr Trp Ser Met Ala Gln Leu Pro Pro Val Gly His Glu Gln
            260                 265                 270

Phe Tyr Ser Ile Leu Ala Ala Asn Asp Glu Met Val Phe Met His Val
        275                 280                 285

Asp Glu Pro Gly Asp Ser Gly Phe Gly Thr Ile Tyr Val Ser Asp Asp
290                 295                 300

Arg Gly Thr Val Tyr Ser Lys Ser Leu Glu Arg His Leu Tyr Thr Thr
305                 310                 315                 320

Thr Gly Gly Glu Thr Asp Phe Ile Asn Val Thr Ser Leu Arg Gly Val
                325                 330                 335

Phe Thr Thr Ser Ile Leu Ala Glu Asp Lys Ser Val Gln Ser Val Ile
            340                 345                 350

Ser Phe Asp Gln Gly Gly Glu Trp Val Pro Leu Arg Lys Pro Ala Asp
        355                 360                 365

Ser Lys Cys Asp Ala Thr Ala Arg Asp Pro Glu Lys Cys Ser Leu His
370                 375                 380

Ile His Ala Ala Tyr Ser Ile Ala Thr Gly Leu Asn Val Pro Met Leu
385                 390                 395                 400

Pro Leu Ser Glu Pro Asn Ala Val Gly Leu Val Leu Ala His Gly Ser
                405                 410                 415

Val Gly Asp Ala Ile Ser Val Met Arg Pro Asp Val Tyr Val Ser Asp
            420                 425                 430

Asp Gly Gly Tyr Thr Trp Ile Lys Ala Leu Glu Gly Pro His His Tyr
        435                 440                 445

Ala Ile Leu Asp Ser Gly Gly Leu Leu Val Ala Val Glu Gln Asn Ala
    450                 455                 460

His Gln Gly Val Asn Gln Ile Lys Phe Ser Thr Asp Glu Gly Gln Cys
465                 470                 475                 480
```

```
Trp Gly Val Tyr Asn Phe Thr Lys Asp Pro Ile Phe Thr Gly Leu
            485                 490                 495

Ala Ser Glu Pro Gly Ala Arg Ser Met Asn Val Ser Leu Trp Gly Tyr
        500                 505                 510

Arg Ser Ser Leu Phe His Gln Tyr Trp Ile Ser Phe Thr Ile Asp Phe
            515                 520                 525

Arg Asp Leu Ile Thr Arg Asn Cys Thr Asp Lys Asp Tyr Val Gln Trp
        530                 535                 540

Leu Ala His Ser Asp Asp Ile Ser Asp Pro Asn Asp Gly Cys Met Leu
545                 550                 555                 560

Gly Tyr Lys Glu Lys Phe Leu Arg Leu Lys Lys Asp Ser Val Cys Leu
            565                 570                 575

Asn Gly Arg Asp Tyr Glu Val Asn Thr Gln Pro Thr Pro Cys Leu Cys
        580                 585                 590

Thr Leu Asp Asp Phe Leu Cys Asp Phe Gly Tyr Tyr Arg Lys Glu Asn
            595                 600                 605

Ser Ser Glu Cys Val Glu Gln Pro Asp Leu Lys Gly Lys Val Leu Glu
        610                 615                 620

Phe Cys Leu His Gly Thr Glu Glu Leu Leu Thr Asn Gly Tyr Arg
625                 630                 635                 640

Lys Ile Pro Gly Asp Lys Cys Glu Gly Gly Gln Ile Pro Glu Arg Lys
            645                 650                 655

Glu Ile Asn Leu Arg Arg Arg Cys Val Ser Asp Leu Leu Gly Pro Glu
        660                 665                 670

Phe Leu Val Lys Lys Ser Ser Gly Ser Ala Gly Gly Ser Gly Gly Leu
            675                 680                 685

Asn Asp Ile Phe Glu Ala Gln Lys Ile Glu Trp His Glu
        690                 695                 700

<210> SEQ ID NO 175
<211> LENGTH: 700
<212> TYPE: PRT
<213> ORGANISM: Artificial
<220> FEATURE:
<223> OTHER INFORMATION: Sortilin  SORTECDBAP_hRIM

<400> SEQUENCE: 175

Ser Ala Pro Gly Glu Asp Glu Cys Gly Arg Val Arg Asp Phe Val
1               5                   10                  15

Ala Lys Leu Ala Asn Asn Thr His Gln His Val Phe Asp Asp Leu Arg
            20                  25                  30

Gly Ser Val Ser Leu Ala Trp Val Gly Asp Gly Thr Gly Val Ile Leu
        35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Asn Phe Lys Asp Ile
65              70                  75                  80

Thr Asp Leu Ile Asn Asn Thr Phe Ile Arg Ser Asp Phe Gly Ile Ala
            85                  90                  95

Ile Gly Pro Glu Asn Ser Gly Lys Val Ile Leu Thr Ala Asp Val Ser
        100                 105                 110

Gly Ser His Gly Ser Arg Ile Phe Arg Ser Ser Asp Phe Ala Lys Asn
    115                 120                 125

Phe Val Gln Thr Asp Leu Pro Phe Val Pro Leu Met Gln Ile Thr Tyr
130                 135                 140
```

```
Asn Pro Glu Asn Ser Asn Val Leu Leu Ala Leu Ser Asn Lys Asn Glu
145                 150                 155                 160

Leu Trp Val Ser Lys Asn Phe Gly Gly Lys Trp Glu Ile His Asp
            165                 170                 175

Thr Val Cys Leu Ala Lys Trp Gly Arg Lys Gly Thr Ile Phe Phe Thr
            180                 185                 190

Ala Asn His Asn Gly Ser Cys Ser Asn Asp Arg Gly Met Leu Glu Leu
            195                 200                 205

Trp Arg Thr Ser Asp Leu Gly Lys Ser Phe Lys Thr Ile Gly Val Lys
            210                 215                 220

Ile Tyr Ser Phe Gly Leu Gly Lys Phe Leu Phe Ala Ser Val Met
225                 230                 235                 240

Thr Gly Lys Gly Thr Leu Arg Arg Ile His Val Ser Thr Asp Gln Gly
            245                 250                 255

Asp Thr Trp Ser Met Ala Gln Leu Pro Ser Val Gly His Glu Gln Phe
            260                 265                 270

Tyr Ser Ile Leu Ala Ala Asn Asp Glu Met Val Phe Met His Val Asp
            275                 280                 285

Glu Pro Gly Asp Ser Gly Phe Gly Thr Ile Phe Thr Ser Asp Asp Arg
290                 295                 300

Gly Ile Val Tyr Ser Lys Ser Leu Asp Arg His Leu Tyr Thr Thr Thr
305                 310                 315                 320

Gly Gly Glu Thr Asp Phe Ile Asn Val Thr Ser Leu Arg Gly Val Phe
            325                 330                 335

Thr Thr Ser Ile Leu Ala Glu Asp Lys Ser Ile Gln Thr Met Ile Thr
            340                 345                 350

Phe Asp Gln Gly Gly Arg Trp Thr His Leu Arg Lys Pro Glu Asn Ser
            355                 360                 365

Glu Cys Asp Ala Thr Ala Lys Asn Lys Asn Glu Cys Ser Leu His Ile
            370                 375                 380

His Ala Ala Tyr Ser Ile Ala Thr Gly Leu Asn Val Pro Met Leu Pro
385                 390                 395                 400

Leu Ser Glu Pro Asn Ala Val Gly Leu Val Leu Ala His Gly Ser Val
            405                 410                 415

Gly Asp Ala Ile Ser Val Met Arg Pro Asp Val Tyr Ile Ser Asp Asp
            420                 425                 430

Gly Gly Tyr Ser Trp Thr Lys Met Leu Glu Gly Pro His His Tyr Ala
            435                 440                 445

Ile Leu Asp Ser Gly Gly Leu Leu Val Ala Val Glu Gln Asn Ala His
            450                 455                 460

Gln Gly Val Asn Val Ile Lys Phe Ser Thr Asp Glu Gly Gln Cys Trp
465                 470                 475                 480

Gln Thr Tyr Thr Phe Thr Arg Asp Pro Ile Phe Phe Thr Gly Leu Ala
            485                 490                 495

Ser Glu Pro Gly Ala Arg Ser Met Asn Val Ser Leu Trp Gly Tyr Arg
            500                 505                 510

Ser Ser Leu Phe His Gln Gln Trp Val Ser Tyr Thr Ile Asp Phe Lys
            515                 520                 525

Asp Ile Leu Glu Arg Asn Cys Glu Glu Lys Asp Tyr Thr Ile Trp Leu
            530                 535                 540

Ala His Ser Thr Asp Pro Glu Asp Tyr Glu Asp Gly Cys Ile Leu Gly
545                 550                 555                 560
```

```
Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
            595                 600                 605

Ser Lys Cys Val Glu Gln Pro Glu Leu Lys Gly His Asp Leu Glu Phe
    610                 615                 620

Cys Leu Tyr Gly Arg Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Lys Cys Thr Ser Asn Phe Leu Ser Pro Glu Lys
                660                 665                 670

Gln Asn Ser Lys Ser Asn Gly Ser Ala Gly Gly Ser Gly Gly Leu Asn
            675                 680                 685

Asp Ile Phe Glu Ala Gln Lys Ile Glu Trp His Glu
            690                 695                 700

<210> SEQ ID NO 176
<211> LENGTH: 699
<212> TYPE: PRT
<213> ORGANISM: Artificial
<220> FEATURE:
<223> OTHER INFORMATION: Sortilin  SORTECDBAP_hB06-10

<400> SEQUENCE: 176

Arg Ser Thr Glu Gln Gly Glu Ser Cys Ser Gly Leu Leu Gly Ala Asp
1               5                   10                  15

Ala Lys Leu Ala Gly Asn Thr His Gln His Ile Phe Asn Asp Leu Ser
                20                  25                  30

Gly Ser Val Ser Leu Ala Trp Val Gly Asp Gly Thr Gly Val Ile Leu
            35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Ser Phe Glu Asp Val
65                  70                  75                  80

Thr Asn Leu Ile Asn Asn Thr Phe Ile Arg Ser Asp Phe Gly Ile Ala
                85                  90                  95

Ile Gly Pro Glu Asn Ser Gly Lys Val Ile Leu Thr Ala Asp Val Ser
                100                 105                 110

Gly Ser His Gly Ser Arg Ile Phe Val Ser Ser Asp Phe Gly Lys Ser
            115                 120                 125

Phe Thr His Gln Glu Leu Pro Phe Val Pro Leu Met Gln Ile Thr Tyr
    130                 135                 140

Asn Pro Glu Asn Ser Asn Val Leu Leu Ala Leu Ser Asn Lys Asn Glu
145                 150                 155                 160

Leu Trp Leu Ser Glu Asp Phe Gly Thr Asn Trp Lys Lys Leu Tyr Asp
                165                 170                 175

Thr Val Cys Leu Ala Lys Trp Gly Arg Lys Gly Thr Ile Phe Phe Thr
                180                 185                 190

Ala Asn His Asn Gly Ser Cys Ser Asn Asp Arg Gly Met Leu Glu Leu
            195                 200                 205

Glu Arg Thr Thr Asp Tyr Gly Lys Ser Phe Lys Thr Val Ala Ser Lys
    210                 215                 220
```

-continued

| | | | | | | | | | | | | | | |
|---|---|---|---|---|---|---|---|---|---|---|---|---|---|---|
Ile | Tyr | Ser | Phe | Gly | Leu | Gly | Gly | Lys | Phe | Leu | Phe | Ala | Ser | Val | Met
225 | | | | 230 | | | | 235 | | | | | | 240

Thr Gly Lys Gly Thr Leu Arg Ala Ile His Val Ser Val Asp Asp Gly
               245                   250                   255

Asp Thr Trp Asn Met Ala Gln Leu Pro Ser Val Gly Gln Glu Gln Phe
         260                   265                   270

Tyr Ser Ile Leu Ala Ala Asn Asp Asp Met Val Phe Met His Val Asp
     275                   280                   285

Glu Pro Gly Asp Thr Gly Phe Gly Thr Ile Phe Thr Ser Asp Asp Arg
     290                   295                   300

Gly Ile Val Tyr Ser Lys Ser Leu Asp Arg His Leu Tyr Thr Thr Thr
305              310                 315                320

Gly Gly Glu Thr Asp Phe Thr Asn Val Thr Ser Leu Arg Gly Val Tyr
               325                   330                335

Ile Thr Ser Val Leu Ser Glu Asp Asn Ser Ile Gln Thr Met Ile Thr
             340                  345              350

Phe Asp Gln Gly Gly Arg Trp Thr His Leu Arg Lys Pro Glu Asn Ser
         355                 360                365

Glu Cys Asp Ala Thr Ala Lys Asn Lys Asn Glu Cys Ser Leu His Ile
    370                 375                   380

His Ala Ser Tyr Ser Ile Ser Gln Lys Leu Asn Val Pro Met Ala Pro
385              390                 395                400

Leu Ser Glu Pro Asn Ala Val Gly Ile Val Ile Ala His Gly Ser Val
             405                  410              415

Gly Asp Ala Ile Ser Val Met Val Pro Asp Val Tyr Ile Ser Asp Asp
         420                 425              430

Gly Gly Tyr Ser Trp Thr Lys Met Leu Glu Gly Pro His Tyr Tyr Thr
         435                 440              445

Ile Leu Asp Ser Gly Gly Ile Ile Val Ala Ile Glu His Ser Ser Arg
450              455                 460

Pro Ile Asn Val Ile Lys Phe Ser Thr Asp Glu Gly Gln Cys Trp Gln
465              470                 475              480

Thr Tyr Thr Phe Thr Arg Asp Pro Ile Tyr Phe Thr Gly Leu Ala Ser
             485                  490              495

Glu Pro Gly Ala Arg Ser Met Asn Ile Ser Ile Trp Gly Phe Thr Glu
         500                 505                510

Ser Phe Leu Thr Ser Gln Trp Val Ser Tyr Thr Ile Asp Phe Lys Asp
         515                 520              525

Ile Leu Glu Arg Asn Cys Glu Glu Lys Asp Tyr Thr Ile Trp Leu Ala
530              535                 540

His Ser Thr Asp Pro Glu Asp Tyr Glu Asp Gly Cys Ile Leu Gly Tyr
545              550               555              560

Lys Glu Gln Phe Leu Arg Leu Arg Lys Ser Ser Val Cys Gln Asn Gly
         565                 570               575

Arg Asp Tyr Val Val Thr Lys Gln Pro Ser Ile Cys Leu Cys Ser Leu
         580                 585              590

Glu Asp Phe Leu Cys Asp Phe Gly Tyr Tyr Arg Pro Glu Asn Asp Ser
     595                   600                  605

Lys Cys Val Glu Gln Pro Glu Leu Lys Gly His Asp Leu Glu Phe Cys
     610                   615                  620

Leu Tyr Gly Arg Glu Glu His Leu Thr Thr Asn Gly Tyr Arg Lys Ile
625              630                 635                640

Pro Gly Asp Lys Cys Gln Gly Gly Val Asn Pro Val Arg Glu Val Lys

```
                    645                 650                 655
Asp Leu Lys Lys Lys Cys Thr Ser Asn Phe Leu Ser Pro Glu Lys Gln
                660                 665                 670

Asn Ser Lys Ser Asn Gly Ser Ala Gly Gly Ser Gly Gly Leu Asn Asp
            675                 680                 685

Ile Phe Glu Ala Gln Lys Ile Glu Trp His Glu
        690                 695

<210> SEQ ID NO 177
<211> LENGTH: 700
<212> TYPE: PRT
<213> ORGANISM: Artificial
<220> FEATURE:
<223> OTHER INFORMATION: Sortilin  SORTECDBAP_hB12390

<400> SEQUENCE: 177

Ser Ala Pro Gly Glu Asp Glu Cys Gly Arg Val Arg Asp Phe Val
1               5                  10                  15

Ala Lys Leu Ala Asn Asn Thr His Gln His Val Phe Asp Asp Leu Arg
                20                  25                  30

Gly Ser Val Ser Leu Ser Trp Val Gly Asp Ser Thr Gly Val Ile Leu
            35                  40                  45

Val Leu Thr Thr Phe His Val Pro Leu Val Ile Met Thr Phe Gly Gln
        50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95

Ile Gly Pro Glu Asn Ser Gly Lys Val Val Leu Thr Ala Glu Val Ser
            100                 105                 110

Gly Gly Ser Arg Gly Gly Arg Ile Phe Arg Ser Ser Asp Phe Ala Lys
        115                 120                 125

Asn Phe Val Gln Thr Asp Leu Pro Phe His Pro Leu Thr Gln Met Met
    130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys Thr Val Cys Leu Ala Lys Trp Gly Arg Lys Gly Thr Ile Phe Phe
            180                 185                 190

Thr Ala Asn His Asn Gly Ser Cys Ser Asn Asp Arg Gly Met Leu Glu
        195                 200                 205

Leu Glu Arg Thr Thr Asp Tyr Gly Lys Ser Phe Lys Thr Val Ala Ser
    210                 215                 220

Lys Ile Tyr Ser Phe Gly Leu Gly Gly Lys Phe Leu Phe Ala Ser Val
225                 230                 235                 240

Met Thr Gly Lys Gly Thr Leu Arg Ala Ile His Val Ser Val Asp Asp
                245                 250                 255

Gly Asp Thr Trp Asn Met Ala Gln Leu Pro Pro Val Gly His Glu Gln
            260                 265                 270

Phe Tyr Ser Ile Leu Ala Ala Asn Asp Glu Met Val Phe Met His Val
        275                 280                 285

Asp Glu Pro Gly Asp Ser Gly Phe Gly Thr Ile Tyr Val Ser Asp Asp
    290                 295                 300

Arg Gly Thr Val Tyr Ser Lys Ser Leu Glu Arg His Leu Tyr Thr Thr
```

```
            305                 310                 315                 320
    Thr Gly Gly Glu Thr Asp Phe Ile Asn Val Thr Ser Leu Arg Gly Val
                    325                 330                 335
    Phe Thr Thr Ser Ile Leu Ala Glu Asp Lys Ser Val Gln Ser Val Ile
                    340                 345                 350
    Ser Phe Asp Gln Gly Gly Glu Trp Val Pro Leu Arg Lys Pro Ala Asp
                    355                 360                 365
    Ser Lys Cys Asp Ala Thr Ala Arg Asp Pro Glu Lys Cys Ser Leu His
                    370                 375                 380
    Ile His Ala Ala Tyr Ser Ile Ala Thr Gly Leu Asn Val Pro Met Leu
    385                 390                 395                 400
    Pro Leu Ser Glu Pro Asn Ala Val Gly Leu Val Leu Ala His Gly Ser
                    405                 410                 415
    Val Gly Asp Ala Ile Ser Val Met Arg Pro Asp Val Tyr Val Ser Asp
                    420                 425                 430
    Asp Gly Gly Tyr Thr Trp Ile Lys Ala Leu Glu Gly Pro His Tyr Tyr
                    435                 440                 445
    Thr Ile Leu Asp Ser Gly Gly Ile Val Ala Ile Glu His Ser Ser
    450                 455                 460
    Arg Pro Ile Asn Val Ile Lys Phe Ser Thr Asp Glu Gly Gln Cys Trp
    465                 470                 475                 480
    Gln Thr Tyr Thr Phe Thr Arg Asp Pro Ile Tyr Phe Thr Gly Leu Ala
                    485                 490                 495
    Ser Glu Pro Gly Ala Arg Ser Met Asn Ile Ser Ile Trp Gly Phe Thr
                    500                 505                 510
    Glu Ser Phe Leu Thr Ser Gln Trp Val Ser Tyr Thr Ile Asp Phe Lys
                    515                 520                 525
    Asp Ile Leu Glu Arg Asn Cys Glu Glu Lys Asp Tyr Thr Ile Trp Leu
                    530                 535                 540
    Ala His Ser Thr Asp Pro Glu Asp Tyr Glu Asp Gly Cys Ile Leu Gly
    545                 550                 555                 560
    Tyr Lys Glu Gln Phe Leu Arg Leu Arg Lys Ser Ser Val Cys Gln Asn
                    565                 570                 575
    Gly Arg Asp Tyr Val Val Thr Lys Gln Pro Ser Ile Cys Leu Cys Ser
                    580                 585                 590
    Leu Glu Asp Phe Leu Cys Asp Phe Gly Tyr Tyr Arg Pro Glu Asn Asp
                    595                 600                 605
    Ser Lys Cys Val Glu Gln Pro Glu Leu Lys Gly His Asp Leu Glu Phe
                    610                 615                 620
    Cys Leu Tyr Gly Arg Glu Glu His Leu Thr Thr Asn Gly Tyr Arg Lys
    625                 630                 635                 640
    Ile Pro Gly Asp Lys Cys Gln Gly Gly Val Asn Pro Val Arg Glu Val
                    645                 650                 655
    Lys Asp Leu Lys Lys Lys Cys Thr Ser Asn Phe Leu Ser Pro Glu Lys
                    660                 665                 670
    Gln Asn Ser Lys Ser Asn Gly Ser Ala Gly Gly Ser Gly Gly Leu Asn
                    675                 680                 685
    Asp Ile Phe Glu Ala Gln Lys Ile Glu Trp His Glu
                    690                 695                 700

<210> SEQ ID NO 178
<211> LENGTH: 700
<212> TYPE: PRT
<213> ORGANISM: Artificial
```

<220> FEATURE:
<223> OTHER INFORMATION: Sortilin SORTECDBAP_hB45678

<400> SEQUENCE: 178

```
Arg Ser Thr Glu Gln Gly Glu Ser Cys Ser Gly Leu Leu Gly Ala Asp
1               5                   10                  15

Ala Lys Leu Ala Gly Asn Thr His Gln His Ile Phe Asn Asp Leu Ser
            20                  25                  30

Gly Ser Val Ser Leu Ala Trp Val Gly Asp Gly Thr Gly Val Ile Leu
        35                  40                  45

Ala Leu Thr Thr Phe Gln Val Pro Ile Phe Met Ile Thr Ile Gly Gln
    50                  55                  60

Ser Lys Leu Tyr Arg Ser Glu Asp Tyr Gly Lys Ser Phe Glu Asp Val
65                  70                  75                  80

Thr Asn Leu Ile Asn Asn Thr Phe Ile Arg Ser Asp Phe Gly Ile Ala
                85                  90                  95

Ile Gly Pro Glu Asn Ser Gly Lys Val Ile Leu Thr Ala Asp Val Ser
            100                 105                 110

Gly Ser His Gly Ser Arg Ile Phe Val Ser Ser Asp Phe Gly Lys Ser
        115                 120                 125

Phe Thr His Gln Glu Leu Pro Phe Val Pro Leu Met Gln Ile Thr Tyr
    130                 135                 140

Asn Pro Glu Asn Ser Asn Val Leu Leu Ala Leu Ser Asn Lys Asn Glu
145                 150                 155                 160

Leu Trp Leu Ser Glu Asp Phe Gly Thr Asn Trp Lys Lys Leu Tyr Asp
                165                 170                 175

Ala Val Cys Leu Ala Lys Trp Gly Ser Asp Asn Thr Ile Phe Phe Thr
            180                 185                 190

Thr Tyr Ala Asn Gly Ser Cys Lys Ala Asp Leu Gly Ala Leu Glu Leu
        195                 200                 205

Trp Arg Thr Ser Asp Leu Gly Lys Ser Phe Lys Thr Ile Gly Val Lys
    210                 215                 220

Ile Tyr Ser Phe Gly Leu Gly Gly Arg Phe Leu Phe Ala Ser Val Met
225                 230                 235                 240

Ala Asp Lys Asp Thr Thr Arg Arg Ile His Val Ser Thr Asp Gln Gly
                245                 250                 255

Asp Thr Trp Ser Met Ala Gln Leu Pro Ser Val Gly Gln Glu Gln Phe
            260                 265                 270

Tyr Ser Ile Leu Ala Ala Asn Asp Asp Met Val Phe Met His Val Asp
        275                 280                 285

Glu Pro Gly Asp Thr Gly Phe Gly Thr Ile Phe Thr Ser Asp Asp Arg
    290                 295                 300

Gly Ile Val Tyr Ser Lys Ser Leu Asp Arg His Leu Tyr Thr Thr Thr
305                 310                 315                 320

Gly Gly Glu Thr Asp Phe Thr Asn Val Thr Ser Leu Arg Gly Val Tyr
                325                 330                 335

Ile Thr Ser Val Leu Ser Glu Asp Asn Ser Ile Gln Thr Met Ile Thr
            340                 345                 350

Phe Asp Gln Gly Gly Arg Trp Thr His Leu Arg Lys Pro Glu Asn Ser
        355                 360                 365

Glu Cys Asp Ala Thr Ala Lys Asn Lys Asn Glu Cys Ser Leu His Ile
    370                 375                 380

His Ala Ser Tyr Ser Ile Ser Gln Lys Leu Asn Val Pro Met Ala Pro
385                 390                 395                 400
```

-continued

```
Leu Ser Glu Pro Asn Ala Val Gly Ile Val Ile Ala His Gly Ser Val
                405                 410                 415

Gly Asp Ala Ile Ser Val Met Val Pro Asp Val Tyr Ile Ser Asp Asp
            420                 425                 430

Gly Gly Tyr Ser Trp Thr Lys Met Leu Glu Gly Pro His His Tyr Ala
        435                 440                 445

Ile Leu Asp Ser Gly Gly Leu Leu Val Ala Val Glu Gln Asn Ala His
    450                 455                 460

Gln Gly Val Asn Gln Ile Lys Phe Ser Thr Asp Gly Gln Cys Trp
465                 470                 475                 480

Gly Val Tyr Asn Phe Thr Lys Asp Pro Ile Phe Phe Thr Gly Leu Ala
                485                 490                 495

Ser Glu Pro Gly Ala Arg Ser Met Asn Val Ser Leu Trp Gly Tyr Arg
            500                 505                 510

Ser Ser Leu Phe His Gln Tyr Trp Ile Ser Phe Thr Ile Asp Phe Arg
        515                 520                 525

Asp Leu Ile Thr Arg Asn Cys Glu Glu Lys Asp Tyr Thr Ile Trp Leu
    530                 535                 540

Ala His Ser Thr Asp Pro Glu Asp Tyr Glu Asp Gly Cys Ile Leu Gly
545                 550                 555                 560

Tyr Lys Glu Gln Phe Leu Arg Leu Arg Lys Ser Ser Val Cys Gln Asn
                565                 570                 575

Gly Arg Asp Tyr Val Val Thr Lys Gln Pro Ser Ile Cys Leu Cys Ser
            580                 585                 590

Leu Glu Asp Phe Leu Cys Asp Phe Gly Tyr Tyr Arg Pro Glu Asn Asp
        595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Gly Val Asn Pro Val Arg Glu Val
                645                 650                 655

Lys Asp Leu Lys Lys Cys Thr Ser Asn Phe Leu Ser Pro Glu Lys
            660                 665                 670

Gln Asn Ser Lys Ser Asn Gly Ser Ala Gly Gly Ser Gly Leu Asn
        675                 680                 685

Asp Ile Phe Glu Ala Gln Lys Ile Glu Trp His Glu
    690                 695                 700

<210> SEQ ID NO 179
<211> LENGTH: 763
<212> TYPE: PRT
<213> ORGANISM: Artificial
<220> FEATURE:
<223> OTHER INFORMATION: Sortilin  SORTECD_HIS

<400> SEQUENCE: 179

Met Glu Arg Pro Trp Gly Ala Ala Asp Gly Leu Ser Arg Trp Pro His
1               5                   10                  15

Gly Leu Gly Leu Leu Leu Leu Leu Gln Leu Leu Pro Ser Thr Leu
            20                  25                  30

Ser Gln Asp Arg Leu Asp Ala Pro Pro Pro Ala Ala Pro Leu Pro
        35                  40                  45

Arg Trp Ser Gly Pro Ile Gly Val Ser Trp Gly Leu Arg Ala Ala Ala
    50                  55                  60
```

```
Ala Gly Gly Ala Phe Pro Arg Gly Gly Arg Trp Arg Ser Ala Pro
 65                  70                  75                  80

Gly Glu Asp Glu Glu Cys Gly Arg Val Arg Asp Phe Val Ala Lys Leu
                 85                  90                  95

Ala Asn Asn Thr His Gln His Val Phe Asp Asp Leu Arg Gly Ser Val
                100                 105                 110

Ser Leu Ser Trp Val Gly Asp Ser Thr Gly Val Ile Leu Val Leu Thr
            115                 120                 125

Thr Phe His Val Pro Leu Val Ile Met Thr Phe Gly Gln Ser Lys Leu
        130                 135                 140

Tyr Arg Ser Glu Asp Tyr Gly Lys Asn Phe Lys Asp Ile Thr Asp Leu
145                 150                 155                 160

Ile Asn Asn Thr Phe Ile Arg Thr Glu Phe Gly Met Ala Ile Gly Pro
                165                 170                 175

Glu Asn Ser Gly Lys Val Val Leu Thr Ala Glu Val Ser Gly Gly Ser
            180                 185                 190

Arg Gly Gly Arg Ile Phe Arg Ser Ser Asp Phe Ala Lys Asn Phe Val
        195                 200                 205

Gln Thr Asp Leu Pro Phe His Pro Leu Thr Gln Met Met Tyr Ser Pro
210                 215                 220

Gln Asn Ser Asp Tyr Leu Leu Ala Leu Ser Thr Glu Asn Gly Leu Trp
225                 230                 235                 240

Val Ser Lys Asn Phe Gly Gly Lys Trp Glu Glu Ile His Lys Ala Val
                245                 250                 255

Cys Leu Ala Lys Trp Gly Ser Asp Asn Thr Ile Phe Phe Thr Thr Tyr
            260                 265                 270

Ala Asn Gly Ser Cys Lys Ala Asp Leu Gly Ala Leu Glu Leu Trp Arg
        275                 280                 285

Thr Ser Asp Leu Gly Lys Ser Phe Lys Thr Ile Gly Val Lys Ile Tyr
290                 295                 300

Ser Phe Gly Leu Gly Gly Arg Phe Leu Phe Ala Ser Val Met Ala Asp
305                 310                 315                 320

Lys Asp Thr Thr Arg Arg Ile His Val Ser Thr Asp Gln Gly Asp Thr
                325                 330                 335

Trp Ser Met Ala Gln Leu Pro Ser Val Gly Gln Glu Gln Phe Tyr Ser
            340                 345                 350

Ile Leu Ala Ala Asn Asp Asp Met Val Phe Met His Val Asp Glu Pro
        355                 360                 365

Gly Asp Thr Gly Phe Gly Thr Ile Phe Thr Ser Asp Asp Arg Gly Ile
370                 375                 380

Val Tyr Ser Lys Ser Leu Asp Arg His Leu Tyr Thr Thr Thr Gly Gly
385                 390                 395                 400

Glu Thr Asp Phe Thr Asn Val Thr Ser Leu Arg Gly Val Tyr Ile Thr
                405                 410                 415

Ser Val Leu Ser Glu Asp Asn Ser Ile Gln Thr Met Ile Thr Phe Asp
            420                 425                 430

Gln Gly Gly Arg Trp Thr His Leu Arg Lys Pro Glu Asn Ser Glu Cys
        435                 440                 445

Asp Ala Thr Ala Lys Asn Lys Asn Glu Cys Ser Leu His Ile His Ala
        450                 455                 460

Ser Tyr Ser Ile Ser Gln Lys Leu Asn Val Pro Met Ala Pro Leu Ser
465                 470                 475                 480
```

```
Glu Pro Asn Ala Val Gly Ile Val Ile Ala His Gly Ser Val Gly Asp
                485                 490                 495

Ala Ile Ser Val Met Val Pro Asp Val Tyr Ile Ser Asp Asp Gly Gly
            500                 505                 510

Tyr Ser Trp Thr Lys Met Leu Glu Gly Pro His Tyr Tyr Thr Ile Leu
        515                 520                 525

Asp Ser Gly Gly Ile Ile Val Ala Ile Glu His Ser Ser Arg Pro Ile
    530                 535                 540

Asn Val Ile Lys Phe Ser Thr Asp Glu Gly Gln Cys Trp Gln Thr Tyr
545                 550                 555                 560

Thr Phe Thr Arg Asp Pro Ile Tyr Phe Thr Gly Leu Ala Ser Glu Pro
                565                 570                 575

Gly Ala Arg Ser Met Asn Ile Ser Ile Trp Gly Phe Thr Glu Ser Phe
            580                 585                 590

Leu Thr Ser Gln Trp Val Ser Tyr Thr Ile Asp Phe Lys Asp Ile Leu
        595                 600                 605

Glu Arg Asn Cys Glu Glu Lys Asp Tyr Thr Ile Trp Leu Ala His Ser
    610                 615                 620

Thr Asp Pro Glu Asp Tyr Glu Asp Gly Cys Ile Leu Gly Tyr Lys Glu
625                 630                 635                 640

Gln Phe Leu Arg Leu Arg Lys Ser Ser Val Cys Gln Asn Gly Arg Asp
                645                 650                 655

Tyr Val Val Thr Lys Gln Pro Ser Ile Cys Leu Cys Ser Leu Glu Asp
            660                 665                 670

Phe Leu Cys Asp Phe Gly Tyr Tyr Arg Pro Glu Asn Asp Ser Lys Cys
        675                 680                 685

Val Glu Gln Pro Glu Leu Lys Gly His Asp Leu Glu Phe Cys Leu Tyr
    690                 695                 700

Gly Arg Glu Glu His Leu Thr Thr Asn Gly Tyr Arg Lys Ile Pro Gly
705                 710                 715                 720

Asp Lys Cys Gln Gly Gly Val Asn Pro Val Arg Glu Val Lys Asp Leu
                725                 730                 735

Lys Lys Lys Cys Thr Ser Asn Phe Leu Ser Pro Glu Lys Gln Asn Ser
            740                 745                 750

Lys Ser Asn His His His His His His His
        755                 760

<210> SEQ ID NO 180
<211> LENGTH: 177
<212> TYPE: PRT
<213> ORGANISM: Artificial
<220> FEATURE:
<223> OTHER INFORMATION: A region

<400> SEQUENCE: 180

Ser Ala Pro Gly Glu Asp Glu Cys Gly Arg Val Arg Asp Phe Val
1               5                   10                  15

Ala Lys Leu Ala Asn Asn Thr His Gln His Val Phe Asp Asp Leu Arg
            20                  25                  30

Gly Ser Val Ser Leu Ser Trp Val Gly Asp Ser Thr Gly Val Ile Leu
        35                  40                  45

Val Leu Thr Thr Phe His Val Pro Leu Val Ile Met Thr Phe Gly Gln
    50                  55                  60

Ser Lys Leu Tyr Arg Ser Glu Asp Tyr Gly Lys Asn Phe Lys Asp Ile
65                  70                  75                  80
```

Thr Asp Leu Ile Asn Asn Thr Phe Ile Arg Thr Glu Phe Gly Met Ala
            85                  90                  95

Ile Gly Pro Glu Asn Ser Gly Lys Val Val Leu Thr Ala Glu Val Ser
        100                 105                 110

Gly Gly Ser Arg Gly Gly Arg Ile Phe Arg Ser Ser Asp Phe Ala Lys
            115                 120                 125

Asn Phe Val Gln Thr Asp Leu Pro Phe His Pro Leu Thr Gln Met Met
        130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175

Lys

<210> SEQ ID NO 181
<211> LENGTH: 6
<212> TYPE: PRT
<213> ORGANISM: Artificial
<220> FEATURE:
<223> OTHER INFORMATION: A region amino acids 109-114

<400> SEQUENCE: 181

Arg Gly Ser Val Ser Leu
1               5

<210> SEQ ID NO 182
<211> LENGTH: 28
<212> TYPE: PRT
<213> ORGANISM: Artificial
<220> FEATURE:
<223> OTHER INFORMATION: A region amino acides 126-153

<400> SEQUENCE: 182

Val Leu Thr Thr Phe His Val Pro Leu Val Ile Met Thr Phe Gly Gln
1               5                   10                  15

Ser Lys Leu Tyr Arg Ser Glu Asp Tyr Gly Lys Asn
            20                  25

<210> SEQ ID NO 183
<211> LENGTH: 19
<212> TYPE: PRT
<213> ORGANISM: Artificial
<220> FEATURE:
<223> OTHER INFORMATION: A region amino acides 126-144

<400> SEQUENCE: 183

Val Leu Thr Thr Phe His Val Pro Leu Val Ile Met Thr Phe Gly Gln
1               5                   10                  15

Ser Lys Leu

<210> SEQ ID NO 184
<211> LENGTH: 6
<212> TYPE: PRT
<213> ORGANISM: Artificial
<220> FEATURE:
<223> OTHER INFORMATION: A region amino acides 154-159

<400> SEQUENCE: 184

Phe Lys Asp Ile Thr Asp
1               5

<210> SEQ ID NO 185

-continued

```
<211> LENGTH: 3
<212> TYPE: PRT
<213> ORGANISM: Artificial
<220> FEATURE:
<223> OTHER INFORMATION: D region amino acids 570-572

<400> SEQUENCE: 185

Thr Gly Leu
1

<210> SEQ ID NO 186
<211> LENGTH: 10
<212> TYPE: PRT
<213> ORGANISM: Artificial
<220> FEATURE:
<223> OTHER INFORMATION: D region amino acids 588-597

<400> SEQUENCE: 186

Phe Thr Glu Ser Phe Leu Thr Ser Gln Trp
1               5                   10

<210> SEQ ID NO 187
<211> LENGTH: 5
<212> TYPE: PRT
<213> ORGANISM: Artificial
<220> FEATURE:
<223> OTHER INFORMATION: D region amino acids 593-597

<400> SEQUENCE: 187

Leu Thr Ser Gln Trp
1               5

<210> SEQ ID NO 188
<211> LENGTH: 696
<212> TYPE: PRT
<213> ORGANISM: Artificial
<220> FEATURE:
<223> OTHER INFORMATION: Sequences used for HDX experiments

<400> SEQUENCE: 188

Ser Ala Pro Gly Glu Asp Glu Glu Cys Gly Arg Val Arg Asp Phe Val
1               5                   10                  15

Ala Lys Leu Ala Asn Asn Thr His Gln His Val Phe Asp Asp Leu Arg
                20                  25                  30

Gly Ser Val Ser Leu Ser Trp Val Gly Asp Ser Thr Gly Val Ile Leu
            35                  40                  45

Val Leu Thr Thr Phe His Val Pro Leu Val Ile Met Thr Phe Gly Gln
        50                  55                  60

Ser Lys Leu Tyr Arg Ser Glu Asp Tyr Gly Lys Asn Phe Lys Asp Ile
65                  70                  75                  80

Thr Asp Leu Ile Asn Asn Thr Phe Ile Arg Thr Glu Phe Gly Met Ala
                85                  90                  95

Ile Gly Pro Glu Asn Ser Gly Lys Val Val Leu Thr Ala Glu Val Ser
            100                 105                 110

Gly Gly Ser Arg Gly Gly Arg Ile Phe Arg Ser Ser Asp Phe Ala Lys
        115                 120                 125

Asn Phe Val Gln Thr Asp Leu Pro Phe His Pro Leu Thr Gln Met Met
    130                 135                 140

Tyr Ser Pro Gln Asn Ser Asp Tyr Leu Leu Ala Leu Ser Thr Glu Asn
145                 150                 155                 160

Gly Leu Trp Val Ser Lys Asn Phe Gly Gly Lys Trp Glu Glu Ile His
                165                 170                 175
```

```
Lys Ala Val Cys Leu Ala Lys Trp Gly Ser Asp Asn Thr Ile Phe Phe
                180                 185                 190
Thr Thr Tyr Ala Asn Gly Ser Cys Lys Ala Asp Leu Gly Ala Leu Glu
        195                 200                 205
Leu Trp Arg Thr Ser Asp Leu Gly Lys Ser Phe Lys Thr Ile Gly Val
    210                 215                 220
Lys Ile Tyr Ser Phe Gly Leu Gly Gly Arg Phe Leu Phe Ala Ser Val
225                 230                 235                 240
Met Ala Asp Lys Asp Thr Thr Arg Arg Ile His Val Ser Thr Asp Gln
                245                 250                 255
Gly Asp Thr Trp Ser Met Ala Gln Leu Pro Ser Val Gly Gln Glu Gln
                260                 265                 270
Phe Tyr Ser Ile Leu Ala Ala Asn Asp Asp Met Val Phe Met His Val
            275                 280                 285
Asp Glu Pro Gly Asp Thr Gly Phe Gly Thr Ile Phe Thr Ser Asp Asp
        290                 295                 300
Arg Gly Ile Val Tyr Ser Lys Ser Leu Asp Arg His Leu Tyr Thr Thr
305                 310                 315                 320
Thr Gly Gly Glu Thr Asp Phe Thr Asn Val Thr Ser Leu Arg Gly Val
                325                 330                 335
Tyr Ile Thr Ser Val Leu Ser Glu Asp Asn Ser Ile Gln Thr Met Ile
            340                 345                 350
Thr Phe Asp Gln Gly Gly Arg Trp Thr His Leu Arg Lys Pro Glu Asn
        355                 360                 365
Ser Glu Cys Asp Ala Thr Ala Lys Asn Lys Asn Glu Cys Ser Leu His
    370                 375                 380
Ile His Ala Ser Tyr Ser Ile Ser Gln Lys Leu Asn Val Pro Met Ala
385                 390                 395                 400
Pro Leu Ser Glu Pro Asn Ala Val Gly Ile Val Ile Ala His Gly Ser
                405                 410                 415
Val Gly Asp Ala Ile Ser Val Met Val Pro Asp Val Tyr Ile Ser Asp
            420                 425                 430
Asp Gly Gly Tyr Ser Trp Thr Lys Met Leu Glu Gly Pro His Tyr Tyr
        435                 440                 445
Thr Ile Leu Asp Ser Gly Gly Ile Ile Val Ala Ile Glu His Ser Ser
    450                 455                 460
Arg Pro Ile Asn Val Ile Lys Phe Ser Thr Asp Glu Gly Gln Cys Trp
465                 470                 475                 480
Gln Thr Tyr Thr Phe Thr Arg Asp Pro Ile Tyr Phe Thr Gly Leu Ala
                485                 490                 495
Ser Glu Pro Gly Ala Arg Ser Met Asn Ile Ser Ile Trp Gly Phe Thr
            500                 505                 510
Glu Ser Phe Leu Thr Ser Gln Trp Val Ser Tyr Thr Ile Asp Phe Lys
        515                 520                 525
Asp Ile Leu Glu Arg Asn Cys Glu Glu Lys Asp Tyr Thr Ile Trp Leu
    530                 535                 540
Ala His Ser Thr Asp Pro Glu Asp Tyr Glu Asp Gly Cys Ile Leu Gly
545                 550                 555                 560
Tyr Lys Glu Gln Phe Leu Arg Leu Arg Lys Ser Ser Val Cys Gln Asn
                565                 570                 575
Gly Arg Asp Tyr Val Val Thr Lys Gln Pro Ser Ile Cys Leu Cys Ser
            580                 585                 590
```

Leu Glu Asp Phe Leu Cys Asp Phe Gly Tyr Tyr Arg Pro Glu Asn Asp
            595                 600                 605

Ser Lys Cys Val Glu Gln Pro Glu Leu Lys Gly His Asp Leu Glu Phe
    610                 615                 620

Cys Leu Tyr Gly Arg Glu Glu His Leu Thr Thr Asn Gly Tyr Arg Lys
625                 630                 635                 640

Ile Pro Gly Asp Lys Cys Gln Gly Val Asn Pro Val Arg Glu Val
                645                 650                 655

Lys Asp Leu Lys Lys Cys Thr Ser Asn Phe Leu Ser Pro Glu Lys
        660                 665                 670

Gln Asn Ser Lys Ser Asn Ser Gly Ser Ala Met Ile Glu Gly Arg Gly
    675                 680                 685

Val Gly His His His His His His
    690                 695

<210> SEQ ID NO 189
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 189

Ser Trp Val Gly Asp Ser Thr Gly Val Ile Leu
1               5                   10

<210> SEQ ID NO 190
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 190

Val Leu Thr Thr Phe His Val Pro Leu Val Ile Met Thr
1               5                   10

<210> SEQ ID NO 191
<211> LENGTH: 15
<212> TYPE: PRT
<213> ORGANISM: Artificial Sequence
<220> FEATURE:
<223> OTHER INFORMATION: Synthetic polypeptide

<400> SEQUENCE: 191

Tyr Arg Ser Glu Asp Tyr Gly Lys Asn Phe Lys Asp Ile Thr Asp
1               5                   10                  15

<210> SEQ ID NO 192
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 192

Phe Thr Arg Asp Pro Ile Tyr Phe Thr Gly Leu
1               5                   10

<210> SEQ ID NO 193
<211> LENGTH: 10
<212> TYPE: PRT
<213> ORGANISM: Artificial Sequence
<220> FEATURE:

-continued

```
<223> OTHER INFORMATION: Synthetic polypeptide

<400> SEQUENCE: 193

Thr Arg Asp Pro Ile Tyr Phe Thr Gly Leu
1               5                   10

<210> SEQ ID NO 194
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 194

Tyr Thr Ile Trp Leu Ala His Ser Thr Asp Pro Glu Asp
1               5                   10

<210> SEQ ID NO 195
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 195

Arg Lys Ser Ser Val Cys Gln Asn Gly Arg Asp
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 196

Tyr Val Val Thr Lys Gln Pro Ser Ile Cys Leu
1               5                   10

<210> SEQ ID NO 197
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 197

Tyr Gly Arg Glu Glu His Leu Thr Thr Asn Gly
1               5                   10

<210> SEQ ID NO 198
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 198

Tyr Arg Lys Ile Pro Gly Asp Lys Cys Gln Gly Gly Val Asn
1               5                   10
```

AGENT, USES AND METHODS FOR TREATMENT

CROSS-REFERENCE TO RELATED APPLICATIONS

This application is a Continuation Application of U.S. application Ser. No. 16/521,279, filed Jul. 24, 2019, which is a Continuation application of U.S. application Ser. No. 15/743,549, filed Jan. 10, 2018, which is a national stage filing under 35 U.S.C. § 371 of International Application No. PCT/EP2016/066516, filed Jul. 12, 2016, which claims priority to Great Britain Application No. 1512215.3, filed Jul. 13, 2015, the entire contents of each of which are incorporated herein by reference.

FIELD OF THE INVENTION

The present invention relates to monoclonal anti-Sortilin antibodies useful in correcting a deficient level of progranulin (PGRN). In particular these antibodies can be used in the treatment of frontotemporal dementia (FTD) and amyotrophic lateral sclerosis (ALS). Furthermore, it anticipated that the monoclonal antibodies may also be useful to treat neurodegenerative disorders such as Alzheimer's Disease (AD).

REFERENCE TO SEQUENCE LISTING

This application includes one or more Sequence Listings pursuant to 37 C.F.R. 1.821 et seq., which are disclosed in computer-readable media (file name: 0993_ST25.txt, created on 22 Jun. 2016, and having a size of 144 kB), which file is herein incorporated by reference in its entirety. This application contains a Sequence Listing which has been submitted in ASCII format via EFS-Web and is hereby incorporated by reference in its entirety. Said ASCII copy, created on Nov. 14, 2022, is named H095270067US02-SUBSEQ-JDH and is 146,619 bytes in size.

BACKGROUND OF THE INVENTION

Sortilin is a receptor that has been reported to mediate pro-apoptotic effects of pro-neurotrophins and to mediate trafficking and sorting of neurotrophin receptors (Nykjær et al, 2012, Trends Neurosci. 2012; 35(4):261-70; Glerup et al, Handb Exp Pharmacol, 2014; 220:165-89, Carlo et al, J Mol Med (Berl). 2014 September; 92(9):905-11). A number of sortilin ligands have been identified including neurotensin for which a high affinity binding site was localized by x-ray crystallography to inside a beta propeller tunnel in the sortilin molecule (Quistgaard et al, Nat Struct Mol Biol. 2009 January; 16(1):96-8; Quistgaard et al, Protein Sci. 2014, September; 23(9):1291-300). More recently, sortilin was shown to function as a high affinity receptor for the growth factor progranulin (PGRN, Hu et al. Neuron. 2010 Nov. 18; 68(4):654-67.

PGRN ((proepithelin, granulin-epithelin precursor, PC-cell-derived growth factor, acrogranin)) is a secreted glycosylated protein with anti-inflammatory and neurotrophic-like actions (For a recent review, see Nguyen, Trends Endocrinol Metab. 2013 December; 24(12):597-606). PGRN is proteolytically cleaved to granulins, but much remains to be learned regarding the physiological role of PGRN and granulins and the identity of their receptors. PGRN has been implicated in several cellular functions including cell cycle regulation and cell motility (He, Z. & Bateman, A., J. Mol. Med. 57:600-612 (2003); Monami, G., et al., Cancer Res. (5(5:7103-7110 (2006)), wound repair, inflammation (Zhu, J., et al., Cell 777:867-878 (2002)), induction of growth factors such as vascular endothelial growth factor (VEGF) (Tangkeangsirrsin, W. & Serrero, G, Carcinogenesis 25.1587-1592 (2004)), and tumorigenesis (He, Z. & Bateman, A., J. Mol. Med. 81:600-612 (2003), Monami, G., et al., Cancer Res (5(5:7103-7110 (2006); Serrero, G., Biochem Biophys. Res. Commun. 505-409-413 (2003), Lu, R & Serrero, G., Proc. Natl Acad Sci U.SA 98 142-147 (2001); Liau, L M., et al., Cancer Res. 60:1353-1360 (2000)). PGRN has been reported to bind the TNF receptor (Tang W et al., Science 2011, 332(6028):478-84). but this observation has been challenged by others (Chen et al., J Neurosci. 2013, 33(21):9202-9213).

The binding of PGRN to sortilin has been mapped to the neurotensin site and reported to be mediated solely through the PGRN C-terminal domain (Zheng et al. PLoS One. 2011; 6(6):e21023; Lee et al. Hum Mol Genet. 2013) in a manner similar to neurotensin and in accordance, neurotensin has been shown to block the interaction of sortilin with PGRN and other ligands. Upon binding, sortilin mediates lysosomal clearance of PGRN and thereby regulates extracellular PGRN levels (Hu et al. 2010). Thus, knockdown or overexpression of sortilin have been shown to regulate extracellular PGRN levels in cell culture (Carrasquillo et al. Am J Hum Genet. 2010 Dec. 10; 87(6):890-7) and in mice, sortilin deficiency was reported to increase PGRN levels and to restore plasma and brain PGRN-levels in PGRN+/−mice (Hu et al. 2010). Interestingly, a single nucleotide polymorphism (SNP) near sortilin was associated with decreased plasma PGRN and increased sortilin mRNA levels (Carrasquillo et al. Am J Hum Genet. 2010 Dec. 10; 87(6):890-7). These observations suggest that sortilin is a key regulator of extracellular PGRN.

PGRN has been linked to frontotemporal dementia (FTD), a progressive dementia characterized by behavioral and semantic changes, as well as frontotemporal lobar degeneration (FTLD) and neuronal inclusions containing TAR DNA Binding Protein-43 (TDP-43) or tau inclusions (Baker et al, 2006, Nature. 2006 Aug. 24; 442(7105):916-9; Cruts et al, Nature 442: 920-924 (2006); Am J Hum Genet. 2010 Dec. 10; 87(6):890-7, M et al, Trends in Genetics 24: 186-194 (2008)). The majority of sporadic and familial FTD cases show TDP-43 pathology (~50%) similar to ALS and FTD-TDP43 and ALS are by some considered to constitute a disease spectrum (Ito D Neurology. 2011 Oct. 25; 77(17): 1636-43; Boxer Ala. et al, Alzheimers Dement. 2013 March; 9(2):176-88; Rademakers et al, Nat Rev Neurol. 2012 August; 8(8): 423-434) due to common pathologies and genetic factors and some overlap in symptomatology. No disease-modifying treatment options are available for FTD. A subset of frontotemporal dementia patients with TDP-43 pathology have loss of function mutations in the granulin gene (GRN) resulting in PGRN haplo-insufficiency. To date, 69 different mutations in the granulin gene, all resulting in reduced PGRN levels and/or function, have been associated with FTD and it is believed that raising extracellular PGRN in plasma and brain would counteract the disease process.

PGRN mutations have also been linked with Alzheimer's disease (AD) (Sheng et al., 2014, Gene. 2014 Jun. 1; 542(2):141-5; Brouwers et al., 2008, Neurology. 2008 Aug. 26; 71(9):656-64) suggesting that PGRN deficiency may play an important role in AD pathogenesis. Furthermore, neuroprotective effects of PGRN in mouse AD models have been observed (Minami et al, 2014, Nat Med. 2014 October; 20(10):1157-64) providing support for the view that enhanced PGRN may be beneficial in AD and possibly other neurodegenerative conditions.

The present application describes the generation and identification of anti-human Sortilin antibodies which can regulate PGRN in cellular models and in mice. Those antibodies surprisingly bind to a region on Sortilin which is distant to the previously reported progranulin binding site, the so-called neurotensin-site, and yet are capable of inhibiting Sortilin-PGRN interaction and of thereby increasing extracellular PGRN.

The inventors have defined six Sortilin binding regions and surprisingly identified that the most efficacious antibodies bind a region ("region D"). As PGRN has neuroprotective and anti-inflammatory effects, the inventors' findings indicate that such antibodies targeting Sortilin are likely to have a beneficial effect in the treatment of a range of neurodegenerative disorders including FTD/FTLD. A subgroup of these patients carry a mutation in the gene encoding PGRN leading to haploinsufficiency. Sortilin antibodies are therefore likely to have similar therapeutic benefits for patients suffering from other TDP-43 proteinopathies and diseases in which PGRN levels may influence TDP43-function and pathology, including ALS and AD.

SUMMARY OF INVENTION

The inventors of the present invention have generated monoclonal antibodies which are able to inhibit the binding of PGRN to Sortilin, and which surprisingly bind to a novel Sortilin region denominated the "D-region" as defined in SEQ ID NO:170. Several antibodies identified by the inventors have properties similar to the D-region antibodies and experimental evidence indicates that they also bind within the D-region, and those antibodies are herein referred to as D+ antibodies. Accordingly, in one aspect, the invention relates to such antibodies, to compositions and/or kits comprising such antibodies, and to methods and uses thereof.

The invention also relates to a method of preventing or treating a disease associated with decreased PGRN levels in the brain of a patient, comprising administering an effective dosage of an antibody or an antigen-binding fragment thereof that binds to the D-region of Sortilin. These diseases include i.a. FTD, ALS and TDP43 proteinopathies such as AD.

BRIEF DESCRIPTION OF THE DRAWINGS

FIG. 1 provides an overview of the generation of region assignment of human antibodies based on Sortilin region binding, effect on PGRN-binding and PGRN-levels and on cross-blocking between the antibodies.

Sortilin-binding antibodies were selected and assigned to regions A-E based on binding to shuffle constructs in which the sequence corresponded to the tetraodon Sortilin sequence within selected regions of the protein (Example 1, FIGS. 2A-2C).

20 antibodies which inhibited Sortilin-PGRN binding (as measured by HTRF analysis) were selected (see Example 10, FIG. 5 and FIG. 6). 15 of these antibodies were D-region antibodies while 3 were D+ antibodies (FIG. 6). Subsequent cross-blocking analysis showed that the 18 D-region and D+ antibodies (D+ antibodies have a different binding pattern to shuffle constructs than D-region antibodies. Nevertheless D+ antibodies cannot with certainty be assigned to a binding region A-E as outlined above but shared functional characteristics (cell assays etc.) similar to the D-region antibodies), all cross-blocked each other supporting that they interacted with the same Sortilin region (Example 9, FIGS. 7A-7C). When sortilin antibodies of other region classes were tested in the HTRF sortilin-PGRN binding assay, only two of 41 antibodies exhibited an inhibitory effect. One of these two antibodies cross-blocked with the D and D+, but had an atypical shuffle construct binding pattern (D-like except that it bound the hB01-05 region), while the other antibody did not cross-block with the other antibodies that inhibited PGRN-sortilin binding, thus supporting the conclusion that it binds to another sortilin region.

These observations show that antibodies binding to an area in sortilin defined by the D-region have the potential to inhibit sortilin-PGRN binding.

Figure 10:
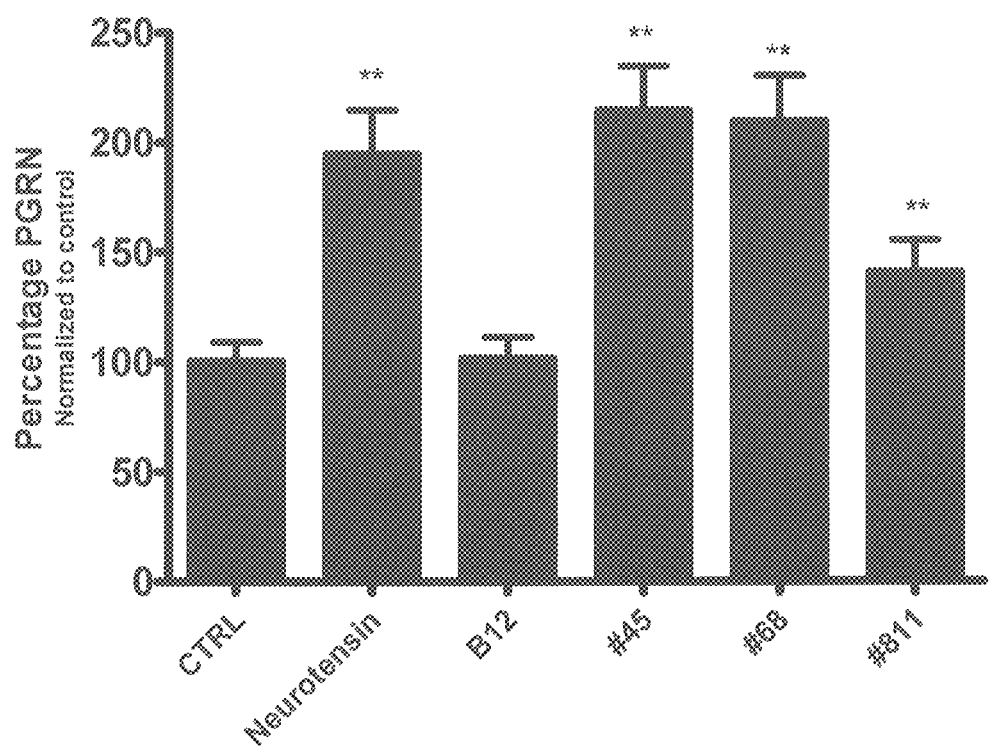
Figure 13A:
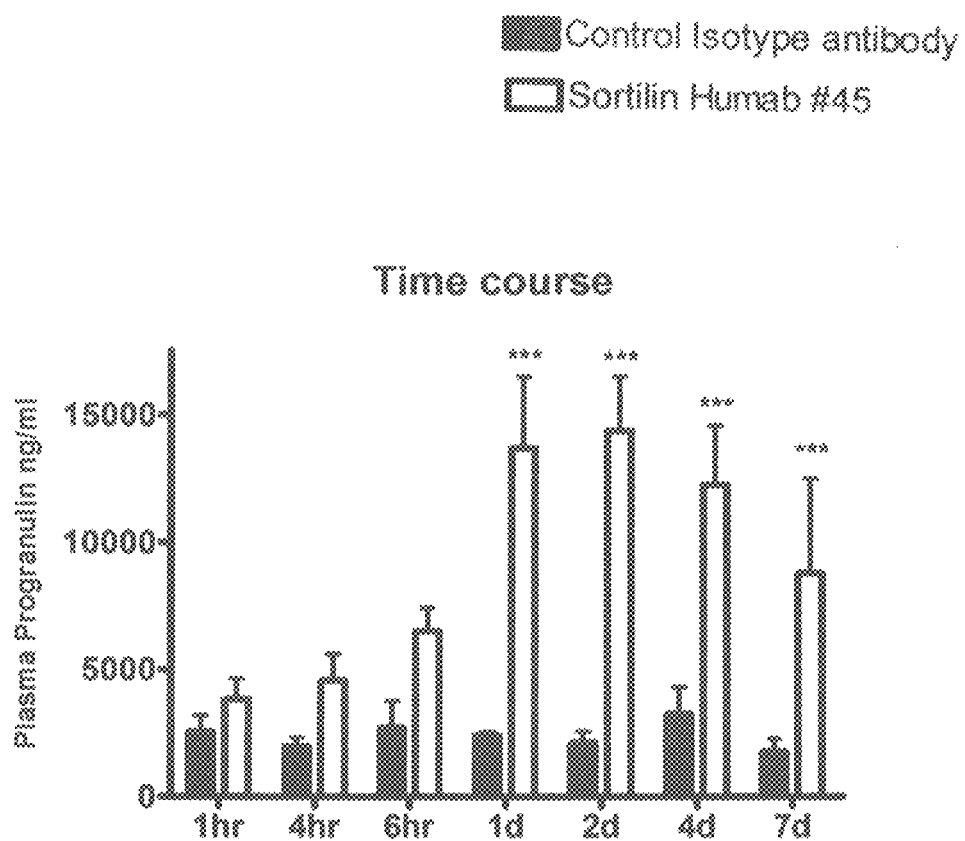
Figure 13B:
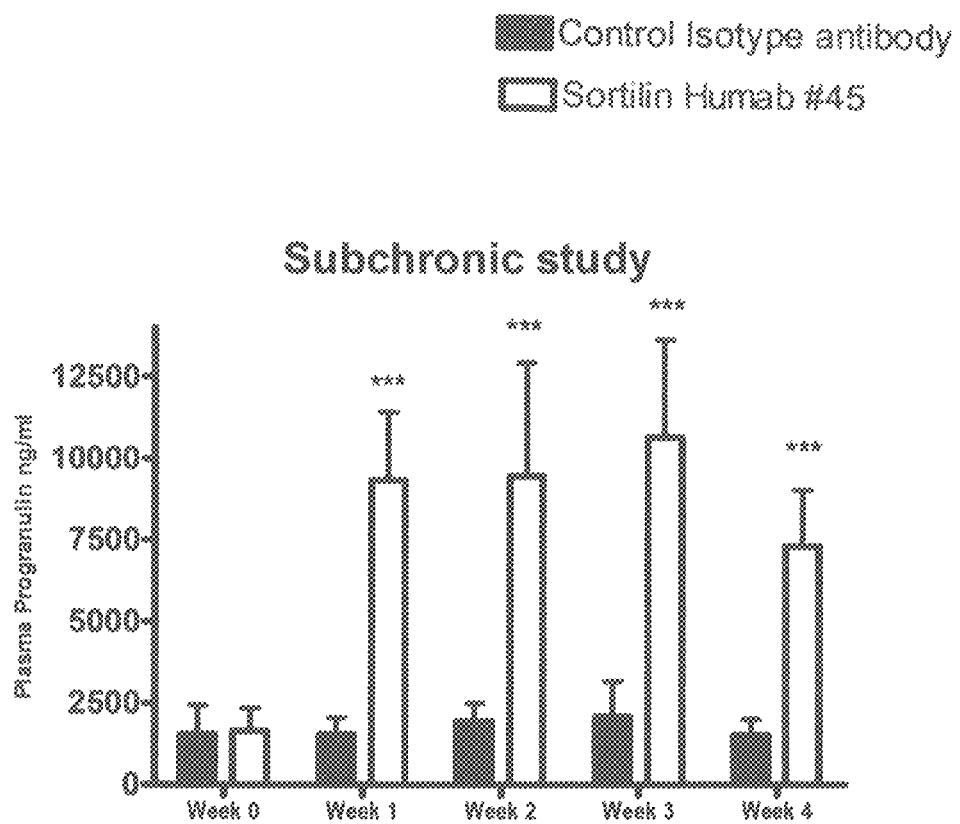
Figure 13C:
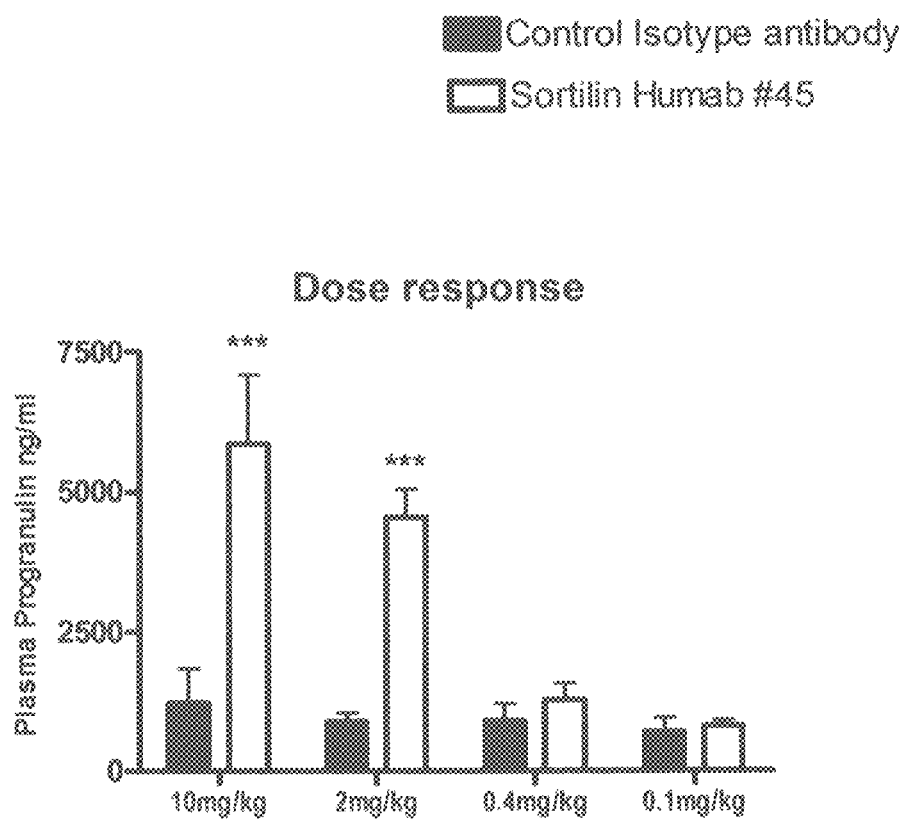

19 cross-blocking antibodies, of which 18 were D-region and D+ antibodies, increased extracellular PGRN in a cellular assay (Example 13, FIG. 10 and FIG. 11). Three of these antibodies were tested in vivo and found to increase plasma PGRN (FIGS. 13A-13C, Example 15).

The boxes in FIG. 1 illustrate steps in the selection of antibodies. A-E refer to the regions to which the respective Sortilin-binding antibodies were assigned based on shuffle constructs as described in Example 1 and SEQ ID NOs:171-179. "Other" refers to an antibody which could not be assigned to one region, and which may bind at the interface between the A- and B-regions. Tet refers to antibodies binding also tetraodon-Sortilin.

In addition to the human antibodies shown, a set of mouse anti-human sortilin antibodies was generated and similarly characterized. Two of these antibodies were assigned to the D Region and shown to cross block with human D-region and D+ antibodies, to inhibit sortilin-PGRN binding and to increase extracellular PGRN (see FIG. 4).

FIGS. 2A-2C show the region assignment of antibodies based on binding to Sortilin shuffle constructs.

FIG. 2A shows a linear illustration of the shuffle constructs used for region assignment of antibodies as described in Example 1. Sortilin shuffle constructs were generated based on the human Sortilin sequence (SEQ ID NO:169) (sections depicted in grey) in which amino acid residues were exchanged to the corresponding amino acid from the tetraodon Sortilin sequence (depicted in black) (SEQ ID NO:173) (Examples 1-3).

FIG. 2B shows predicted structure of the shuffle constructs illustrated linearly in A. Dark residues indicate residues changed to the corresponding tetraodon sequence in the shuffle constructs.

FIG. 2C illustrates the binding pattern of antibodies assigned to the D-region and the E region classes respectively. A "+" indicates binding to a given shuffle construct and a "−" indicates lack of binding. Based on the binding pattern to the different shuffle constructs, antibodies were assigned to regions. The resultant antibody region classes are indicated by A-E. For the illustrated D and E region antibodies, both bound the human sequences (all grey) as indicated by "+" and neither bound the tetraodon sequence (all black) as indicated by "−", whereas the E region antibody bound the hB45678 shuffle construct while the D Region antibody did not bind resulting in the localisation of binding as illustrated in FIG. 2A. For D Region antibodies, binding to the following shuffle regions was observed: hsort, hB06-10, B12390. The antibodies did not bind to hB01-05, B45678, tet. For D+ antibodies, binding to the following shuffle region was observed: hsort, B12390. The antibodies did not bind to hB01-05, hB06-10, B45678, tet. The F binding pattern was similar to the D binding pattern except that no binding to the hB06-10 was observed for D+ antibodies.

The antibodies did not bind to the fully tetraodon Sortilin protein, except two. The two antibodies capable of binding the tetraodon sequence were denoted "tet". "Other" refers to an antibody which could not be assigned to one region.

FIG. 3 shows the binding affinities of human D-region and D+ antibodies. Binding affinities to sortilin shuffle constructs by bioLayer interferometry using Octet 384RED as described in Example 8 (EC50, ng/ml). No shading indicates EC50 of 0.1-10 ng/ml, light grey shading indicates EC50 >10 ng/ml and grey shading indicates no binding (NB). Region assignment was based on binding patterns is illustrated in FIGS. 2A-2C. Shuffle constructs are illustrated in FIGS. 2A-2C and sequences are given in SEQ ID NOs: 171-179. mAb=monoclonal antibody.

FIG. 4 shows the binding affinities of mouse anti-human antibodies to Sortilin shuffle constructs as obtained by bioLayer interferometry using Octet 384RED as described in Example 8 (EC50, ng/ml). No shading indicates binding and grey shading indicates no binding (NB). Region assignment based on binding patterns is illustrated in FIGS. 2A-2C.

FIG. 5 shows the effect of Sortilin antibody on Sortilin PGRN binding. The D Region Sortilin human monoclonal (humAb) antibody 45 (filled circles) prevented PGRN binding to Sortilin, in contrast to a control Sortilin E region antibody (filled triangles) and an IgG control, IgG1-b12 (open triangles) that did not interfere with the binding. The binding of antibodies was determined by measuring the displacement of PGRN binding to Sortilin using Homogenous Time Resolved Fluorescent (HTRF) (Example 10). Dose-response evaluation of antibodies was performed with ten concentrations covering 50 μM to 1 μM in a 3-fold dilution curve. The half-maximal inhibitory concentration (IC50) values were calculated by non-linear regression using sigmoidal concentration response (variable slope) in XLfit 4 (IDBS, UK).

FIG. 6 Summary of effect of antibodies on Sortilin-PGRN binding determined by homogenous time resolved fluorescent (HTRF) analysis as shown in FIG. 5. In total, 62 antibodies were tested—15 D-region antibodies and 3 D+ antibodies were found to inhibit sortilin-PGRN binding and the IC50 values were determined. For two additional antibodies (E and other regions), an inhibitory effect was observed. All remaining antibodies were negative in the test. * antibody too weak to fit a dose-response curve. 6% inhibition at 1 μM. ** control (ctrl) antibody too weak to fir a dose-response curve. 37% inhibition at 1 PM.

These observations show that sortilin antibodies characterized by their D-region or D+ assignment inhibit sortilin's binding to PGRN directly and are capable of inhibiting sortilin-PGRN binding.

FIGS. 7A-7C show cross-blocking between antibodies. Human antibodies and the mouse antibodies were all tested in a single experiment where each antibody was bound to human wild type (WT) Sortilin (FIGS. 7A-7C). Subsequently all other antibodies were tested for binding to the preformed sortilin:antibody complex (Example 9). The selected 15 D-region and 3 D+ human antibodies (based on their effect in the HTRF PGRN-sortilin assay, (FIG. 5 and FIG. 6) and two mouse D Region antibodies all inhibited binding of each other to human WT Sortilin.

The antibodies did not cross-block with antibodies designated to other region classes (as illustrated for A-region, E-region and tetraodon recognizing antibodies numbered AbA1-x, AbE1-x and Abtet in the table respectively) except for one cross blocking A region antibody, one antibody with unknown region assignment ("other") and a partial block for a D+ antibody 548. These data support that the D-region and D+ antibodies capable of inhibiting sortilin-PGRN binding in the HTRF assay all interact with the same region in sortilin.

Cross blocking between Sortilin antibodies from the same or different regions (regions based on binding to shuffle constructs as illustrated in FIGS. 2A-2C) was determined by analyzing interference with antibody-Sortilin binding. Binding of antibodies to Sortilin-ECD-His was measured by BioLayer Interferometry using Octet 384RED (Example 9). The left column indicates primary (immobilized) antibodies and the top row indicates the secondary antibodies (antibodies being tested against the immobilized antibodies). Binding of both the primary and secondary antibodies to Sortilin-ECD-His would results in a response value higher than 0.1 and indicate that both antibodies were binding to different regions of the protein. Response value less than 0.1 shows lack of binding of the secondary antibody and an effective cross blocking by the immobilized (primary) antibody, which suggests that both antibodies bind to the same region of Sortilin.

FIG. 8 shows the effect of D-region and D+ Sortilin antibodies on the binding of the selective small molecule ligand AF38469 to Sortilin. The binding site for AF38469 has been shown to be similar to the binding site of neurotensin and characterized by X-ray crystallography (Schrçder et al. Bioorg Med Chem Lett. 2014 Jan. 1; 24(1):177-80). PGRN has been reported to bind to the same site (Lee et al. Hum Mol Genet. 2013) antibodies 45 and 68, binding to D-region, and D+ respectively, did not inhibit the binding of AF38469 to sortilin. This data suggests that these antibodies have a binding site for Sortilin distinct from the binding site for AF38469. Therefore, antibodies 45 and 68 inhibit PGRN-sortilin binding through a binding site distinct from the hitherto presumed PGRN binding site in sortilin.

FIG. 9 Effect of antibodies 45 and 68 on cellular binding and endocytosis of PGRN (Example 12). Antibodies 45 and 68 inhibited the binding and/or endocytosis of PGRN by sortilin overexpressing cells. Addition of neurotensin (NT, 10 uM) similarly reduced binding or endocytosis of PGRN as reflected in reduced fluorescence as expected whereas the isotype control antibody B12 did not influence PGRN fluorescence levels.

Antibodies (100 nM) to be tested were added to S18 cells 30 min before addition of recombinant PGRN for 4 hr. The cells were then fixed, stained for PGRN and analyzed by Cellomics. PGRN fluorescence was measured as mean fluorescence per cell. Data is presented as mean±SD. Data analyzed by one-way Anova followed by Dunnett's analysis, all groups were compared to PGRN. $*p<0.05$; $p<0.01$ FIG. 10** Extracellular PGRN levels estimated by ELISA in media from cultures of sortilin over-expressing HEK cells (S18). Sortilin D-region (45, 811) and D+ (68) antibodies increased PGRN levels and a similar effect of the sortilin ligand neurotensin was observed whereas the control antibody B12 had no effect. These observations indicate that D-region and D+ Sortilin antibodies were capable of inhibiting sortilin-mediated clearance of PGRN thereby increasing extracellular PGRN. All antibodies were tested at 100 nM. Neurotensin was tested at 10 uM. PGRN levels have been normalized to control. Data is presented as mean±SD. Data was analyzed by one-way Anova followed by Dunnett's analysis, all groups were compared to CTRL $*p<0.05$; $**p<0.01$. (Example 13).

FIG. 11 shows the effect of antibodies on extracellular PGRN in human Sortilin over-expressing HEK cells measured by ELISA as described in example 13. All selected D-region antibodies and the three selected D+ antibodies increased extracellular PGRN. PGRN levels were analysed the same as above. PGRN levels are normalized to untreated controls and given in %. Two antibodies were raised in mouse against human Sortilin (1F2F4 & 5E1F6) and the rest are human antibodies. Ab=monoclonal antibody.

Figure 12:
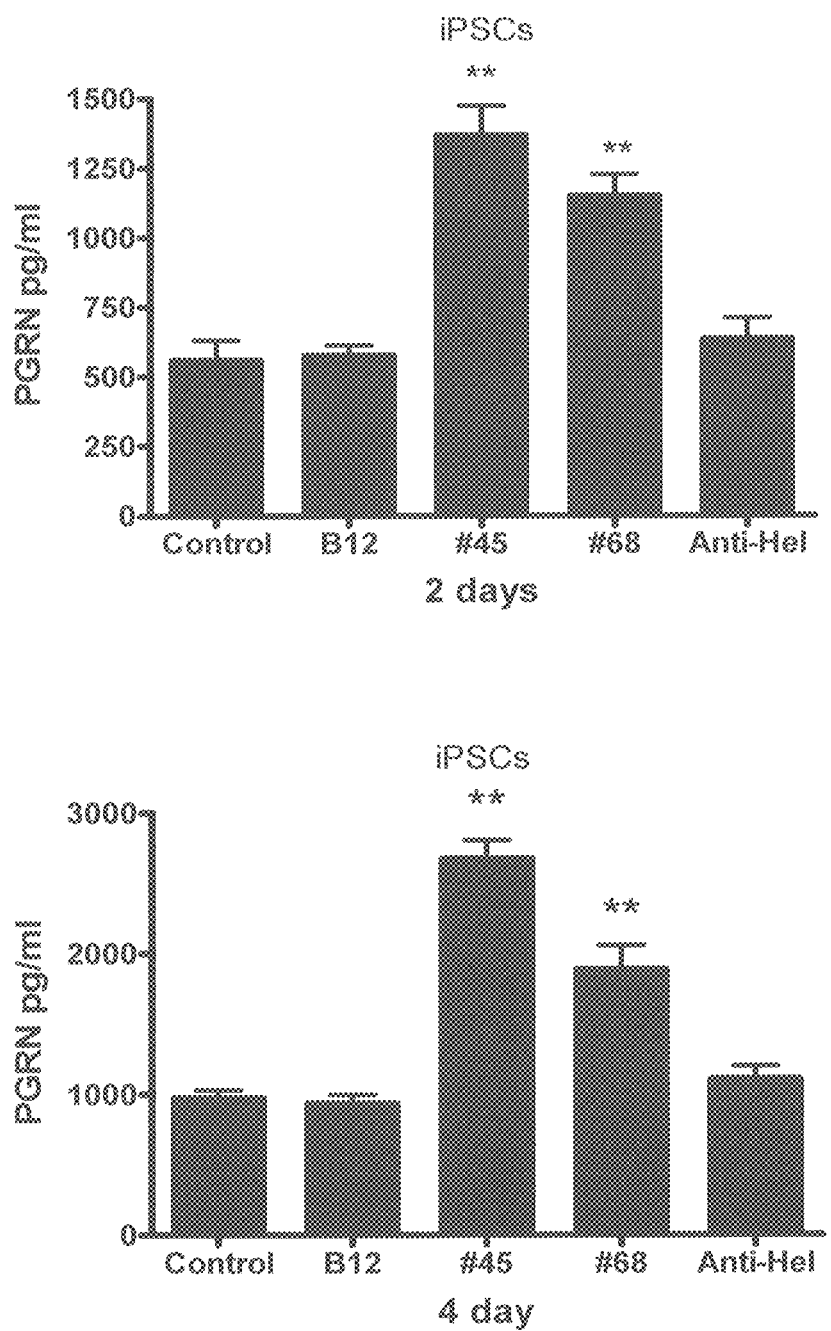

FIG. 12 shows the effect of Sortilin antibody on extracellular PGRN in neuronally differentiated iPSC cells (Example 14). The sortilin D-region antibody 45 and the D+ antibody 68 increased PGRN levels whereas the control antibodies B12 and anti-HEL had no effect.

Neuronally differentiated iPSC cells were plated into 96 wells plate. One week later, antibodies were added to the cells. Media from the cells were collected at 48 hrs or 96 hrs and analysed by human PGRN ELISA (Enzo Life sciences) and samples analysed as per the manufacturer's instructions. Sortilin human antibodies 45 and 68 increased PGRN levels in the media at both time points. Control isotype antibodies B12 and Anti-Hel (negative control) did not change extracellular PGRN. Data is presented as mean±SD. Data was analyzed by one-way Anova followed by Dunnett's analysis *p<0.05; **p<0.01 (Example 14)

FIGS. 13A-13C show plasma PGRN levels in human Sortilin expressing knock in (KI) mice treated with Sortilin human antibody (Example 15). Sortilin antibody 45 increased plasma PGRN levels whereas the control antibody had no effect.

FIG. 13A shows results of a Time course study: Increased plasma levels of PGRN were observed after injection of antibody 45 (D Region). Mice were injected with 45 (n=5) or control (n=3) antibody sc at a dose of 10 mg/kg. Each group was sacrificed at different time points. In mice treated with control antibodies (Anti-Hel) there was no change in plasma PGRN, whereas in mice treated with 45 there was a gradual increase in PGRN levels. Effect appeared to peak between 24 and 48 hrs and gradually decreased by day 4-7.

FIG. 13B shows results of a Subchronic study: Mice were treated twice a week with 10 mg/kg of 45 and control antibody (Anti-Hel). Samples were collected from cheek blood every week. Plasma PGRN was elevated at week 1 and remained at approximately the same level throughout the entire study as compared to the animals treated with control antibody (n=20).

FIG. 13C shows results of a Dose response study: Different doses (4 doses: 0.1, 0.4, 2 and 10 mg/kg) of the Sortilin (45) and control antibodies (Anti-Hel) were injected and mice were sacrificed on day 2. Plasma PGRN was elevated in mice treated with 45 (10 and 2 mg/kg). lower doses (0.4 and 0.1 mg/kg) did not have an effect on plasma PGRN. Data is presented as mean±SD. Data was analyzed by two-way Anova followed by Bonferroni's analysis *p<0.05; p<0.01; *p<0.001 (Example 15).

Figure 14:
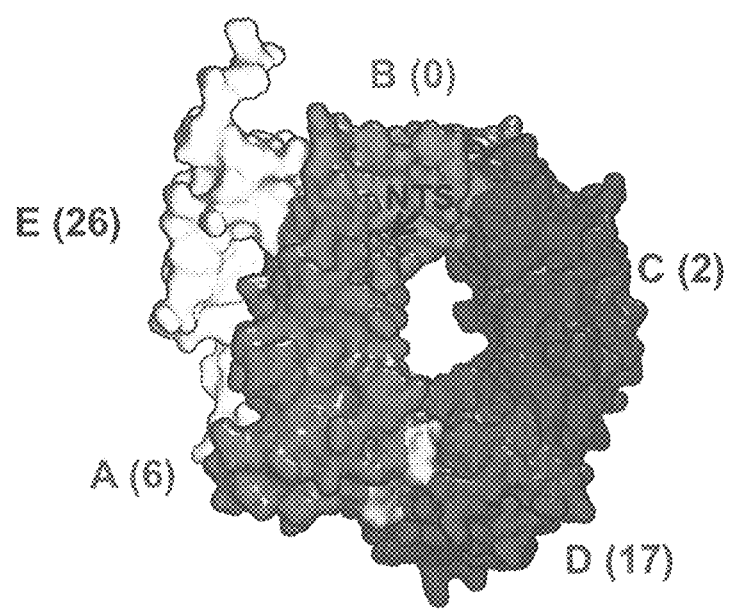
Figure 15A:
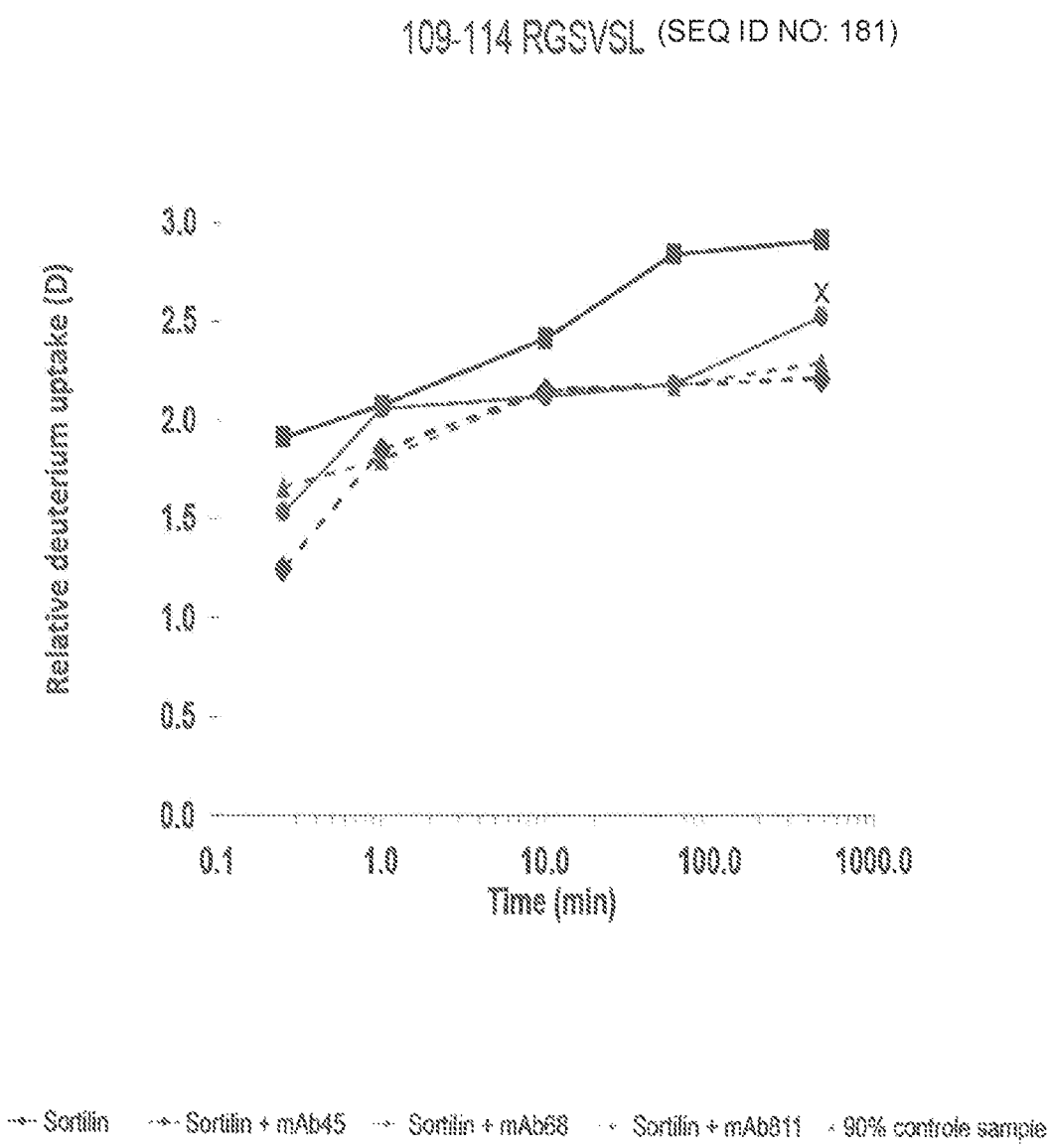
Figure 15B:
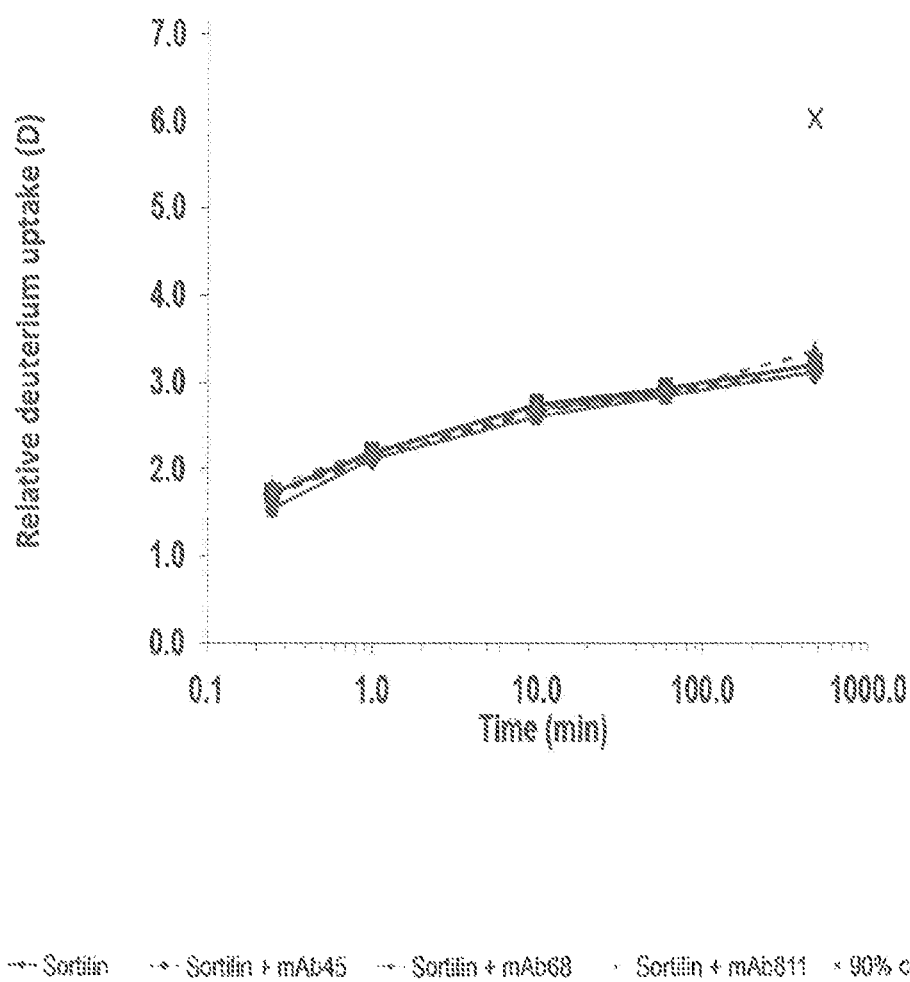
Figure 15C:
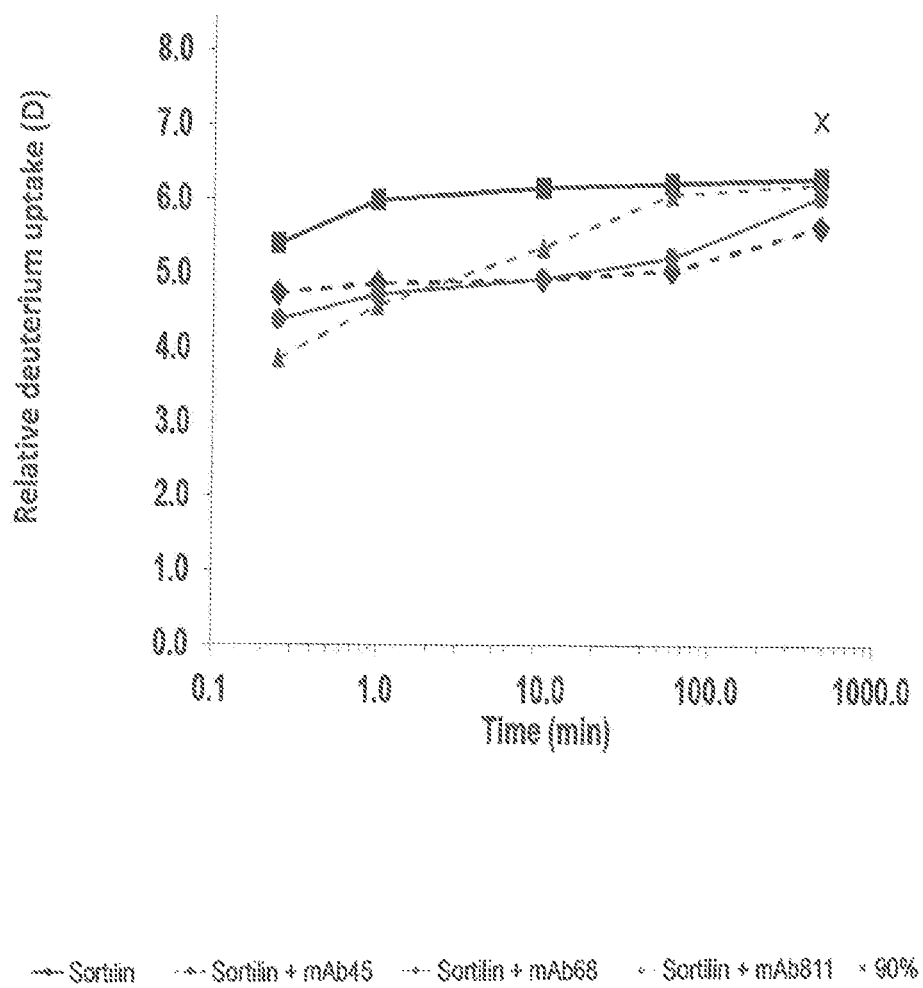
Figure 15D:
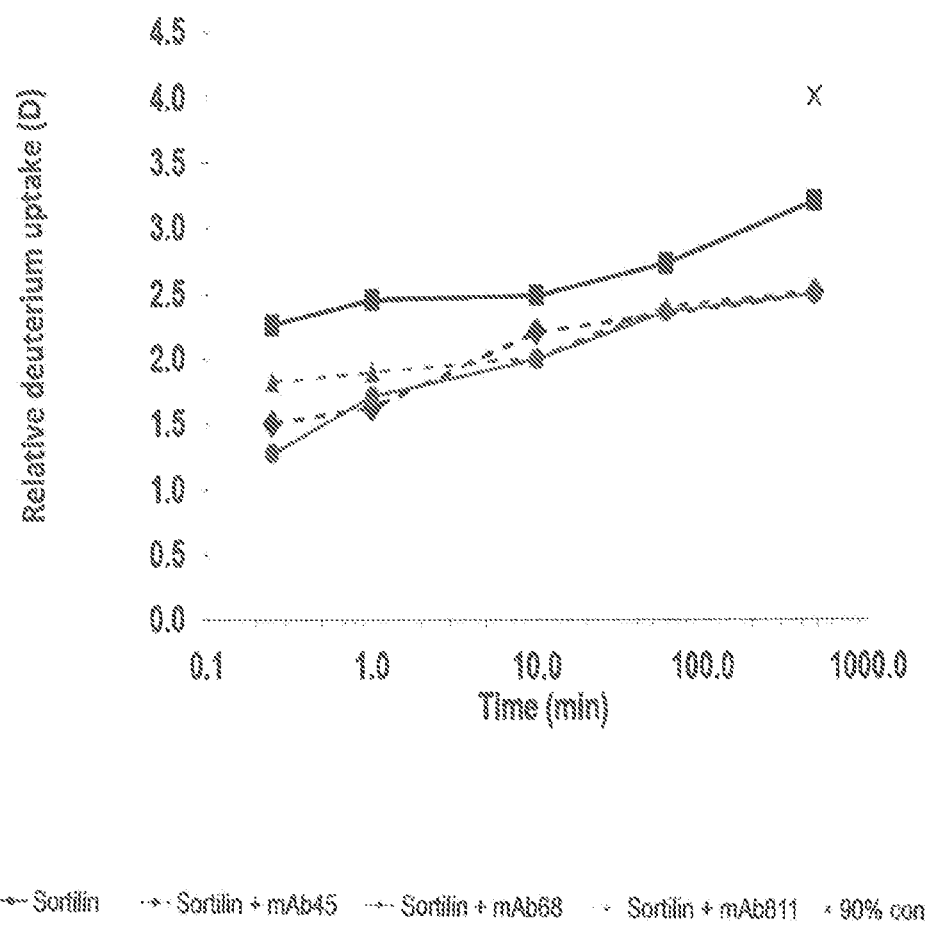
Figure 15E:
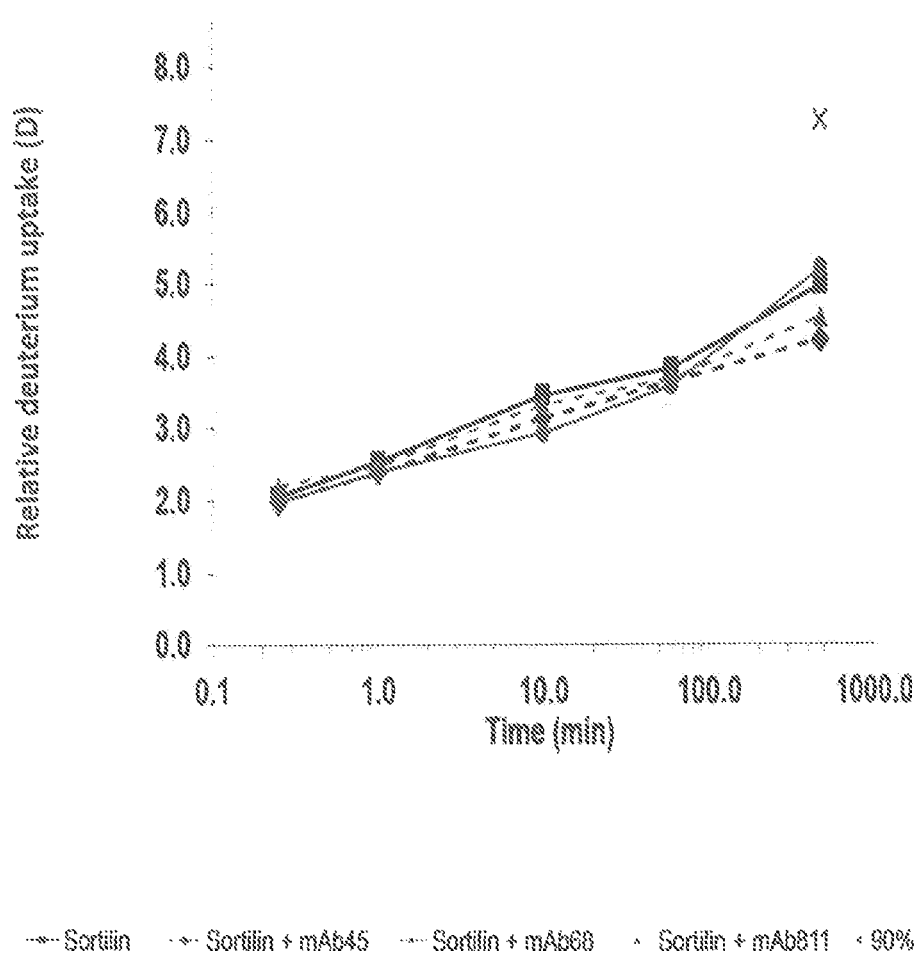
Figure 15F:
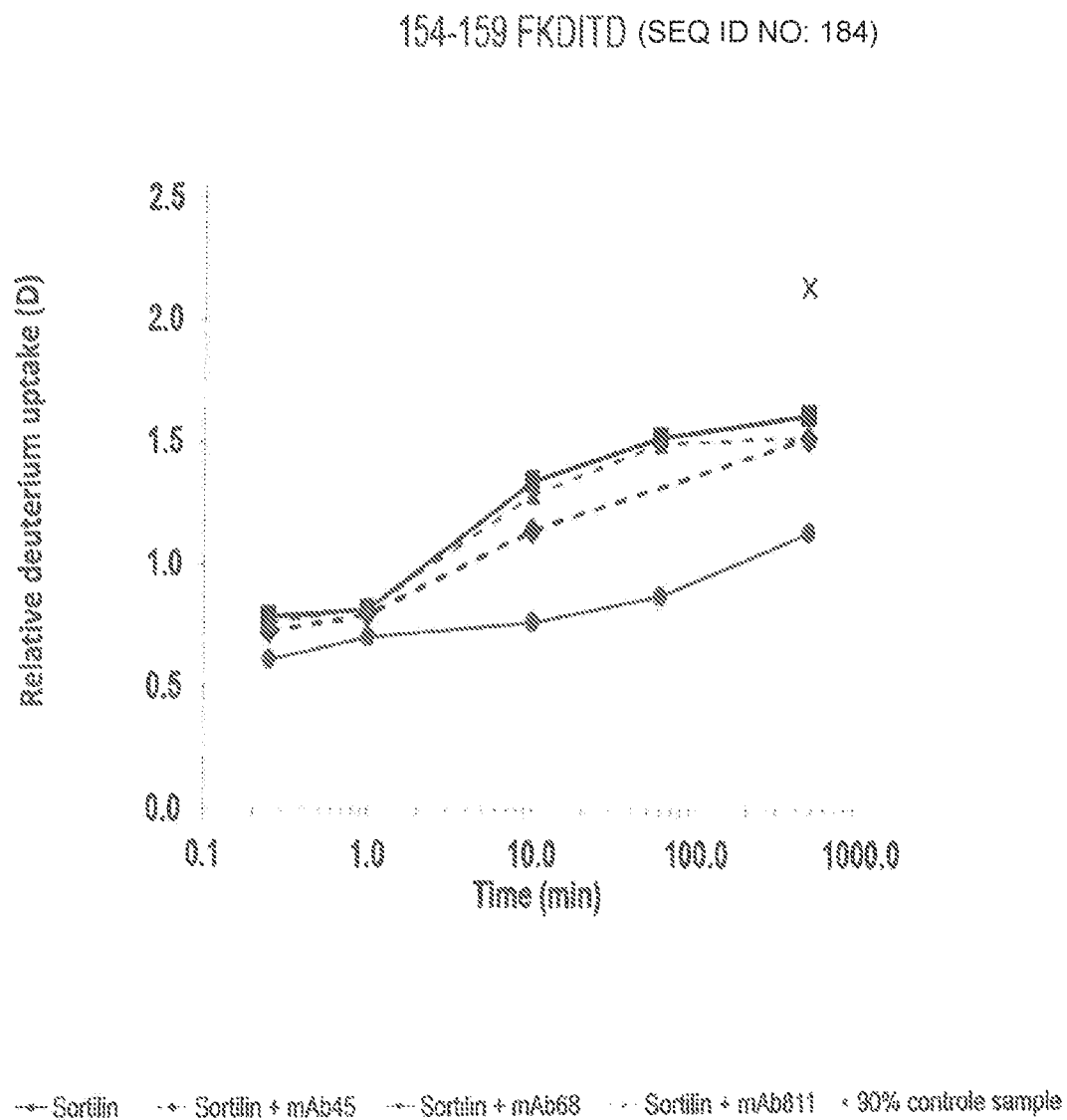
Figure 15G:
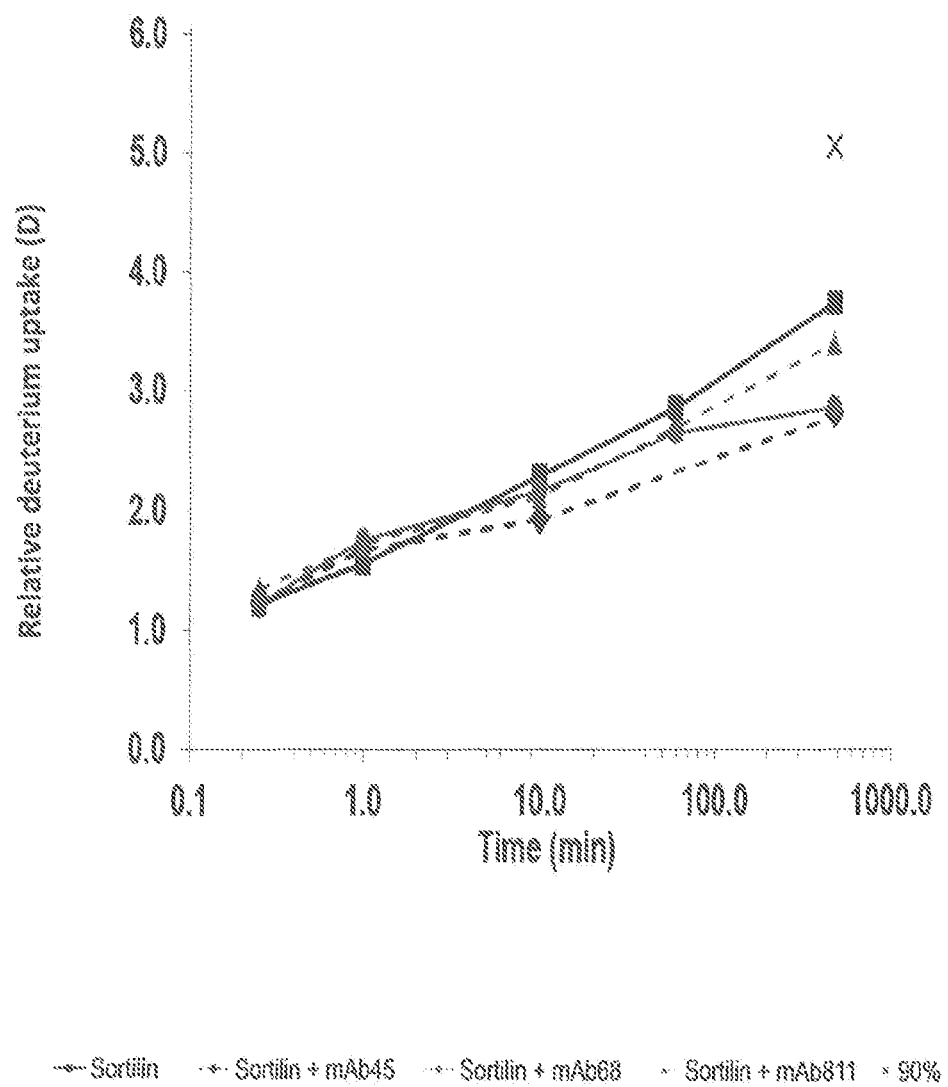
Figure 15H:
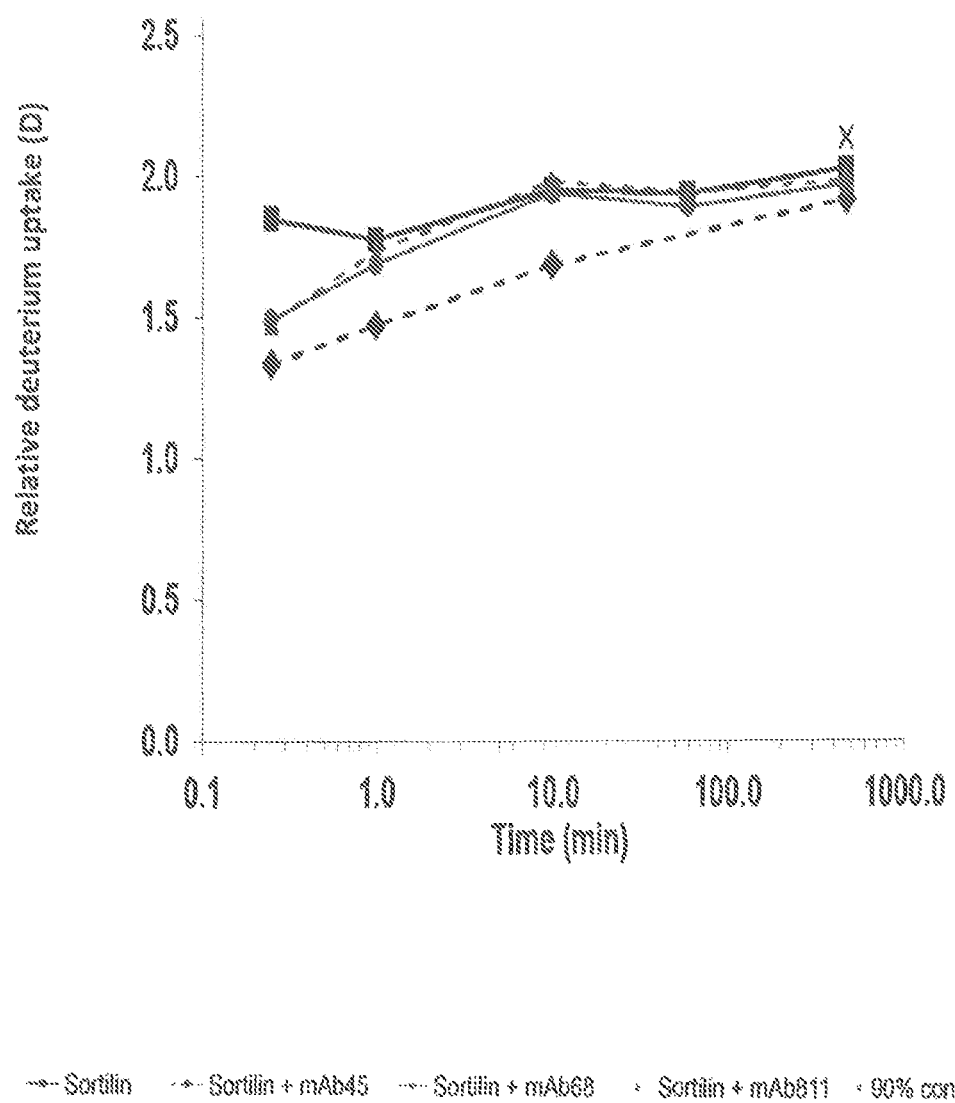
Figure 15I:
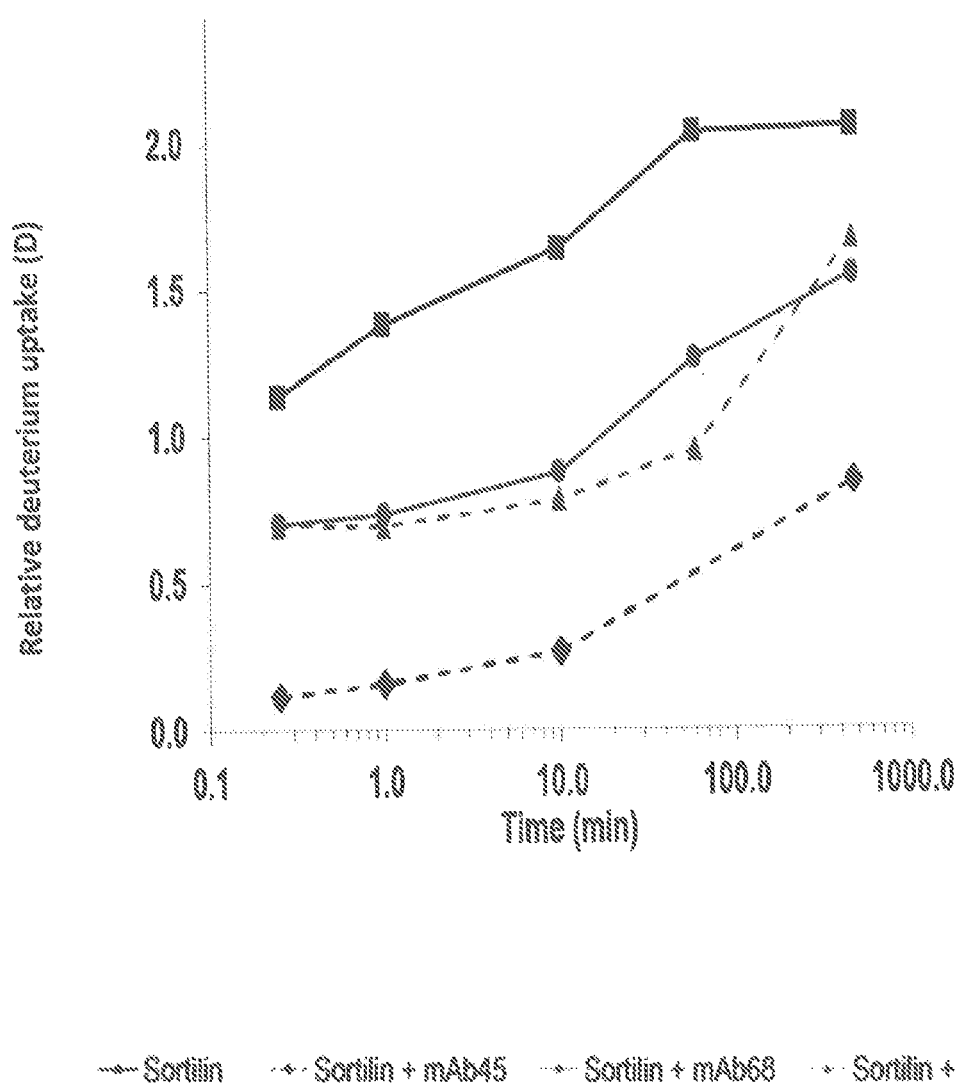
Figure 16A:
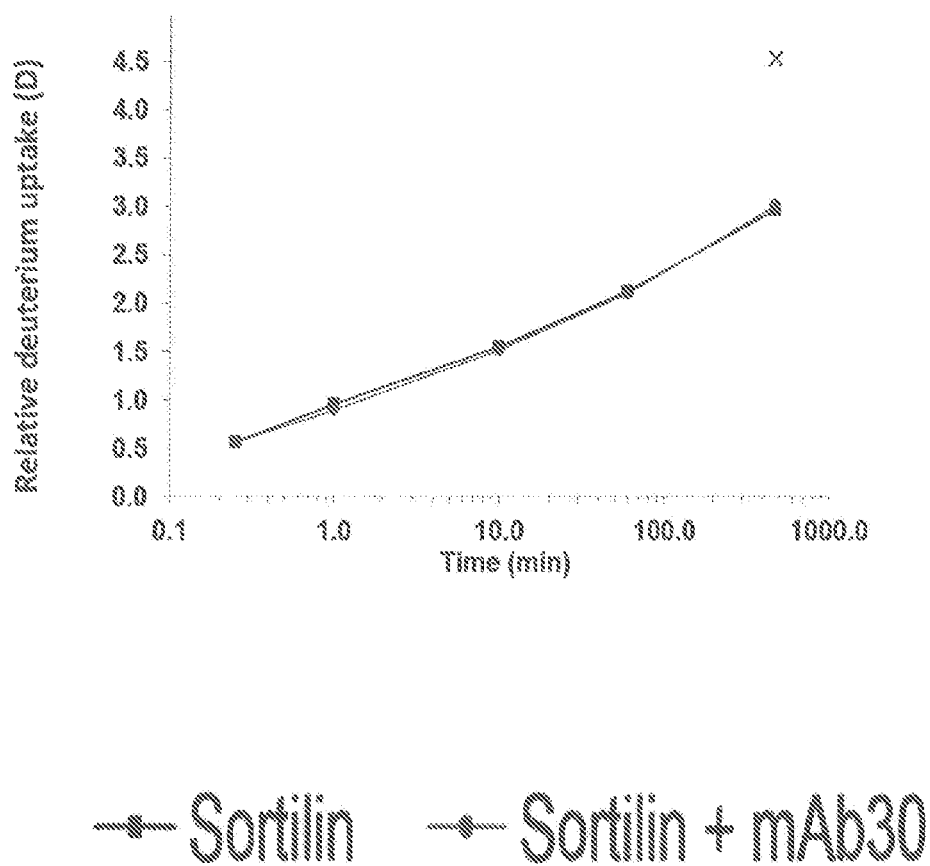
Figure 16B:
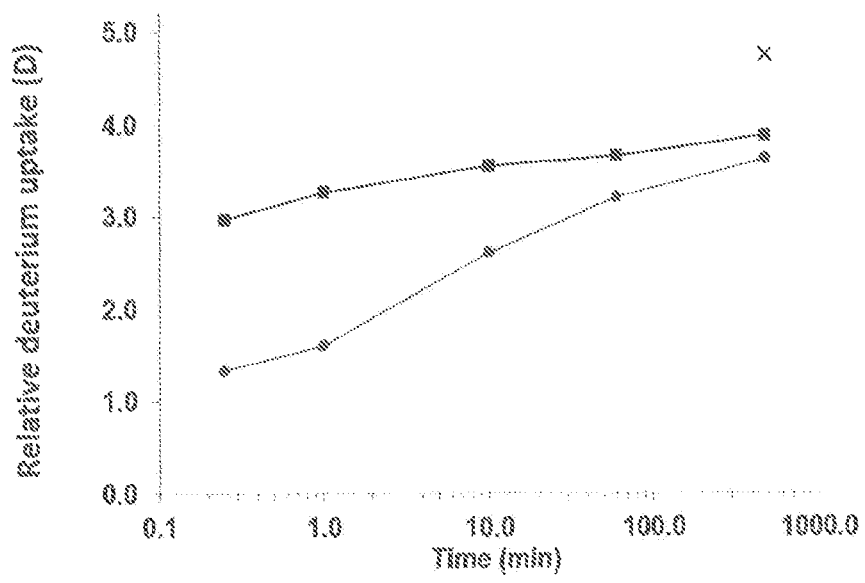
Figure 16C:
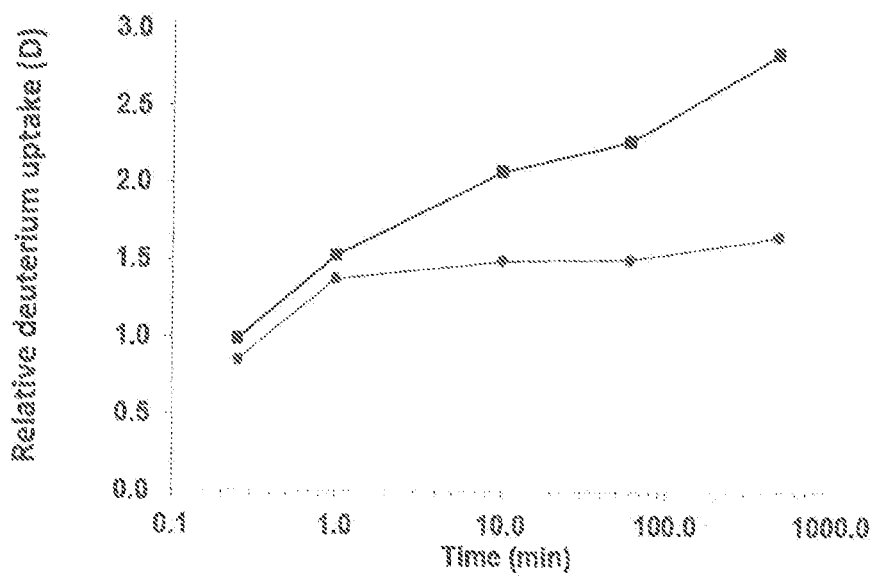
Figure 16D:
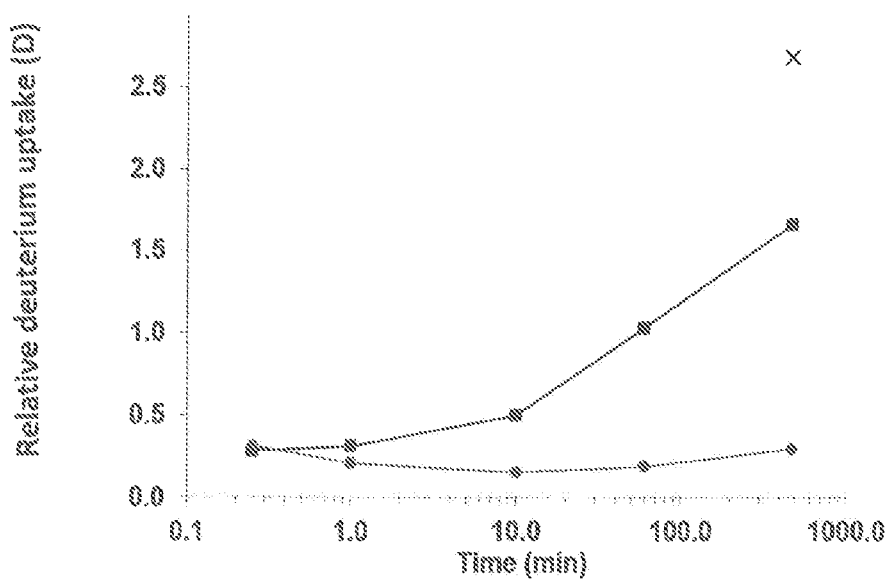
Figure 16E:
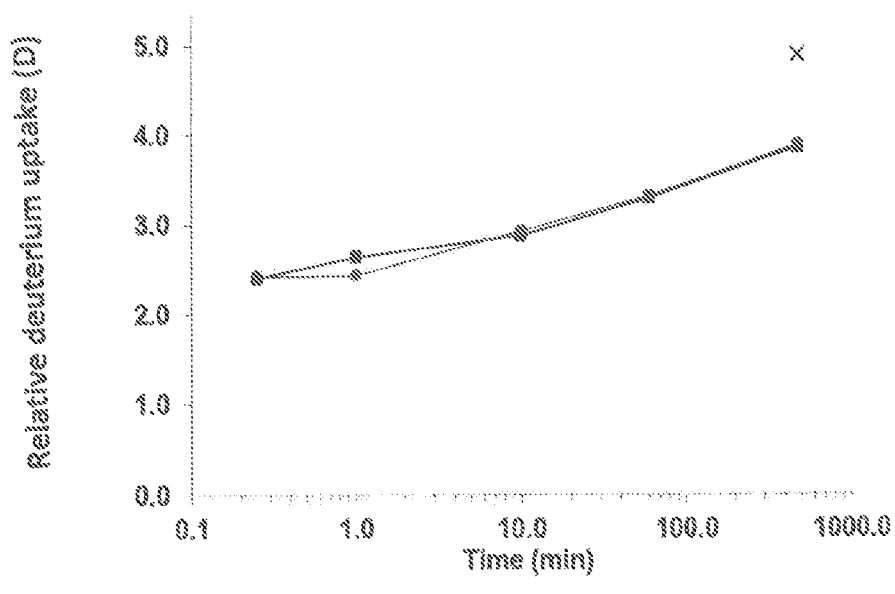
Figure 16F:
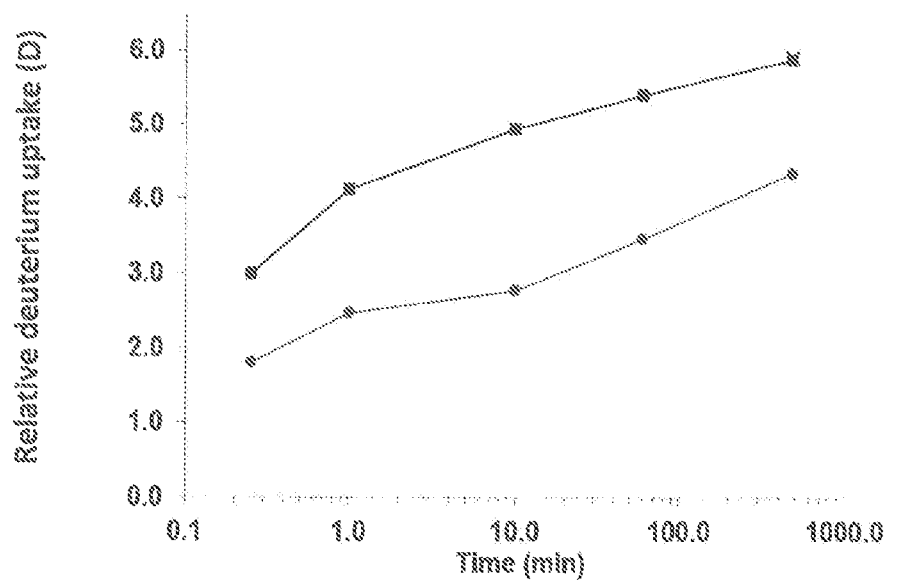
Figure 16G:
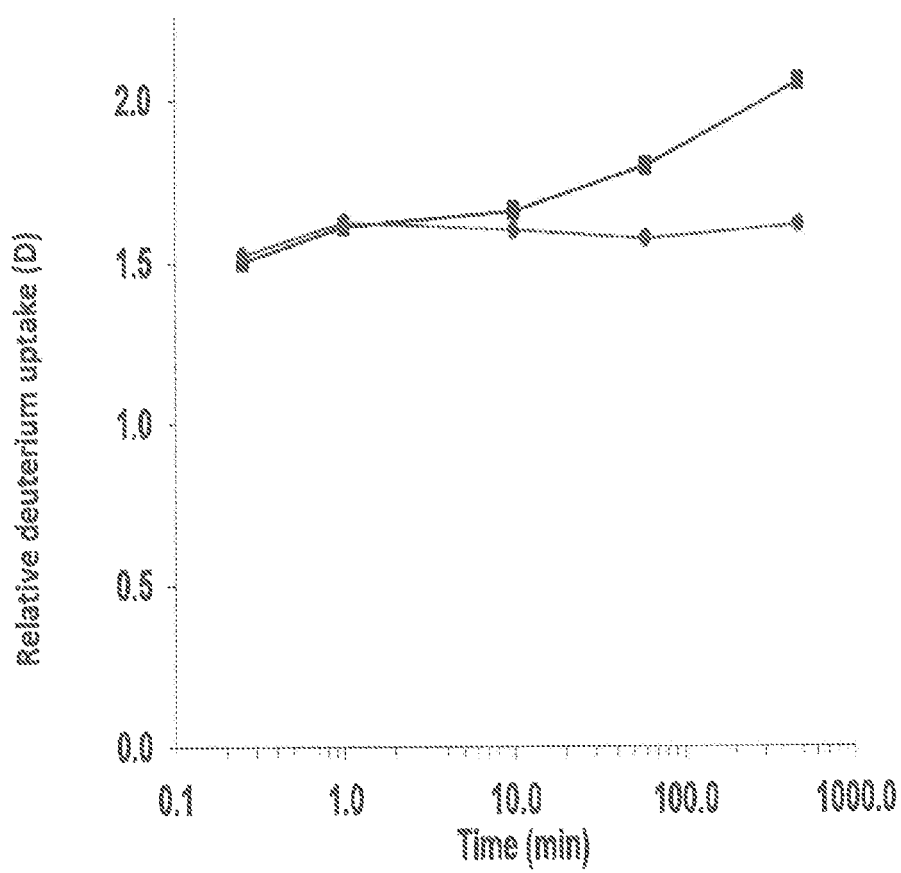
Figure 16H:
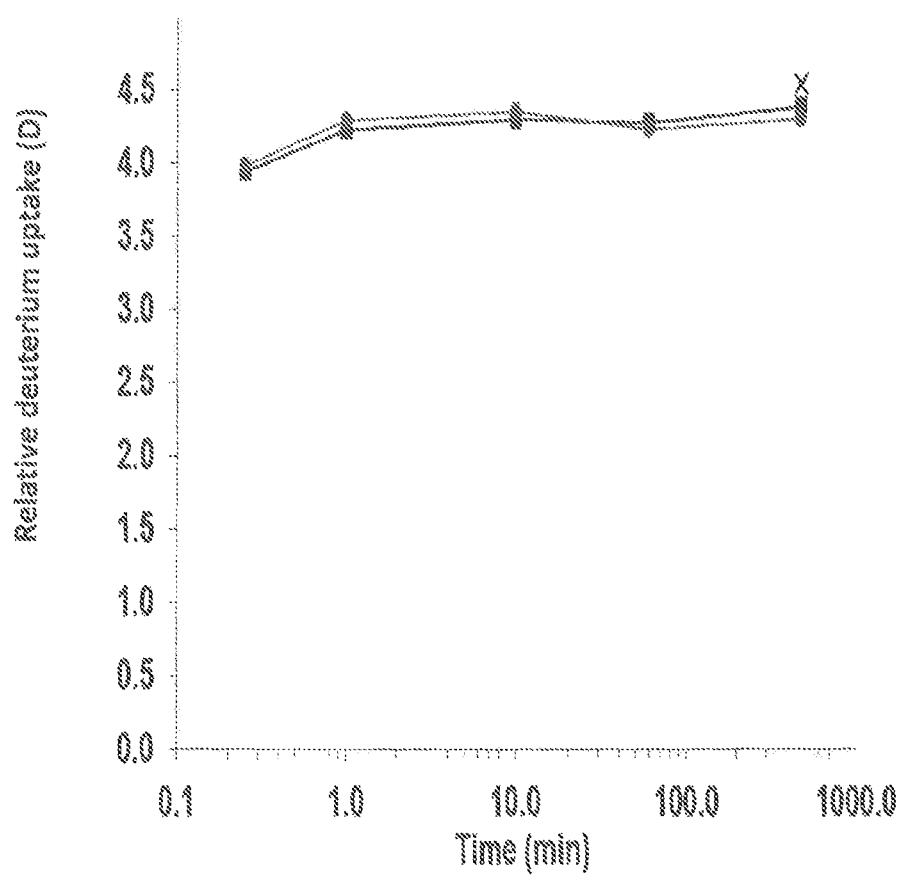
Figure 16I:
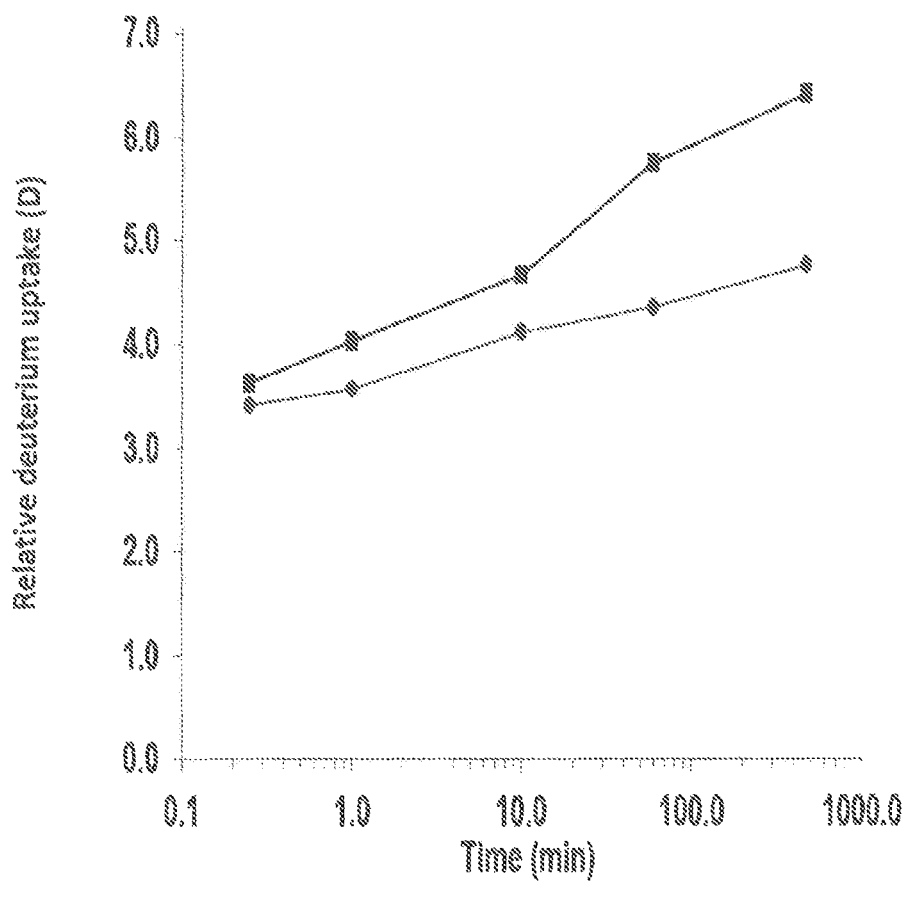

FIG. 14 provides an illustration of sortilin regions, based on sortilin shuffle constructs, imposed onto the predicted sortilin structure. The regions constitute the sections of the sortilin protein in which the change of selected amino acid residues from the human sequence to the tetraodon sequence inhibited binding for antibodies of that region class. The arrow indicates the reported high affinity binding site of neurotensin and PGRN (Quistgaard Nat Struct Mol Biol. 2009 January; 16(1):96-8, Lee et al, Hum Mol Genet. 2013).

FIG. 15A-15I show representative peptides covering the conformational epitope of antibody 45, 68 and 811. All of the shown peptides show a protection from exchange larger than 0.5D, except peptide 115-125. Peptide 115-125 is an example of a peptide which is unaffected by the presence of antibody 45, 68 or 811, and thereby is not a part of the conformational binding epitope (Example 16)

FIGS. 16A-16I show representative peptides covering the conformational epitope of antibody 30. All of the shown peptides show a protection from exchange larger than 0.5D, except peptide 563-572, peptide 646-656 and peptide 704-714. These three peptides are examples of peptides which are unaffected by the presence of antibody 30, and thereby is not a part of the conformational binding (Example 16)

Figure 17:
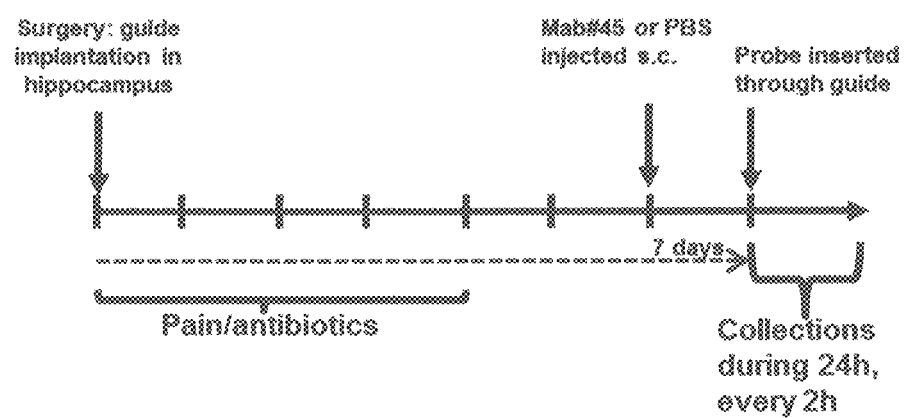

FIG. 17 shows an illustration of the microdialysis for procedure.

Figure 18A:
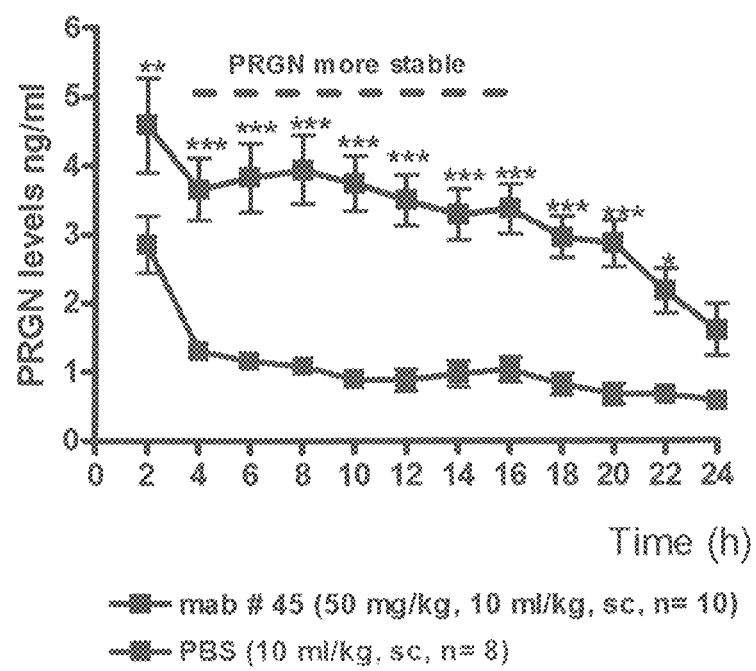

FIG. 18A shows a time course: effect of systemic administration of antibody 45 or PBS (50 mg/kg, 10 ml/kg, s.c.) 24 h prior to the microdialysis experiments on the levels of PRGN in the hippocampus of freely moving hSORT1 mice over time (24 h). (Example 17)

Figure 18B:
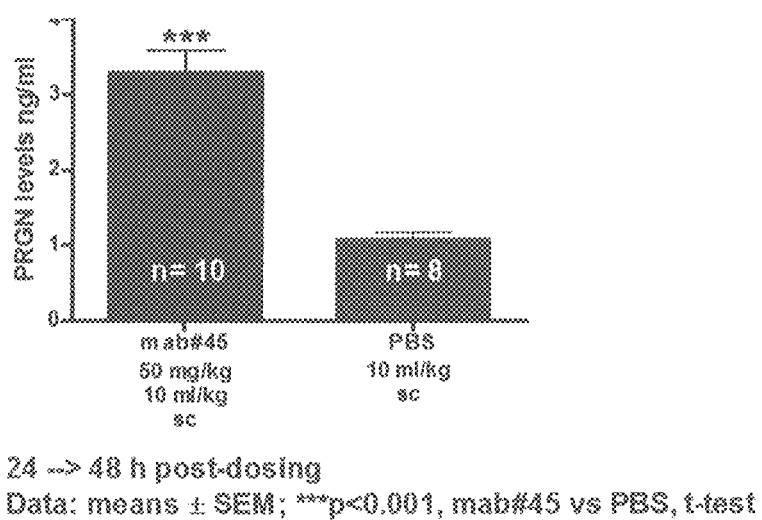

FIG. 18B shows the results of a pooled 24 h dialysis: basal PRGN in the hippocampus of freely moving hSORT1 mice in mab #45- and PBS-treated mice, 3.3±0.3 ng/ml and 1.1±0.1 ng/ml, respectively, as assessed by push-pull microdialysis (Example 17).

FIG. 18C presents a table showing PRGN levels (means±SEM) in the hippocampus of freely moving hSORT1 mice measured every 2 h during 24 h, 1d after the animals were treated with mab #45 (n=10) or PBS (n=8) (Example 17).

DETAILED DESCRIPTION OF THE INVENTION

As used herein, the term "Sortilin" is synonymous with the Sortilin protein (identified in for example UniProt as Q99523, 1 and 2). The amino acid numbering of Sortilin is given with respect to SEQ ID NO:169 as shown below, Met being amino acid 1:

```
MERPWGAADG LSRWPHGLGL LLLLQLLPPS TLSQDRLDAP
PPPAAPLPRW SGPIGVSWGL RAAAAGGAFP RGGRWRRSAP
GEDEECGRVR DFVAKLANNT HQHVFDDLRG SVSLSWVGDS
TGVILVLTTF HVPLVIMTFG QSKLYRSEDY GKNFKDITDL
INNTFIRTEF GMAIGPENSG KVVLTAEVSG GSRGGRIFRS
SDFAKNFVQT DLPFHPLTQM MYSPQNSDYL LALSTENGLW
VSKNFGGKWE EIHKAVCLAK WGSDNTIFFT TYANGSCKAD
LGALELWRTS DLGKSFKTIG VKIYSFGLGG RPLFASVMAD
KDTTRRIHVS TDQGDTWSMA QLPSVGQEQF YSILAANDDM
VFMHVDEPGD TGFGTIFTSD DRGIVYSKSL DRHLYTTTGG
ETDFTNVTSL RGVYITSVLS EDNSIQTMIT FDQGGRWTHL
RKPENSECDA TAKNKNECSL HIHASYSISQ KLNVPMAPLS
EPNAVGIVIA HGSVGDAISV MVPDVYISDD GGYSWTKMLE
GPHYYTILDS GGIIVAIEHS SRPINVIKFS TDEGQCWQTY
TFTRDPIYFT GLASEPGARS MNISIWGFTE SFLTSQWVSY
TIDFKDILER NCEEKDYTIW LAHSTDPEDY EDGCILGYKE
QFLRLRKSSV CQNGRDYVVT KQPSICLCSL EDFLCDFGYY
RPENDSKCVE QPELKGHDLE FCLYGREEHL TTNGYRKIPG
```

-continued

```
DKCQGGVNPV REVKDLKKKC TSNFLSPEKQ NSKSNSVPII

LAIVGLMLVT VVAGVLIVKK YVCGGRFLVH RYSVLQQHAE

ANGVDGVDAL DTASHTNKSG YHDDSDEDLLE
```

As used herein, the term "D Region" is intended to refer to the region on Sortilin (corresponding to residues 523-610 of SEQ ID NO:169) consisting of the amino acids in SEQ ID NO:170 as shown below:

```
HYYTILDSGG IIVAIEHSSR PINVIKFSTD EGQCWQTYTF

TRDPIYFTGL ASEPGARSMN ISIWGFTESF LTSQWVSYTI

DFKDILER
```

For D Region antibodies, binding to the following shuffle regions was observed: hsort, hB06-10, B12390. The antibodies did not bind to hB01-05, B45678, tet. For D+ antibodies, binding to the following shuffle regions was observed: hsort, B12390. The antibodies did not bind to hB01-05, hB06-10, B45678, tet. For the antibodies named "D+" a similar binding pattern was observed as for "D" region antibodies except that no binding to the hB06-10 was observed for D+ antibodies. Despite the different binding pattern to shuffle constructs, D+ antibodies shared functional characteristics (cell assays etc.) to D-region antibodies.

Certain D and D+ binding antibodies binds particular the region as defined in SEQ ID NO:185, 186 or 187. Thus, the invention relates in certain embodiments to antibodies or antigen binding fragments thereof that binds to the D region sequences of SEQ ID 170, and within that region SEQ ID NO:185, 186 or 187. By binding, these antibodies or antigen-binding fragments, influence the PGRN levels and thus may be used to treat disease associated with PGRN, such as FTD, ALS and AD.

By further analysing the binding of the D and D+ antibodies of the invention, partial binding to the neighbouring region (the A region) was identified for some of the antibodies. This region corresponds to amino acids 78-254 of SEQ ID NO:169, as shown in SEQ ID NO:180 and below:

SAPGEDEECG RVRDFVAKLA NNTHQHVFDD LRGSVSLSWV

GDSTGVILVL TTFHVPLVIM TFGQSKLYRS EDYGKNFKDI

TDLINNTFIR TEFGMAIGPE NSGKVVLTAE VSGGSRGGRI

FRSSDFAKNF VQTDLPFHPL TQMMYSPQNS DYLLALSTEN

GLWVSKNFGG KWEEIHK

This region has been given the term "A region".

Thus, in certain embodiments the invention relates to antibodies or antigen binding fragments thereof that binds the D region as defined above and in SEQ ID Nos 170, 185, 186 or 187, and further have affinity for the A region identified in SEQ ID NO 180. Within the A region certain antibodies or antigen binding fragments thereof have affinity for the A region amino acids identified in SEQ ID NOs 181, 182, 183 or 184.

PGRN (proepithelin, granulin-epithelin precursor, PC-cell-derived growth factor, acrogranin) encodes a 68.5 kDa secreted glycoprotein that has 7.5 repeats of smaller granulin motifs, ranging from 6-25 kDa, which can be proteolytically cleaved from the precursor PGRN (He, Z. & Bateman, A., J. Mol. Med. 81:600-6X2 (2003)). In non-neuronal cells, PGRN has been associated with a variety of events, such as cell cycle regulation and cell motility (He, Z. & Bateman, A., J. Mol. Med. 57:600-612 (2003); Monami, G., et ah, Cancer Res. (5(5:7103-7110 (2006)), wound repair, inflammation (Zhu, J., et ah, Cell 777:867-878 (2002)), induction of growth factors such as vascular endothelial growth factor (VEGF) (Tangkeangsirrsin, W. & Serrero, G, Carcinogenesis 25.1587-1592 (2004)), and tumorigenesis (He, Z. & Bateman, A., J. Mol. Med. 81:600-612 (2003), Monami, G., et al., Cancer Res (5(5:7103-7110 (2006); Serrero, G., Biochem Biophys. Res. Commun. 505-409-413 (2003), Lu, R & Serrero, G., Proc. Natl Acad Sa U.SA 98 142-147 (2001); Liau, L M., et al., Cancer Res. 60:1353-1360 (2000)).

PGRN mutations result in haploinsufficiency (Baker, M., et ah, Nature 442:916-919 (2006); Cruts, M., et ah, Nature 442:920-924 (2006)) and are known to be present in nearly 50% of familial FTD cases, making PGRN mutation a major genetic contributor to FTD (Cruts, M. & Van Broeckhoven, C, Trends Genet. 24:186-194 (2008); Le Ber, I., et ah, Brain 129:3051-3065 (2006)). The loss-of-function heterozygous character of PGRN mutations implies that in healthy individuals, PGRN expression plays a dose-dependent, critical role in protecting healthy individuals from the development of FTD.

The term "antibody" (Ab) in the context of the present invention refers to an immunoglobulin molecule or according to some embodiments of the invention, a fragment of an immunoglobulin molecule which has the ability to bind to an epitope of a molecule ("antigen"). Naturally occurring antibodies typically comprise a tetramer which is usually composed of at least two heavy (H) chains and at least two light (L) chains. Each heavy chain is comprised of a heavy chain variable domain (abbreviated herein as VH) and a heavy chain constant domain, usually comprised of three domains (CH1, CH2 and CH3). Heavy chains can be of any isotype, including IgG (IgG1, IgG2, IgG3 and IgG4 subtypes), IgA (IgA1 and IgA2 subtypes), IgM and IgE. Each light chain is comprised of a light chain variable domain (abbreviated herein as VL) and a light chain constant domain (CL). Light chains include kappa chains and lambda chains. The heavy and light chain variable domain is typically responsible for antigen recognition, while the heavy and light chain constant domain may mediate the binding of the immunoglobulin to host tissues or factors, including various cells of the immune system (e.g., effector cells) and the first component (C1q) of the classical complement system. The VH and VL domains can be further subdivided into regions of hypervariability, termed "complementarity determining regions," that are interspersed with domains of more conserved sequence, termed "framework regions" (FR). Each VH and VL is composed of three CDR Domains and four FR Domains arranged from amino-terminus to carboxy-terminus in the following order: FR1-CDR1-FR2-CDR2-FR3-CDR3-FR4. The variable domains of the heavy and light chains contain a binding domain that interacts with an antigen. Of particular relevance are antibodies and their antigen-binding fragments that have been "isolated" so as to exist in a physical milieu distinct from that in which it may occur in nature or that have been modified so as to differ from a naturally occurring antibody in amino acid sequence.

The term "epitope" means an antigenic determinant capable of specific binding to an antibody. Epitopes usually consist of surface groupings of molecules such as amino acids or sugar side chains and usually have specific three dimensional structural characteristics, as well as specific charge characteristics. Conformational and linear epitopes are distinguished in that the binding to the former, but not the latter, is always lost in the presence of denaturing solvents. The epitope may comprise amino acid residues directly involved in the binding and other amino acid residues, which are not directly involved in the binding, such as amino acid residues which are effectively blocked by the specifically antigen-binding peptide (in other words, the amino acid residue is within the footprint of the specifically antigen-binding peptide).

As used herein, the term "antigen-binding fragment of an antibody" means a fragment, portion, region or domain of an antibody (regardless of how it is produced (e.g., via cleavage, recombinantly, synthetically, etc.)) that is capable of binding to an epitope, and thus the term "antigen-binding" is intended to mean the same as "epitope-binding" so that, for example, an "antigen-binding fragment of an antibody" is intended to be the same as an "epitope-binding fragment of an antibody". An antigen-binding fragment may contain 1, 2, 3, 4, 5 or all 6 of the CDR Domains of such antibody and, although capable of binding to such epitope, may exhibit a specificity, affinity or selectivity toward such epitope that differs from that of such antibody. Preferably, however, an antigen-binding fragment will contain all 6 of the CDR Domains of such antibody. An antigen-binding fragment of an antibody may be part of, or comprise, a single polypeptide chain (e.g., an scFv), or may be part of, or comprise, two or more polypeptide chains, each having an amino-terminus and a carboxyl terminus (e.g., a diabody, a Fab fragment, a $Fab_2$ fragment, etc.). Fragments of antibodies that exhibit antigen-binding ability can be obtained, for example, by protease cleavage of intact antibodies. More preferably, although the two domains of the Fv fragment, VL and VH, are naturally encoded by separate genes, or polynucleotides that encode such gene sequences (e.g., their encoding cDNA) can be joined, using recombinant methods, by a flexible linker that enables them to be made as a single protein chain in which the VL and VH regions associate to form monovalent antigen-binding molecules (known as single-chain Fv (scFv); see e.g., Bird et al. , (1988) Science 242:423-426; and Huston et al. (1988) Proc. Natl. Acad. Sci. (U.S.A.) 85:5879-5883). Alternatively, by employing a flexible linker that is too short (e.g., less than about 9 residues) to enable the VL and VH domains of a single polypeptide chain to associate together, one can form a bispecific antibody, diabody, or similar molecule (in which two such polypeptide chains associate together to form a bivalent antigen-binding molecule) (see for instance PNAS USA 90(14), 6444-8 (1993) for a description of diabodies). Examples of antigen-binding fragments encompassed within the present invention include (i) a Fab' or Fab fragment, a monovalent fragment consisting of the VL, VH, CL and CH1 domains, or a monovalent antibody as described in WO2007059782; (ii) F(ab')2 fragments, bivalent fragments comprising two Fab fragments linked by a disulfide bridge at the hinge domain; (iii) an Fd fragment consisting essentially of the VH and CH1 domains; (iv) a Fv fragment consisting essentially of a VL and VH domains, (v) a dAb fragment (Ward et al., Nature 341, 544-546 (1989)), which consists essentially of a VH domain and also called domain antibodies (Holt et al; Trends Biotechnol. 2003 November; 2i(II):484-90); (vi) camelid or nanobodies (Revets et al; Expert Opin Biol Ther. 2005 January; 5_(I): I 11-24) and (vii) an isolated complementarity determining region (CDR). Furthermore, although the two domains of the Fv fragment, VL and VH, are coded for by separate genes, they may be joined, using recombinant methods, by a synthetic linker that enables them to be made as a single protein chain in which the VL and VH domains pair to form monovalent molecules (known as single chain antibodies or single chain Fv (scFv), see for instance Bird et al., Science 242, 423-426 (1988) and Huston et al., PNAS USA 85, 5879-5883 (1988)). These and other useful antibody fragments in the context of the present invention are discussed further herein. It also should be understood that the term antibody, unless specified otherwise, also includes antibody-like polypeptides, such as chimeric antibodies and humanized antibodies, and antibody fragments retaining the ability to bind to the antigen (antigen-binding fragments) provided by any known technique, such as enzymatic cleavage, peptide synthesis, and recombinant techniques. An antibody as generated can possess any isotype. As used herein, "isotype" refers to the immunoglobulin class (for instance IgG1, IgG2, IgG3 or IgG4) that is encoded by heavy chain constant domain genes. Such antibody fragments are obtained using conventional techniques known to those of skill in the art; suitable fragments capable of binding to a desired epitope may be readily screened for utility in the same manner as an intact antibody.

The term "bispecific antibody" refers to an antibody containing two independent antigen-binding fragments that each target independent targets. These targets can be epitopes present on different proteins or different epitopes present on the same target. Bispecific antibody molecules can be made using compensatory amino acid changes in the constant domains of the HCs of the parent monospecific bivalent antibody molecules. The resulting heterodimeric antibody contains one Fabs contributed from two different parent monospecific antibodies. Amino acid changes in the Fc domain leads to increased stability of the heterodimeric antibody with bispecificity that is stable over time. (Ridgway et al., Protein Engineering 9, 617-621 (1996), Gunasekaran et al., JBC 285, 19637-1(2010), Moore et al., MAbs 3:6 546-557 (2011), Strop et al., JMB 420, 204-219 (2012), Metz et al., Protein Engineering 25:10 571-580 (2012), Labrijn et al., PNAS 110:113, 5145-5150 (2013), Spreter Von Kreudenstein et al., MAbs 5:5 646-654 (2013)). Bispecific antibodies can also include molecules that are generated using ScFv fusions. Two monospecific scfv are then independently joined to Fc domains able to form stable heterodimers to generate a single bispecific molecule (Mabry et al., PEDS 23:3 115-127 (2010). Bispecific molecules have dual binding capabilities.

An "anti-Sortilin antibody" or "Sortilin antibody" (used interchangeably herein, depending on the context wherein its written) is an antibody an antigen-binding fragment thereof which binds specifically to Sortilin, and especially to the Sortilin D Region, SEQ ID NO:170. An anti-Sortilin antibody that binds to the Sortilin D Region will usually bind to a conformational epitope or a linear epitope of 3, 4, 5, 6 or 7 consecutive amino acids within the D-Region (for example SEQ ID NOs:185, 186 or 187) with an affinity (IC50) at or below 22 nM, such as between 22 nM and 1 nM, between 10 nM and 1 nM or between 5 nM and 1 nM. According to some embodiments the anti-Sortilin antibodies may also bind to the A region (SEQ ID NOs:180, 181, 182, 183 or 184) although it's emphasized that their main biological function is believed to be achieved by binding to the D Region.

The binding site identified is rather unique as shown with for example the binding of the selective small molecule ligand AF38469 to Sortilin. The binding site for AF38469 has been shown to be similar to the binding site of neurotensin and characterized by X-ray crystallography (Schroder et al. Bioorg Med Chem Lett. 2014 Jan. 1; 24(1):177-80).

PGRN has been reported to bind to the same site (Lee et al. Hum Mol Genet. 2013). Antibodies 45 and 68, binding to D-region, and D+ respectively, did not inhibit the binding of AF38469 to sortilin. This data suggests that these antibodies have a binding site for Sortilin distinct from the binding site for AF38469 and neurotensin. Therefore, in certain embodiments the invention relates to an antibody, or an antigen-binding fragment thereof, capable of specifically binding to Sortilin and inhibiting the binding of PGRN to Sortilin, but which binding does not inhibit or substantially inhibit the binding of neurotensin or AF38469 to Sortilin. This can be shown using for example displacement of binding to Sortilin using a scintillation proximity assay (SPA) (Example 11). One way of explaining this finding could be that the antibodies, or antigen-binding fragments thereof, are binding to surface areas of Sortilin whereas the small molecules like neurotensine are binding inside the binding pocket.

The term "human antibody" (which may be abbreviated to "humAb" or "HuMab"), as used herein, is intended to include antibodies having variable and constant domains derived from human germline immunoglobulin sequences. The human antibodies of the invention may include amino acid residues not encoded by human germline immunoglobulin sequences (e.g., mutations introduced by random or site-specific mutagenesis in vitro or during gene rearrangement or by somatic mutation in vivo).

The terms "monoclonal antibody" or "monoclonal antibody composition" as used herein refer to a preparation of antibody molecules of single molecular composition. A conventional monoclonal antibody composition displays a single binding specificity and affinity for a particular epitope. In certain embodiments a monoclonal antibody can be composed of more than one Fab domain thereby increasing the specificity to more than one target. The terms "monoclonal antibody" or "monoclonal antibody composition" are not intended to be limited by any particular method of production (e.g., recombinant, transgenic, hybridoma, etc.).

The antibodies of the present invention, and their sortilin antigen-binding fragments will preferably be human or, for example for the mouse antibodies (denoted 1F2, 5E1), "humanized," particularly if employed for therapeutic purposes. The term "humanized" refer to a molecule, generally prepared using recombinant techniques, having an antigen-binding site derived from an immunoglobulin from a non-human species and a remaining immunoglobulin structure based upon the structure and/or sequence of a human immunoglobulin. The antigen-binding site may comprise either complete non-human antibody variable domains fused to human constant domains, or only the complementarity determining regions (CDRs) of such variable domains grafted to appropriate human framework regions of human variable domains. The framework residues of such humanized molecules may be wild type (e.g., fully human) or they may be modified to contain one or more amino acid substitutions not found in the human antibody whose sequence has served as the basis for humanization. Humanization lessens or eliminates the likelihood that a constant domain of the molecule will act as an immunogen in human individuals, but the possibility of an immune response to the foreign variable domain remains (LoBuglio, A. F. et al. (1989) "*Mouse/Human Chimeric Monoclonal Antibody In Man: Kinetics And Immune Response*," Proc. Natl. Acad. Sci. (U.S.A.) 86:4220-4224). Another approach focuses not only on providing human-derived constant domains, but modifying the variable domains as well so as to reshape them as closely as possible to human form. It is known that the variable domains of both heavy and light chains contain three complementarity-determining regions (CDRs) which vary in response to the antigens in question and determine binding capability, flanked by four framework regions (FRs) which are relatively conserved in a given species and which putatively provide a scaffolding for the CDRs. When non-human antibodies are prepared with respect to a particular antigen, the variable domains can be "reshaped" or "humanized" by grafting CDRs derived from nonhuman antibody on the FRs present in the human antibody to be modified. Application of this approach to various antibodies has been reported by Sato, K. et al. (1993) Cancer Res 53:851-856. Riechmann, L. et al. (1988) "*Reshaping Human Antibodies for Therapy*," Nature 332:323-327; Verhoeyen, M. et al. (1988) "*Reshaping Human Antibodies: Grafting An Antilysozyme Activity*," Science 239:1534-1536; Kettleborough, C. A. et al. (1991) "*Humanization Of A Mouse Monoclonal Antibody By CDR-Grafting: The Importance Of Framework Residues On Loop Conformation*," Protein Engineering 4:773-3783; Maeda, H. et al. (1991) "*Construction Of Reshaped Human Antibodies With HIV-Neutralizing Activity*," Human Antibodies Hybridoma 2:124-134; Gorman, S. D. et al. (1991) "*Reshaping A Therapeutic CD4 Antibody*," Proc. Natl. Acad. Sci. (U.S.A.) 88:4181-4185; Tempest, P. R. et al. (1991) "*Reshaping A Human Monoclonal Antibody To Inhibit Human Respiratory Syncytial Virus Infection in vivo*," Bio/Technology 9:266-271; Co, M. S. et al. (1991) "*Humanized Antibodies For Antiviral Therapy*," Proc. Natl. Acad. Sci. (U.S.A.) 88:2869-2873; Carter, P. et al. (1992) "*Humanization Of An Anti-p185her2 Antibody For Human Cancer Therapy*," Proc. Natl. Acad. Sci. (U.S.A.) 89:4285-4289; and Co, M. S. et al. (1992) "*Chimeric And Humanized Antibodies With Specificity For The CD33 Antigen*," J. Immunol. 148:1149-1154. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody. The ability to humanize an antigen is well known (see, e.g., U.S. Pat. Nos. 5,225,539; 5,530,101; 5,585,089; 5,859,205; 6,407,213; 6,881,557).

The term "antibody XX" is intended to denote an antibody or antigen-binding fragment thereof (for example antibody "5E1"), comprising or consisting of the Light Chain, the Light Chain Variable domain, or the Light Chain Variable domain CDR1-3, as defined by its respective SEQ ID NO, and the Heavy Chain, Heavy Chain Variable Domain, or Heavy Chain Variable Domain CDR1-3 as defined by its respective SEQ ID NO. In certain embodiments the antibody or antigen-binding fragment thereof are defined by their entire Heavy Chain Variable Domain comprising as defined by their SEQ ID NO and their Light Chain Variable Domain as defined by their SEQ ID NO.

The numbering of amino acid residues in this region is according to IMGT®, the international ImMunoGeneTics information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and Human Services; Chothia, C. & Lesk, A. M. (1987). Canonical structures For The Hypervariable domains Of Immunoglobulins. J. Mol. Biol. 196, 901-917.

As used herein, an antibody or an antigen-binding fragment thereof is said to "specifically" bind a region of another molecule (i.e., an epitope) if it reacts or associates more frequently, more rapidly, with greater duration and/or with greater affinity or avidity with that epitope relative to alternative epitopes. In one embodiment, the antibody, or antigen-binding fragment thereof, of the invention binds at least 10-fold more strongly to its target (Sortilin) than to another molecule; preferably at least 50-fold more strongly and more preferably at least 100-fold more strongly. Preferably, the antibody, or antigen-binding fragment thereof, binds under physiological conditions, for example, in vivo. Thus, by "specifically binding to Sortilin", we include the ability of the antibody, or antigen-binding fragment thereof, to bind to Sortilin with such specificity and/or under such conditions. Methods suitable for determining such binding will be known to those skilled in the art, and exemplary methods are described in the accompanying Examples. As used herein, the term "binding" in the context of the binding of an antibody to a predetermined antigen typically refers to binding with an affinity corresponding to a KD of about $10^{-7}$ M or less, such as about $10^{-8}$ M or less, such as about $10^{-9}$ M or less when determined by for instance surface plasmon resonance (SPR) technology in either a BIAcore® 3000 or T200instrument using the antigen as the ligand and the antibody as the analyte, and binds to the predetermined antigen with an affinity corresponding to a KD that is at least ten-fold lower, such as at least 100 fold lower, for instance at least 1,000 fold lower, such as at least 10,000 fold lower, for instance at least 100,000 fold lower than its affinity for binding to a non-specific antigen (e.g., BSA, casein) other than the predetermined antigen or a closely-related antigen. The amount with which the affinity is lower is dependent on the KD of the antibody, so that when the KD of the antibody is very low (that is, the antibody is highly specific), then the amount with which the affinity for the antigen is lower than the affinity for a non-specific antigen may be at least 10,000 fold. In particular, the invention pertains to anti-Sortilin antibodies that exhibit a binding affinity corresponding to at or below 22 nM, such as between 22 nM and 1 nM, between 10 nM and 1 nM or between 5 nM and 1 nM, when determined by, for instance, bioLayer interferometry using an Octet 384RED (Example 8).

In certain embodiments of the invention the invention relates to an antibody or antigen-binding fragment thereof able to compete with humAb antibody 45 or humAb antibody 68 for binding to Sortilin. In another embodiment the invention relates to an antibody or antigen-binding fragment thereof that is able to compete with antibody 45 for binding to the D Region of Sortilin as defined in SEQ ID NO:170. Such competitive binding inhibition can be determined using assays and methods well known in the art, for example using BIAcore® chips with immobilised human Sortilin and incubating with a reference antibody (such as antibody "45" or "68") with and without an antibody polypeptide to be tested. Alternatively, a pair-wise mapping approach can be used, in which a reference antibody (such as antibody "45" or "68") is immobilised to the surface of the BIAcore® chip, human Sortilin antigen is bound to the immobilised antibody, and then a second antibody is tested for simultaneous binding ability to human Sortilin (see 'BIAcore® Assay Handbook', GE Healthcare Life Sciences, 29-0194-00 AA 05/2012; the disclosures of which are incorporated herein by reference).

The term "kd" (sec–1 or 1/s), as used herein, refers to the dissociation rate constant of a particular antibody-antigen interaction. Said value is also referred to as the koff value.

The term "ka" (M–1×sec–1 or 1/Msec), as used herein, refers to the association rate constant of a particular antibody-antigen interaction.

The term "KD" (M), as used herein, refers to the dissociation equilibrium constant of a particular antibody-antigen interaction and is obtained by dividing the kd by the ka.

The term "KA" (M–1 or 1/M), as used herein, refers to the association equilibrium constant of a particular antibody-antigen interaction and is obtained by dividing the ka by the kd.

In one embodiment, the invention relates to an antibody, or antigen-binding fragment thereof, which exhibits one or more of the following properties:
(i) a binding affinity ($K_D$) for Sortilin of between 0.5-10 nM, such as 1-5 nM or 1-2 nM;
(ii) capability to reduce and/or inhibit PGRN binding to Sortilin; (iii) capability to reduce and/or inhibit clearance of PGRN by Sortilin-expressing cells;
(iv) capability to reduce and/or inhibit the endocytosis of PGRN by Sortilin-expressing cells;
(v) capability to increase the amount and/or concentration of PGRN in the plasma in human-Sortilin-expressing knock-in mice.

The term "capability to reduce and/or inhibit PGRN binding to Sortilin" includes an antibody that has the ability to inhibit binding to PGRN at an IC50 less than 50 nM but preferably between 10 nM and 0.2 nM using a time resolved fluorescence assay (HTFR) disclosed in Example 10.

The term "capability to reduce and/or inhibit clearance of PGRN by Sortilin-expressing cells" includes the ability to increase the concentration of PGRN in the medium by at least 25%, such as between 25% and 500%, between 25% and 400% or between 25% and 200% as measured by an ELISA assay as disclosed in Example 13.

The "capability to reduce and/or inhibit the endocytosis of PGRN by Sortilin-expressing cells" includes the ability reduce the intracellular concentration of PGRN by at least 10% but preferably between 20 and 100% as measured by a cellomics based assay as disclosed in Example 12.

The "capability to increase the amount and/or concentration of PGRN in the plasma in human-Sortilin-expressing knock-in mice" includes the ability to increase the concentration of PGRN in the plasma by at least 25% but preferably between 50 and 500 percent as measured by an ELISA assay as disclosed in Example 15.

It's envisaged that the capability to increase PGRN in the brain may also be assayed by for example microdialysis. Thus by "capability to increase the amount and/or concentration of PGRN in the brain" includes the ability to increase the concentration of PGRN in the brain by at least 25% but preferably between 50 and 500 percent as measured by microdialysis.

In some antibodies, only part of a CDR, namely the subset of CDR residues required for binding, termed the SDRs, are needed to retain binding in a humanized antibody. CDR residues not contacting the relevant epitope and not in the SDRs can be identified based on previous studies (for example residues H60-H65 in CDR H2 are often not required), from regions of Kabat CDRs lying outside Chothia hypervariable loops (see, Kabat et al. (1992) SEQUENCES OF PROTEINS OF IMMUNOLOGICAL INTEREST, National Institutes of Health Publication No. 91-3242; Chothia, C. et al. (1987) "*Canonical Structures For The Hypervariable Regions Of Immunoglobulins*," J. Mol. Biol. 196:901-917), by molecular modeling and/or empirically, or as described in Gonzales, N. R. et al. (2004) "*SDR Grafting Of A Murine Antibody Using Multiple*

Human Germline Templates To Minimize Its Immunogenicity," Mol. Immunol. 41:863-872. In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Currently, the most advanced BLOSUM database is the BLOSUM62 database (BLOSUM62.iij). Table 1 presents the BLOSUM62.iij substitution scores (the higher the score the more conservative the substitution and thus the more likely the substitution will not affect function). If an antigen-binding fragment comprising the resultant CDR fails to bind to Sortilin, for example, then the BLOSUM62.iij substitution score is deemed to be insufficiently conservative, and a new candidate substitution is selected and produced having a higher substitution score. Thus, for example, if the original residue was glutamate (E), and the non-functional substitute residue was histidine (H), then the BLOSUM62.iij substitution score will be 0, and more conservative changes (such as to aspartate, asparagine, glutamine, or lysine) are preferred.

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | +4 | −1 | −2 | −2 | 0 | −1 | −1 | 0 | −2 | −1 | −1 | −1 | −1 | −2 | −1 | +1 | 0 | −3 | −2 | 0 |
| R | −1 | +5 | 0 | −2 | −3 | +1 | 0 | −2 | 0 | −3 | −2 | +2 | −1 | −3 | −2 | −1 | −1 | −3 | −2 | −3 |
| N | −2 | 0 | +6 | +1 | −3 | 0 | 0 | 0 | +1 | −3 | −3 | 0 | −2 | −3 | −2 | +1 | 0 | −4 | −2 | −3 |
| D | −2 | −2 | +1 | +6 | −3 | 0 | +2 | −1 | −1 | −3 | −4 | −1 | −3 | −3 | −1 | 0 | −1 | −4 | −3 | −3 |
| C | 0 | −3 | −3 | −3 | +9 | −3 | −4 | −3 | −3 | −1 | −1 | −3 | −1 | −2 | −3 | −1 | −1 | −2 | −2 | −1 |
| Q | −1 | +1 | 0 | 0 | −3 | +5 | +2 | −2 | 0 | −3 | −2 | +1 | 0 | −3 | −1 | 0 | −1 | −2 | −1 | −2 |
| E | −1 | 0 | 0 | +2 | −4 | +2 | +5 | −2 | 0 | −3 | −3 | +1 | −2 | −3 | −1 | 0 | −1 | −3 | −2 | −2 |
| G | 0 | −2 | 0 | −1 | −3 | −2 | −2 | +6 | −2 | −4 | −4 | −2 | −3 | −3 | −2 | 0 | −2 | −2 | −3 | −3 |
| H | −2 | 0 | +1 | −1 | −3 | 0 | 0 | −2 | +8 | −3 | −3 | −1 | −2 | −1 | −2 | −1 | −2 | −2 | +2 | −3 |
| I | −1 | −3 | −3 | −3 | −1 | −3 | −3 | −4 | −3 | +4 | +2 | −3 | +1 | 0 | −3 | −2 | −1 | −3 | −1 | +3 |
| L | −1 | −2 | −3 | −4 | −1 | −2 | −3 | −4 | −3 | +2 | +4 | −2 | +2 | 0 | −3 | −2 | −1 | −2 | −1 | +1 |
| K | −1 | +2 | 0 | −1 | −3 | +1 | +1 | −2 | −1 | −3 | −2 | +5 | −1 | −3 | −1 | 0 | −1 | −3 | −2 | −2 |
| M | −1 | −1 | −2 | −3 | −1 | 0 | −2 | −3 | −2 | +1 | +2 | −1 | +5 | 0 | −2 | −1 | −1 | −1 | −1 | +1 |
| F | −2 | −3 | −3 | −3 | −2 | −3 | −3 | −3 | −1 | 0 | 0 | −3 | 0 | +6 | −4 | −2 | −2 | +1 | +3 | −1 |
| P | −1 | −2 | −2 | −1 | −3 | −1 | −1 | −2 | −2 | −3 | −3 | −1 | −2 | −4 | +7 | −1 | −1 | −4 | −3 | −2 |
| S | +1 | −1 | +1 | 0 | −1 | 0 | 0 | 0 | −1 | −2 | −2 | 0 | −1 | −2 | −1 | +4 | +1 | −3 | −2 | −2 |
| T | 0 | −1 | 0 | −1 | −1 | −1 | −1 | −2 | −2 | −1 | −1 | −1 | −1 | −2 | −1 | +1 | +5 | −2 | −2 | 0 |
| W | −3 | −3 | −4 | −4 | −2 | −2 | −3 | −2 | −2 | −3 | −2 | −3 | −1 | +1 | −4 | −3 | −2 | +11 | +2 | −3 |
| Y | −2 | −2 | −2 | −3 | −2 | −1 | −2 | −3 | +2 | −1 | −1 | −2 | −1 | +3 | −3 | −2 | −2 | +2 | +7 | −1 |
| V | 0 | −3 | −3 | −3 | −1 | −2 | −2 | −3 | −3 | +3 | +1 | −2 | +1 | −1 | −2 | −2 | 0 | −3 | −1 | +4 |

The fact that a single amino acid alteration of a CDR residue can result in loss of functional binding (Rudikoff, S. etc. (1982) "Single Amino Acid Substitution Altering Antigen-binding Specificity," Proc. Natl. Acad. Sci. (USA) 79(6):1979-1983) provides a means for systematically identifying alternative functional CDR sequences. In one preferred method for obtaining such variant CDRs, a polynucleotide encoding the CDR is mutagenized (for example via random mutagenesis or by a site-directed method (e.g., polymerase chain-mediated amplification with primers that encode the mutated locus)) to produce a CDR having a substituted amino acid residue. By comparing the identity of the relevant residue in the original (functional) CDR sequence to the identity of the substituted (non-functional) variant CDR sequence, the BLOSUM62.iij substitution score for that substitution can be identified. The BLOSUM system provides a matrix of amino acid substitutions created by analyzing a database of sequences for trusted alignments (Eddy, S. R. (2004) "Where Did The BLOSUM62 Alignment Score Matrix Come From?," Nature Biotech. 22(8):1035-1036; Henikoff, J. G. (1992) "Amino acid substitution matrices from protein blocks," Proc. Natl. Acad. Sci. (USA) 89:10915-10919; Karlin, S. et al. (1990) "Methods For Assessing The Statistical Significance Of Molecular Sequence Features By Using General Scoring Schemes," Proc. Natl. Acad. Sci. (USA) 87:2264-2268; Altschul, S. F. (1991) "Amino Acid Substitution Matrices From An Information Theoretic Perspective," J. Mol. Biol. 219, 555-565.

The invention thus contemplates the use of random mutagenesis to identify improved CDRs. In the context of the present invention, conservative substitutions may be defined by substitutions within the classes of amino acids reflected in one or more of the following three tables:

Amino Acid Residue Classes For Conservative Substitutions:

TABLE 2

| | |
|---|---|
| Acidic Residues | Asp (D) and Glu (E) |
| Basic Residues | Lys (K), Arg (R), and His (H) |
| Hydrophilic Uncharged Residues | Ser (S), Thr (T), Asn (N), and Gln (Q) |
| Aliphatic Uncharged Residues | Gly (G), Ala (A), Val (V), Leu (L), and Ile (I) |
| Non-polar Uncharged Residues | Cys (C), Met (M), and Pro (P) |
| Aromatic Residues | Phe (F), Tyr (Y), and Trp (W) |

Alternative Conservative Amino Acid Residue Substitution Classes:

TABLE 3

| | | | |
|---|---|---|---|
| 1 | A | S | T |
| 2 | D | E | |
| 3 | N | Q | |
| 4 | R | K | |
| 5 | I | L | M |
| 6 | F | Y | W |

Alternative Physical and Functional Classifications of Amino Acid Residues:

TABLE 4

| | |
|---|---|
| Alcohol Group-Containing Residues | S and T |
| Aliphatic Residues | I, L, V and M |
| Cycloalkenyl-Associated Residues | F, H, W and Y |
| Hydrophobic Residues | A, C, F, G, H, I, L, M, R, T, V, W and Y |
| Negatively Charged Residues | D and E |
| Polar Residues | C, D, E, H, K, N, Q, R, S and T |
| Positively Charged Residues | H, K and R |
| Small Residues | A, C, D, G, N, P, S, T and V |
| Very Small Residues | A, G and S |
| Residues Involved In Turn Formation | A, C, D, E, G, H, K, N, Q, R, S, P and T |
| Flexible Residues | Q, T, K, S, G, P, D, E and R |

More conservative substitutions groupings include: valine-leucine-isoleucine, phenylalanine-tyrosine, lysine-arginine, alanine-valine, and asparagine-glutamine.

Additional groups of amino acids may also be formulated using the principles described in, e.g., Creighton (1984) Proteins: Structure and Molecular Properties (2d Ed. 1993), W. H. Freeman and Company.

Phage display technology can alternatively be used to increase (or decrease) CDR affinity. This technology, referred to as affinity maturation, employs mutagenesis or "CDR walking" and re-selection uses the target antigen or an antigenic antigen-binding fragment thereof to identify antibodies having CDRs that bind with higher (or lower) affinity to the antigen when compared with the initial or parental antibody (See, e.g. Glaser et al. (1992) J. Immunology 149:3903). Mutagenizing entire codons rather than single nucleotides results in a semi-randomized repertoire of amino acid mutations. Libraries can be constructed consisting of a pool of variant clones each of which differs by a single amino acid alteration in a single CDR and which contain variants representing each possible amino acid substitution for each CDR residue. Mutants with increased (or decreased) binding affinity for the antigen can be screened by contacting the immobilized mutants with labeled antigen. Any screening method known in the art can be used to identify mutant antibodies with increased or decreased affinity to the antigen (e.g., ELISA) (See Wu et al. 1998, Proc. Natl. Acad. Sci. (U.S.A.) 95:6037; Yelton et al., 1995, J. Immunology 155:1994). CDR walking which randomizes the Light Chain may be used possible (see, Schier et al., 1996, J. Mol. Bio. 263:551).

Methods for accomplishing such affinity maturation are described for example in: Krause, J. C. et al. (2011) "*An Insertion Mutation That Distorts Antibody Binding Site Architecture Enhances Function Of A Human Antibody*," MBio. 2(1) pii: e00345-10. doi: 10.1128/mBio.00345-10; Kuan, C. T. et al. (2010) "*Affinity-Matured Anti-Glycoprotein NMB Recombinant Immunotoxins Targeting Malignant Gliomas And Melanomas*," Int. J. Cancer 10.1002/ijc.25645; Hackel, B. J. et al. (2010) "*Stability And CDR Composition Biases Enrich Binder Functionality Landscapes*," J. Mol. Biol. 401(1):84-96; Montgomery, D. L. et al. (2009) "*Affinity Maturation And Characterization Of A Human Monoclonal Antibody Against HIV-1 gp41*," MAbs 1(5):462-474; Gustchina, E. et al. (2009) "*Affinity Maturation By Targeted Diversification Of The CDR-H2 Loop Of A Monoclonal Fab Derived From A Synthetic Naïve Human Antibody Library And Directed Against The Internal Trimeric Coiled-Coil Of Gp41 Yields A Set Of Fabs With Improved HIV-1 Neutralization Potency And Breadth*," Virology 393(1):112-119; Finlay, W. J. et al. (2009) "*Affinity Maturation Of A Humanized Rat Antibody For Anti-RAGE Therapy: Comprehensive Mutagenesis Reveals A High Level Of Mutational Plasticity Both Inside And Outside The Complementarity-Determining Regions*," J. Mol. Biol. 388(3):541-558; Bostrom, J. et al. (2009) "*Improving Antibody Binding Affinity And Specificity For Therapeutic Development*," Methods Mol. Biol. 525: 353-376; Steidl, S. et al. (2008) "*In Vitro Affinity Maturation Of Human GM-CSF Antibodies By Targeted CDR-Diversification*," Mol. Immunol. 46(1):135-144; and Barderas, R. et al. (2008) "*Affinity Maturation Of Antibodies Assisted By In Silico Modeling*," Proc. Natl. Acad. Sci. (USA) 105(26): 9029-9034.

Thus, the sequence of CDR variants of encompassed antibodies or their antigen-binding fragments may differ from the sequence of the CDR of the parent antibody through substitutions; for instance substituted 4 amino acid residue, 3 amino acid residue, 2 amino acid residue or 1 of the amino acid residues. According to an embodiment of the invention it is furthermore envisaged that the amino acids in the CDR regions may be substituted with conservative substitutions, as defined in the below 3 tables.

The term "transgenic non-human animal" refers to a non-human animal having a genome comprising one or more human heavy and/or light chain transgenes or trans-chromosomes (either integrated or non-integrated into the animal's natural genomic DNA) and which is capable of expressing fully human antibodies. For example, a transgenic mouse can have a human light chain transgene and either a human heavy chain transgene or human heavy chain trans-chromosome, such that the mouse produces human anti-Sortilin antibody when immunized with Sortilin antigen and/or cells expressing Sortilin. The human heavy chain transgene may be integrated into the chromosomal DNA of the mouse, as is the case for transgenic mice, for instance HuMAb mice, such as HCo7 or HCo12 mice, or the human heavy chain transgene may be maintained extra-chromosomally, as is the case for trans-chromosomal KM mice as described in WO02/43478. Such transgenic and trans-chromosomal mice (collectively referred to herein as "transgenic mice") are capable of producing multiple isotypes of human monoclonal antibodies to a given antigen (such as IgG, IgA, IgM, IgD and/or IgE) by undergoing V-D-J recombination and isotype switching.

Transgenic, nonhuman animal can also be used for production of antibodies against a specific antigen by introducing genes encoding such specific antibody, for example by operatively linking the genes to a gene which is expressed in the milk of the animal.

The term "treatment" or "treating" as used herein means ameliorating, slowing, attenuating or reversing the progress or severity of a disease or disorder, or ameliorating, slowing, attenuating or reversing one or more symptoms or side effects of such disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of the progression a disease or disorder state, amelioration or palliation of a disease or disorder state, and remission of a disease or disorder, whether partial or total detectable or undetectable.

An "effective amount," when applied to an antibody or antigen-binding fragment thereof of the invention, refers to an amount sufficient, at dosages and for periods of time necessary, to achieve an intended biological effect or a desired therapeutic result including, without limitation, clinical results. The phrase "therapeutically effective amount," when applied to an antibody or antigen-binding fragment thereof of the invention, is intended to denote an amount of the antibody, or antigen-binding fragment thereof, that is sufficient to ameliorate, palliate, stabilize, reverse, slow, attenuate or delay the progression of a disorder or disease state, or of a symptom of the disorder or disease. In an embodiment, the method of the present invention provides for administration of the antibody, or antigen-binding fragment thereof, in combinations with other compounds. In such instances, the "effective amount" is the amount of the combination sufficient to cause the intended biological effect.

A therapeutically effective amount of an anti-Sortilin antibody or antigen-binding fragment thereof of the invention may vary according to factors such as the disease state, age, sex, and weight of the individual, and the ability of the anti-Sortilin antibody or antigen-binding fragment thereof to elicit a desired response in the individual. A therapeutically effective amount is also one in which any toxic or detrimental effects of the antibody or antibody portion are outweighed by the therapeutically beneficial effects.

The antibodies are preferably a human or humanized antibody.

The numbering of amino acid residues in this region is according to IMGT®, the international ImMunoGeneTics Information System® or, Kabat, E. A., Wu, T. T., Perry, H. M., Gottesmann, K. S. & Foeller, C. (1991). Sequences of Proteins of Immunological Interest, 5th edit., NIH Publication no. 91-3242 U.S. Department of Health and Human Services; Chothia, C. & Lesk, A. M. (1987). Canonical structures For The Hypervariable domains Of Immunoglobulins. J. Mol. Biol. 196, 901-917.

Antibody 5E1:

Accordingly, the invention relates to an antibody, or an antigen-binding fragment thereof, comprising or consisting of:
(a) a Light Chain CDR1 having the amino acid sequence of SEQ ID NO:1;
(b) a Light Chain CDR2 having the amino acid sequence of SEQ ID NO:2;
(c) a Light Chain CDR3 having the amino acid sequence of SEQ ID NO:3;
(d) a Heavy Chain CDR1 having the amino acid sequence of SEQ ID NO:4;
(e) a Heavy Chain CDR2 having the amino acid sequence of SEQ ID NO:5; and
(f) a Heavy Chain CDR3 having the amino acid sequence of SEQ ID NO:6.

Preferably, the monoclonal antibody may comprise or consist of the heavy chain variable domain of SEQ ID NO:8 and the light chain variable domain of SEQ ID NO:7.

Antibody 1F2:

According to another embodiment the invention relates to an antibody, or an antigen-binding fragment thereof, comprising or consisting of:
(a) a Light Chain CDR1 having the amino acid sequence of SEQ ID NO:9;
(b) a Light Chain CDR2 having the amino acid sequence of SEQ ID NO:10;
(c) a Light Chain CDR3 having the amino acid sequence of SEQ ID NO:11;
(d) a Heavy Chain CDR1 having the amino acid sequence of SEQ ID NO:12;
(e) a Heavy Chain CDR2 having the amino acid sequence of SEQ ID NO:13; and
(f) a Heavy Chain CDR3 having the amino acid sequence of SEQ ID NO:14.

Preferably, the monoclonal antibody may comprise or consist of the heavy chain variable domain of SEQ ID NO:16 and the light chain variable domain of SEQ ID NO:15.

Antibody 068:

According to another embodiment the invention relates to an antibody, or an antigen-binding fragment thereof, comprising or consisting of:
(a) a Light Chain CDR1 having the amino acid sequence of SEQ ID NO:17;
(b) a Light Chain CDR2 having the amino acid sequence of SEQ ID NO:18;
(c) a Light Chain CDR3 having the amino acid sequence of SEQ ID NO:19;
(d) a Heavy Chain CDR1 having the amino acid sequence of SEQ ID NO:20;
(e) a Heavy Chain CDR2 having the amino acid sequence of SEQ ID NO:21; and
(f) a Heavy Chain CDR3 having the amino acid sequence of SEQ ID NO:22.

Preferably, the monoclonal antibody may comprise or consist of the heavy chain variable domain of SEQ ID NO:24 and the light chain variable domain of SEQ ID NO:23.

Antibody 1320:

According to another embodiment the invention relates to an antibody, or an antigen-binding fragment thereof, comprising or consisting of:
(a) a Light Chain CDR1 having the amino acid sequence of SEQ ID NO:25;
(b) a Light Chain CDR2 having the amino acid sequence of SEQ ID NO:26;
(c) a Light Chain CDR3 having the amino acid sequence of SEQ ID NO:27;
(d) a Heavy Chain CDR1 having the amino acid sequence of SEQ ID NO:28;
(e) a Heavy Chain CDR2 having the amino acid sequence of SEQ ID NO:29; and
(f) a Heavy Chain CDR3 having the amino acid sequence of SEQ ID NO:30.

Preferably, the monoclonal antibody may comprise or consist of the heavy chain variable domain of SEQ ID NO:32 and the light chain variable domain of SEQ ID NO:31.

Antibody 93-05:

According to another embodiment the invention relates to an antibody, or an antigen-binding fragment thereof, comprising or consisting of:
(a) a Light Chain CDR1 having the amino acid sequence of SEQ ID NO:33;
(b) a Light Chain CDR2 having the amino acid sequence of SEQ ID NO:34;
(c) a Light Chain CDR3 having the amino acid sequence of SEQ ID NO:35;
(d) a Heavy Chain CDR1 having the amino acid sequence of SEQ ID NO:36;
(e) a Heavy Chain CDR2 having the amino acid sequence of SEQ ID NO:37; and
(f) a Heavy Chain CDR3 having the amino acid sequence of SEQ ID NO:38.

Preferably, the monoclonal antibody may comprise or consist of the heavy chain variable domain of SEQ ID NO:40 and the light chain variable domain of SEQ ID NO:39.

Antibody 93-01:

According to another embodiment the invention relates to an antibody, or an antigen-binding fragment thereof, comprising or consisting of:
(a) a Light Chain CDR1 having the amino acid sequence of SEQ ID NO:41;
(b) a Light Chain CDR2 having the amino acid sequence of SEQ ID NO:42;
(c) a Light Chain CDR3 having the amino acid sequence of SEQ ID NO:43;
(d) a Heavy Chain CDR1 having the amino acid sequence of SEQ ID NO:44;
(e) a Heavy Chain CDR2 having the amino acid sequence of SEQ ID NO:45; and
(f) a Heavy Chain CDR3 having the amino acid sequence of SEQ ID NO:46.

Preferably, the monoclonal antibody may comprise or consist of the heavy chain variable domain of SEQ ID NO:48 and the light chain variable domain of SEQ ID NO:47.

Antibody 924:

According to another embodiment the invention relates to an antibody, or an antigen-binding fragment thereof, comprising or consisting of:
(a) a Light Chain CDR1 having the amino acid sequence of SEQ ID NO:49;
(b) a Light Chain CDR2 having the amino acid sequence of SEQ ID NO:50;
(c) a Light Chain CDR3 having the amino acid sequence of SEQ ID NO:51;
(d) a Heavy Chain CDR1 having the amino acid sequence of SEQ ID NO:52;
(e) a Heavy Chain CDR2 having the amino acid sequence of SEQ ID NO:53; and
(f) a Heavy Chain CDR3 having the amino acid sequence of SEQ ID NO:54.

Preferably, the monoclonal antibody may comprise or consist of the heavy chain variable domain of SEQ ID NO:56 and the light chain variable domain of SEQ ID NO:55.

Antibody 1276:

According to another embodiment the invention relates to an antibody, or an antigen-binding fragment thereof, comprising or consisting of:
(a) a Light Chain CDR1 having the amino acid sequence of SEQ ID NO:57;
(b) a Light Chain CDR2 having the amino acid sequence of SEQ ID NO:58;
(c) a Light Chain CDR3 having the amino acid sequence of SEQ ID NO:59;
(d) a Heavy Chain CDR1 having the amino acid sequence of SEQ ID NO:60;
(e) a Heavy Chain CDR2 having the amino acid sequence of SEQ ID NO:61; and
(f) a Heavy Chain CDR3 having the amino acid sequence of SEQ ID NO:62.

Preferably, the monoclonal antibody may comprise or consist of the heavy chain variable domain of SEQ ID NO:64 and the light chain variable domain of SEQ ID NO:63.

Antibody 849:

According to another embodiment the invention relates to an antibody, or an antigen-binding fragment thereof, comprising or consisting of:
(a) a Light Chain CDR1 having the amino acid sequence of SEQ ID NO:65;
(b) a Light Chain CDR2 having the amino acid sequence of SEQ ID NO:66;
(c) a Light Chain CDR3 having the amino acid sequence of SEQ ID NO:67;
(d) a Heavy Chain CDR1 having the amino acid sequence of SEQ ID NO:68;
(e) a Heavy Chain CDR2 having the amino acid sequence of SEQ ID NO:69; and
(f) a Heavy Chain CDR3 having the amino acid sequence of SEQ ID NO:70.

Preferably, the monoclonal antibody may comprise or consist of the heavy chain variable domain of SEQ ID NO:72 and the light chain variable domain of SEQ ID NO:71.

Antibody 531-02:

According to another embodiment the invention relates to an antibody, or an antigen-binding fragment thereof, comprising or consisting of:
(a) a Light Chain CDR1 having the amino acid sequence of SEQ ID NO:73;
(b) a Light Chain CDR2 having the amino acid sequence of SEQ ID NO:74;
(c) a Light Chain CDR3 having the amino acid sequence of SEQ ID NO:75;
(d) a Heavy Chain CDR1 having the amino acid sequence of SEQ ID NO:76;
(e) a Heavy Chain CDR2 having the amino acid sequence of SEQ ID NO:77; and
(f) a Heavy Chain CDR3 having the amino acid sequence of SEQ ID NO:78.

Preferably, the monoclonal antibody may comprise or consist of the heavy chain variable domain of SEQ ID NO:80 and the light chain variable domain of SEQ ID NO:79.

Antibody 548-01:

According to another embodiment the invention relates to an antibody, or an antigen-binding fragment thereof, comprising or consisting of:
(a) a Light Chain CDR1 having the amino acid sequence of SEQ ID NO:81;
(b) a Light Chain CDR2 having the amino acid sequence of SEQ ID NO:82;
(c) a Light Chain CDR3 having the amino acid sequence of SEQ ID NO:83;
(d) a Heavy Chain CDR1 having the amino acid sequence of SEQ ID NO:84;
(e) a Heavy Chain CDR2 having the amino acid sequence of SEQ ID NO:85; and
(f) a Heavy Chain CDR3 having the amino acid sequence of SEQ ID NO:86.

Preferably, the monoclonal antibody may comprise or consist of the heavy chain variable domain of SEQ ID NO:88 and the light chain variable domain of SEQ ID NO:87.

Antibody 548-02:

According to another embodiment the invention relates to an antibody, or an antigen-binding fragment thereof, comprising or consisting of:
(a) a Light Chain CDR1 having the amino acid sequence of SEQ ID NO:89;
(b) a Light Chain CDR2 having the amino acid sequence of SEQ ID NO:90;

(c) a Light Chain CDR3 having the amino acid sequence of SEQ ID NO:91;
(d) a Heavy Chain CDR1 having the amino acid sequence of SEQ ID NO:92;
(e) a Heavy Chain CDR2 having the amino acid sequence of SEQ ID NO:93; and
(f) a Heavy Chain CDR3 having the amino acid sequence of SEQ ID NO:94.

Preferably, the monoclonal antibody may comprise or consist of the heavy chain variable domain of SEQ ID NO:96 and the light chain variable domain of SEQ ID NO:95.

Antibody 1289-02:

According to another embodiment the invention relates to an antibody, or an antigen-binding fragment thereof, comprising or consisting of:
(a) a Light Chain CDR1 having the amino acid sequence of SEQ ID NO:97;
(b) a Light Chain CDR2 having the amino acid sequence of SEQ ID NO:98;
(c) a Light Chain CDR3 having the amino acid sequence of SEQ ID NO:99;
(d) a Heavy Chain CDR1 having the amino acid sequence of SEQ ID NO:100;
(e) a Heavy Chain CDR2 having the amino acid sequence of SEQ ID NO:101; and
(f) a Heavy Chain CDR3 having the amino acid sequence of SEQ ID NO:102.

Preferably, the monoclonal antibody may comprise or consist of the heavy chain variable domain of SEQ ID NO:104 and the light chain variable domain of SEQ ID NO:103.

Antibody 811-02:

According to another embodiment the invention relates to an antibody, or an antigen-binding fragment thereof, comprising or consisting of:
(a) a Light Chain CDR1 having the amino acid sequence of SEQ ID NO:105;
(b) a Light Chain CDR2 having the amino acid sequence of SEQ ID NO:106;
(c) a Light Chain CDR3 having the amino acid sequence of SEQ ID NO:107;
(d) a Heavy Chain CDR1 having the amino acid sequence of SEQ ID NO:108;
(e) a Heavy Chain CDR2 having the amino acid sequence of SEQ ID NO:109; and
(f) a Heavy Chain CDR3 having the amino acid sequence of SEQ ID NO:110.

Preferably, the monoclonal antibody may comprise or consist of the heavy chain variable domain of SEQ ID NO:112 and the light chain variable domain of SEQ ID NO:111.

Antibody 566-01:

According to another embodiment the invention relates to an antibody, or an antigen-binding fragment thereof, comprising or consisting of:
(a) a Light Chain CDR1 having the amino acid sequence of SEQ ID NO:113;
(b) a Light Chain CDR2 having the amino acid sequence of SEQ ID NO:114;
(c) a Light Chain CDR3 having the amino acid sequence of SEQ ID NO:115;
(d) a Heavy Chain CDR1 having the amino acid sequence of SEQ ID NO:116;
(e) a Heavy Chain CDR2 having the amino acid sequence of SEQ ID NO:117; and
(f) a Heavy Chain CDR3 having the amino acid sequence of SEQ ID NO:118.

Preferably, the monoclonal antibody may comprise or consist of the heavy chain variable domain of SEQ ID NO:120 and the light chain variable domain of SEQ ID NO:119.

Antibody 562:

According to another embodiment the invention relates to an antibody, or an antigen-binding fragment thereof, comprising or consisting of:
(a) a Light Chain CDR1 having the amino acid sequence of SEQ ID NO:121;
(b) a Light Chain CDR2 having the amino acid sequence of SEQ ID NO:122;
(c) a Light Chain CDR3 having the amino acid sequence of SEQ ID NO:123;
(d) a Heavy Chain CDR1 having the amino acid sequence of SEQ ID NO:124;
(e) a Heavy Chain CDR2 having the amino acid sequence of SEQ ID NO:125; and
(f) a Heavy Chain CDR3 having the amino acid sequence of SEQ ID NO:126.

Preferably, the monoclonal antibody may comprise or consist of the heavy chain variable domain of SEQ ID NO:128 and the light chain variable domain of SEQ ID NO:127.

Antibody 193:

According to another embodiment the invention relates to an antibody, or an antigen-binding fragment thereof, comprising or consisting of:
(a) a Light Chain CDR1 having the amino acid sequence of SEQ ID NO:129;
(b) a Light Chain CDR2 having the amino acid sequence of SEQ ID NO:130;
(c) a Light Chain CDR3 having the amino acid sequence of SEQ ID NO:131;
(d) a Heavy Chain CDR1 having the amino acid sequence of SEQ ID NO:132;
(e) a Heavy Chain CDR2 having the amino acid sequence of SEQ ID NO:133; and
(f) a Heavy Chain CDR3 having the amino acid sequence of SEQ ID NO:134.

Preferably, the monoclonal antibody may comprise or consist of the heavy chain variable domain of SEQ ID NO:136 and the light chain variable domain of SEQ ID NO:135.

Antibody 88:

According to another embodiment the invention relates to an antibody, or an antigen-binding fragment thereof, comprising or consisting of:
(a) a Light Chain CDR1 having the amino acid sequence of SEQ ID NO:137;
(b) a Light Chain CDR2 having the amino acid sequence of SEQ ID NO:138;
(c) a Light Chain CDR3 having the amino acid sequence of SEQ ID NO:139;
(d) a Heavy Chain CDR1 having the amino acid sequence of SEQ ID NO:140;
(e) a Heavy Chain CDR2 having the amino acid sequence of SEQ ID NO:141; and
(f) a Heavy Chain CDR3 having the amino acid sequence of SEQ ID NO:142.

Preferably, the monoclonal antibody may comprise or consist of the heavy chain variable domain of SEQ ID NO:144 and the light chain variable domain of SEQ ID NO:143.

Antibody 045:

According to another embodiment the invention relates to an antibody, or an antigen-binding fragment thereof, comprising or consisting of:
(a) a Light Chain CDR1 having the amino acid sequence of SEQ ID NO:145;
(b) a Light Chain CDR2 having the amino acid sequence of SEQ ID NO:146;
(c) a Light Chain CDR3 having the amino acid sequence of SEQ ID NO:147;
(d) a Heavy Chain CDR1 having the amino acid sequence of SEQ ID NO:148;
(e) a Heavy Chain CDR2 having the amino acid sequence of SEQ ID NO:149; and
(f) a Heavy Chain CDR3 having the amino acid sequence of SEQ ID NO:150.

Preferably, the monoclonal antibody may comprise or consist of the heavy chain variable domain of SEQ ID NO:152 and the light chain variable domain of SEQ ID NO:151.

Antibody 044:

According to another embodiment the invention relates to an antibody, or an antigen-binding fragment thereof, comprising or consisting of:
(a) a Light Chain CDR1 having the amino acid sequence of SEQ ID NO:153;
(b) a Light Chain CDR2 having the amino acid sequence of SEQ ID NO:154;
(c) a Light Chain CDR3 having the amino acid sequence of SEQ ID NO:155;
(d) a Heavy Chain CDR1 having the amino acid sequence of SEQ ID NO:156;
(e) a Heavy Chain CDR2 having the amino acid sequence of SEQ ID NO:157; and
(f) a Heavy Chain CDR3 having the amino acid sequence of SEQ ID NO:158.

Preferably, the monoclonal antibody may comprise or consist of the heavy chain variable domain of SEQ ID NO:160 and the light chain variable domain of SEQ ID NO:159.

Antibody 002:

According to another embodiment the invention relates to an antibody, or an antigen-binding fragment thereof, comprising or consisting of:
(a) a Light Chain CDR1 having the amino acid sequence of SEQ ID NO:161;
(b) a Light Chain CDR2 having the amino acid sequence of SEQ ID NO:162;
(c) a Light Chain CDR3 having the amino acid sequence of SEQ ID NO:163;
(d) a Heavy Chain CDR1 having the amino acid sequence of SEQ ID NO:164;
(e) a Heavy Chain CDR2 having the amino acid sequence of SEQ ID NO:165; and
(f) a Heavy Chain CDR3 having the amino acid sequence of SEQ ID NO:166.

Preferably, the monoclonal antibody may comprise or consist of the heavy chain variable domain of SEQ ID NO:168 and the light chain variable domain of SEQ ID NO:167.

The antibodies mentioned above may, according to one embodiment, further comprise a variant with no more than 4 amino acid differences, or no more than 3 amino acid differences, or no more than 2 amino acid differences, or no more than 1 amino acid difference from said CDR1, CDR2, and/or CDR3 (VH and/or VL) sequences.

Further, the antibodies may be in a composition together with a pharmaceutically acceptable carrier. The antibodies of the invention may be used in therapy. In particular, the antibodies of the invention may be used in treating FTD or ALS or TDP43 proteinopathies such as Alzheimer's Disease (AD).

The treatment envisioned by the present invention may be chronic and the patient may be treated at least 2 weeks, such as at least for 1 month, 6, months, 1 year or more.

The antibodies of the present invention may, for example, be monoclonal antibodies produced by the hybridoma method first described by Kohler et al., Nature 256, 495 (1975), or may be monoclonal antibodies produced by recombinant DNA or other methods. Monoclonal antibodies may also be isolated from phage antibody libraries using the techniques described in, for example, Clackson et al., Nature 352, 624-628 (1991) and Marks et al., J. Mol. Biol. 222, 581-597 (1991). Monoclonal antibodies may be obtained from any suitable source. Thus, for example, monoclonal antibodies may be obtained from hybridomas prepared from murine splenic B lymphocyte cells obtained from mice immunized with an antigen of interest, for instance, in the form of cells expressing the antigen on the surface, or a nucleic acid encoding an antigen of interest. Monoclonal antibodies may also be obtained from hybridomas derived from antibody-expressing cells of immunized humans or from non-human mammals such as rats, rabbits, dogs, sheep, goats, primates, etc.

In one embodiment, the antibody of the invention is a human antibody. Human monoclonal antibodies directed against Sortilin may be generated using transgenic or transchromosomal mice carrying parts of the human immune system rather than the mouse system. Such transgenic and trans-chromosomic mice include mice referred to herein as HuMAb mice and KM mice, respectively.

The HuMAb mouse contains a human immunoglobulin gene minilocus that encodes unrearranged human heavy variable and constant (p and Y) and light variable and constant (K) chain immunoglobulin sequences, together with targeted mutations that inactivate the endogenous p and K chain loci (Lonberg, N. et al., Nature 368, 856-859 (1994)). Accordingly, the mice exhibit reduced expression of mouse IgM or K and in response to immunization, the introduced human heavy and light chain transgenes, undergo class switching and somatic mutation to generate high affinity human IgG, K monoclonal antibodies (Lonberg, N. et al. (1994), supra; reviewed in Lonberg, N., Handbook of Experimental Pharmacology 113, 49-101 (1994), Lonberg, N. and Huszar, D., Intern. Rev. Immunol. Vol. 13 65-93 (1995) and Harding, F. and Lonberg, N., Ann. N. Y. Acad. Sci 764 536-546 (1995)). The preparation of HuMAb mice is described in detail in Taylor, L. et al., Nucleic Acids Research 20, 6287-6295 (1992), Chen, J. et al., International Immunology 5, 647-656 (1993), Tuaillon et al., J. Immunol. 152, 2912-2920 (1994), Taylor, L. et al., International Immunology 6, 579-591 (1994), Fishwild, D. et al., Nature Biotechnology 14, 845-851 (1996). See also U.S. Pat. Nos. 5,545,806, 5,569,825, 5,625,126, 5,633,425, 5,789,650, 5,877,397, 5,661,016, 5,814,318, 5,874,299, 5,770,429, 5,545,807, WO 98/24884, WO 94/25585, WO 93/1227, WO 92/22645, WO 92/03918 and WO 01/09187.

The HCo7, HCo12, HCo17 and HCo20 mice have a JKD disruption in their endogenous light chain (kappa) genes (as described in Chen et al., EMBO J. 12, 811-820 (1993)), a CMD disruption in their endogenous heavy chain genes (as described in Example 1 of WO 01/14424), and a KCo5 human kappa light chain transgene (as described in Fishwild et al., Nature Biotechnology 14, 845-851 (1996)). Additionally, the HCo7 mice have a HCo7 human heavy chain transgene (as described in U.S. Pat. No. 5,770,429), the HCo12 mice have a HCo12 human heavy chain transgene (as described in Example 2 of WO 01/14424), the HCo17 mice have a HCo17 human heavy chain transgene (as described in Example 2 of WO 01/09187) and the HCo20 mice have a HCo20 human heavy chain transgene. The resulting mice express human immunoglobulin heavy and kappa light chain transgenes in a background homozygous for disruption of the endogenous mouse heavy and kappa light chain loci.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain transchromosome composed of chromosome 14 fragment hCF (SC20) as described in WO 02/43478. HCo12-Balb/c, HCo17-Balb/c and HCo20-Balb/c mice can be generated by crossing HCo12, HCo17 and HCo20 to KCo5[J/K](Balb) as described in WO 09/097006.

In the KM mouse strain, the endogenous mouse kappa light chain gene has been homozygously disrupted as described in Chen et al., EMBO J. 12, 811-820 (1993) and the endogenous mouse heavy chain gene has been homozygously disrupted as described in Example 1 of WO 01/09187. This mouse strain carries a human kappa light chain transgene, KCo5, as described in Fishwild et al., Nature Biotechnology 14, 845-851 (1996). This mouse strain also carries a human heavy chain trans-chromosome composed of chromosome 14 antigen-binding fragment hCF (SC20) as described in WO 02/43478.

Splenocytes from these transgenic mice may be used to generate hybridomas that secrete human monoclonal antibodies according to well-known techniques. Human monoclonal or polyclonal antibodies of the present invention, or antibodies of the present invention originating from other species may also be generated transgenically through the generation of another non-human mammal or plant that is transgenic for the immunoglobulin heavy and light chain sequences of interest and production of the antibody in a recoverable form therefrom. In connection with the transgenic production in mammals, antibodies may be produced in, and recovered from, the milk of goats, cows, or other mammals. See for instance U.S. Pat. Nos. 5,827,690, 5,756,687, 5,750,172 and 5,741,957.

The antibody of the invention may be of any isotype. The choice of isotype typically will be guided by the desired effector functions, such as ADCC induction. Exemplary isotypes are IgG1, IgG2, IgG3, and IgG4. Either of the human light chain constant domains, kappa or lambda, may be used. If desired, the class of an anti-Sortilin antibody of the present invention may be switched by known methods. For example, an antibody of the present invention that was originally IgM may be class switched to an IgG antibody of the present invention. Further, class switching techniques may be used to convert one IgG subclass to another, for instance from IgG1 to IgG2. Thus, the effector function of the antibodies of the present invention may be changed by isotype switching to, e.g., an IgG1, IgG2, IgG3, IgG4, IgD, IgA, IgE, or IgM antibody for various therapeutic uses. In one embodiment an antibody of the present invention is an IgG1 antibody, for instance an IgG1, κ. An antibody is said to be of a particular isotype if its amino acid sequence is most homologous to that isotype, relative to other isotypes.

In one embodiment, the antibody of the invention is a full-length antibody, preferably an IgG antibody, in particular an IgG1, κ antibody. In another embodiment, the antibody of the invention is an antibody antigen-binding fragment or a single-chain antibody.

Antibodies and antigen-binding fragments thereof may e.g. be obtained by antigen-binding fragmentation using conventional techniques, and antigen-binding fragments screened for utility in the same manner as described herein for whole antibodies. For example, F(ab')2 antigen-binding fragments may be generated by treating antibody with pepsin. The resulting F(ab')2 antigen-binding fragment may be treated to reduce disulfide bridges to produce Fab' antigen-binding fragments. Fab antigen-binding fragments may be obtained by treating an IgG antibody with papain; Fab' antigen-binding fragments may be obtained with pepsin digestion of IgG antibody. An F(ab') antigen-binding fragment may also be produced by binding Fab'-described below via a thioether bond or a disulfide bond. A Fab' antigen-binding fragment is an antibody antigen-binding fragment obtained by cutting a disulfide bond of the hinge domain of the F(ab')$_2$. A Fab'-antigen-binding fragment may be obtained by treating an F(ab')$_2$ antigen-binding fragment with a reducing agent, such as dithiothreitol. Antibody antigen-binding fragment may also be generated by expression of nucleic acids encoding such antigen-binding fragments in recombinant cells (see for instance Evans et al., J. Immunol. Meth. 184, 123-38 (1995)). For example, a chimeric gene encoding a portion of an F(ab')2 antigen-binding fragment could include DNA sequences encoding the CH1 domain and hinge domain of the H chain, followed by a translational stop codon to yield such a truncated antibody antigen-binding fragment molecule.

In one embodiment, the anti-Sortilin antibody is a monovalent antibody, preferably a monovalent antibody as described in WO2007059782 (which is incorporated herein by reference in its entirety) having a deletion of the hinge region. Accordingly, in one embodiment, the antibody is a monovalent antibody, wherein said anti-Sortilin antibody is constructed by a method comprising: i) providing a nucleic acid construct encoding the light chain of said monovalent antibody, said construct comprising a nucleotide sequence encoding the VL region of a selected antigen specific anti-Sortilin antibody and a nucleotide sequence encoding the constant CL region of an Ig, wherein said nucleotide sequence encoding the VL region of a selected antigen specific antibody and said nucleotide sequence encoding the CL region of an Ig are operably linked together, and wherein, in case of an IgG1 subtype, the nucleotide sequence encoding the CL region has been modified such that the CL region does not contain any amino acids capable of forming disulfide bonds or covalent bonds with other peptides comprising an identical amino acid sequence of the CL region in the presence of polyclonal human IgG or when administered to an animal or human being; ii) providing a nucleic acid construct encoding the heavy chain of said monovalent antibody, said construct comprising a nucleotide sequence encoding the VH region of a selected antigen specific antibody and a nucleotide sequence encoding a constant CH region of a human Ig, wherein the nucleotide sequence encoding the CH region has been modified such that the region corresponding to the hinge region and, as required by the Ig subtype, other regions of the CH region, such as the CH3 region, does not comprise any amino acid residues which participate in the formation of disulphide bonds or covalent or stable non-covalent inter-heavy chain bonds with other peptides comprising an identical amino acid sequence of the CH region of the human Ig in the presence of polyclonal human IgG or when administered to an animal human being, wherein said nucleotide sequence encoding the VH region of a selected antigen specific antibody and said nucleotide sequence encoding the CH region of said Ig are operably linked together; iii) providing a cell expression system for producing said monovalent antibody; iv) producing said monovalent antibody by co-expressing the nucleic acid constructs of (i) and (ii) in cells of the cell expression system of (iii).

Similarly, in one embodiment, the anti-Sortilin antibody is a monovalent antibody, which comprises:
(i) a variable domain of an antibody of the invention as described herein or an antigen-binding part of the said domain, and
(ii) a CH domain of an immunoglobulin or a domain thereof comprising the CH2 and CH3 domains, wherein the CH domain or domain thereof has been modified such that the domain corresponding to the hinge domain and, if the immunoglobulin is not an IgG4 subtype, other domains of the CH domain, such as the CH3 domain, do not comprise any amino acid residues, which are capable of forming disulfide bonds with an identical CH domain or other covalent or stable non-covalent inter-heavy chain bonds with an identical CH domain in the presence of polyclonal human IgG.

In a further embodiment, the heavy chain of the monovalent antibody has been modified such that the entire hinge region has been deleted.

In another further embodiment, the sequence of the monovalent antibody has been modified so that it does not comprise any acceptor sites for N-linked glycosylation.

The invention also includes "Bispecific Antibodies," wherein an anti-Sortilin binding region (e.g., a Sortilin-binding region of an anti-Sortilin monoclonal antibody) is part of a bivalent or polyvalent bispecific scaffold that targets more than one epitope, (for example a second epitope could comprise an epitope of an active transport receptor, such that the Bispecific Antibody would exhibit improved transcytosis across a biological barrier, such as the Blood Brain Barrier). Thus, in another further embodiment, the monovalent Fab of an anti-Sortilin antibody may be joined to an additional Fab or scfv that targets a different protein to generate a bispecific antibody. A bispecific antibody can have a dual function, for example a therapeutic function imparted by an anti-sortilin binding domain and a transport function that can bind to a receptor molecule to enhance transfer cross a biological barrier, such as the blood brain barrier.

Antibodies and antigen-binding fragments thereof of the invention also include single chain antibodies. Single chain antibodies are peptides in which the heavy and light chain Fv domains are connected. In one embodiment, the present invention provides a single-chain Fv (scFv) wherein the heavy and light chains in the Fv of an anti-Sortilin antibody of the present invention are joined with a flexible peptide linker (typically of about 10, 12, 15 or more amino acid residues) in a single peptide chain. Methods of producing such antibodies are described in for instance U.S. Pat. No. 4,946,778, Pluckthun in The Pharmacology of Monoclonal Antibodies, vol. 113, Rosenburg and Moore eds. Springer-Verlag, New York, pp. 269-315 (1994), Bird et al., Science 242, 423-426 (1988), Huston et al., PNAS USA 85, 5879-5883 (1988) and McCafferty et al., Nature 348, 552-554 (1990). The single chain antibody may be monovalent, if only a single VH and VL are used, bivalent, if two VH and VL are used, or polyvalent, if more than two VH and VL are used.

The antibodies and antigen-binding fragments thereof described herein may be modified by inclusion of any suitable number of modified amino acids and/or associations with such conjugated substituents. Suitability in this context is generally determined by the ability to at least substantially retain the Sortilin selectivity and/or Sortilin specificity associated with the non-derivatized parent anti-Sortilin antibody. The inclusion of one or more modified amino acids may be advantageous in, for example, increasing polypeptide serum half-life, reducing polypeptide antigenicity, or increasing polypeptide storage stability. Amino acid(s) are modified, for example, co-translationally or post-translationally during recombinant production (e.g., N-linked glycosylation at N-X-S/T motifs during expression in mammalian cells) or modified by synthetic means. Non-limiting examples of a modified amino acid include a glycosylated amino acid, a sulfated amino acid, a prenylated (e. g., farnesylated, geranyl-geranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols On CD-Rom, Humana Press, Totowa, N.J. The modified amino acid may, for instance, be selected from a glycosylated amino acid, a PEGylated amino acid, a farnesylated amino acid, an acetylated amino acid, a biotinylated amino acid, an amino acid conjugated to a lipid moiety, or an amino acid conjugated to an organic derivatizing agent.

The antibodies and antigen-binding fragments thereof of the invention, may also be chemically modified by covalent conjugation to a polymer to for instance increase their circulating half-life. Exemplary polymers, and methods to attach them to peptides, are illustrated in for instance U.S. Pat. Nos. 4,766,106; 4,179,337; 4,495,285 and 4,609,546. Additional illustrative polymers include polyoxyethylated polyols and polyethylene glycol (PEG) (e.g., a PEG with a molecular weight of between about 1,000 and about 40,000, such as between about 2,000 and about 20,000, e.g., about 3,000-12,000 g/mol).

The antibodies and antigen-binding fragments thereof of the present invention may further be used in a diagnostic method or as a diagnostic imaging ligand.

In one embodiment, antibodies and antigen-binding fragments thereof of the invention comprising one or more radiolabeled amino acids are provided. A radiolabeled anti-Sortilin antibody may be used for both diagnostic and therapeutic purposes (conjugation to radiolabeled molecules is another possible feature). Non-limiting examples of such labels include, but are not limited to bismuth ($^{213}$Bi), carbon ($^{11}$C, $^{13}$C, $^{14}$C), chromium ($^{51}$Cr), cobalt ($^{57}$Co, $^{60}$Co), copper ($^{64}$Cu), dysprosium ($^{165}$Dy), erbium ($^{169}$Er), fluorine ($^{18}$F), gadolinium ($^{153}$Gd, $^{159}$Gd), gallium ($^{68}$Ga, $^{67}$Ga), germanium ($^{68}$Ge), gold ($^{198}$Au), holmium ($^{166}$Ho), hydrogen ($^{3}$H), indium ($^{111}$In, $^{112}$In, $^{113}$In, $^{115}$In), iodine ($^{121}$I, $^{123}$I $^{125}$I, $^{131}$I), iridium ($^{192}$Ir), iron ($^{59}$Fe), krypton ($^{81m}$Kr), lanthanium ($^{140}$La), lutelium ($^{177}$Lu), manganese ($^{54}$Mn), molybdenum ($^{99}$Mo), nitrogen ($^{13}$N, $^{15}$N), oxygen ($^{15}$O), palladium ($^{103}$Pd), phosphorus ($^{32}$P), potassium ($^{42}$K), praseodymium ($^{142}$Pr), promethium ($^{149}$Pm), rhenium ($^{186}$Re, $^{188}$Re), rhodium ($^{105}$Rh), rubidium ($^{81}$Rb, $^{82}$Rb), ruthenium ($^{82}$Ru, $^{97}$Ru), samarium ($^{153}$Sm), scandium ($^{47}$Sc), selenium ($^{75}$Se), sodium ($^{24}$Na), strontium ($^{85}$Sr, $^{89}$Sr, $^{92}$Sr), sulfur ($^{35}$S), technetium ($^{99}$Tc), thallium ($^{201}$Tl), tin ($^{113}$Sn, $^{117}$Sn), xenon ($^{133}$Xe), ytterbium ($^{169}$Yb, $^{175}$Yb, $^{177}$Yb), yttrium ($^{90}$Y) and zinc ($^{65}$Zn). Methods for preparing radiolabeled amino acids and related peptide derivatives are known in the art (see for instance Junghans et al., in Cancer Chemotherapy and Biotherapy 655-686 (2nd edition, Chafner and Longo, eds., Lippincott Raven (1996)) and U.S. Pat. Nos. 4,681,581, 4,735,210, 5,101,827, 5,102,990 (U.S. RE35, 500), U.S. Pat. Nos. 5,648,471 and 5,697,902. For example, a radioisotope may be conjugated by a chloramine T method (Lindegren, S. et al. (1998) "*Chloramine-T In High-Specific-Activity Radioiodination Of Antibodies Using N-Succinimidyl-3-(Trimethylstannyl)Benzoate As An Intermediate*," Nucl. Med. Biol. 25(7):659-665; Kurth, M. et al. (1993) "*Site-Specific Conjugation Of A Radioiodinated Phenethylamine Derivative To A Monoclonal Antibody Results In Increased Radioactivity Localization In Tumor*," J. Med. Chem. 36(9):1255-1261; Rea, D. W. et al. (1990) "Site-specifically radioiodinated antibody for targeting tumors," Cancer Res. 50(3 Suppl):857s-861 s).

The invention also provides anti-Sortilin antibodies and antigen-binding fragments thereof that are detectably labeled using a fluorescent label (such as a rare earth chelate (e.g., a europium chelate)), a fluorescein-type label (e.g., fluorescein, fluorescein isothiocyanate, 5-carboxyfluorescein, 6-carboxy fluorescein, dichlorotriazinylamine fluorescein), a rhodamine-type label (e.g., ALEXA FLUOR® 568 (Invitrogen), TAMRA® or dansyl chloride), VIVOTAG 680 XL FLUOROCHROME™ (Perkin Elmer), phycoerythrin; umbelliferone, Lissamine; a cyanine; a phycoerythrin, Texas Red, BODIPY FL-SE® (Invitrogen) or an analogue thereof, all of which are suitable for optical detection. Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin.

Chemiluminescent labels may be employed (e.g., luminol, luciferase, luciferin, and aequorin). Such diagnosis and detection can also be accomplished by coupling the diagnostic molecule of the present invention to detectable substances including, but not limited to, various enzymes, enzymes including, but not limited to, horseradish peroxidase, alkaline phosphatase, beta-galactosidase, or acetylcholinesterase, or to prosthetic group complexes such as, but not limited to, streptavidin/biotin and avidin/biotin. Paramagnetic labels can also be employed, and are preferably detected using Positron Emission Tomography (PET) or Single-Photon Emission Computed Tomography (SPECT). Such paramagnetic labels include, but are not limited to compounds containing paramagnetic ions of Aluminum (Al), Barium (Ba), Calcium (Ca), Cerium (Ce), Dysprosium (Dy), Erbium (Er), Europium (Eu), Gandolinium (Gd), Holmium (Ho), Iridium (Ir), Lithium (Li), Magnesium (Mg), Manganese (Mn), Molybdenum (M), Neodymium (Nd), Osmium (Os), Oxygen (O), Palladium (Pd), Platinum (Pt), Rhodium (Rh), Ruthenium (Ru), Samarium (Sm), Sodium (Na), Strontium (Sr), Terbium (Tb), Thulium (Tm), Tin (Sn), Titanium (Ti), Tungsten (W), and Zirconium (Zi), and particularly, $Co^{+2}$, $CR^{+2}$ $Cr^{+3}$, $Cu^{+2}$, $Fe^{+2}$, $Fe^{+3}$, $Ga^{+3}$, $Mn^{+3}$, $Ni^{+2}$, $Ti^{+3}$, $V^{+3}$, and $V^{+4}$, positron emitting metals using various positron emission tomographies, and non-radioactive paramagnetic metal ions.

Thus in one embodiment the anti-Sortilin antibody or Sortilin-binding fragment thereof of the invention may be labelled with a fluorescent label, a chemiluminescent label, a paramagnetic label, a radioisotopic label or an enzyme label. The labelled antibody of fragment may be used in detecting or measuring the presence or amount of said Sortilin in the brain of a subject. This method may comprise the detection or measurement of in vivo imaging of anti-Sortilin antibody or Sortilin-binding fragment bound to said Sortilin and may comprises ex vivo imaging of said anti-Sortilin antibody or Sortilin-binding fragment bound to such Sortilin.

In a further aspect, the invention relates to an expression vector encoding one or more polypeptide chains of an antibody of the invention or an antigen-binding-domain thereof. Such expression vectors may be used for recombinant production of the antibodies and antigen-binding fragments of the invention.

An expression vector in the context of the present invention may be any suitable DNA or RNA vector, including chromosomal, non-chromosomal, and synthetic nucleic acid vectors (a nucleic acid sequence comprising a suitable set of expression control elements). Examples of such vectors include derivatives of SV40, bacterial plasmids, phage DNA, baculovirus, yeast plasmids, vectors derived from combinations of plasmids and phage DNA, and viral nucleic acid (RNA or DNA) vectors. In one embodiment, an anti-Sortilin antibody-encoding nucleic acid is comprised in a naked DNA or RNA vector, including, for example, a linear expression element (as described in, for instance, Sykes and Johnston, Nat Biotech 12, 355-59 (1997)), a compacted nucleic acid vector (as described in for instance U.S. Pat. No. 6,077,835 and/or WO 00/70087), a plasmid vector such as pBR322, pUC 19/18, or pUC 118/119, a "midge" minimally-sized nucleic acid vector (as described in, for instance, Schakowski et al., Mol Ther 3, 793-800 (2001)), or as a precipitated nucleic acid vector construct, such as a $CaPO_4$-precipitated construct (as described in, for instance, WO 00/46147, Benvenisty and Reshef, PNAS USA 83, 9551-55 (1986), Wigler et al., Cell 14, 725 (1978), and Coraro and Pearson, Somatic Cell Genetics 2, 603 (1981)). Such nucleic acid vectors and the usage thereof are well known in the art (see for instance U.S. Pat. Nos. 5,589,466 and 5,973,972).

In one embodiment, the vector is suitable for expression of anti-Sortilin antibodies or antigen-binding fragments thereof in a bacterial cell. Examples of such vectors include expression vectors such as BlueScript (Stratagene), pIN vectors (Van Heeke & Schuster, J Biol Chem 264, 5503-5509 (1989), pET vectors (Novagen, Madison, Wis.) and the like).

An expression vector may also or alternatively be a vector suitable for expression in a yeast system. Any vector suitable for expression in a yeast system may be employed. Suitable vectors include, for example, vectors comprising constitutive or inducible promoters such as alpha factor, alcohol oxidase and PGH (reviewed in: F. Ausubel et al., ed. Current Protocols in Molecular Biology, Greene Publishing and Wiley InterScience New York (1987), Grant et al., Methods in Enzymol 153, 516-544 (1987), Mattanovich, D. et al. Methods Mol. Biol. 824, 329-358 (2012), Celik, E. et al. Biotechnol. Adv. 30(5), 1108-1118 (2012), Li, P. et al. Appl. Biochem. Biotechnol. 142(2), 105-124 (2007), Böer, E. et al. Appl. Microbiol. Biotechnol. 77(3), 513-523 (2007), van der Vaart, J. M. Methods Mol. Biol. 178, 359-366 (2002), and Holliger, P. Methods Mol. Biol. 178, 349-357 (2002)).

In an expression vector of the invention, anti-Sortilin antibody-encoding nucleic acids may comprise or be associated with any suitable promoter, enhancer, and other expression-facilitating elements. Examples of such elements include strong expression promoters (e. g., human CMV IE promoter/enhancer as well as RSV, SV40, SL3-3, MMTV, and HIV LTR promoters), effective poly (A) termination sequences, an origin of replication for plasmid product in E. coli, an antibiotic resistance gene as selectable marker, and/or a convenient cloning site (e.g., a polylinker). Nucleic acids may also comprise an inducible promoter as opposed to a constitutive promoter such as CMV IE (the skilled artisan will recognize that such terms are actually descriptors of a degree of gene expression under certain conditions).

In an even further aspect, the invention relates to a recombinant eukaryotic or prokaryotic host cell, such as a transfectoma, which produces an antibody or antigen-binding fragment thereof of the invention as defined herein or a bispecific molecule of the invention as defined herein. Examples of host cells include yeast, bacteria, and mammalian cells, such as CHO or HEK cells.

For example, in one embodiment, the present invention provides a cell comprising a nucleic acid stably integrated into the cellular genome that comprises a sequence coding for expression of an anti-Sortilin antibody of the present invention or an antigen-binding fragment thereof. In another embodiment, the present invention provides a cell comprising a non-integrated nucleic acid, such as a plasmid, cosmid, phagemid, or linear expression element, which comprises a sequence coding for expression of an anti-Sortilin antibody or antigen-binding fragment thereof of the invention.

In a further aspect, the invention relates to a method for producing an anti-Sortilin antibody of the invention, said method comprising the steps of a) culturing a hybridoma or a host cell of the invention as described herein above, and b) purifying the antibody of the invention from the culture media.

In one embodiment, the invention relates to a preparation that, as such term is used herein, comprises an anti-Sortilin antibody as defined herein, and that is substantially free of naturally-arising antibodies that are either not capable of binding to sortilin or that do not materially alter the anti-Sortilin functionality of the preparation. Thus, such a preparation does not encompass naturally-arising serum, or a purified derivative of such serum, that comprises a mixture of an anti-Sortilin antibody and another antibody that does not alter the functionality of the anti-Sortilin antibody of the preparation, wherein such functionality is:
(i) a binding affinity ($K_D$) for Sortilin;
(ii) a capability to reduce and/or inhibit PGRN binding to Sortilin;
(iii) a capability to reduce and/or inhibit clearance of PGRN by Sortilin-expressing cells;
(iv) a capability to reduce and/or inhibit the endocytosis of PGRN by Sortilin-expressing cells;
(v) a capability to increase the amount and/or concentration of PGRN in the plasma in human-Sortilin-expressing knock-in mice; a capability to increase the amount and/or concentration of PGRN in the brain and/or
(vi) a capability, when administered chronically, to provide treatment of frontotemporal dementia (FTD) and/or amyotrophic lateral sclerosis (ALS).

The invention particularly relates to preparations of such an anti-Sortilin antibody having a structural change in its amino acid sequence (in any of its CDRs, variable domains, framework residues and/or constant domains) relative to the structure of a naturally-occurring anti-Sortilin antibody, wherein said structural change causes the anti-Sortilin antibody monoclonal antibody to exhibit a markedly altered functionality (i.e., more than a 20% difference, more than a 40% difference, more than a 60% difference, more than an 80% difference, more than a 100% difference, more than a 150% difference, more than a 2-fold difference, more than a 4-fold difference, more than a 5-fold difference, or more than a 10-fold difference in functionality) relative to the functionality exhibited by said naturally-occurring anti-Sortilin antibody; wherein such functionality is:
(i) a binding affinity ($K_D$) for Sortilin;
(ii) a capability to reduce and/or inhibit PGRN binding to Sortilin;
(iii) a capability to reduce and/or inhibit clearance of PGRN by Sortilin-expressing cells;
(iv) a capability to reduce and/or inhibit the endocytosis of PGRN by Sortilin-expressing cells;
(vi) a capability to increase the amount and/or concentration of PGRN in the plasma in human-Sortilin-expressing knock-in mice;
(vii) a capability to increase the amount and/or concentration of PGRN in the brain and/or
(vi) a capability, when administered chronically, to provide treatment of frontotemporal dementia (FTD), amyotrophic lateral sclerosis (ALS) and/or Alzheimer's Disease (AD).
especially wherein such altered functionality is a result of the structural change and thus is inseparable from it.

The term "substantially free" of naturally-arising antibodies refers to the complete absence of such naturally-arising antibodies in such preparations, or of the inclusion of a concentration of such naturally-arising antibodies in such preparations that does not materially affect the Sortilin-binding properties of the preparations. An antibody is said to be "isolated" if it has no naturally-arising counterpart or has been separated or purified from components which naturally accompany it.

The term "naturally-arising antibodies," as it relates to such preparations, refers to antibodies (including naturally-arising autoantibodies) elicited within living humans or other animals, as a natural consequence to the functioning of their immune systems.

Thus, the preparations of the present invention do not exclude, and indeed explicitly encompass, such preparations that contain an anti-Sortilin antibody and a deliberately added additional antibody capable of binding to an epitope that is not possessed by Sortilin. Such preparations particularly include embodiments thereof wherein the preparation exhibits enhanced efficacy in treating frontotemporal dementia (FTD) and/or amyotrophic lateral sclerosis (ALS).

The antibodies of antigen-binding fragments thereof of the present invention may be produced in different cell lines, such as a human cell line, a mammal non-human cell line, and insect cell line, for example a CHO cell line, HEK cell line, BHK-21 cell line, murine cell line (such as a myeloma cell line), fibrosarcoma cell line, PER.C6 cell line, HKB-11 cell line, CAP cell line and HuH-7 human cell line (Dumont et al, 2015, Crit Rev Biotechnol. September 18:1-13., the contents which is included herein by reference).

In an even further aspect, the invention relates to a pharmaceutical composition comprising:
(i) an anti-Sortilin antibody or antigen-binding fragment thereof, both as defined herein, or a preparation, as such term is defined herein, that comprises such an anti-Sortilin antibody or antigen-binding fragment thereof; and (ii) a pharmaceutically-acceptable carrier.

The pharmaceutical compositions may be formulated with pharmaceutically acceptable carriers or diluents as well as any other known adjuvants and excipients in accordance with conventional techniques such as those disclosed in Remington: The Science and Practice of Pharmacy, 22nd Edition, Gennaro, Ed., Mack Publishing Co., Easton, Pa., 2013.

The pharmaceutically acceptable carriers or diluents as well as any other known adjuvants and excipients should be suitable for the chosen compound of the present invention and the chosen mode of administration. Suitability for carriers and other components of pharmaceutical compositions is determined based on the lack of significant negative impact on the desired biological properties of the chosen compound or pharmaceutical composition of the present invention (e.g., less than a substantial impact (10% or less relative inhibition, 5% or less relative inhibition, etc.)) on epitope binding.

A pharmaceutical composition of the present invention may also include diluents, fillers, salts, buffers, detergents (e.g., a non-ionic detergent, such as Tween-20 or Tween-80), stabilizers (e.g., sugars or protein-free amino acids), preservatives, tissue fixatives, solubilizers, and/or other materials suitable for inclusion in a pharmaceutical composition. The diluent is selected to not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, or non-toxic, nontherapeutic, non-immunogenic stabilizers and the like. The compositions may also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes).

The actual dosage levels of the active ingredients in the pharmaceutical compositions of the present invention may be varied so as to obtain an amount of the active ingredient which is effective to achieve the desired therapeutic response for a particular patient, composition, and mode of administration. The selected dosage level will depend upon a variety of pharmacokinetic factors including the activity of the particular compositions of the present invention employed, or the amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

The pharmaceutical composition may be administered by any suitable route and mode, including: parenteral, topical, oral or intranasal means for prophylactic and/or therapeutic treatment. In one embodiment, a pharmaceutical composition of the present invention is administered parenterally. The phrases "parenteral administration" and "administered parenterally" as used herein means modes of administration other than enteral and topical administration, usually by injection, and include epidermal, intravenous, intramuscular, intraarterial, intrathecal, intracapsular, intraorbital, intracardiac, intradermal, intraperitoneal, intratendinous, transtracheal, subcutaneous, subcuticular, intraarticular, subcapsular, subarachnoid, intraspinal, intracranial, intrathoracic, epidural and intrasternal injection and infusion. Additional suitable routes of administering a compound of the present invention in vivo and in vitro are well known in the art and may be selected by those of ordinary skill in the art. In one embodiment that pharmaceutical composition is administered by intravenous or subcutaneous injection or infusion.

Pharmaceutically acceptable carriers include any and all suitable solvents, dispersion media, coatings, antibacterial and antifungal agents, isotonicity agents, antioxidants and absorption delaying agents, and the like that are physiologically compatible with a compound of the present invention.

Examples of suitable aqueous and non-aqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, such as olive oil, corn oil, peanut oil, cottonseed oil, and sesame oil, carboxymethyl cellulose colloidal solutions, tragacanth gum and injectable organic esters, such as ethyl oleate, and/or various buffers. Other carriers are well known in the pharmaceutical arts.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated.

Proper fluidity may be maintained, for example, by the use of coating materials, such as lecithin, by the maintenance of the required particle size in the case of dispersions, and by the use of surfactants.

Pharmaceutical compositions of the present invention may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical compositions of the present invention may also comprise isotonicity agents, such as sugars, polyalcohols, such as mannitol, sorbitol, glycerol or sodium chloride in the compositions.

The pharmaceutical compositions of the present invention may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The compounds of the present invention may be prepared with carriers that will protect the compound against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art. See, e.g., Sustained and Controlled Release Drug Delivery Systems, J. R. Robinson, ed., Marcel Dekker, Inc., New York, 1978.

In one embodiment, the compounds of the present invention may be formulated to ensure proper distribution in vivo. Pharmaceutically acceptable carriers for parenteral administration include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the present invention is contemplated. Supplementary active compounds may also be incorporated into the compositions.

Pharmaceutical compositions for injection must typically be sterile and stable under the conditions of manufacture and storage. The composition may be formulated as a solution, micro-emulsion, liposome, or other ordered structure suitable to high drug concentration. The carrier may be an aqueous or non-aqueous solvent or dispersion medium containing for instance water, ethanol, polyols (such as glycerol, propylene glycol, polyethylene glycol, and the like), and suitable mixtures thereof, vegetable oils, such as olive oil, and injectable organic esters, such as ethyl oleate. The proper fluidity may be maintained, for example, by the use of a coating such as lecithin, by the maintenance of the required particle size in the case of dispersion and by the use of surfactants. In many cases, it will be preferable to include isotonic agents, for example, sugars, polyalcohols such as glycerol, mannitol, sorbitol, or sodium chloride in the composition. Prolonged absorption of the injectable compositions may be brought about by including in the composition an agent that delays antibody absorption, for example, monostearate salts and gelatin. Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Sterile injectable solutions may be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Dosage regimens in the above methods of treatment and uses described herein are adjusted to provide the optimum desired response (e.g., a therapeutic response). For example, a single bolus may be administered, several divided doses may be administered over time or the dose may be proportionally reduced or increased as indicated by the exigencies of the therapeutic situation. Parenteral compositions may be formulated in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the present invention are dictated by and directly dependent on (a) the unique characteristics of the active compound and the particular therapeutic effect to be achieved, and (b) the limitations inherent in the art of compounding such an active compound for the treatment of sensitivity in individuals.

The effective dosages and the dosage regimens for the anti-Sortilin antibodies depend on the disease or condition to be treated and may be determined by the persons skilled in the art. An exemplary, non-limiting range for a therapeutically effective amount of an antibody of the present invention is about 0.1-10 mg/kg/body weight, such as about 0.1-5 mg/kg/body weight, for example about 0.1-2 mg/kg/body weight, such as about 0.1-1 mg/kg/body weight, for instance about 0.15, about 0.2, about 0.5, about 1, about 1.5 or about 2 mg/kg/body weight.

A physician or veterinarian having ordinary skill in the art may readily determine and prescribe the effective amount of the pharmaceutical composition required. For example, the physician or veterinarian could start doses of the anti-Sortilin antibody employed in the pharmaceutical composition at levels lower than that required in order to achieve the desired therapeutic effect and gradually increase the dosage until the desired effect is achieved. In general, a suitable daily dose of a composition of the present invention will be that amount of the compound which is the lowest dose effective to produce a therapeutic effect. Such an effective dose will generally depend upon the factors described above. Administration may e.g. be intravenous, intramuscular, intraperitoneal, or subcutaneous, and for instance administered proximal to the site of the target. If desired, the effective daily dose of a pharmaceutical composition may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical composition as described above.

The labelled antibodies or antigen-binding fragments thereof of the invention can be used for diagnostic purposes to detect, diagnose, or monitor diseases or disorders. The invention provides for the detection or diagnosis of a neurodegenerative or cognitive disease or disorder, including but not limited to FTD, ALS or TDP43 proteinopathies such as Alzheimer's Disease (AD), comprising: (a) assaying the existence of pyroglutamated Aβ fragments in cells or tissue samples of a subject using one or more antibodies that specifically bind to Sortilin; and (b) comparing the level of the antigen with a control level, e.g. levels in normal tissue samples, whereby an increase in the assayed level of antigen compared to the control level of antigen is indicative of the disease or disorder, or indicative of the severity of the disease or disorder.

The antibodies or antigen-binding fragments thereof of the invention can be used to assay Sortilin or antigen-binding fragments of Sortilin in a biological sample using immuno-histochemical methods well-known in the art. Other antibody-based methods useful for detecting protein include immunoassays such as the enzyme linked immunoassay (ELISA) and the radioimmunoassay assay (RIA) and mesoscale discovery platform based assays (MSD). Suitable antibody labels may be used in such kits and methods, and labels known in the art include enzyme labels, such as alkaline phosphatase and glucose oxidase; radioisotope labels, such as iodine ($^{125}$I, $^{131}$I), carbon ($^{14}$C), sulfur ($^{35}$S), tritium ($^{3}$H), indium ($^{121}$In), and technetium ($^{99m}$Tc); and luminescent labels, such as luminol and luciferase; and fluorescent labels, such as fluorescein and rhodamine.

The presence of labeled anti-Sortilin antibodies or their Sortilin-binding fragments may be detected in vivo for diagnostic purposes. In one embodiment, diagnosis comprises: a) administering to a subject an effective amount of such labeled molecule; b) waiting for a time interval following administration to allow the labeled molecule to concentrate at sites (if any) of Aβ deposition and to allow for unbound labeled molecule to be cleared to background level; c) determining a background level; and d) detecting the labeled molecule in the subject, such that detection of labeled molecule above the background level is indicative that the subject has the disease or disorder, or is indicative of the severity of the disease or disorder. In accordance with such embodiment, the molecule is labeled with an imaging moiety suitable for detection using a particular imaging system known to those skilled in the art. Background levels may be determined by various methods known in the art, including comparing the amount of labeled antibody detected to a standard value previously determined for a particular imaging system. Methods and systems that may be used in the diagnostic methods of the invention include, but are not limited to, computed tomography (CT), whole body scan such as positron emission tomography (PET), magnetic resonance imaging (MRI), and sonography.

In a further aspect, the invention relates to an antibody, or antigen-binding fragment thereof, of the invention, for use in medicine.

In a further aspect, the invention relates to an antibody, or antigen-binding fragment thereof, of the invention, for use in treating a disease associated with decreased PGRN levels in the brain of a patient.

In a further aspect, the invention relates to the use of the antibody, or antigen-binding fragment thereof, of the invention, in the manufacture of a medicament for treating a disease associated with decreased PGRN levels in the brain of a patient.

In a further aspect, the invention relates to a method of preventing or treating a disease associated with decreased PGRN levels in the brain of a patient, comprising administering an effective dosage of an antibody of the invention, or an antigen-binding fragment thereof.

It is preferred that in the uses and methods of those aspects of the invention the disease is: FTD; ALS; or TDP43 proteinopathies, such as AD.

Preferably, in the uses and methods of those aspects of the invention, the treatment is chronic, and is preferably for at least 2 weeks, such as at least for 1 month, 6, months, 1 year or more.

In a further aspect, the invention provides a kit comprising the antibody, or antigen-binding fragment thereof, of the invention.

TABLE 5

| Antibody Sequences | |
|---|---|
| Ab 5E1 | |
| Seq ID No: 1 | 5E1 CDR1 Light Chain |
| Seq ID No: 2 | 5E1 CDR2 Light Chain |
| Seq ID No: 3 | 5E1 CDR3 Light Chain |
| Seq ID No: 4 | 5E1 CDR1 Heavy Chain |

TABLE 5-continued

| Antibody Sequences | |
|---|---|
| Seq ID No: 5 | 5E1 CDR2 Heavy Chain |
| Seq ID No: 6 | 5E1 CDR3 Heavy Chain |
| Seq ID No: 7 | 5E1 VL |
| Seq ID No: 8 | 5E1 VH |
| Ab 1F2 | |
| Seq ID No: 9 | 1F2 CDR1 Light Chain |
| Seq ID No: 10 | 1F2 CDR2 Light Chain |
| Seq ID No: 11 | 1F2 CDR3 Light Chain |
| Seq ID No: 12 | 1F2 CDR1 Heavy Chain |
| Seq ID No: 13 | 1F2 CDR2 Heavy Chain |
| Seq ID No: 14 | 1F2 CDR3 Heavy Chain |
| Seq ID No: 15 | 1F2 VL |
| Seq ID No: 16 | 1F2 VH |
| Ab 068 | |
| Seq ID No: 17 | 068 CDR1 Light Chain |
| Seq ID No: 18 | 068 CDR2 Light Chain |
| Seq ID No: 19 | 068 CDR3 Light Chain |
| Seq ID No: 20 | 068 CDR1 Heavy Chain |
| Seq ID No: 21 | 068 CDR2 Heavy Chain |
| Seq ID No: 22 | 068 CDR3 Heavy Chain |
| Seq ID No: 23 | 068 VL |
| Seq ID No: 24 | 068 VH |
| Ab 1320 | |
| Seq ID No: 25 | 1320 CDR1 Light Chain |
| Seq ID No: 26 | 1320 CDR2 Light Chain |
| Seq ID No: 27 | 1320 CDR3 Light Chain |
| Seq ID No: 28 | 1320 CDR1 Heavy Chain |
| Seq ID No: 29 | 1320 CDR2 Heavy Chain |
| Seq ID No: 30 | 1320 CDR3 Heavy Chain |
| Seq ID No: 31 | 1320 VL |
| Seq ID No: 32 | 1320 VH |
| Ab 93-05 | |
| Seq ID No: 33 | 93-05 CDR1 Light Chain |
| Seq ID No: 34 | 93-05 CDR2 Light Chain |
| Seq ID No: 35 | 93-05 CDR3 Light Chain |
| Seq ID No: 36 | 93-05 CDR1 Heavy Chain |
| Seq ID No: 37 | 93-05 CDR2 Heavy Chain |
| Seq ID No: 38 | 93-05 CDR3 Heavy Chain |
| Seq ID No: 39 | 93-05 VL |
| Seq ID No: 40 | 93-05 VH |
| Ab 93-01 | |
| Seq ID No: 41 | 93-01 CDR1 Light Chain |
| Seq ID No: 42 | 93-01 CDR2 Light Chain |
| Seq ID No: 43 | 93-01 CDR3 Light Chain |
| Seq ID No: 44 | 93-01 CDR1 Heavy Chain |
| Seq ID No: 45 | 93-01 CDR2 Heavy Chain |
| Seq ID No: 46 | 93-01 CDR3 Heavy Chain |
| Seq ID No: 47 | 93-01 VL |
| Seq ID No: 48 | 93-01 VH |
| Ab 924 | |
| Seq ID No: 49 | 924 CDR1 Light Chain |
| Seq ID No: 50 | 924 CDR2 Light Chain |
| Seq ID No: 51 | 924 CDR3 Light Chain |
| Seq ID No: 52 | 924 CDR1 Heavy Chain |
| Seq ID No: 53 | 924 CDR2 Heavy Chain |
| Seq ID No: 54 | 924 CDR3 Heavy Chain |
| Seq ID No: 55 | 924 VL |
| Seq ID No: 56 | 924 VH |
| Ab 1276 | |
| Seq ID No: 57 | 1276 CDR1 Light Chain |
| Seq ID No: 58 | 1276 CDR2 Light Chain |
| Seq ID No: 59 | 1276 CDR3 Light Chain |
| Seq ID No: 60 | 1276 CDR1 Heavy Chain |
| Seq ID No: 61 | 1276 CDR2 Heavy Chain |
| Seq ID No: 62 | 1276 CDR3 Heavy Chain |
| Seq ID No: 63 | 1276 VL |
| Seq ID No: 64 | 1276 VH |
| Ab 849 | |
| Seq ID No: 65 | 849 CDR1 Light Chain |
| Seq ID No: 66 | 849 CDR2 Light Chain |

TABLE 5-continued

Antibody Sequences

| | |
|---|---|
| Seq ID No: 67 | 849 CDR3 Light Chain |
| Seq ID No: 68 | 849 CDR1 Heavy Chain |
| Seq ID No: 69 | 849 CDR2 Heavy Chain |
| Seq ID No: 70 | 849 CDR3 Heavy Chain |
| Seq ID No: 71 | 849 VL |
| Seq ID No: 72 | 849 VH |

Ab 531-02

| | |
|---|---|
| Seq ID No: 73 | 531-02 CDR1 Light Chain |
| Seq ID No: 74 | 531-02 CDR2 Light Chain |
| Seq ID No: 75 | 531-02 CDR3 Light Chain |
| Seq ID No: 76 | 531-02 CDR1 Heavy Chain |
| Seq ID No: 77 | 531-02 CDR2 Heavy Chain |
| Seq ID No: 78 | 531-02 CDR3 Heavy Chain |
| Seq ID No: 79 | 531-02 VL |
| Seq ID No: 80 | 531-02 VH |

Ab 548-01

| | |
|---|---|
| Seq ID No: 81 | 548-01 CDR1 Light Chain |
| Seq ID No: 82 | 548-01 CDR2 Light Chain |
| Seq ID No: 83 | 548-01 CDR3 Light Chain |
| Seq ID No: 84 | 548-01 CDR1 Heavy Chain |
| Seq ID No: 85 | 548-01 CDR2 Heavy Chain |
| Seq ID No: 86 | 548-01 CDR3 Heavy Chain |
| Seq ID No: 87 | 548-01 VL |
| Seq ID No: 88 | 548-01 VH |

Ab 548-02

| | |
|---|---|
| Seq ID No: 89 | 548-02 CDR1 Light Chain |
| Seq ID No: 90 | 548-02 CDR2 Light Chain |
| Seq ID No: 91 | 548-02 CDR3 Light Chain |
| Seq ID No: 92 | 548-02 CDR1 Heavy Chain |
| Seq ID No: 93 | 548-02 CDR2 Heavy Chain |
| Seq ID No: 94 | 548-02 CDR3 Heavy Chain |
| Seq ID No: 95 | 548-02 VL |
| Seq ID No: 96 | 548-02 VH |

Ab1289-02

| | |
|---|---|
| Seq ID No: 97 | 1289-02 CDR1 Light Chain |
| Seq ID No: 98 | 1289-02 CDR2 Light Chain |
| Seq ID No: 99 | 1289-02 CDR3 Light Chain |
| Seq ID No: 100 | 1289-02 CDR1 Heavy Chain |
| Seq ID No: 101 | 1289-02 CDR2 Heavy Chain |
| Seq ID No: 102 | 1289-02 CDR3 Heavy Chain |
| Seq ID No: 103 | 1289-02 VL |
| Seq ID No: 104 | 1289-02 VH |

Ab 811-02

| | |
|---|---|
| Seq ID No: 105 | 811-02 CDR1 Light Chain |
| Seq ID No: 106 | 811-02 CDR2 Light Chain |
| Seq ID No: 107 | 811-02 CDR3 Light Chain |
| Seq ID No: 108 | 811-02 CDR1 Heavy Chain |
| Seq ID No: 109 | 811-02 CDR2 Heavy Chain |
| Seq ID No: 110 | 811-02 CDR3 Heavy Chain |
| Seq ID No: 111 | 811-02 VL |
| Seq ID No: 112 | 811-02 VH |

Ab 566-01

| | |
|---|---|
| Seq ID No: 113 | 566-01 CDR1 Light Chain |
| Seq ID No: 114 | 566-01 CDR2 Light Chain |
| Seq ID No: 115 | 566-01 CDR3 Light Chain |
| Seq ID No: 116 | 566-01 CDR1 Heavy Chain |
| Seq ID No: 117 | 566-01 CDR2 Heavy Chain |
| Seq ID No: 118 | 566-01 CDR3 Heavy Chain |
| Seq ID No: 119 | 566-01 VL |
| Seq ID No: 120 | 566-01 VH |

Ab 562

| | |
|---|---|
| Seq ID No: 121 | 562 CDR1 Light Chain |
| Seq ID No: 122 | 562 CDR2 Light Chain |
| Seq ID No: 123 | 562 CDR3 Light Chain |
| Seq ID No: 124 | 562 CDR1 Heavy Chain |
| Seq ID No: 125 | 562 CDR2 Heavy Chain |
| Seq ID No: 126 | 562 CDR3 Heavy Chain |
| Seq ID No: 127 | 562 VL |
| Seq ID No: 128 | 562 VH |

Ab 193

| | |
|---|---|
| Seq ID No: 129 | 193 CDR1 Light Chain |
| Seq ID No: 130 | 193 CDR2 Light Chain |
| Seq ID No: 131 | 193 CDR3 Light Chain |
| Seq ID No: 132 | 193 CDR1 Heavy Chain |
| Seq ID No: 133 | 193 CDR2 Heavy Chain |
| Seq ID No: 134 | 193 CDR3 Heavy Chain |
| Seq ID No: 135 | 193 VL |
| Seq ID No: 136 | 193 VH |

Ab 88

| | |
|---|---|
| Seq ID No: 137 | 88 CDR1 Light Chain |
| Seq ID No: 138 | 88 CDR2 Light Chain |
| Seq ID No: 139 | 88 CDR3 Light Chain |
| Seq ID No: 140 | 88 CDR1 Heavy Chain |
| Seq ID No: 141 | 88 CDR2 Heavy Chain |
| Seq ID No: 142 | 88 CDR3 Heavy Chain |
| Seq ID No: 143 | 88 VL |
| Seq ID No: 144 | 88 VH |

Ab 045

| | |
|---|---|
| Seq ID No: 145 | 045 CDR1 Light Chain |
| Seq ID No: 146 | 045 CDR2 Light Chain |
| Seq ID No: 147 | 045 CDR3 Light Chain |
| Seq ID No: 148 | 045 CDR1 Heavy Chain |
| Seq ID No: 149 | 045 CDR2 Heavy Chain |
| Seq ID No: 150 | 045 CDR3 Heavy Chain |
| Seq ID No: 151 | 045 VL |
| Seq ID No: 152 | 045 VH |

Ab 044

| | |
|---|---|
| Seq ID No: 153 | 044 CDR1 Light Chain |
| Seq ID No: 154 | 044 CDR2 Light Chain |
| Seq ID No: 155 | 044 CDR3 Light Chain |
| Seq ID No: 156 | 044 CDR1 Heavy Chain |
| Seq ID No: 157 | 044 CDR2 Heavy Chain |
| Seq ID No: 158 | 044 CDR3 Heavy Chain |
| Seq ID No: 159 | 044 VL |
| Seq ID No: 160 | 044 VH |

Ab 002

| | |
|---|---|
| Seq ID No: 161 | 002 CDR1 Light Chain |
| Seq ID No: 162 | 002 CDR2 Light Chain |
| Seq ID No: 163 | 002 CDR3 Light Chain |
| Seq ID No: 164 | 002 CDR1 Heavy Chain |
| Seq ID No: 165 | 002 CDR2 Heavy Chain |
| Seq ID No: 166 | 002 CDR3 Heavy Chain |
| Seq ID No: 167 | 002 VL |
| Seq ID No: 168 | 002 VH |
| Seq ID No: 169 | Full human Sortilin sequence isoform 1 |
| Seq ID No: 170 | "D Region" as identified by present invention |
| Seq ID No: 171 | Sortilin "hSORTECDBAP" |
| Seq ID No: 172 | Sortilin SORTECDBAP_hBACK |
| Seq ID No: 173 | Sortilin SORTECDBAP_tetra |
| Seq ID No: 174 | Sortilin SORTECDBAP_hB01-05 |
| Seq ID No: 175 | Sortilin SORTECDBAP_hRIM |
| Seq ID No: 176 | Sortilin SORTECDBAP_hB06-10 |
| Seq ID No: 177 | Sortilin SORTECDBAP_hB12390 |
| Seq ID No: 178 | Sortilin SORTECDBAP_hB45678 |
| Seq ID No: 179 | Sortilin SORTECD_HIS |
| Seq ID No: 180 | "A region" as identified by the present invention |
| Seq ID No: 181 | A region 109-114 |
| Seq ID No: 182 | A region 126-153 |
| Seq ID No: 183 | A region 126-144 |
| Seq ID No: 184 | A region 154-159 |
| Seq ID No: 185 | D Region 570-572 |
| Seq ID No: 186 | D Region 588-597 |
| Seq ID No: 187 | D Region 593-597 |
| Seq ID No: 188 | Sequences used for HDX |

The listing or discussion in this specification of an apparently prior-published document should not necessarily be taken as an acknowledgement that the document is part of the state of the art or is common general knowledge.

EMBODIMENTS

As would be apparent from the text and the Examples the invention further relates to the below embodiments:

1. An antibody, or an antigen-binding fragment thereof, capable of specifically binding to Sortilin and inhibiting binding of PGRN to Sortilin.
2. The antibody, or antigen-binding fragment thereof, according to Embodiment 1, wherein the antibody comprises or consists of an intact antibody.
3. The antibody, or antigen-binding fragment thereof, according to Embodiment 1 or 2, wherein the antigen-binding fragment comprises or consists of an antigen-binding fragment selected from the group consisting of: an Fv fragment (e.g. single chain Fv or a disulphide-bonded Fv); a Fab-like fragment (e.g. Fab fragment or F(ab')$_2$ fragment); and a domain antibody (e.g. a single VH variable domain or VL variable domain).
4. The antibody, or antigen-binding fragment thereof, according to any preceding Embodiment, wherein the antibody is selected from the group consisting of: an antibody of subtype IgG1, IgG2, IgG3 or IgG4.
5. The antibody, or antigen-binding fragment thereof, according to any preceding Embodiment, wherein said antibody or antigen-binding fragment thereof binds specifically to the D Region of Sortilin as defined in SEQ ID NO:170.
6. The antibody, or antigen-binding fragment thereof, according to any preceding Embodiment, wherein said antibody or fragment thereof binds specifically to at least 3 consecutive amino acids, such as 4, 5, 6 or 7 consecutive amino acids, of the D Region of Sortilin as defined in SEQ ID NO:170.
7. The antibody, or antigen-binding fragment thereof, according to any preceding Embodiment, wherein the antibody or antigen-binding fragment exhibits one or more of the following properties:
   (i) a binding affinity ($K_D$) for Sortilin of between 0.5-10 nM, such as 1-5 nM or 1-2 nM
   (ii) capability to reduce and/or inhibit PGRN binding to Sortilin;
   (iii) capability to reduce and/or inhibit clearance of PGRN by Sortilin-expressing cells;
   (iv) capability to reduce and/or inhibit the endocytosis of PGRN by Sortilin-expressing cells;
   (v) capability to increase the amount and/or concentration of PGRN in the plasma in human-Sortilin-expressing knock-in mice.
8. The antibody, or antigen-binding fragment thereof, according to Embodiment 7, wherein the capability of the antibody or fragment thereof to reduce PGRN binding to Sortilin comprises reducing PGRN binding to Sortilin by 10% or more; for example, by 20% or more; or by 30% or more.
9. The antibody, or antigen-binding fragment thereof, according to Embodiment 7 or 8, wherein the capability of said antibody or fragment thereof the antibody or fragment thereof to reduce and/or inhibit PGRN binding to Sortilin comprises reducing and/or inhibiting PGRN binding to Sortilin with an IC50 at or below 22 nM, such as between 22 nM and 1 nM, or between 10 nM and 1 nM, or between 5 nM and 1 nM.
10. The antibody, or antigen-binding fragment thereof, according to any previous Embodiment, wherein the antibody or antigen-binding fragment thereof is human or is humanized.
11. The antibody, or antigen-binding fragment thereof, according to any preceding Embodiment, comprising a light chain variable domain comprising one or more of the CDR 1-3 Light Chain as listed for each of the antibodies defined in Table 5, or an amino acid sequence having no more than 4 amino acid differences, or no more than 3 amino acid differences, or no more than 2 amino acid differences, or no more than 1 amino acid difference.
12. The antibody, or antigen-binding fragment thereof, according to Embodiment 11, comprising a light chain variable domain comprising the CDR 1-3 Light Chain as listed for each of the antibodies defined in Table 5.
13. The antibody, or antigen-binding fragment thereof, according to Embodiment 11 or 12, comprising a light chain variable domain comprising or consisting of the amino acid sequence VL as listed for each of the antibodies defined in Table 5.
14. The antibody, or antigen-binding fragment thereof, according to any of Embodiments 11 to 13, comprising a light chain comprising or consisting of the amino acid sequence of VL as listed for each of the antibodies defined in Table 5.
15. The antibody, or antigen-binding fragment thereof, according to any preceding Embodiment, comprising a heavy chain variable domain comprising one or more CDR 1-3 Heavy Chain as listed for each of the antibodies defined in Table 5, or an amino acid sequence having no more than 4 amino acid differences, or no more than 3 amino acid differences, or no more than 2 amino acid differences, or no more than 1 amino acid difference.
16. The antibody, or antigen-binding fragment thereof, according to Embodiment 15, comprising a heavy chain variable domain comprising the CDR 1-3 Heavy Chain as listed for each of the antibodies defined in Table 5.
17. An antibody, or antigen-binding fragment thereof, according to Embodiment 15 or 16 comprising a heavy chain variable domain comprising or consisting of the amino acid sequence of VH as listed for each of the antibodies defined in Table 5.
18. The antibody, or antigen-binding fragment thereof, according to any of Embodiments 15 to 17, comprising a heavy chain comprising or consisting of the amino acid sequence VL as listed for each of the antibodies defined in Table 5.
19. The antibody, or antigen-binding fragment thereof, according to any preceding embodiment, comprising a light chain variable domain comprising or consisting of the amino acid sequence of VL as listed for each of the antibodies defined in Table 5, and a heavy chain variable domain comprising or consisting of the amino acid sequence of VH as listed for each of the antibodies defined in Table 5.
20. The antibody, or antigen-binding fragment thereof, according to any preceding embodiment, comprising a light chain comprising or consisting of the amino acid sequence of VL as listed for each of the antibodies defined in Table 5, and a heavy chain comprising or consisting of the amino acid sequence of VH as listed for each of the antibodies defined in Table 5.
21. The antibody, or antigen-binding fragment thereof, according to any preceding Embodiment, wherein said antibody or antigen-binding fragment thereof competes with the antibody or antigen-binding fragment thereof defined in Embodiment 20 for binding to Sortilin.

22. The antibody, or antigen-binding fragment thereof, according to any preceding Embodiment, wherein the antibody or antigen-binding fragment comprises an Fc region.
23. The antibody, or antigen-binding fragment thereof, according to any preceding Embodiment, wherein the antibody or antigen-binding fragment further comprises a moiety for increasing in vivo half-life.
24. The antibody, or antigen-binding fragment thereof, according to Embodiment 22, wherein the moiety for increasing the in vivo half-life is selected from the group consisting of polyethylene glycol (PEG), human serum albumin, glycosylation groups, fatty acids and dextran.
25. The antibody, or antigen-binding fragment thereof, according to any preceding Embodiment, wherein the antibody or antigen-binding fragment further comprises a detectable moiety.
26. The antibody, or antigen-binding fragment thereof, according to Embodiment 25, wherein the detectable moiety is selected from the group consisting of: a fluorescent label; a chemiluminescent label; a paramagnetic label; a radio-isotopic label; or an enzyme label.
27. The antibody, or antigen-binding fragment thereof, according to Embodiment 25 or 26, wherein the detectable moiety comprises or consists of a radioisotope.
28. The antibody, or antigen-binding fragment thereof, according to Embodiment 26 or 27, wherein the radioisotope is selected from the group consisting of $^{99m}$Tc, $^{111}$In, $^{67}$Ga, $^{68}$Ga, $^{72}$As, $^{89}$Zr, $^{123}$I and $^{201}$Tl.
29. The antibody, or antigen-binding fragment thereof, according to Embodiment 25, wherein the detectable moiety comprises or consists of a paramagnetic isotope.
30. The antibody, or antigen-binding fragment thereof, according to Embodiment 29 wherein the paramagnetic isotope is selected from the group consisting of $^{157}$Gd, $^{55}$Mn, $^{162}$Dy, $^{52}$Cr and $^{56}$Fe.
31. The antibody, or antigen-binding fragment thereof, according to any of Embodiments 25 to 30, wherein the detectable moiety is detectable by an imaging technique such as SPECT, PET, MRI, optical or ultrasound imaging.
32. The antibody, or antigen-binding fragment thereof, according to any of Embodiments 25 to 31, wherein the detectable moiety is joined to the antibody or antigen-binding fragment thereof indirectly, via a linking moiety.
33. The antibody, or antigen-binding fragment thereof, according to Embodiment 32 wherein the linking moiety is selected from the group consisting of: derivatives of 1,4,7,10-tetraazacyclododecane-1,4,7,10,tetraacetic acid (DOTA); deferoxamine (DFO); derivatives of diethylenetriaminepentaacetic avid (DTPA); derivatives of S-2-(4-Isothiocyanatobenzyl)-1,4,7-triazacyclononane-1,4,7-triacetic acid (NOTA); and derivatives of 1,4,8,11-tetraazacyclodocedan-1,4,8,11-tetraacetic acid (TETA).
34. An isolated nucleic acid molecule encoding an antibody or antigen-binding fragment thereof as defined in any of Embodiments 1-33.
35. A nucleic acid molecule according to Embodiment 34 wherein the molecule is a cDNA molecule.
36. A vector comprising a nucleic acid molecule as defined in Embodiment 34 or 35.
37. A recombinant host cell comprising a nucleic acid molecule as defined in any of Embodiments 34-36.
38. A method for producing an antibody or antigen-binding fragment as defined in any of Embodiments 1-33, the method comprising culturing a host cell as defined in Embodiment 37 under conditions which permit expression of the encoded antibody or antigen-binding fragment thereof.
39. A preparation comprising the antibody or antigen-binding fragment thereof according to any one of the previous Embodiments, wherein said preparation is substantially free of naturally-arising antibodies that are either not capable of binding to Sortilin or that do not materially alter an anti-Sortilin functionality of the preparation, said functionality being selected from the group consisting of:
(i) a binding affinity ($K_D$) for Sortilin;
(ii) a capability to reduce and/or inhibit PGRN binding to Sortilin;
(iii) a capability to reduce and/or inhibit clearance of PGRN by Sortilin-expressing cells;
(iv) a capability to reduce and/or inhibit the endocytosis of PGRN by Sortilin-expressing cells;
(v) a capability to increase the amount and/or concentration of PGRN in the plasma in human-Sortilin-expressing knock-in mice; and/or
(vi) a capability, when administered chronically, to provide treatment of frontotemporal dementia (FTD) and/or amyotrophic lateral sclerosis (ALS).
40. A preparation comprising the monoclonal antibody or antigen-binding fragment thereof according to any one of the previous Embodiments, wherein said monoclonal antibody possesses a structural change in its amino acid sequence, relative to the structure of a naturally-occurring anti-Sortilin antibody, wherein said structural change causes said monoclonal antibody to exhibit an altered functionality relative to the functionality exhibited by said naturally-occurring anti-Sortilin antibody, wherein said functionality is:
(i) a binding affinity (KD) for Sortilin;
(ii) a capability to reduce and/or inhibit PGRN binding to Sortilin;
(iii) a capability to reduce and/or inhibit clearance of PGRN by Sortilin-expressing cells;
(iv) a capability to reduce and/or inhibit the endocytosis of PGRN by Sortilin-expressing cells;
(v) a capability to increase the amount and/or concentration of PGRN in the plasma in human-Sortilin-expressing knock-in mice; and/or
(vi) a capability, when administered chronically, to provide treatment of frontotemporal dementia (FTD) and/or amyotrophic lateral sclerosis (ALS).
41. A pharmaceutical composition comprising an antibody, or antigen-binding fragment thereof, as defined in any of Embodiments 1-33, or the preparation of any one of embodiments 39-40, and a pharmaceutically-acceptable carrier.
42. The antibody, or antigen-binding fragment thereof, as defined in any of Embodiments 1-33, or the preparation of any one of embodiments 39-40, for use in medicine.
43. The antibody, or antigen-binding fragment thereof, as defined in any of Embodiments 1-33, or the preparation of any one of embodiments 39-40, for use in preventing and/or treating a disease associated with decreased PGRN levels in the brain of a patient.
44. Use of an antibody, or antigen-binding fragment thereof, as defined in any of Embodiments 1-33, or the preparation of any one of embodiments 39-40, in the manufacture of a medicament for preventing and/or treating a disease associated with decreased PGRN levels in the brain of a patient.
45. The antibody or antigen-binding fragment thereof for use according to Embodiment 43, or the use according to Embodiment 44, wherein the disease is selected from the group consisting of: FTD; ALS; TDP43 proteinopathies, such as AD.

46. A method of preventing or treating a disease associated with decreased PGRN levels in the brain of a patient, comprising administering an effective dosage of an antibody or a fragment thereof as defined in any of Embodiments 1-33, the preparation of any one of Embodiments 39-40, or the pharmaceutical composition of Embodiment 41.

47. The antibody, or antigen-binding fragment thereof, for use according to Embodiment 43, or the use according to Embodiment 44, or the method according to Embodiment 46, wherein the disease is selected from the group consisting of: FTD; ALS; or TDP43 proteinopathies, such as AD.

48. The antibody, or antigen-binding fragment thereof, for use; or the use; or the method according to Embodiment 46 or 47, wherein the treatment is chronic.

49. The antibody, or antigen-binding fragment thereof, for use; or the use; or the method, according to Embodiment 48, wherein the chronic treatment is for at least 2 weeks, such as at least for 1 month, 6, months, 1 year or more 50. The antibody, or antigen-binding fragment thereof, as defined in any of Embodiments 1-33, the preparation of any one of Embodiments 39-40, or the pharmaceutical composition of Embodiment 41, which is capable of specifically binding to Sortilin and inhibiting the binding of PGRN to Sortilin, but which binding does not inhibit or substantially inhibit the binding of neurotensin or AF38469 to Sortilin.

51. A kit comprising the antibody, or antigen-binding fragment thereof, as defined in any of Embodiments 1-33, the preparation, as defined in any one of Embodiments 39-40, or the pharmaceutical composition as defined in Embodiment 41.

Preferred, non-limiting examples which embody certain aspects of the invention will now be described, with reference to the accompanying figures.

EXAMPLES

Examples 1-3 describe the generation of sortilin constructs

Example 1 discloses the shuffle constructs. Example 2 discloses the expression of sortilin constructs. Example 3 discloses the purification of sortilin constructs.

Examples 4-7 describe the generation of sortilin antibodies

Example 4 discloses the immunization and the hybridomas.

Example 5 discloses the sequence analysis. Example 6 discloses the purification of antibodies. Example 7 discloses the generation of mouse antibodies.

Examples 8-17 describe the characterization of sortilin antibodies

Example 8 discloses the binding to sortilin. Example 9 discloses the cross blocking ability of Sortilin antibodies. Example 10 discloses HTRF PGRN-sortilin binding. Example 11 discloses NTS binding. Example 12 discloses cellular PGRN binding and endocytosis. Example 13 discloses extracellular PGRN levels. Example 14 discloses iPSC PGRN levels. Example 15 discloses a plasma PGRN levels. Example 16 disclose epitope mapping by HDX.

Example 17 disclose microdialysis of PGRN in the brain.

Example 1

For use in both the hybridoma screening process and as a diversification of the panel of antibodies, so called "shuffle constructs" were designed, constructed and produced, making a set of chimeric sortilin molecules containing amino acid sequences derived from both human sortilin and a distantly related species (tetraodon) with significantly reduced sequence homology. The rationale being that the overall sortilin structure and functionality of these chimeric constructs would be retained but that loss of binding of antibodies to certain chimeric constructs would indicate the involvement of the specific exchanged regions in binding. Soluble extracellular region (ECD, aa 1-755) constructs were tagged with either a BAP tag (biotin acceptor peptide), enabling the "in vitro" biotinylation of the proteins by co-expression of biotin ligase or a His tag, enabling easy purification. Expression vectors encoding the following proteins were prepared: SORT-ECDBAP, SORT-ECDBAP-hB01-05, SORT-ECDBAP-hB06-10, SORT-ECDBAP-hB12390, SORT-ECDBAP-hB45678, SORT-ECDBAP-tetra, SORT, SORT-tetra.

The Sortilin sequences can be found in SEQ ID NOs: 169-180 and FIGS. 2A-2C show schematic presentation of the region assignment of antibodies based on binding to Sortilin shuffle constructs.

Example 2

In the case of antibody expression, the appropriate heavy chain and light chain vectors, as described in Examples 4, 5 and 6, were co-expressed in HEK-293F cells.

Example 3: Purification of His-Tagged Sortilin

SORTECDHis was expressed in HEK-293F cells. The His-tag in the proteins enables purification with immobilized metal affinity chromatography. In this process NiNTA Superflow Cartridge (Qiagen) is equilibrated with 50 mM $NAH_2PO_4$, 300 mM NaCl and 10 mM Imidazole pH 8.0. Column is loaded with His tagged protein with a residence time of 1 minute. Column is washed with 50 mM $NAH_2PO_4$, 300 mM NaCl and 20 mM Imidazole pH 8.0. Protein is eluted with 50 mM $NAH_2PO_4$, 300 mM NaCl and 250 mM Imidazole pH 8.0. Subsequently the protein is dialyzed to PBS using a Slide-A-Lyzer with a cut off of 10.000 mwco (Thermo Scientific). After dialyzing the protein is sterile filtered using a 0.2 micron SFCA filter(Thermo Scientific).

The S18-HEK cell line was generated by transfecting HEK293 cells with a human wild type (WT) sortilin expression vector. Stable transfected cells were derived after passage in the presence of a selection agent. Individual clones were selected by dilution cloning. Clones were characterized for sortilin mRNA expression using QPCR. Highest expressing clones were than analyzed by FACS (Guava, Millipore) using an anti-sortilin polyclonal antibody (Polyclonal Goat Sortilin Biotinylated Ab, Cat. No: BAF2934_ (R&D Systems)) to determine the surface expressed levels of Sortilin.

Example 4

A—Immunization Procedure of Transgenic Mice

Antibodies HuMab Sortilin were derived from the immunizations of HuMAb mouse strains HCo12, HCo17, HCo20, HCo12-BALB/c, HCo17-BALB/c and HCo20-BALB/c (human monoclonal antibody; Medarex Inc., San Jose, Calif., USA), These mice are double knock out for the mouse immunoglobulin (Ig) heavy and mouse kappa light chain, which substantially inactivate the expression of antibodies that are completely murine. The various mouse strains were made transgenic by the insertion of human Ig heavy and human Ig kappa light chain loci and differ in the number of human VH (variable domain of heavy chain) and VL (variable domain of light chain) genes. HCo12-BALB/c mice were derived by crossbreeding with KCo5-BALB/c (kappa light chain transgenic) mice.

48 mice were immunized alternating intraperitoneally (IP) with 20 μg SORTECDHis (SEQ ID NO: 179) and subcutaneously (SC, at the tail base) with the same protein, with an interval of 14 days. A maximum of eight immunizations were performed, 4 IP and 4 SC.

In one protocol, the first immunization was performed with SORTECDHis in complete Freund's adjuvant (CFA; Difco Laboratories, Detroit, Mich., USA), the following immunizations in incomplete Freund's adjuvant (IFA). A second protocol used SAS as an adjuvant in all immunization steps. When serum titers were found to be sufficient (dilution of serum of 1/50 or lower found positive in antigen specific screening assay on at least two sequential, biweekly, screening events), mice were additionally boosted twice intravenously (IV) with 10 μg SORTECDHis protein in 100 μL PBS, four and three days before fusion.

B—HuMab Hybridoma-Generation

HuMAb mice with sufficient antigen-specific titer development as defined above were sacrificed and the spleen and lymph nodes flanking the abdominal aorta and caval vein were collected. Fusion of splenocytes and lymph node cells with a mouse myeloma cell line was done by electrofusion using a CEEF 50 Electrofusion System (Cyto Pulse Sciences, Glen Burnie, Md., USA), essentially according to the manufacturer's instructions. Fused cells were seeded in fusion medium containing 10% Fetal Clone I Bovine serum (Perbio), 1 mM sodium pyruvate (Cambrex), 0.5 U/mL penicillin, 0.5 U/mL streptomycin (Cambrex), 50 μM 2-mercaptoethanol (Invitrogen), 600 ng/mL interleukin 6 (IL-6) (Strathmann), 1×HAT (Sigma) and 0.5 mg/mL kanamycin (Invitrogen) in HyQ mADCF-Mab (Perbio). After ten days, supernatant was harvested and cells were refreshed with harvest medium, containing 10% Fetal Clone I Bovine serum, 0.5 U/mL penicillin, 0.5 U/mL streptomycin, 600 ng/mL IL-6 and 1×proHT (Cambrex) in HyQ mADCF-Mab. Supernatants of the hybridoma cultures were screened by primary screening assays and streptavidin beads coupled to SORTECDBAP (SEQ ID NO 171), SORTECDBAPhB06-10 (SEQ ID NO 176), SORTECDBAPhB12390 (SEQ ID NO 177), to detect hybridomas producing human (or chimeric) anti-Sortilin antibodies. Hybridoma cells from the best primary wells were seeded in semisolid medium made from 40% CloneMedia (Genetix, Hampshire, UK) and 60% HyQ 2× complete medium (Hyclone, Waltham, USA). For each primary well, a well of a Genetix black 6-well plate was seeded. From each well, 25 sub clones were picked, using the ClonePix system (Genetix). The sub clones were picked in harvest medium. After seven days, the supernatants of the sub clones were screened again for Sortilin-specific human IgG binding and the human IgG concentration was measured using Octet 384red (Fortebio, Menlo Park, USA). From each primary well, the best sub clone was selected and expanded in expansion medium containing only 600 ng/mL IL-6, 0.5 U/mL penicillin, 0.5 U/mL streptomycin and 1×proHT. The sub clones were expanded from one 96-well plate well to one 24-well plate well to four 24-well plate wells to six 6-well plate wells. Clones derived by this process were designated as primary clones (PC).

The anti-sortilin HuMab antibodies of the invention were identified and subjected to sequence analysis.

Example 5: Sequence Analysis of the Sortilin-Specific HuMab Variable Domains and Cloning in Expression Vectors Total RNA was prepared from 0.2 to 5×106 hybridoma cells and 5'-RACE-Complementary DNA (cDNA) was prepared from 100 ng total RNA, using the SMART RACE cDNA Amplification kit (Clontech), according to the manufacturer's instructions. VH and VL coding regions were amplified by PCR and cloned directly, in frame, in the p33G1f and p33Kappa expression vectors (containing the human IgG1./kappa constant domain encoding sequences), by ligation independent cloning (Aslanidis, C. and P. J. de Jong, Nucleic Acids Res 1990; 18(20): 6069-74). For each antibody, 16 VL clones and 16 VH clones were sequenced. Clones with a correct Open Reading Frame (ORF) were selected for further study and expression. Vectors of all combinations of heavy chains and light chains were transiently co-expressed in Freestyle™ 293-F cells using 293fectin.

The resulting sequences are shown in the Sequence Listing (SEQ ID NOs:1-168) herein. CDR sequences were defined according to the published guidelines.

Example 6: Purification of Antibodies

Culture supernatant was filtered over 0.2 μm dead-end filters, loaded on 5 mL Protein A columns (rProtein A FF, Amersham Bioscience) and eluted with 0.1 M citric acid-NaOH, pH 3. The eluate was immediately neutralized with 2M Tris-HCl, pH 9 and dialyzed to 12.6 mM $NaH_2PO_4$, 140 mM NaCl, pH 7.4 (B. Braun), O/N (over night). After dialysis, samples were sterile-filtered over 0.2 μm dead-end filters. Purity was determined by SDS-PAGE and concentration was measured by nephelometry and absorbance at 280 nm. Purified antibodies were aliquoted and stored at −80° C. Once thawed, purified antibody aliquots were kept at 4° C. Mass spectrometry was performed to identify the molecular mass of the antibody heavy and light chains expressed by the hybridomas.

Example 7: Generation of Mouse Antibodies (1F2 and 5E1) Immunogen

A synthetic gene coding for the chimeric immunogen hSortilin-FC, (human Sortilin AA (78-756) from SEQ ID NO:169) and human IgG1-FC AA (104-330) from SEQ ID NO:169 was cloned into pcDNA3.1 and used for expression using the freestyle system from Invitrogen. The antigen was purified from cell culture supernatants by protein-A affinity chromatography using standard procedures for antibody purification as described above for human antibodies.

Hybridoma Generation hSortilin-FC was used as immunogen and 5 BALB/c mice were immunized. A mouse with satisfactory immune response was selected for cell fusion and hybridoma generation. Hybridoma supernatants were screened by ELISA using hSortilin-ECD as coating antigen. A total of eighteen hybridoma cell lines derived from nine parental clones were generated.

Expression

Hybridomas were initially grown in complete growth medium, DMEM with 10% FBS+ antibiotics, and subsequently adapted to CDhybridoma media (Invitrogen) for expression experiments.

Purification

Mouse monoclonal antibodies were purified from hybridoma cell culture supernatants by protein-G sepharose according to standard procedures recommended by the supplier (GE healthcare).

Example 8: Affinity of Sortilin Specific HuMab and Mouse Antibodies to Recombinant Extracellular Region of Sortilin Binding kinetics of anti-Sortilin HuMab antibodies to Sortilin were determined using Octet 384RED (Fortebio, Menlo Park, USA). HuMab solutions of 2 µg/ml were made by dilution in sample diluent (ForteBio, art. No. 18-5028). Prot A sensors (ForteBio, art.no. 18-0004) were prewetted with kinetics buffer (1:10 sample diluent in PBS) for at least 600 seconds. Subsequently sensors were immobilized with HuMab solution for 600 seconds. A baseline response was obtained by dipping in kinetics buffer for 120 seconds. Association of SORTECD constructs was performed during a 1000 seconds incubation. This was followed by dissociation in kinetics buffer for 100 seconds. After dissociation, sensors were regenerated (10 mM Glycine pH 1.0) and neutralized (kinetics buffer) 3 times for 5 seconds. All HuMab were analysed using four concentrations of SORTECD constructs (10, 5, 2.5 and 1.25 µg/ml). A molecular weight of 76.8 kDA was used for SORTECDHis. Data was fitted with ForteBio Analysis 6.4 software, using a global full fit. Results are shown in FIG. 3 and FIG. 4.

Example 9: Antibody Cross Block of Anti-Sortilin HuMabs

Antibody cross-block studies were performed using Octet 384RED (Fortebio, Menlo Park, USA). HuMab antibody solutions of 2 µg/ml were made by dilution in sample diluent (ForteBio, art. No. 18-5028). Amine reactive sensors (ForteBio, art.no. 18-0008) were used for immobilization of HuMabs. Prior to coupling to amine reactive sensors, HuMabs were diluted in MES pH 6.0 buffer (18-5027). Coupling was performed at 30° C. and 1000 rpm as follows: Amine reactive sensors were prewet in PBS and subsequently activated with EDC/NHS (ForteBio. Art.no. 18-1033/18-1034) activation solution (according to manufacturer's instruction) for 300 seconds. Activated sensors were immobilized with HuMabs during 600 seconds. Immobilized sensors were quenched for remaining amine reactivity with Ethanolamine (ForteBio, cat no. 18-1039). After quenching sensors were placed in PBS until use. Cross block analysis starts with establishing a baseline response at 30° C. and 1000 rpm. Baseline response was obtained by dipping in sample diluent for 120 seconds. Association of SORTEC-DHis was performed during 300 seconds directly followed by association of HuMab for 300 seconds. After association of HuMab, sensors were regenerated (10 mM Glycine pH 1.0) and neutralized (sample diluent) 3 times for 5 seconds. Data was processed using ForteBio Analysis 6.4 software.

Antibodies were grouped based on their binding profiles on the different Sortilin shuffle constructs (FIGS. 2A-2C, FIG. 3 and FIG. 4). To confirm that all the antibodies from Region D (and region F) bind to the same region on human wild type Sortilin ECD, their ability to block each other's binding to the wild type human Sortilin ECD was characterised in a cross blocking study using the Octet384 red. For example, when antibodies from the same region were tested, the primary antibody would block binding of the secondary antibody and vice versa. Whereas, when antibodies from different regions were tested, there would be no cross blocking as only one region is blocked by the primary antibody and the remaining regions are available for the secondary antibody to bind. FIGS. 7A-7C show that all D-region and D+ antibodies cross block each other which confirms classification of the antibodies to Region D and D+ based on shuffle constructs. Further, these data also confirm that the chimeric Sortilin constructs retain similarity to the native human wild type Sortilin ECD.

Example 10: Characterization of Sortilin—PGRN Ligand Binding in the Presence of Anti-Sortilin Antibodies IC50 values for antibodies were determined by measuring the displacement of PGRN binding to Sortilin using a homogenous time resolved fluorescent (HTRF, CisBio) assay, see FIG. 5 and FIG. 6.

Experiments were performed in assay buffer (50 mM Phosphate, pH 7.0, 0.1% BSA) in a total volume of 20 µl in a Greiner 384 well, white, low volume microtiter plate, (784075, Greiner).

The antibodies were pre-incubated for 15 min at room temperature with 50 nM HIS-tagged Sortilin ECD and 4 nM PGRN (SULU20110924) before 7 nM anti-6HIS-d2 and 0.7 nM anti-PGRN-Eu cryptate (Cisbio) diluted in conjugate buffer (50 mM Phosphate, pH 7.0, 0.8 mM KF, 0.1% BSA) were added. 20 µM neurotensin was used as positive control and DMSO in buffer was used as negative control.

The assay plate was incubated for 60 min at room temperature and overnight at 4° C. before the plate was read in EnVision reader (Perkin Elmer).

Unlabelled neurotensin and DMSO blank were used as positive and negative controls for the assay set up, respectively. Dose-response evaluation of antibodies was performed with ten concentrations between 1 µM and 50 µM in a 3-fold dilution curve.

Figure 5:
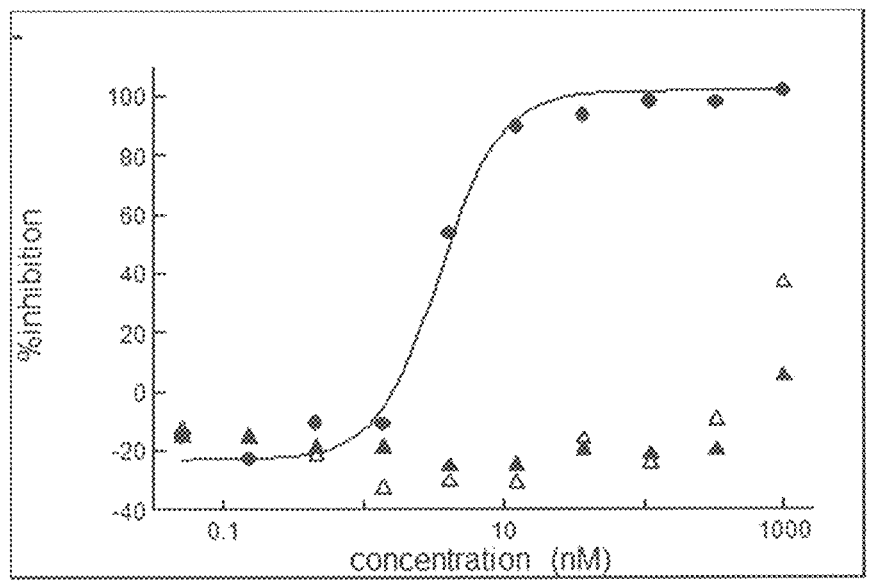

The half-maximal inhibitory concentration (IC50) were calculated by non-linear regression using a sigmoidal concentration response (variable slope) in XLfit 4 (IDBS, UK). (FIGS. 5 and 6).

Example 11: Characterization of Sortilin—Neurotensin Binding in the Presence of Anti-Sortilin Antibodies The IC50 for the Sortilin specific compound AF38469 (Schroder et al, Bioorg Med Chem Lett. 2014 Jan. 1; 24(1):177-80, 2014) was determined by measuring the displacement of $^3$H-Neurotensin binding to Sortilin using a scintillation proximity assay (SPA).

Experiments were performed in assay buffer (50 mM HEPES, pH 7.4, 100 mM NaCl, 2 mM $CaCl_2$), 0.1% BSA, 0.1% Tween-20) in a total volume of 40 µl in a 384-well Optiplate, white opaque, (6007299, Perkin Elmer).

150 nM HIS-tagged Sortilin was pre-incubated for 15 min at room temperature with or without 1 µM Sortilin specific antibody (IgG1-6003-045 or IgG1-6003-068) or with human IgG1 isotype control before the protein solutions were added to wells containing AF38469 in a concentration series 50 µM to 2.5 nM. The mixture was incubated for 15 min at room temperature on a shaker before 5 nM $^3$H-Neurotensin and Ni-chelate imaging beads (RPNQ0266, Perkin Elmer) were added. The assay was incubated additionally for 60 min under same conditions.

After 6 h, the plate was read on ViewLux (360 s exposure time). Unlabelled neurotensin and DMSO blank were used as positive and negative controls, respectively.

Figure 8:
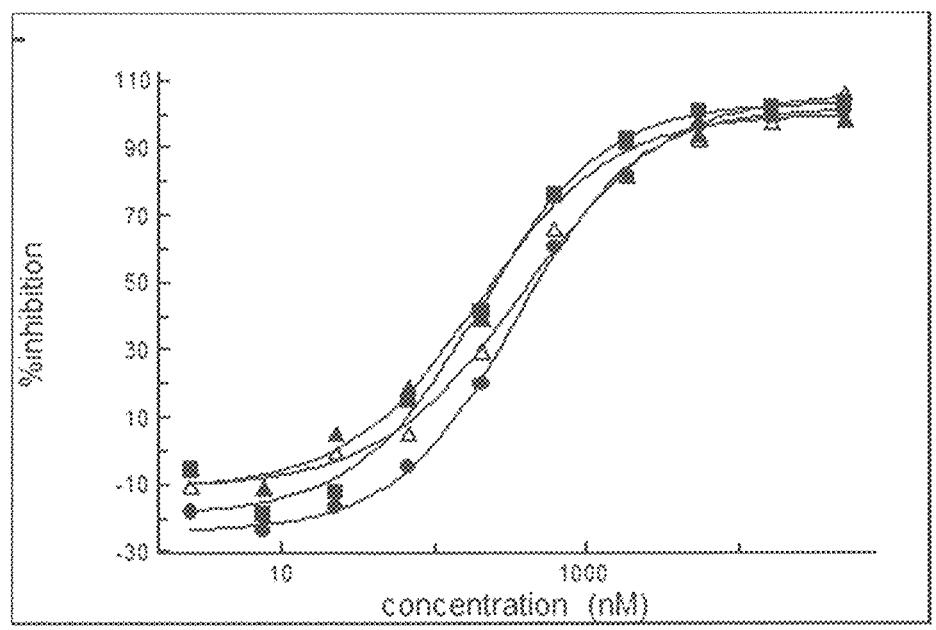

Dose-response evaluation for AF38469 was performed with ten concentrations between 50 µM and 2.5 nM in a 3-fold dilution curve. The half-maximal inhibitory concentration (IC50) were calculated by non-linear regression using sigmoidalconcentration response (variable slope) in XLfit 4 (IDBS, UK). Results can be seen in FIG. 8.

Example 12: Characterization of Sortilin—PGRN Ligand Binding on the Surface of Cells in the Presence of Anti-Sortilin Antibodies Both Sortilin transiently transfected cells and the stable cell line S18-HEK cells (human Sortilin over-expressing HEK cells) were used in this assay. Cells were trypsinized and plated at density of 42,000 cells per well in a 96 well plate. In the case of transiently transfected cells, the cells were plated 24 hrs after transfection in 96 well plates. Next day, media was changed completely and test compounds diluted in media were added to cells for 30 min. followed by addition of PGRN for 4 hr. At the end of the study (after 4.5 hrs), the cells were fixed and stained for PGRN. All stained plates were analyzed by Cellomics Array Scan (Thermo Fischer) and average staining intensity for PGRN/cell/well was used for analysis.

PGRN used in the assay was harvested from media following transient transfection of PGRN expression plasmids in HEK 293 cells. PGRN levels were measured using PGRN ELISA kit (R&D).

PGRN added to cells was readily bound and endocytosed which led to an increased fluorescence signal in Sortilin transfected wells. Addition of neurotensin, prevented Sortilin binding to PGRN and a PGRN fluorescence intensity is similar to control levels indicating that PGRN was not bound and endocytosed in the presence of neurotensin.

Figure 9:
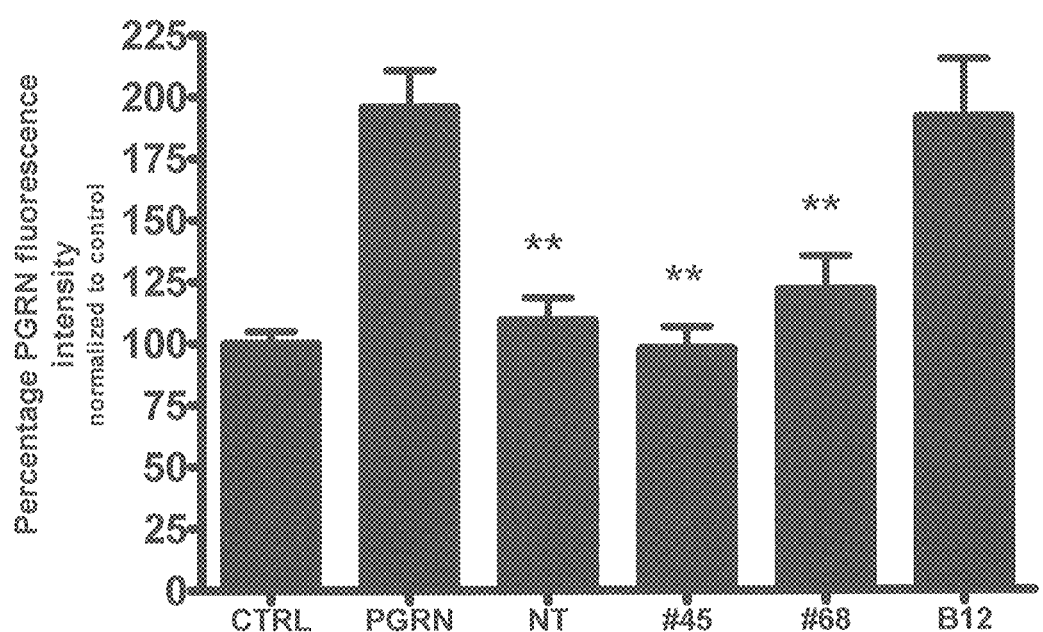

Both Sortilin HumAbs (45 and 68) blocked the uptake of PGRN with an efficacy similar to neurotensin. The isotype control antibody, B12, did not have any effect on PGRN endocytosis or binding. Results can be seen in FIG. 9.

Example 13: Effect of Antibodies on Extracellular PGRN Levels

Both HEK293 cells and S18-HEK cells were found to secrete PGRN continuously into the medium without any stimulation.

Antibodies and control agents were added to S18-HEK cells to evaluate the effect on PGRN. Addition of Neurotensin, a known peptide sortilin ligand, or human antibodies, 45, 68 and 811 to S18-HEK cells led to an increase of PGRN in the cell culture medium. Two of the Sortilin human antibodies (45 and 68) had an effect similar to neurotensin elevating PGRN levels to 202% and 201% respectively. The antibody 811 increased PGRN to 146% in the medium as compared to the controls B12, an isotype control antibody was used as negative control in all our studies and did not show any effect on PGRN levels. These observations indicate that the tested sortilin antibodies inhibited sortilin-mediated internalization of PGRN, thereby increasing extracellular PGRN.

On day1, S18-HEK cells were seeded in a 96 well plate. After 24 hrs, medium was completely replaced with either medium alone (control) or medium supplemented with test compound. All compounds were tested at 10 uM and antibodies at 100 nM unless otherwise specified. Medium was collected on day 3 and analyzed using PGRN ELISA (R&D). Cell viability was assessed by Cell TiterGlo (Pro Mega) to evaluate cytotoxic effect of the compounds. PGRN levels in media were analysed by ELISA and values were normalized to control wells. Results can be seen in FIG. 10.

Example 14: ELISA Assay for Extracellular PGRN in iPSCs

Induced pluripotent stem cells (iPSCs) were generated by non-integrative reprogramming of human fibroblasts (Normal human dermal fibroblasts 18 y male; Lonza) as described elsewhere (Rasmussen et al., Stem Cell Reports. 2014 Sep. 9; 3(3):404-13.). The NHDF K1_shp53 line was used for these studies. The iPSCs were initially generated in mTESR media and subsequently cultured in monolayer in Pluripro (Cell Guidance System). Neuronal differentiation was initiated day 0 by replating the cells on poly-L-ornithine/laminin coated dishes and culturing them in N3 media (50% DMEM/F12+50% Neurobasal media supplemented with 0.5% N2, 1% B27 with RA, 0.5 mM GlutaMAX, 0.5& NEA, 50 µM 2-mercaptoethanol and 2.5 mg/mL insulin) with 500 ng/mL noggin and 10 µM SB431542. The media was refreshed every day. After 11 days of noggin/SB431542 induction, the cells were split with dispase and re-plated on poly-L-ornithine/laminin in N3 media. From that point forward, N3 media was refreshed every 2-3 days and the cells were split approximately every 10-14 day using accutase.

Neuronal differentiated iPSC cells were plated into 96 wells plate. One week later, antibodies were added to the cells. Media from the cells were collected at 48 hrs or 96 hrs and analysed by human PGRN ELISA (Enzo Life sciences) and samples analysed as per the manufacturer's instructions.

The tested Sortilin human antibodies (45 and 68) increased PGRN levels at varying levels in the media at 48 hrs and 96 hrs. B12 and Anti-Hel are the control isotype antibodies (negative control). Data is presented as mean±SD. Data was analyzed by one-way Anova followed by Dunnett's analysis $*p<0.05$; $p<0.01$. Results can be seen in FIG. 12**.

Example 15

To analyze the effect of antibodies on PGRN levels in plasma, humanized Sortilin KI mice were given a single or multiple injections (10 mg/kg) of the sortilin antibodies or isotype control by subcutaneous injections. The animals were anaesthetized and sacrificed at various time points after dosing and plasma PGRN levels determined by ELISA.

A. Time course study: Mice were treated with antibodies (a Sortilin humab or a control ab) and sacrificed at different time points. Mice treated with control antibodies (Anti-Hel), did not show change in plasma PGRN whereas in mice treated with Sortilin humab 45, there was an increase in PGRN levels which seemed to peak between 24 and 48 hrs and then gradually decreased from around day 4. PGRN levels were still elevated at day 7.

B. Subchronic study: Based on the data from time course study, Sortilin KI mice were dosed twice a week with 10 mg/kg, s.c, with either Sortilin human antibody 45 or isotype control antibody, in order to maintain a steady antibody level for a subchronic study (4 weeks).

Blood samples were collected at the start of the study and every week to follow plasma PGRN changes. Plasma PGRN levels at the start of the study were similar in both group of animals. Higher levels of plasma PGRN were seen in mice treated with Sortilin antibody45 from week 1 and remain elevated throughout the study. Mice treated with control ab, did not show any increase in plasma PGRN and remained at baseline levels (week 0).

C. Dose response study: Different doses (4 doses: 10, 2, 0.4 and 0.1 mg/kg) of the Sortilin (45) and control antibody (Anti-Hel) were injected and mice sacrificed on day 2. Plasma PGRN was elevated with 10 mg/kg and 2 mg/kg in mice treated with Sortilin humab and the lower doses did not have an effect on the plasma PGRN which clearly shows a dose dependent effect of the Sortilin antibody on the plasma PGRN levels. Mice treated with control antibody did not show any change in PGRN levels.

Mice were anaesthetized with 0.4 ml Avertin IP and heart blood was collected and transferred to a 500 ul kEDTA vial. Samples were kept on ice until centrifuged at 3600 G for 15 min at 4 C. The plasma was pipetted in to a micronic vial and frozen at −20 C. PGRN in the samples was measured using PGRN ELISA kit (Adipogen) as per the manufacturer's instructions. Results can be seen in FIGS. 13A-13C.

Example 16: Epitope Mapping of Antibodies Targeting the Progranulin-Sortilin Interaction by Hydrogen/Deuterium Exchange Followed by Mass Spectrometry In hydrogen/deuterium exchange followed by mass spectrometry (HDX-MS) the exchange rate of backbone amide hydrogens in a protein is measured. Hereby, it is possible to probe the conformational dynamics of the entire protein backbone except at proline residues. The rate of the exchange reaction is determined by the hydrogen bonding status of the backbone amide and to a lesser extent its solvent accessibility. Subtle changes in these two parameters e.g. caused by the presence of a ligand can be observed as a change in deuterium incorporation.

To sub-localize the changes in deuterium incorporation the protein is treated with an acid stable protease (e.g. pepsin), which generates local regions of typically ten to fifteen amino acids. Regions that shows a perturbation in the presence of a ligand is either directly involved in the binding interface or allosterically affected by the binding event.

Epitope Mapping of Antibodies

The deuterium incorporation of the extra cellular region of Sortilin (SEQ ID NO:188) was measured in the absence and presence of mAb45, mAb68, mAb811 and an antibody denominated mAb30 which does not bind the D region. To secure that the measurements were conducted at steady-state conditions the complexes were equilibrated for 15 min at 25° C. before the exchange reaction was initiated. The exchange reaction was initiated by dilution of the protein samples 1:9 (v/v) into deuterated buffer (99% D2O, 20 mM tris, 150 mM NaCl, pDread=7.6). After various time points (15 s, 1 min, 10 min, 1 h and 8 h) the exchange reaction was quenched by 1:1 (v/v) dilution with ice-cold quench buffer (2M glycine, 0.8M tris-(2-carboxyethyl)phosphine (TCEP), pH=2.3), thereby decreasing the pH to 2.46. The quenched samples were immediately placed inside a −80° freezer and stored until analysis. Fully deuterated control samples were prepared by diluting sortilin samples 1:9 (v/v) into a deuterated denaturation buffer (6M guanidinium chloride, 99% D2O, 20 mM tris, 150 mM NaCl, pDread=7.6) followed by incubation at 25° C. for 16 h before they were quenched and handled as described above.

The quenched samples were thawed and injected into a cooled (0° C.) reverse-phase UPLC-HDX-system (Waters Inc., USA) equipped with a home-packed pepsin column (internal volume of 60 μL, pepsin beads acquired from Thermo Scientific Inc.). Here, the deuterated protein samples were subjected to online pepsin digestion at 20° C., and the resulting peptic peptides were separated by reverse-phase UPLC. The peptides were ionized by electrospray ionization into a mass spectrometer (Synapt G2 mass spectrometer, Waters Inc, UK), where the peptides were further separated by ion mobility before final mass determination.

The Identification of peptides was performed on fully reduced and non-deuterated samples by tandem mass spectrometry using a combination of data independent (MSe) and data dependent acquisition.

Data Analysis

Identification of Peptides

The acquired mass spectra were lock mass corrected against GFP and analyzed in PLGS 3.0, which matched precursor and fragment ions to a local protein database. All peptide identifications were carefully assessed manually.

Determination of deuterium incorporation: The acquired mass spectra were lock mass corrected against GFP and the software DynamX 3.0 (Waters Inc., USA) was used to determine the deuterium incorporation for all peptides of sortilin either in absence or presence of antibodies.

A peptide was considered to be a part of the binding epitope if a protection from exchange larger than 0.5D was observed in presence of an antibody.

TABLE 1

Table of identified conformational epitopes by HDX-MS.

| Antibody | Epitope mapping by HDX-MS relative to SEQ ID NO: 169 | | | | |
| --- | --- | --- | --- | --- | --- |
| 45 | 109-114 | 126-153 | | 570-572 | 588-597 |
| 68 | 109-114 | 126-144 | 154-159 | 570-572 | 593-597 |
| 811-02 | 109-114 | 126-144 | | | 593-597 |

Example 17: Microdialysis to Assess Progranulin Levels in the Brain of Awake Freely Moving Animals Push-pull microdialysis method was used to assess brain ISF progranulin (PRGN) from awake and freely moving mice. Mice were single-housed in controlled temperature (22±1.5° C.) and humidity conditions (55-65%) and kept in a 12:12 hour light/dark cycle (lights on at 06:00 h). Food and water were available ad libitum. The current study was performed in the hippocampus of human sortilin knock-in (hSORT1) mice (22 weeks old). To enable microdialysis in the hippocam-pus, mice were anaesthetized with isoflurane and an intracerebral guide cannula (CMA) was stereotaxically implanted into the brain, positioning the microdialysis probe in the hippocampus (co-ordinates of probe tip: 3.1 mm posterior and 2.8 mm lateral from bregma, and 1.3 mm relative dura mater) according to the atlas of Paxinos and Franklin 2001. Acrylic cement was used for the fixation of the guide cannulas. After implantation of the cannula mice were allowed to recover from the surgery for 7 days before dialysis. During the first 5 days, including the surgery day, animals had pain and antibiotics treatments (Rimadyl and Noromox Prolongatum). 24 h before the starting of microdialysis experiments pump was also connected to the outlet tubing in order to prevent perfusion fluid loss from the probe, by pulling the fluid through the tubing. As a perfusion buffer, 25% bovine albumin fraction V (Sigma) was diluted to 0.2% with artificial CSF (aCSF; in mM: 147 NaCl, 2.7 KCl, 1.2 CaCl2, 0.85 MgCl2) on the day of use and filtered through a 0.1-μm membrane. The actual flow rate of the pump was determined without having the probe connected. The sample tubes were weighed before and after sampling for a given time period and the flow rate was calculated. The pump was then set to have a constant flow of 1 μL/min. A 120-min sampling regimen was used throughout the experiment period and 12 samples (12 h of collection) were collected (FIG. 17, for procedure). At the end of experiments, blood was taken from animals, animals were perfused and brains collected. The dialysates, plasma and brains were stored at −80° C. until PRGN determination by ELISA.

The measurement of PRGN levels every 2 h during 24 h is depicted in FIG. 17. At every time period, except 24 h after starting collecting di dialysates, PRGN levels are significantly increased in animals-treated with mab #45 increased when compared to the ones from animals treated with PBS (FIG. 18A). PRGN levels are stable over time from 4 h until 16 h after probe insertion in hippocampus. In the first dialysate PRGN are elevated likely due to the probe insertion into hippocampus. It is speculated that PRGN levels are decreasing >18 h/20 h after probe insertion, likely due to the clogging of the probe membrane, as it occurred in both groups (and has been previously observed in other push-pull studies).

The average±SEM of the 12 dialysis samples 24 h after antibody or vehicle treatment, for each animal and then all animals pooled, was taken as baseline (FIG. 18B). Differences between animals-treated with mab #45 and PBS were analyzed with unpaired t-test. The basal levels of PRGN in animals-treated with mab #45 were significantly increased when compared to the ones from animals treated with PBS ($p<0.001$, F10.0, DFn, 9 Dfd 7; 3.3±0.3 ng/ml, n=10 versus 1.1±0.1 ng/ml, n=8) (FIG. 18B).

The invention claimed is:

1. An antibody, or an antigen-binding fragment thereof, comprising:

(a) a light chain variable domain L-CDR1 comprising SEQ ID NO:137;
(b) a light chain variable domain L-CDR 2 comprising SEQ ID NO:138;
(c) a light chain variable domain L-CDR 3 comprising SEQ ID NO:139;
(d) a heavy chain variable domain H-CDR 1 comprising SEQ ID NO:140;

(e) a heavy chain variable domain H-CDR 2 comprising SEQ ID NO:141; and
(f) a heavy chain variable domain H-CDR 3 comprising SEQ ID NO:142.

2. The antibody, or antigen-binding fragment thereof, according to claim 1, wherein said antibody or antigen-binding fragment thereof comprises a heavy chain variable domain comprising SEQ ID NO:144.

3. The antibody, or antigen-binding fragment thereof, according to claim 1, wherein said antibody or antigen-binding fragment thereof comprises a light chain variable domain comprising SEQ ID NO:143.

4. The antibody, or antigen-binding fragment thereof, according to claim 1, wherein the antibody or antigen-binding fragment thereof comprises both the heavy chain variable domain comprising SEQ ID NO:144 and light chain variable domain comprising SEQ ID NO:143.

5. The antibody, or antigen-binding fragment thereof, of claim 1, wherein the antigen-binding fragment is selected from the group consisting of an Fv fragment and a Fab-like fragment.

6. The antibody, or antigen-binding fragment thereof, of claim 1, wherein the antibody is selected from the group consisting of an antibody of subtypes IgG1, IgG2, IgG3 or IgG4.

7. The antibody, or antigen-binding fragment thereof, of claim 1, wherein said antibody or antigen-binding fragment thereof binds to the D Region of Sortilin as defined by SEQ ID NO:170.

8. The antibody, or antigen-binding fragment thereof, of claim 1, wherein said antibody or antigen-binding fragment thereof binds to at least 3-7 consecutive amino acids within the D Region of Sortilin as defined in SEQ ID NO:170.

9. The antibody, or antigen-binding fragment thereof, of claim 1, wherein the antibody or antigen-binding fragment exhibits one or more of the following properties:
  (a) a binding affinity (KD) for Sortilin between 0.5-10 nM;
  (b) capability to reduce and/or inhibit PGRN binding to Sortilin;
  (c) capability to reduce and/or inhibit clearance of PGRN by Sortilin-expressing cells;
  (d) capability to reduce and/or inhibit the endocytosis of PGRN by Sortilin-expressing cells;
  (e) capability to increase the amount and/or concentration of PGRN in the brain, and/or
  (f) capability to increase the amount and/or concentration of PGRN in the plasma in human-Sortilin-expressing knock-in mice.

10. The antibody, or antigen-binding fragment thereof, of claim 1, wherein the antibody or antigen-binding fragment thereof is a human, humanized, recombinant or chimeric antibody.

11. A pharmaceutical composition comprising an antibody, or an antigen-binding fragment thereof, of claim 1 and a pharmaceutically-acceptable carrier.

12. A method of treating a disease associated with decreased PGRN levels in the brain of a patient, comprising administering an effective dosage of an antibody, or an antigen-binding fragment thereof, of claim 1.

13. The method according to claim 12, wherein the disease is frontotemporal dementia, amyotrophic lateral sclerosis or Alzheimer's disease.

14. A kit comprising an antibody, or antigen-binding fragment thereof, of claim 1.

15. An antibody, or antigen-binding fragment thereof, of claim 1 which has been produced or manufactured in a cell line comprising a mammal non-human cell line, an insect, yeast or bacterial cell line.

16. The antibody, or antigen binding fragment thereof, of claim 15 produced in a CHO cell line, HEK cell line, BHK-21 cell line, murine cell line, myeloma cell line, fibrosarcoma cell line, PER.C6 cell line, HKB-11 cell line, CAP cell line and HuH-7 human cell line.

17. A method of making a pharmaceutical composition comprising combining an antibody, or an antigen-binding fragment thereof, of claim 1, with a pharmaceutically-acceptable carrier.

18. A nucleic acid sequence encoding an antibody or antibody binding fragment of claim 1.

19. A cell line comprising the nucleic acid sequence of claim 18.

* * * * *